(12) United States Patent
Masuda et al.

(10) Patent No.: US 11,472,782 B2
(45) Date of Patent: Oct. 18, 2022

(54) RIP1 INHIBITORY COMPOUNDS AND METHODS FOR MAKING AND USING THE SAME

(71) Applicant: Rigel Pharmaceuticals, Inc., South San Francisco, CA (US)

(72) Inventors: Esteban Masuda, Menlo Park, CA (US); Simon Shaw, Oakland, CA (US); Vanessa Taylor, San Francisco, CA (US); Somasekhar Bhamidipati, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 68 days.

(21) Appl. No.: 17/072,862

(22) Filed: Oct. 16, 2020

(65) Prior Publication Data

US 2021/0040053 A1 Feb. 11, 2021

Related U.S. Application Data

(63) Continuation of application No. 16/402,111, filed on May 2, 2019, now Pat. No. 10,815,206.

(60) Provisional application No. 62/666,462, filed on May 3, 2018.

(51) Int. Cl.
| | |
|---|---|
| C07D 267/14 | (2006.01) |
| C07D 487/04 | (2006.01) |
| C07D 413/06 | (2006.01) |
| C07D 413/14 | (2006.01) |
| C07D 403/12 | (2006.01) |
| C07D 493/04 | (2006.01) |
| C07D 407/06 | (2006.01) |
| A61P 35/00 | (2006.01) |
| C07D 413/12 | (2006.01) |

(52) U.S. Cl.
CPC ............ C07D 267/14 (2013.01); A61P 35/00 (2018.01); C07D 413/12 (2013.01); C07D 413/14 (2013.01); C07D 487/04 (2013.01)

(58) Field of Classification Search
CPC .. C07D 267/14; C07D 487/04; C07D 413/06; C07D 413/14; C07D 403/12; C07D 493/04; C07D 407/06
See application file for complete search history.

(56) References Cited

U.S. PATENT DOCUMENTS

| | | | |
|---|---|---|---|
| 8,658,689 | B2 | 2/2014 | Cuny et al. |
| 9,556,152 | B2 | 1/2017 | Harris et al. |
| 9,624,202 | B2 | 4/2017 | Jeong |
| 9,815,850 | B2 | 11/2017 | Estrada et al. |
| 9,896,458 | B2 | 2/2018 | Estrada et al. |
| 10,815,206 | B2 | 10/2020 | Masuda et al. |
| 10,975,064 | B2 | 4/2021 | Taylor et al. |
| 2015/0353533 | A1 | 12/2015 | Bandyopadhyay et al. |
| 2017/0008877 | A1 | 1/2017 | Patel et al. |
| 2017/0226127 | A1 | 8/2017 | Estrada et al. |
| 2019/0337907 | A1 | 11/2019 | Masuda et al. |
| 2019/0337934 | A1 | 11/2019 | Taylor et al. |
| 2021/0070743 | A1 | 3/2021 | Chen et al. |
| 2021/0070744 | A1 | 3/2021 | Shaw et al. |

FOREIGN PATENT DOCUMENTS

| | | |
|---|---|---|
| CN | 20180676651.0 A | 6/2018 |
| CN | 201811301267.9 A | 5/2020 |
| EP | 3816163 A1 | 5/2021 |
| EP | 3872077 A1 | 8/2021 |
| WO | WO 2014/125444 | 8/2014 |
| WO | WO 2014/145022 | 9/2014 |
| WO | WO 2016/027253 | 2/2016 |
| WO | WO 2016/128936 | 8/2016 |
| WO | WO 2017/064217 | 4/2017 |
| WO | WO 2017/069279 | 4/2017 |
| WO | WO 2017/109724 | 6/2017 |
| WO | WO 2018/073193 | 4/2018 |
| WO | WO 2018/109097 | 6/2018 |
| WO | 2018/154520 | 8/2018 |
| WO | 2020/001420 A1 | 1/2020 |
| WO | 2020/088194 A1 | 5/2020 |

OTHER PUBLICATIONS

Harris et al., "Discovery of a first-in-class receptor interacting protein 1 (RIP1) kinase specific clinical candidate (GSK2982772) for the treatment of inflammatory diseases," *J. Med. Chem.*, 60(4): 1247-1261, Feb. 23, 2017.
International Search Report issued for International Application No. PCT/US2019/030476 dated Sep. 11, 2019.
International Search Report issued for International Application No. PCT/US2019/030473 dated Jul. 4, 2019.
Najjar et al., "Structure guided design of potent and selective ponatinib-based hybrid inhibitors for RIPK1," *Cell Reports*, vol. 10, pp. 1850-1860, Mar. 24, 2015.
Takeda et al., "CETSA quantitatively verifies in vivo target engagement of novel RIPK1 inhibitors in various biospecimens," *Scientific Reports*, vol. 7, Oct. 11, 2017.
Harris et al., "Identification of a RIP1 Kinase Inhibitor Clinical Candidate (GSK3145095) for the Treatment of Pancreatic Cancer," *ACS Medicinal Chemistry Letters*, pp. 857-862, vol. 10, No. 6, (2019).
Harris et al., "Discovery and Lead-Optimization of 4,5-Dihydropyrazoles as Mono-Kinase Selective, Orally Bioavailable and Efficacious Inhibitors of Receptor Interacting Protein 1 (RIP1) Kinase," Journal of Medicinal Chemistry, pp. 5096-5110, vol. 62, No. 10, (2019).

(Continued)

*Primary Examiner* — Brenda L Coleman
(74) *Attorney, Agent, or Firm* — Gabriel Magallanes

(57) ABSTRACT

Disclosed herein are kinase inhibitory compounds, such as a receptor-interacting protein-1 (RIP1) kinase inhibitor compounds, as well as pharmaceutical compositions and combinations comprising such inhibitory compounds. The disclosed compounds, pharmaceutical compositions, and/or combinations may be used to treat or prevent a kinase-associated disease or condition, particularly a RIP1-associated disease or condition.

17 Claims, No Drawings

(56) References Cited

OTHER PUBLICATIONS

Yoshikawa et al., "Discovery of 7-Oxo-2,4,5,7-tetrahydro-6 H-pyrazolo [3,4- C ] pyridine Derivatives as Potent, Orally Available, and Brain-Penetrating Receptor Interacting Protein 1 (RIP1) Kinase Inhibitors: Analysis of Structure-Kinetic Relationships," Journal of Medicinal Chemistry, pp. 2384-2409, vol. 61, No. 6, (2018).

U.S. Appl. No. 17/221,493, filed Apr. 2, 2021 (Rigel Pharmaceuticals, Inc.).

Harris, et al., "DNA-Encoded Library Screening Identifies Benzo[b][1,4]oxazepin-4-ones as Highly Potent and Monoselective Receptor Interacting Protein 1 Kinase Inhibitors," Journal of Medicinal Chemistry, vol. 59, No. 5, pp. 2163-2178 (Mar. 10, 2016).

RIP1 INHIBITORY COMPOUNDS AND METHODS FOR MAKING AND USING THE SAME

CROSS REFERENCE TO RELATED APPLICATION

This application is a continuation of U.S. application Ser. No. 16/402,111, filed on May 2, 2019, which claims the benefit of the earlier filing date of U.S. Provisional Application No. 62/666,462, filed on May 3, 2018; the entirety of each of these prior applications is incorporated herein by reference.

FIELD

The present disclosure concerns compounds and methods of making and using the compounds, such as for inhibiting receptor-interacting protein-1 kinase ("RIP1"), and for treating diseases and/or conditions related to RIP1.

BACKGROUND

Receptor-interacting protein-1 kinase (referred to herein as "RIP1") belongs to the tyrosine kinase-like family and is a serine/threonine protein kinase involved in innate immune signaling. RIP1 plays a central role in regulating cell signaling and its role in programmed cell death has been linked to various inflammatory diseases, such as inflammatory bowel disease, psoriasis, and other diseases and/or conditions associated with inflammation and/or necroptotic cell death.

SUMMARY

Disclosed herein are compound embodiments having a Formula I

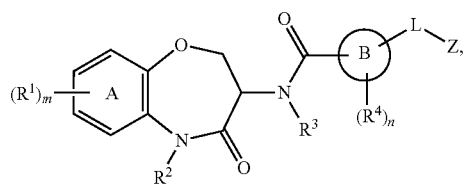

Formula I or a pharmaceutically acceptable salt thereof. A person of ordinary skill in the art will appreciate that compounds within the scope of Formula I also include stereoisomers, N-oxides, tautomers, hydrates, solvates, isotopes, and/or prodrugs thereof.

With reference to Formula I, ring B is 5-membered or 6-membered heteroaryl; L is a heteroatom or $R^a$, provided that $R^a$ is not H or D; Z is $C_{1-10}$aliphatic (such as $C_{1-10}$alkyl, $C_{2-10}$alkenyl, $C_{2-10}$ alkynyl, or $C_{3-6}$cycloalkyl); or $R^1$ is a halogen, —C≡CH, or a -linker-$R^6$ group, wherein the linker is $R^a$, provided that $R^a$ is not H or D, and $R^6$ is $R^b$, —C($R^f$)$_3$, or —C($R^f$)=C($R^f$)$_2$; $R^2$ and $R^3$ independently are $R^a$; $R^4$ and $R^5$ independently are $R^e$; $R^a$ is independently for each occurrence H, D, $C_{1-10}$aliphatic, $C_{1-10}$haloaliphatic, $C_{5-10}$aromatic, or $C_{3-6}$heterocyclic; $R^b$ is independently for each occurrence —OH, —SH, —OR$^c$, —SR$^c$, —NR$^d$R$^d$, —Si($R^a$)$_3$, —C(O)OH, —C(O)OR$^c$, or —C(O)NR$^d$R$^d$; $R^c$ is independently for each occurrence $C_{1-10}$alkyl, $C_{2-10}$alkenyl, $C_{2-10}$alkynyl, $C_{3-6}$cycloalkyl (which can be substituted with 1, 2 or 3 $R^e$), or $C_{5-10}$aromatic (which can be substituted with 1, 2 or 3 $R^e$); $R^d$ is independently for each occurrence H; $C_{1-6}$alkyl (which can be substituted with 1, 2 or 3 $R^e$); $C_{3-6}$cycloalkyl (which can be substituted with 1, 2 or 3 $R^e$); $C_{3-6}$heterocyclic (which can be substituted with 1, 2 or 3 $R^e$); $C_{5-10}$aryl (which can be substituted with 1, 2 or 3 $R^e$); $C_{5-10}$heteroaryl (which can be substituted with 1, 2 or 3 $R^e$); or two $R^d$ groups together with the nitrogen bound thereto provide a $C_{3-9}$heterocyclic (which can be substituted with one or more $R^e$), or a $C_{5-10}$heteroaryl (which can be substituted with one or more $R^e$); $R^e$ is independently for each occurrence halogen, $C_{1-6}$alkyl, $C_{2-10}$alkenyl, $C_{2-10}$alkynyl, $C_{1-6}$haloalkyl $C_{3-6}$cycloalkyl, $C_{5-10}$heteroaryl, or —OR$^a$; $R^f$ is independently for each occurrence $R^a$, $R^b$, or $R^c$, or two $R^f$ groups together with the carbon atom bound thereto provide a $C_{3-6}$cycloalkyl group (which can be substituted with one or more $R^e$), or a $C_{3-10}$heterocyclic (which can be substituted with one or more $R^e$); m is 1 to 4; n is 0, 1 or 2; and p is 0, 1, 2, 3, 4, or 5.

Disclosed compounds may have a structure satisfying the formula below

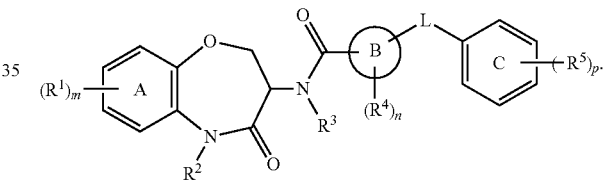

In any or all of the above embodiments, ring B can have a structure satisfying a formula

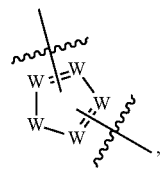

wherein at least one W is nitrogen, and each remaining W independently is selected from carbon, CH, oxygen, sulfur, nitrogen, or NH, with particular ring B embodiments being a diazole, a triazole, an oxadiazole, an oxazole, or a pyridinyl. Suitable exemplary triazoles include any of the following:

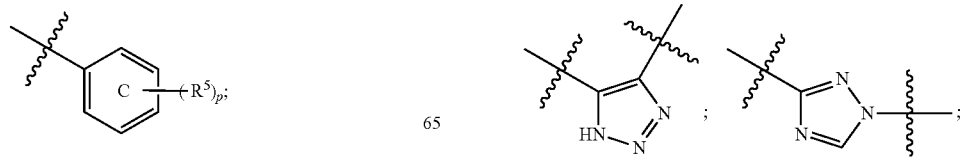

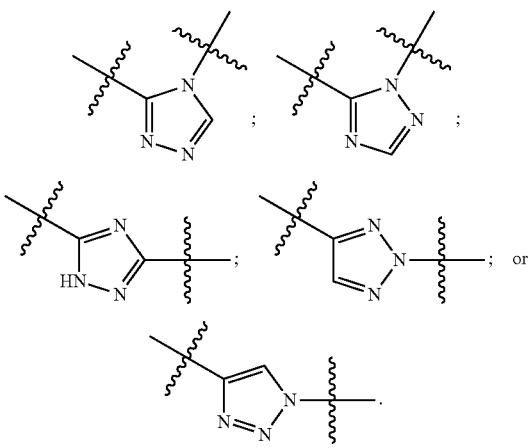

Suitable exemplary diazole include any of the following:

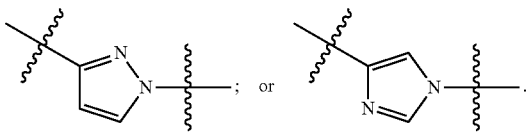 [SMILES: *c1ccn(*)n1 ; *c1cn(*)cn1]

Suitable exemplary oxadiazoles include any of the following:

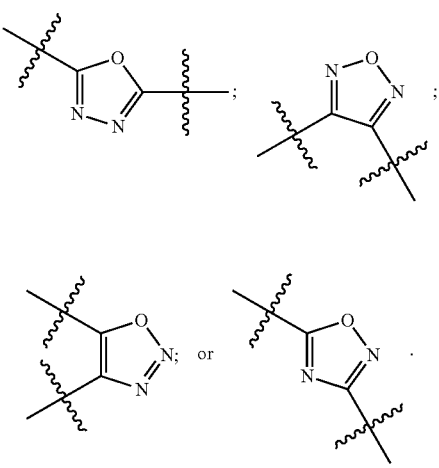

Suitable exemplary oxazoles include any of the following:

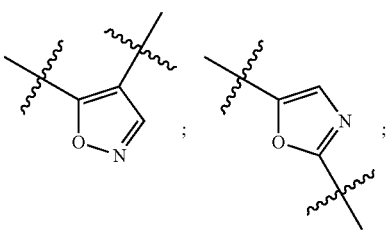

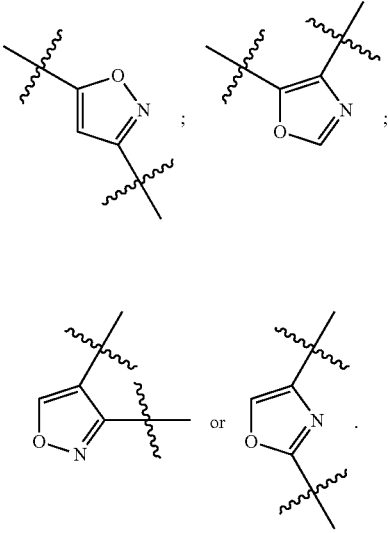

Certain disclosed compounds comprise an $R^5$ group that is an $R^e$ group, wherein $R^e$ is $C_1$-$C_4$aliphatic, or halogen, $R^2$ is $R^a$ wherein $R^a$ is $C_1$-$C_4$aliphatic, and $R^3$ is $R^a$, wherein $R^a$ is hydrogen.

For certain disclosed embodiments, $R^1$ is a linker-$R^6$ group wherein the linker is $R^a$ and $R^a$ is a $C_1$, $C_2$, $C_3$, or $C_4$ aliphatic group. The $C_2$ aliphatic group may be an alkyl, alkenyl, or alkynyl group. The $R^6$ group may be R wherein R is —C($R^f$)$_3$, wherein one $R^f$ is $R^e$, particularly —O$R^a$, wherein $R^a$ is H; and each other $R^f$ independently for each occurrence is $R^a$, wherein $R^a$ is $C_{1-4}$alkyl, particularly methyl. In particular embodiments, the $C_2$ group is an alkyne. In any or all of the above embodiments, ring B can be selected from

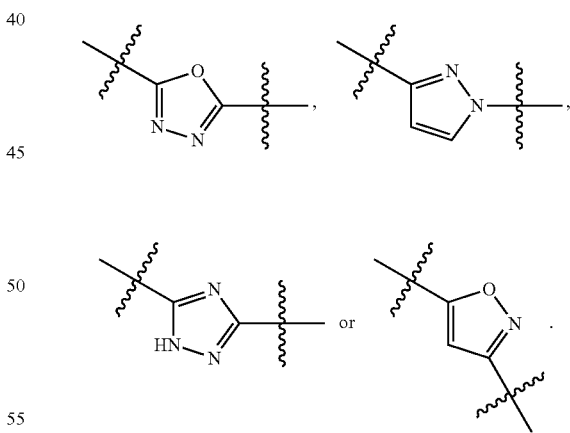

In some embodiments, $R^6$ may be $R^b$ wherein $R^b$ is —C(O)OEt; or $R^b$ may be —C(O)N$R^d R^d$, wherein each $R^d$ is independently for each occurrence H, $C_{5-10}$heteroaryl (which can be substituted with 1, 2 or 3 $R^e$), $C_{1-6}$alkyl (which can be substituted with 1, 2 or 3 $R^e$), or two $R^d$ groups together with the nitrogen bound thereto provide a $C_{3-9}$heterocyclic (which can be substituted with one or more $R^e$), or a $C_{5-10}$heteroaryl (which can be substituted with one or more $R^e$). More particularly, one $R^d$ is H and the other $R^d$ is aromatic, such as

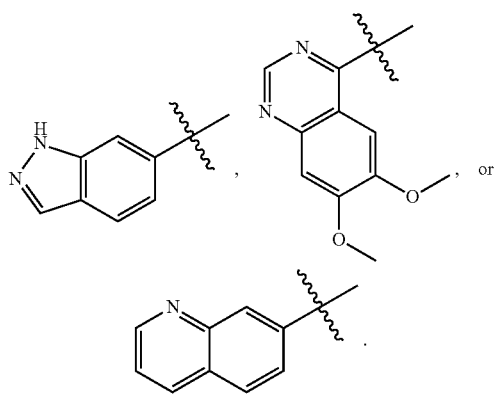

Certain compounds can comprise an $R^6$ group that is $R^b$ wherein $R^b$ is —OH; $OR^c$, wherein $R^c$ is $C_{1-10}$alkyl (which can be substituted with 1, 2 or 3 $R^e$), $C_{2-10}$alkenyl (which can be substituted with 1, 2 or 3 $R^e$), $C_{2-10}$alkynyl (which can be substituted with 1, 2 or 3 $R^e$), or $C_{5-10}$aromatic (which can be substituted with 1, 2 or 3 $R^e$); or $NR^dR^d$, wherein one $R^d$ is H and the other $R^d$ is $C_{5-10}$aromatic (which can be substituted with 1, 2 or 3 $R^e$). In some embodiments, $R^b$ is $OR^c$, wherein $R^c$ is $C_2$alkyl substituted with pyridinyl. In some other embodiments, $R^b$ may be —$NR^dR^d$, wherein one $R^d$ is H and the other $R^d$ is pyridinyl.

The linker group of the linker-$R^6$ group can be a $C_1$ group and the corresponding $R^6$ group is $R^b$ wherein $R^b$ is —$NR^dR^d$, wherein two $R^d$ groups together with the nitrogen bound thereto provide a $C_{3-9}$heterocyclic (which can be substituted with one or more $R^e$), or a $C_{5-10}$heteroaryl (which can be substituted with one or more $R^e$), particularly wherein two $R^d$ groups together with the nitrogen bound thereto provide a $C_{3-9}$heterocyclic substituted with one $R^e$. In such embodiments, $R^e$ may be $C_{5-10}$heteroaryl, such as pyridinyl. In other embodiments, the two $R^d$ groups together with the nitrogen to which they are bound may provide a $C_{5-10}$heteroaryl optionally may be substituted with one or more $R^e$. The $C_{5-10}$heteroaryl without $R^e$ substituents can be

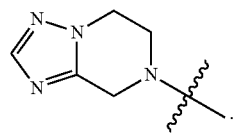

In some embodiments, $R^5$ is $R^e$, wherein $R^e$ is halogen or methyl. In some embodiments, the linker of the linker-$R^6$ group is $R^a$ wherein $R^a$ is a $C_1$, $C_2$, $C_3$, or $C_4$ aliphatic group comprising an alkyl, alkenyl, or alkynyl group. In some such embodiments, the $C_2$ group comprises an alkyne and wherein $R^6$ is $R^b$ wherein $R^b$ is —$C(R^f)_3$, wherein one $R^f$ is $R^e$ and each other $R^f$ independently for each occurrence is $R^a$, wherein $R^a$ is $C_{1-4}$alkyl. In particular embodiments, $R^e$ is —$OR^a$, wherein $R^a$ is H. $R^a$ is methyl in some such embodiments and ring B is

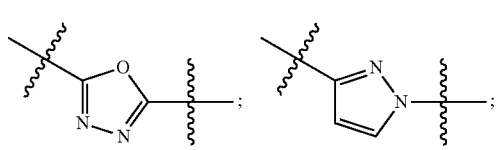

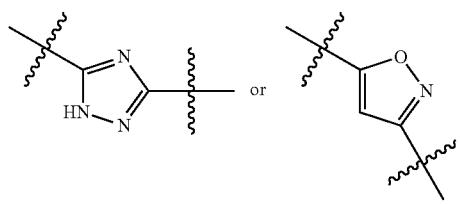

$R^1$ can be positioned on any suitable carbon atom(s) of phenyl ring A, such as at the 1, 2, 3, or 4 position, illustrated in Formula I. Exemplary $R^1$ groups are as follows:

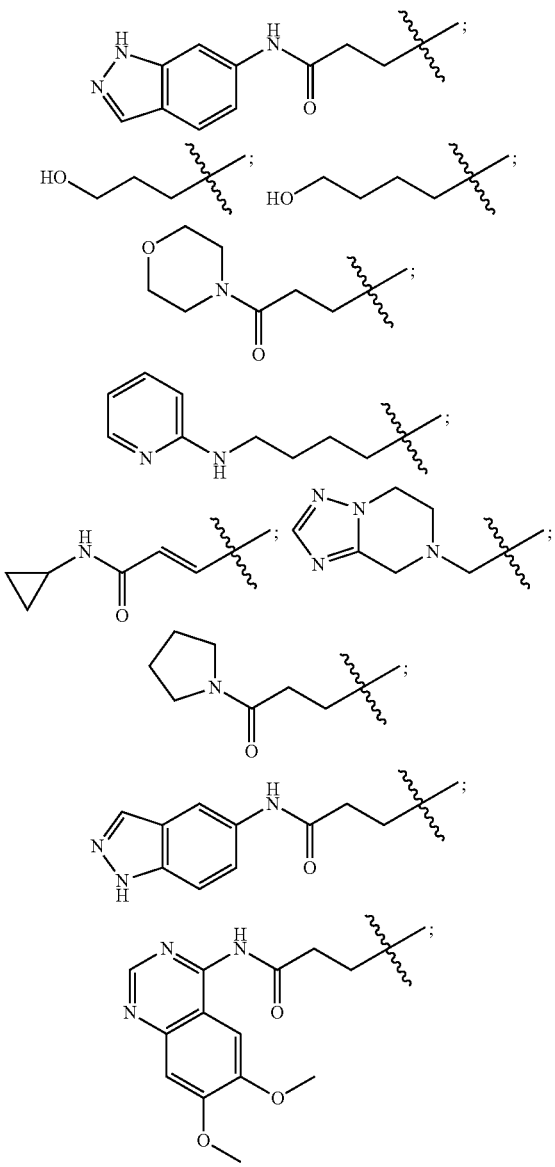

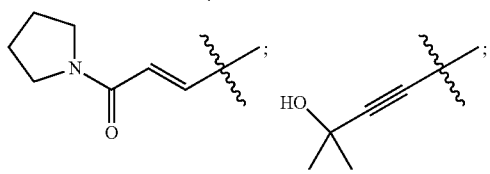

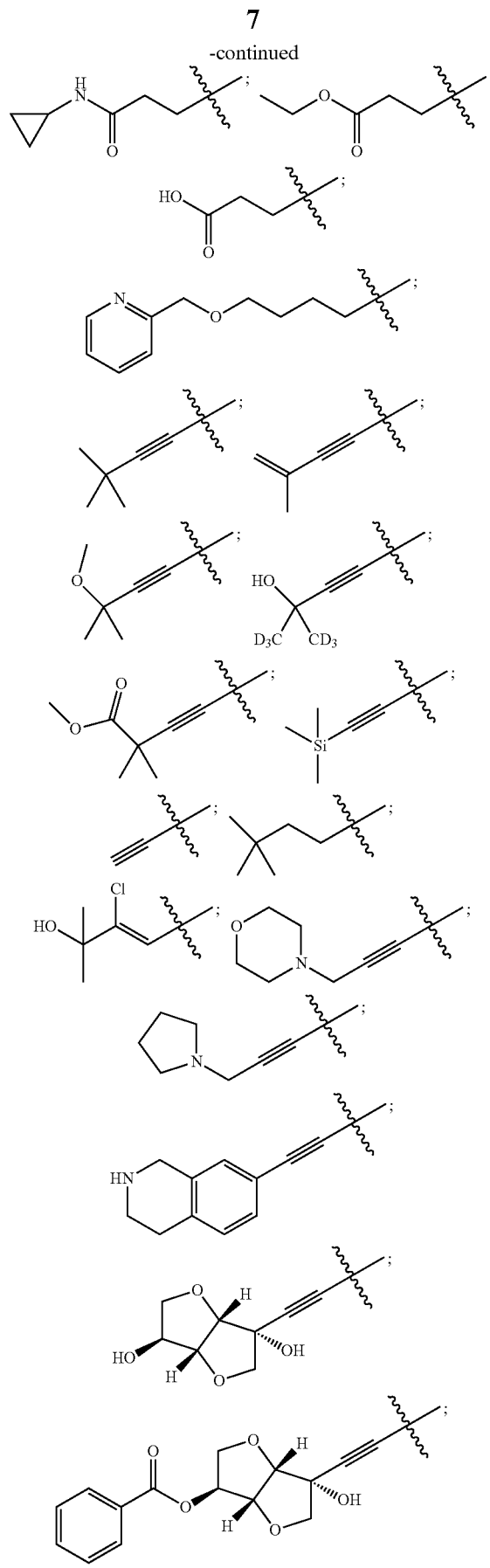
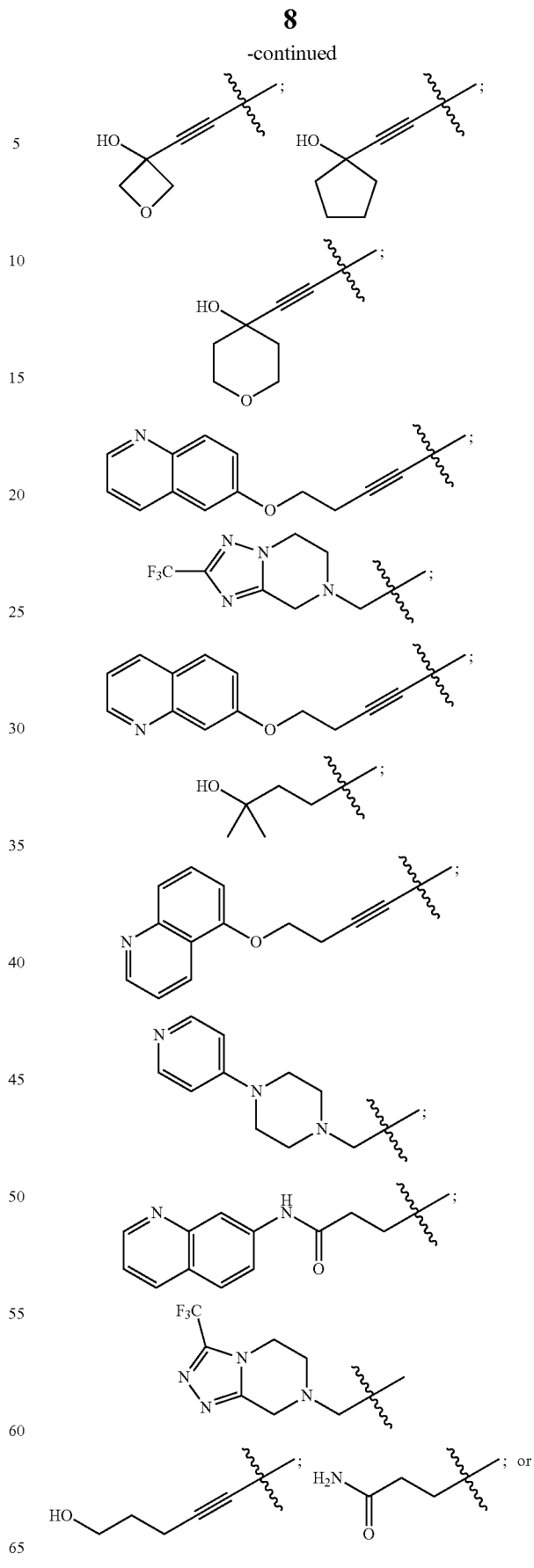

-continued

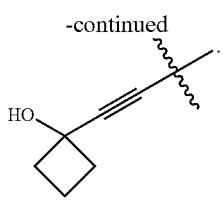

Exemplary compound species are provided herein.

Also disclosed herein are pharmaceutical composition embodiments comprising a compound (or compounds) according to any of the formulas and/or species disclosed herein (or a pharmaceutically acceptable salt, a stereoisomer, an N-oxide, a tautomer, a hydrate, a solvate, an isotope, or a prodrug thereof), and at least one additional active and/or non-active agent, such as an excipient, a therapeutic agent, an adjuvant, or combinations thereof.

Also disclosed herein are embodiments of a method for using disclosed compounds. One such embodiment comprises contacting a receptor-interacting protein-1 (RIP1) kinase with a compound according to any of the formulas and/or species disclosed herein (or a pharmaceutically acceptable salt, a stereoisomer, an N-oxide, a tautomer, a hydrate, a solvate, an isotope, or a prodrug thereof), or a pharmaceutical composition embodiment described herein. Contacting can occur ex vivo or in vivo.

Also disclosed is a method for treating a disease in a subject, comprising administering to the subject (i) a therapeutically effective amount of the compound according to any of the formulas and/or species disclosed herein (or a pharmaceutically acceptable salt, a stereoisomer, an N-oxide, a tautomer, a hydrate, a solvate, an isotope, or a prodrug thereof); and/or (ii) a therapeutically effective amount of a pharmaceutical composition embodiment described herein; wherein the subject has, or is suspected of having or developing a disease involving a receptor-interacting protein-1 (RIP1) kinase.

Method embodiments for making the compound embodiments disclosed herein also are described. In some embodiments, the method can comprise coupling a starting material having a Formula A with an R-containing reagent, by combining the starting material and the $R^1$-containing reagent, wherein $R^1$ comprises a linker-$R^6$ group, with a transition metal catalyst, a base, and a solvent to form a functionalized product; deprotecting an amine group of the functionalized product to provide an amine compound; and forming an amide bond between the amine compound and an acid-containing coupling partner to provide an amide-containing compound; wherein Formula A is Formula A

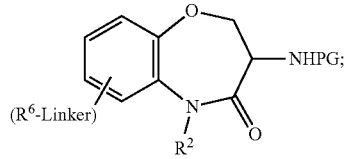

the functionalized product has a structure satisfying Formula B

Formula B

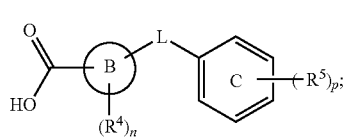

and the acid-containing coupling partner has a structure satisfying Formula C

Formula C and wherein
X is a halogen or a triflate;
PG is an amine protecting group;
and each of ring B, L, $R^1$, $R^2$, $R^4$, $R^5$, m, n, and p are as recited for any one or more of the above compound embodiments.

The foregoing and other objects and features of the present disclosure will become more apparent from the following detailed description.

DETAILED DESCRIPTION

I. Overview of Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

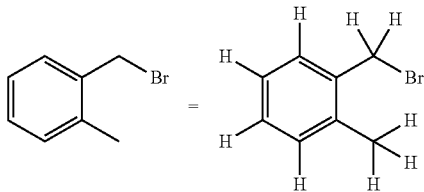

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

If an R group is depicted as "floating" on a ring system, as for example with $R^1$ in the group:

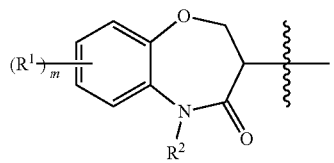

then, unless otherwise defined, a substituent R (e.g., $R^1$ above) can reside on any atom of the fused bicyclic ring system, excluding the atom carrying the bond with the "⭨" symbol, so long as a stable structure is formed.

When a group R is depicted as existing on a ring system containing saturated carbons, as for example in the formula:

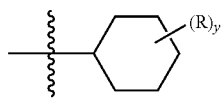

where, in this example, y can be more than one, assuming each replaces a currently depicted, implied, or expressly defined hydrogen on the ring; then, unless otherwise defined, two R's can reside on the same carbon. A simple example is when R is a methyl group. The depicted structure can exist as a geminal dimethyl on a carbon of the depicted ring (an "annular" carbon). In another example, two R's on the same carbon, including that same carbon, can be included in a ring, thus creating a spirocyclic ring (a "spirocyclyl" group) structure.

As used herein, the term "substituted" refers to all subsequent modifiers in a term, for example in the term "substituted arylC$_{1-8}$alkyl," substitution may occur on the "C$_{1-8}$alkyl" portion, the "aryl" portion or both portions of the arylC$_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted unless the context indicates otherwise or a particular structural formula precludes substitution. In particular embodiments, a substituent may or may not be expressly defined as substituted, but is still contemplated to be optionally substituted. For example, an "aliphatic" or a "cyclic" moiety may be unsubstituted or substituted, but an "unsubstituted aliphatic" or an "unsubstituted cyclic" is not substituted.

"Substituents" or "substituent groups" for substituting for one or more hydrogen atoms on saturated carbon atoms in the specified group or moiety can be, unless otherwise specified, —$R^{60}$, halo, =O, —$OR^{70}$, —$SR^{70}$, —$N(R^{80})_2$, haloalkyl, perhaloalkyl, —CN, —NO$_2$, =N$_2$, —N$_3$, —SO$_2R^{70}$, —SO$_3^-M^+$, —SO$_3R^{70}$, —OSO$_2R^{70}$, —OSO$_3^-M^+$, —OSO$_3R^{70}$, —P(O)(O$^-$)$_2$(M$^+$)$_2$, —P(O)(O$^-$)$_2$M$^{2+}$, —P(O)(OR$^{70}$)O$^-M^+$, —P(O)(OR$^{70}$)$_2$, —C(O)R$^{70}$, —C(S)R$^{70}$, —C(NR$^{70}$)R$^{70}$, —CO$_2^-M^+$, —CO$_2R^{70}$, —C(S)OR$^{70}$, —C(O)N(R$^{80}$)$_2$, —C(NR$^{70}$)(R$^{80}$)$_2$, —OC(O)R$^{70}$, —OC(S)R$^{70}$, —OCO$_2^-M^+$, —OCO$_2R^{70}$, —OC(S)OR$^{70}$, —NR$^{70}$C(O)R$^{70}$, —NR$^{70}$C(S)R$^{70}$, —NR$^{70}$CO$_2^-M^+$, —NR$^{70}$CO$_2R^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where $R^{60}$ is C$_{1-10}$aliphatic, heteroaliphatic, or cycloaliphatic, typically, C$_{1-6}$aliphatic, more typically C$_{1-6}$alkyl, where $R^{60}$ optionally may be substituted; each $R^{70}$ is independently for each occurrence hydrogen or $R^{60}$; each $R^{80}$ is independently for each occurrence $R^{70}$ or alternatively, two $R^{80}$ groups, taken together with the nitrogen atom to which they are bonded, form a 3- to 7-membered heterocycloaliphatic, which optionally includes from 1 to 4 of the same or different additional heteroatoms selected from O, N and S, of which N optionally has $R^{70}$ substitution, such as H or C$_1$-C$_3$alkyl substitution; and each M$^+$ is a counter ion with a net single positive charge. Each M$^+$ is independently for each occurrence, for example, an alkali metal ion, such as K$^+$, Na$^+$, Li$^+$; an ammonium ion, such as $^+$N(R$^{60}$)$_4$; a protonated amino acid ion, such as a lysine ion, or an arginine ion; or an alkaline metal earth ion, such as [Ca$^{2+}$]$_{0.5}$, [Mg$^{2+}$]$_{0.5}$, or [Ba$^{2+}$]$_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —N(R$^{80}$)$_2$ includes —NH$_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon also can be replaced with, for example, =O, =NR$^{70}$, =N—OR$^{70}$, =N$_2$ or =S.

Substituent groups for replacing hydrogen atoms on unsaturated carbon atoms in groups containing unsaturated carbons are, unless otherwise specified, —R$^{60}$, halo, —O$^-M^+$, —OR$^{70}$, —SR$^{70}$, —S$^-M^+$, —N(R$^{80}$)$_2$, perhaloalkyl, —CN, —OCN, —SCN, —NO, —NO$_2$, —N$_3$, —SO$_2R^{70}$, —SO$_3^-M^+$, —SO$_3R^{70}$, —OSO$_2R^{70}$, —OSO$_3^-M^+$, —OSO$_3R^{70}$, —PO$_3^{-2}$(M$^+$)$_2$, —PO$_3^{-2}$M$^{2+}$, —P(O)(OR$^{70}$)O$^-M^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)N(R$^{80}$)$_2$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined. In an independent embodiment, the substituents are not —O$^-$M$^+$, —OR$^{70}$, —SR$^{70}$, or —S$^-$M$^+$.

Substituent groups for replacing hydrogen atoms on nitrogen atoms in groups containing such nitrogen atoms are, unless otherwise specified, —R$^{60}$, —O$^-$M$^+$, —OR$^{70}$, —SR$^{70}$, —S$^-$M$^+$, —N(R$^{80}$)$_2$, perhaloalkyl, —CN, —NO, —NO$_2$, —S(O)$_2$R$^{70}$, —SO$_3$$^-$M$^+$, —SO$_3$R$^{70}$, —OS(O)$_2$R$^{70}$, —OSO$_3$$^-$M$^+$, —OSO$_3$R$^{70}$, —PO$_3$$^{2-}$(M$^+$)$_2$, —PO$_3$$^{2-}$M$^{2+}$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, heteroaliphatic, or aromatic (including both aryl and heteroaryl). Exemplary acyl moieties include, but are not limited to, —C(O)H, —C(O)alkyl, —C(O)C$_1$-C$_6$alkyl, —C(O)C$_1$-C$_6$haloalkyl, —C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety. An aliphatic group or moiety can be acyclic, including alkyl, alkenyl, or alkynyl groups (as well as alkylene, alkenylene, or alkynylene groups), cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms (C$_{1-25}$); for example, from one to fifteen (C$_{1-15}$), from one to ten (C$_{1-10}$) from one to six (C$_{1-6}$), or from one to four carbon atoms (C$_{1-4}$) for an acyclic aliphatic group or moiety, or from three to fifteen (C$_{3-15}$) from three to ten (C$_{3-10}$), from three to six (C$_{3-6}$), or from three to four (C$_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

"Lower aliphatic" refers to an aliphatic group containing from one to ten carbon atoms (C$_{1-10}$), such as from one to six (C$_{1-6}$), or from one to four (C$_{1-4}$) carbon atoms; or from three to ten (C$_{3-10}$), such as from three to six (C$_{3-6}$) carbon atoms for a lower cycloaliphatic group.

"Alkoxy" refers to the group —OR, where R is a substituted or unsubstituted alkyl or a substituted or unsubstituted cycloalkyl group. In certain examples R is a C$_{1-6}$ alkyl group or a C$_{3-6}$cycloalkyl group. Methoxy (—OCH$_3$) and ethoxy (—OCH$_2$CH$_3$) are exemplary alkoxy groups. In a substituted alkoxy, R is substituted alkyl or substituted cycloalkyl, examples of which in the presently disclosed compounds include haloalkoxy groups, such as —OCF$_2$H.

"Alkoxyalkyl" refers to the group -alkyl-OR, where R is a substituted or unsubstituted alkyl or a substituted or unsubstituted cycloalkyl group; —CH$_2$CH$_2$—O—CH$_2$CH$_3$ is an exemplary alkoxyalkyl group.

"Alkyl" refers to a saturated aliphatic hydrocarbyl group having from 1 to at least 25 (C$_{1-25}$) carbon atoms, more typically 1 to 10 (C$_{1-10}$) carbon atoms such as 1 to 6 (C$_{1-6}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Amino" refers to the group —NH$_2$, —NHR, or —NRR, where each R independently is selected from H, aliphatic, heteroaliphatic, aromatic, including both aryl and heteroaryl, or heterocycloaliphatic, or two R groups together with the nitrogen attached thereto form a heterocyclic ring. Examples of such heterocyclic rings include those wherein two R groups together with the nitrogen to which they are attached form a —(CH$_2$)$_{2-5}$— ring optionally interrupted by one or two heteroatom groups, such as —O— or —N(R$^g$) such as in the groups

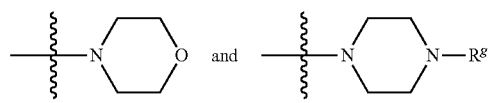

wherein R$^g$ is R$^{70}$, —C(O)R$^{70}$, —C(O)OR$^{60}$ or —C(O)N(R$^{80}$)$_2$.

"Amide" refers to the group —N(R)acyl, wherein R is hydrogen, heteroaliphatic, or aliphatic, such as alkyl, particularly C$_{1-6}$alkyl.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example, However, in certain examples, context or express disclosure may indicate that the point of attachment is through a non-aromatic portion of the condensed ring system. For example, An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Unless otherwise stated, an aromatic group may be substituted or unsubstituted.

"Aryl" refers to an aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxyl" refers to —CO$_2$H.

"Carboxamide" refers to —C(O)amino.

"Carboxyl ester" or "carboxy ester" refers to the group —C(O)OR, where R is aliphatic, heteroaliphatic, or aromatic (including both aryl and heteroaryl).

"Carboxylate" refers to —C(O)O or salts thereof.

"Cyano" refers to the group —CN.

"Cycloaliphatic" refers to a cyclic aliphatic group having a single ring (e.g., cyclohexyl), or multiple rings, such as in a fused, bridged or spirocyclic system, the ring or at least one of the rings in the system is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. Exemplary haloalkyl moieties include —CH$_2$F, —CHF$_2$ and —CF$_3$.

"Heteroaliphatic" refers to an aliphatic compound or group having at least one heteroatom and at least one carbon atom, i.e., at least one carbon atom from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heteroaryl" refers to an aromatic group or moiety having, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heteroalicyclyl or heterocycloaliphatic moieties, which are heterocyclyl rings that are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO$_2$.

"Phosphate" refers to the group —O—P(O)(OR')$_2$, where each —OR' independently is —OH; —O-aliphatic, such as —O-alkyl or —O-cycloalkyl; —O-aromatic, including both —O-aryl and —O-heteroaryl; —O-aralkyl; or —OR' is —O$^-$M$^+$, where M$^+$ is a counter ion with a single positive charge. Each M$^+$ may be an alkali ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth ion, such as [Ca$^{2+}$]$_{0.5}$, [Mg$^{2+}$]$_{0.5}$, or [Ba$^{2+}$]$_{0.5}$. Phosphonooxyalkyl refers to the group -alkyl-phosphate, such as, for example, —CH$_2$OP(O)(OH)$_2$, or a salt thereof, such as —CH$_2$OP(O)(O—Na$^+$)$_2$, and (((dialkoxyphosphoryl)oxy)alkyl) refers to the dialkyl ester of a phosphonooxyalkyl group, such as, for example, —CH$_2$OP(O)(O-tert-butyl)$_2$.

"Phosphonate" refers to the group —P(O)(OR')$_2$, where each —OR' independently is —OH; —O-aliphatic such as —O-alkyl or —O-cycloalkyl; —O-aromatic, including both —O-aryl and —O-heteroaryl; or —O-aralkyl; or —OR' is —O$^-$M$^+$, and M$^+$ is a counter ion with a single positive charge. Each M$^+$ is a positively charged counterion and may be, by way of example, an alkali metal ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth metal ion, such as [Ca$^{2+}$]$_{0.5}$, [Mg$^{2+}$]$_{0.5}$, or [Ba$^{2+}$]$_{0.5}$. Phosphonoalkyl refers to the group -alkyl-phosphonate, such as, for example, —CH$_2$P(O)(OH)$_2$, or —CH$_2$P(O)(O$^-$Na$^+$)$_2$, and ((dialkoxyphosphoryl)alkyl) refers to the dialkyl ester of a phosphonoalkyl group, such as, for example, —CH$_2$P(O)(O-tert-butyl)$_2$.

"Patient" or "Subject" may refer generally to any living being, but more typically refers to mammals and other animals, particularly humans. Thus disclosed methods are applicable to both human therapy and veterinary applications.

"Pharmaceutically acceptable excipient" refers to a substance, other than the active ingredient, that is included in a composition comprising the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is a component that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, Pa., 21$^{st}$ Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as amino acids, formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the compounds may be a formate, trifluoroactate, hydrochloride or sodium salt.

"Effective amount" with respect to a compound or pharmaceutical composition refers to an amount of the compound or pharmaceutical composition sufficient to achieve a particular desired result, such as to inhibit a protein or enzyme. In particular embodiments, an "effective amount" is an amount sufficient to inhibit RIP1; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the size, age, and gender of the patient to be treated and the like, as will be understood by a person of ordinary skill in the art.

"Prodrug" refers to compounds that are transformed in vivo to yield a biologically active compound, or a compound more biologically active than the parent compound. In vivo transformation may occur, for example, by hydrolysis or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—P(O)(OR')$_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —$SO_2$amino, or —N(R)sulfonyl, where R is H, aliphatic, heteroaliphatic, or aromatic (including both aryl and heteroaryl).

"Sulfanyl" refers to the group or —SH, —S-aliphatic, —S-heteroaliphatic, —S-aromatic, (including both-S-aryl and —S-heteroaryl).

"Sulfinyl" refers to the group or moiety —S(O)H, —S(O) aliphatic, —S(O)heteroaliphatic, or —S(O)aromatic (including both —S(O)aryl and —S(O)heteroaryl).

"Sulfonyl" refers to the group: —$SO_2$H, —$SO_2$aliphatic, —$SO_2$heteroaliphatic, —$SO_2$aromatic (including both —$SO_2$aryl and —$SO_2$heteroaryl).

"Treating" or "treatment" as used herein concerns treatment of a disease or condition of interest in a patient or subject, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing diminution of a symptom or regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. Mixtures of different isomeric forms, including mixtures of enantiomers and/or stereoisomers, can be separated to provide each separate enantiomers and/or stereoisomer using techniques known to those of ordinary skill in the art, particularly with the benefit of the present disclosure. In cases of limited rotation, e.g. around the amide bond or between two directly attached rings such as pyridinyl rings, biphenyl groups, and the like, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl refers to both $C_2H_5$ or $C_2H_5$ where from 1 to 5 hydrogens are replaced by deuterium, such as in $C_2D_xH_{5-x}$.

II. RIP1-Active Compounds and Pharmaceutical Compositions Comprising RIP1-Active Compounds

A. Compounds

Disclosed herein are compounds and pharmaceutical compositions comprising such compounds that are useful for inhibiting RIP1 and/or for treating diseases and/or conditions associated with RIP1. In some embodiments, the compounds are selective kinase inhibitors. For example, exemplary compounds are able to selectively inhibit RIP1 over RIP2, RIP3, or both RIP2 and RIP3. In some embodiments, a compound of the present disclosure can have a structure satisfying Formula I

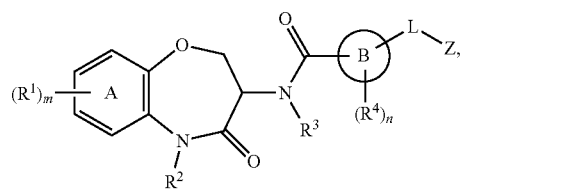

Formula I or a pharmaceutically acceptable salt thereof. A person of ordinary skill in the art will appreciate that the disclosed general formulas include within their scope all stereoisomers, N-oxides, tautomers, hydrates, solvates, isotopes, and/or prodrugs of compounds otherwise having structural features required by such formulas.

With reference to Formula I:

ring B is 5-membered or 6-membered heteroaryl;

L is a heteroatom or $R^a$, provided that $R^a$ is not H or D;

Z is $C_{1-10}$aliphatic (such as $C_{1-10}$alkyl, $C_{2-10}$alkenyl, $C_{2-10}$alkynyl, or $C_{3-6}$cycloalkyl); or

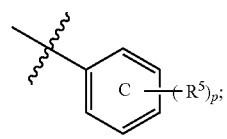

$R^1$ is a halogen, —C≡CH, or a -linker-$R^6$ group, wherein the linker is $R^a$, provided that $R^a$ is not H or D, and $R^6$ is $R^b$, —C($R^f$)$_3$, or —C($R^f$)=C($R^f$)$_2$;

$R^2$ and $R^3$ independently are $R^a$;

$R^4$ and $R^5$ independently are $R^e$;

$R^a$ is independently for each occurrence H or D (except for embodiments where L is $R^a$), $C_{1-10}$aliphatic (such as $C_{1-10}$alkyl, $C_{2-10}$alkenyl, $C_{2-10}$alkynyl, or $C_{3-6}$cycloalkyl), $C_{1-10}$haloaliphatic, $C_{5-10}$aromatic, or $C_{3-6}$heterocyclic;

$R^b$ is independently for each occurrence —OH, —SH, —OR$^c$, —SR$^c$, —NR$^d$R$^d$, —Si(R$^a$)$_3$, —C(O)OH, —C(O)OR$^c$, or —C(O)NR$^d$R$^d$;

$R^c$ is independently for each occurrence $C_{1-10}$alkyl (which can be substituted with 1, 2 or 3 $R^e$), $C_{2-10}$alkenyl (which can be substituted with 1, 2 or 3 $R^e$), $C_{2-10}$alkynyl (which can be substituted with 1, 2 or 3 $R^e$), $C_{3-6}$cycloalkyl (which can be substituted with 1, 2 or 3 $R^e$), or $C_{5-10}$aromatic (which can be substituted with 1, 2 or 3 $R^e$);

$R^d$ is independently for each occurrence H; $C_{1-6}$alkyl (which can be substituted with 1, 2 or 3 $R^e$); $C_{3-6}$cycloalkyl (which can be substituted with 1, 2 or 3 $R^e$); $C_{3-6}$heterocyclic (which can be substituted with 1, 2 or 3 $R^e$); $C_{5-10}$aryl (which can be substituted with 1, 2 or 3 $R^e$); $C_{5-10}$heteroaryl (which can be substituted with 1, 2 or 3 $R^e$); or two $R^d$ groups together with the nitrogen bound thereto provide a $C_{3-9}$heterocyclic (which can be substituted with one or more $R^e$), or a $C_{5-10}$heteroaryl (which can be substituted with one or more $R^e$);

$R^e$ is independently for each occurrence halogen, $C_{1-6}$alkyl, $C_{2-10}$alkenyl, $C_{2-10}$alkynyl, $C_{1-6}$haloalkyl, $C_{3-6}$cycloalkyl, $C_{5-10}$heteroaryl, or —OR$^a$; and $R^f$ is independently for each occurrence $R^a$, $R^b$, or $R^e$, or two $R^f$ groups together with the carbon atom bound thereto provide a $C_{3-6}$cycloalkyl group (which can be substituted with one or more $R^e$), or a $C_{3-10}$heterocyclic (which can be substituted with one or more $R^e$);

m is 1 to 4, such as 1, 2, 3, or 4, with particular embodiments being 1 or 2;

n is 0, 1 or 2; and p is 0, 1, 2, 3, 4, or 5.

In some embodiments, a compound of the present disclosure can have a structure satisfying Formula IA

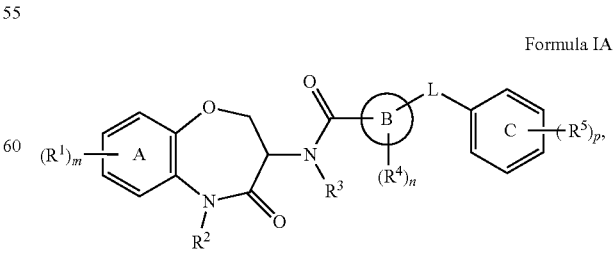

Formula IA or a pharmaceutically acceptable salt thereof. A person of ordinary skill in the art will appreciate that the disclosed general formulas include within their scope all stereoisomers, N-oxides, tautomers, hydrates, solvates, isotopes, and/or prodrugs of compounds otherwise having structural features required by such formulas.

With reference to Formula IA:
ring B is 5-membered or 6-membered heteroaryl;
L is a heteroatom or $R^a$, provided that $R^a$ is not H or D;
$R^1$ is a halogen, —C≡CH, or a -linker-$R^6$ group, wherein the linker is $R^a$, provided that $R^a$ is not H or D, and $R^6$ is R, —C($R^f$)$_3$, or —C($R^f$)=C($R^f$)$_2$;
$R^2$ and $R^3$ independently are $R^a$;
$R^4$ and $R^5$ independently are $R^e$;
$R^a$ is independently for each occurrence H or D (except for embodiments where L is $R^a$), $C_{1-10}$aliphatic (such as $C_{1-10}$alkyl, $C_{2-10}$alkenyl, $C_{2-10}$alkynyl, or $C_{3-6}$cycloalkyl), $C_{1-10}$haloaliphatic, $C_{5-10}$aromatic, or $C_{3-6}$heterocyclic;
$R^b$ is independently for each occurrence —OH, —SH, —OR$^c$, —SR$^c$, —NR$^d$R$^d$, —Si(R$^a$)$_3$, —C(O)OH, —C(O)OR$^c$, or —C(O)NR$^d$R$^d$;
$R^c$ is independently for each occurrence $C_{1-10}$alkyl (which can be substituted with 1, 2 or 3 $R^e$), $C_{2-10}$alkenyl (which can be substituted with 1, 2 or 3 $R^e$), $C_{2-10}$alkynyl (which can be substituted with 1, 2 or 3 $R^e$), $C_{3-6}$cycloalkyl (which can be substituted with 1, 2 or 3 $R^e$), or $C_{5-10}$aromatic (which can be substituted with 1, 2 or 3 $R^e$);
$R^d$ is independently for each occurrence H; $C_{1-6}$alkyl (which can be substituted with 1, 2 or 3 $R^e$); $C_{3-6}$cycloalkyl (which can be substituted with 1, 2 or 3 $R^e$); $C_{3-6}$heterocyclic (which can be substituted with 1, 2 or 3 $R^e$); $C_{5-10}$aryl (which can be substituted with 1, 2 or 3 $R^b$); $C_{5-10}$heteroaryl (which can be substituted with 1, 2 or 3 $R^e$); or two $R^d$ groups together with the nitrogen bound thereto provide a $C_{3-9}$heterocyclic (which can be substituted with one or more $R^e$), or a $C_{5-10}$heteroaryl (which can be substituted with one or more $R^e$);
$R^e$ is independently for each occurrence halogen, $C_{1-6}$alkyl, $C_{2-10}$alkenyl, $C_{2-10}$alkynyl, $C_{1-6}$haloalkyl, $C_{3-6}$cycloalkyl, $C_{5-10}$heteroaryl, or —OR$^a$; and
$R^f$ is independently for each occurrence $R^a$, $R^b$, or $R^e$ or two $R^f$ groups together with the carbon atom bound thereto provide a $C_{3-6}$cycloalkyl group (and in some embodiments, the $C_{3-6}$cycloalkyl group is substituted with one or more $R^e$), or a $C_{3-10}$heterocyclic (and in some embodiments, the $C_{3-10}$heterocyclic group is substituted with one or more $R^e$);
m is 1 to 4, such as 1, 2, 3, or 4, with particular embodiments being 1 or 2;
n is 0, 1 or 2; and
p is 0, 1, 2, 3, 4, or 5.

In particular embodiments of Formulas I or IA, the 5-membered heteroaryl group can have structure satisfying formula

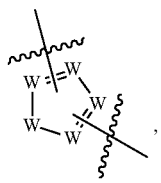

wherein at least one W is nitrogen, and each remaining W independently is selected from carbon, CH, oxygen, sulfur, nitrogen, or NH. In some embodiments, the 5-membered heteroaryl group is a diazole, a triazole, an oxadiazole, or an oxazole. Exemplary triazoles include any of the following:

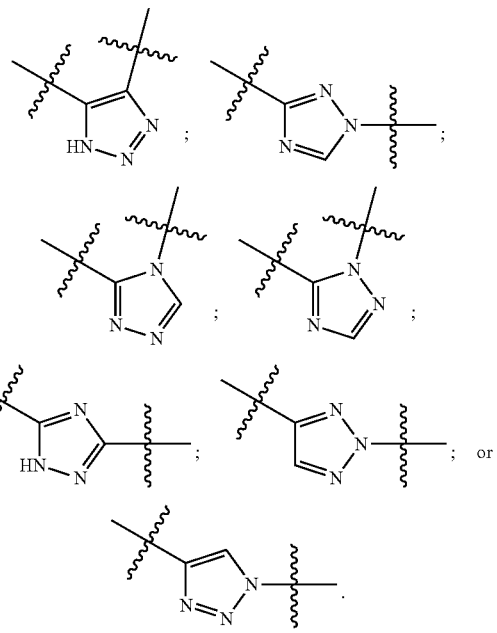

Exemplary diazoles are selected from any of the following:

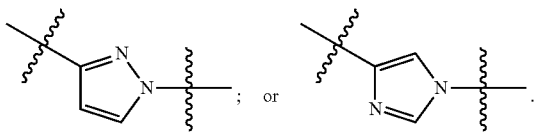 [SMILES: *c1ccn(*)n1 ; *c1cn(*)cn1]

Exemplary oxazoles are selected from any of the following:

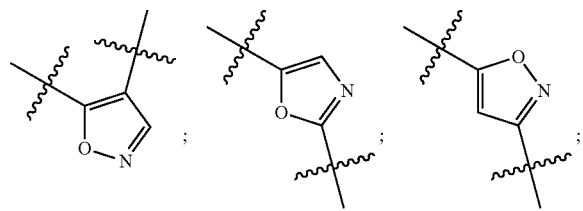

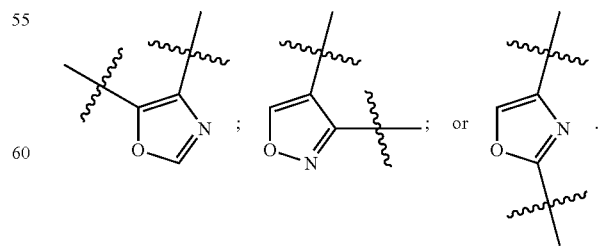

Exemplary oxadiazoles are selected from any of the following:

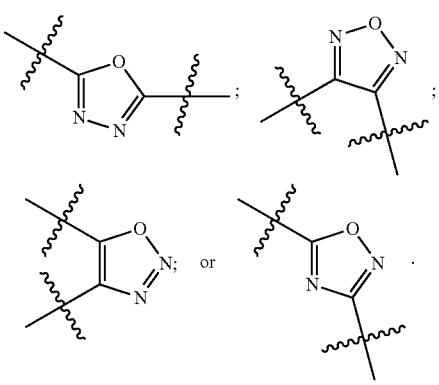

In particular embodiments of Formulas I or IA, L is oxygen or $R^a$ wherein $R^a$ is $C_1$-$C_4$alkyl, such as —CH$_2$—, —CH$_2$CH$_2$—, —CH$_2$CH$_2$CH$_2$—, or —CH$_2$CH$_2$CH$_2$CH$_2$—. In some embodiments, L is —CH$_2$— or oxygen.

The linker group of $R^1$ groups where $R^2$ is linker-$R^6$ is a $C_1$, $C_2$, $C_3$, or $C_4$ aliphatic group, such a $C_2$ alkyl group, an alkenyl group, or an alkynyl group, or a $C_1$, $C_2$, $C_3$, or $C_4$ haloaliphatic group, such as a $C_2$ haloalkyl group, or an haloalkenyl group. In some embodiments, the linker group of $R^1$ is $R^a$ wherein $R^a$ is $C_1$-$C_4$alkyl, such as —CH$_2$—, —CH$_2$CH$_2$—, —CH$_2$CH$_2$CH$_2$—, or —CH$_2$CH$_2$CH$_2$CH$_2$—; or the linker group is $C_2$-$C_4$alkenyl, such as —CH=CH—, —CH=CHCH$_2$—, —CH$_2$CH=CH—, or —CH$_2$CH=CHCH$_2$—; or the linker group is $C_2$-$C_4$alkynyl, such as —C≡C—, —C≡CCH$_2$—, —CH$_2$C≡C—, or —CHC≡C—CH$_2$—. In some embodiments, the linker group is $C_2$-$C_4$haloalkenyl, such as —CF=CH—, —CCl=CH—, —CH=CCl—, —CH=CF—, —CCl=CCl—, —CF=CF—, or —CCl=CF—, —CF=CCl—. In some embodiments, linker group is is —CH$_2$—, —CH$_2$CH$_2$—, —CH$_2$CH$_2$CH$_2$—, —CH$_2$CH$_2$CH$_2$CH$_2$—, —CH=CH—, —CCl=CH—, —CH=CCl—, or —C≡C—.

The $R^6$ group of $R^1$ is $C(R^f)_3$ in some embodiments, wherein one $R^f$ is $R^e$, wherein $R^e$ is —OR$^a$ (e.g., hydroxyl or OMe) and each other $R^f$ independently is $R^a$, wherein $R^a$ is $C_{1-4}$aliphatic and preferably each other $R^f$ is $R^a$ wherein $R^a$ is independently for each occurrence $C_{1-4}$alkyl. In particular embodiments, each other $R^f$ is $R^a$ wherein $R^a$ is methyl or CD$_3$. In yet some additional embodiments, $R^6$ is —C(R$^f$)$_3$ wherein each $R^f$ is $R^a$ wherein $R^a$ is methyl or H or wherein each $R^f$ is $R^a$ wherein $R^a$ is methyl or $R^b$ wherein $R^b$ is —C(O)OR$^c$. In some additional embodiments, one $R^f$ is $R^e$ is —OR$^a$ (e.g., hydroxyl or OMe) and the other two $R^f$ groups join together to provide a alicyclic (e.g., cyclopropane, cyclobutane, cyclopentane, or cyclohexane) or heterocyclic group (e.g., epoxide, oxetane, tetrahydrofuran, tetrahydropyran, or hexahydrofuro[3,2-b]furan) with the carbon atom to which they are bound. In some such embodiments, the alicyclic and/or heterocyclic group can be substituted, with some particular embodiments being substituted with one or more hydroxyl groups or benzyl-carbonyl groups.

Some compound embodiments have a linker group that is a $C_{2-4}$ group, which can comprise an alkyne. In particular embodiments, $R^1$ is a -linker-$R^6$ group and the linker is $R^a$ wherein $R^a$ is —CH$_2$—, —CH$_2$CH$_2$—, —CH$_2$CH$_2$CH$_2$—, —CH$_2$CH$_2$CH$_2$CH$_2$—, —CH=CH—, or —C≡C—, —CH$_2$C≡C—, and $R^6$ is $R^b$ wherein $R^b$ is —C(O)OEt or is —C(O)NR$^d$R$^d$ or —NR$^d$R$^d$ wherein each $R^d$ independently for each occurrence is hydrogen, $C_{5-10}$heteroaryl, $C_{3-6}$cycloalkyl, or both $R^d$ groups join together to provide a heterocyclic group with the nitrogen atom to which they are bound, which may further comprise one or more additional heteroatoms aside from the nitrogen atom to which the $R^d$ groups are bound. In some embodiments, one $R^d$ is hydrogen and the other $R^d$ is $C_{5-10}$heteroaryl, which can be substituted with one or more $R^e$, such as one of the following:

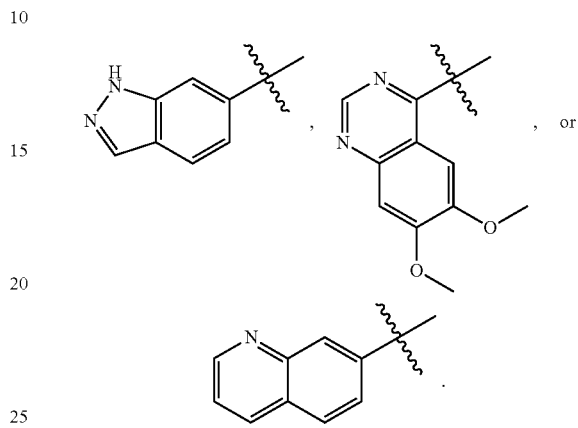

$R^6$ also can be $R^b$ wherein $R^b$ is —OH or —OR$^c$ (wherein $R^c$ is $C_{1-6}$alkyl and in some embodiments the $C_{1-6}$alkyl is substituted with $C_{5-10}$heteroaryl, such as pyridinyl; or wherein $R^c$ is $C_{5-10}$heteroaryl, such as quinolinyl), or $R^b$ can be —NR$^d$R$^d$ wherein $R^d$ is independently for each occurrence H, $C_{5-10}$heteroaryl (and in some embodiments, the $C_{5-10}$heteroaryl group is substituted with one or more $R^e$ groups), or two $R^d$ groups together with the nitrogen bound thereto provide a $C_{3-9}$heterocyclic (and in some embodiments, the $C_{3-9}$heterocyclic is substituted with one or more $R^e$ groups) or a $C_{5-10}$heteroaryl (and in some embodiments, the $C_{5-10}$heteroaryl is substituted with one or more $R^e$ groups). In embodiments with $R^e$ substitution, $R^e$ independently for each occurrence $C_{5-10}$heteroaryl, or —OR$^a$, wherein $R^a$ is $C_{1-10}$alkyl.

Some compounds comprise a linker that is a $C_1$ group and an $R^6$ group that is $R^b$, wherein $R^b$ is —NR$^d$R$^d$ wherein one $R^d$ is H and the other $R^d$ is pyridinyl, or wherein both $R^d$ groups together with the nitrogen bound thereto provide a $C_{5-10}$heteroaryl; or $R^b$ is OR$^c$, wherein $R^c$ is $C_{1-4}$alkyl substituted with a pyridinyl group. In some embodiments, $R^b$ is

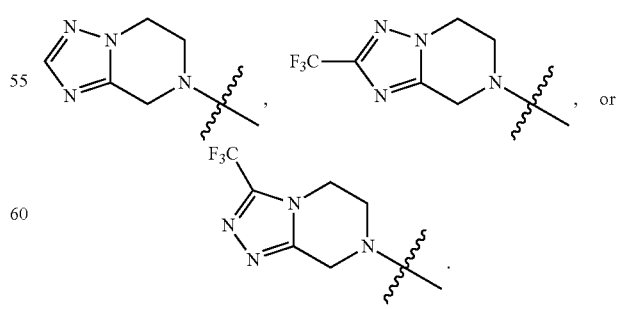

In some embodiments, $R^1$ can be selected from any of the following:

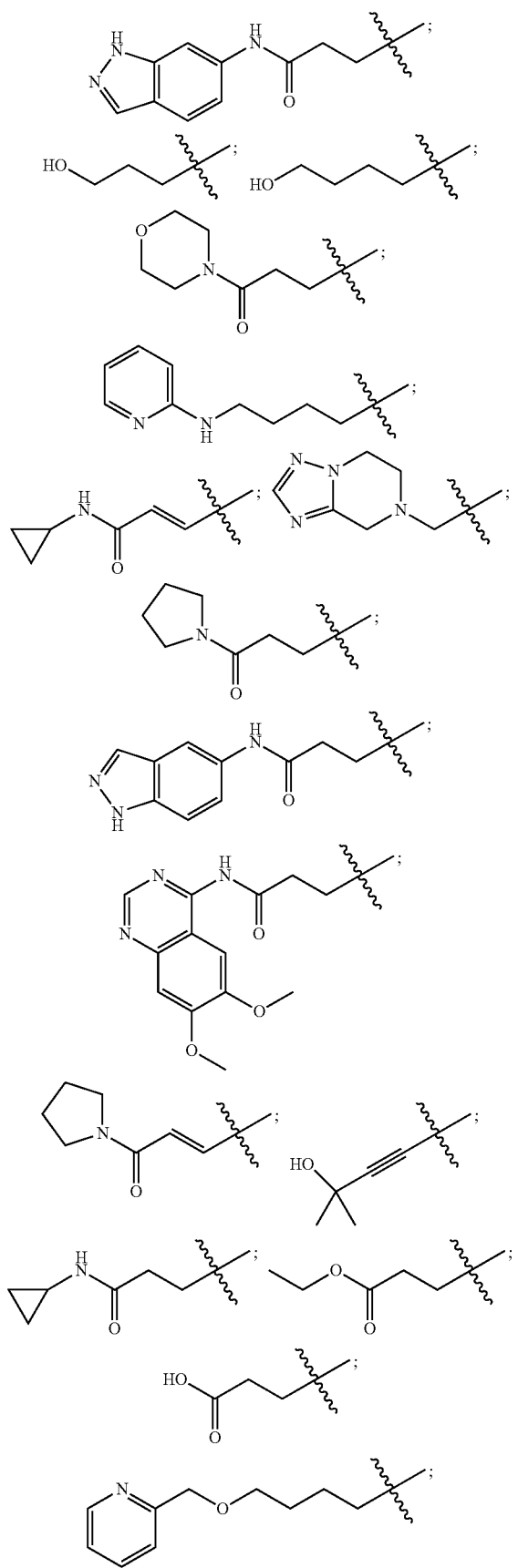
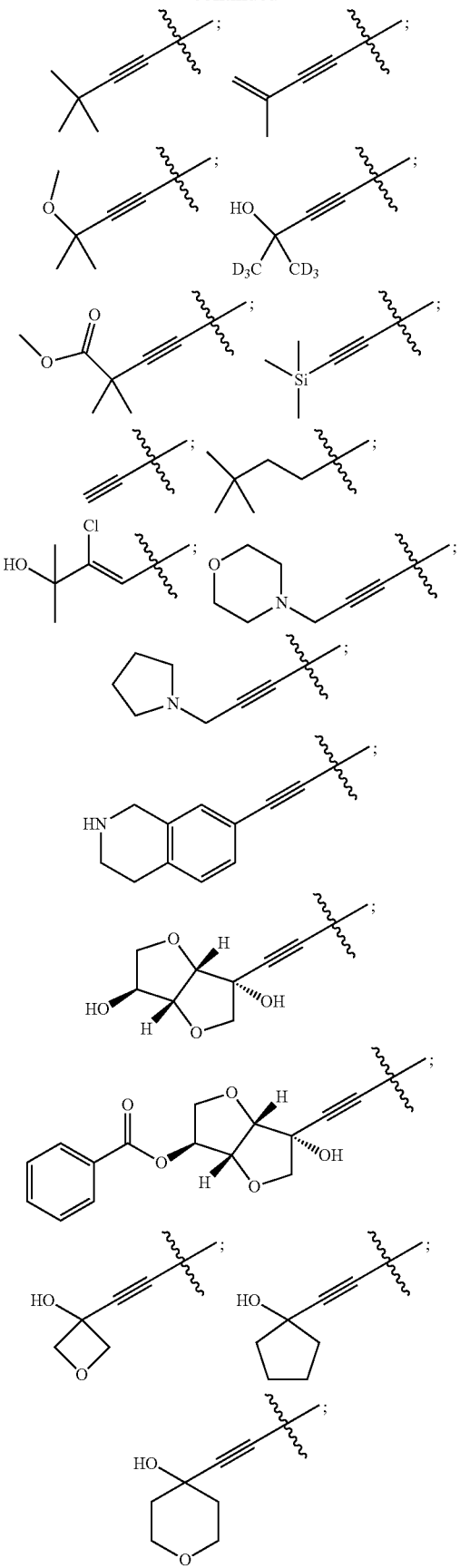

29

-continued

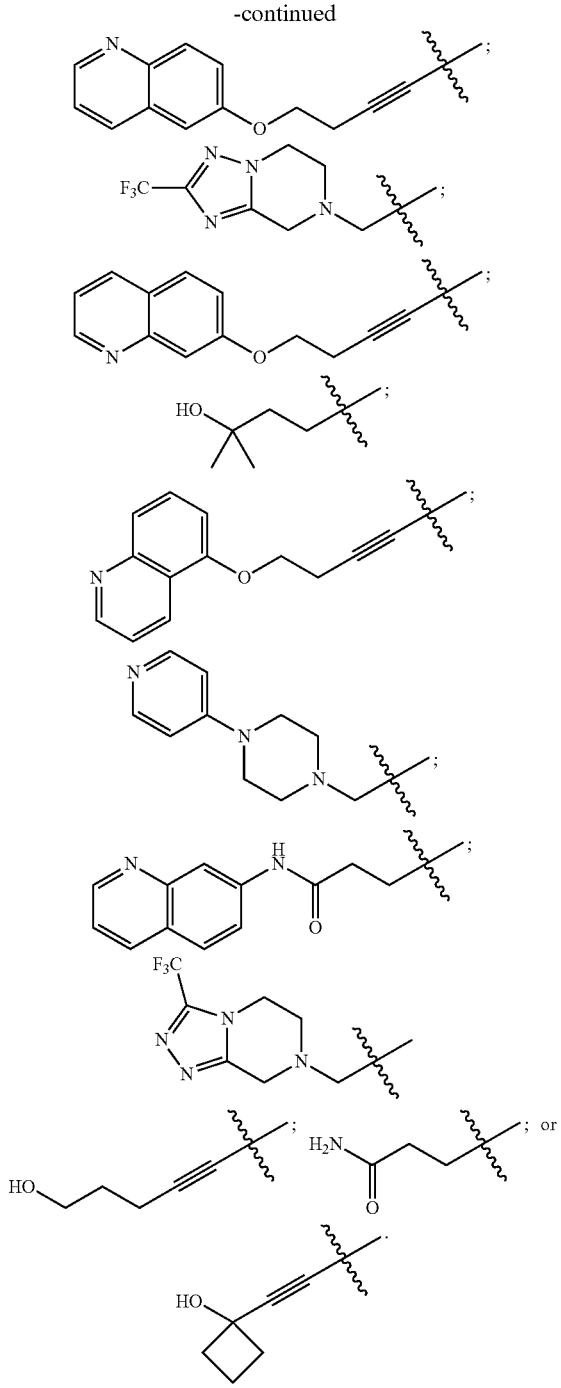

In some embodiments, m is 1; n is 0 or 1; and p is 0, 1, or 2. In particular embodiments, m is 1, n is 0 and p is 0, 1, or 2.

The compounds of Formulas I or IA can also have structures satisfying any one or more of Formulas II and IIA-IIF.

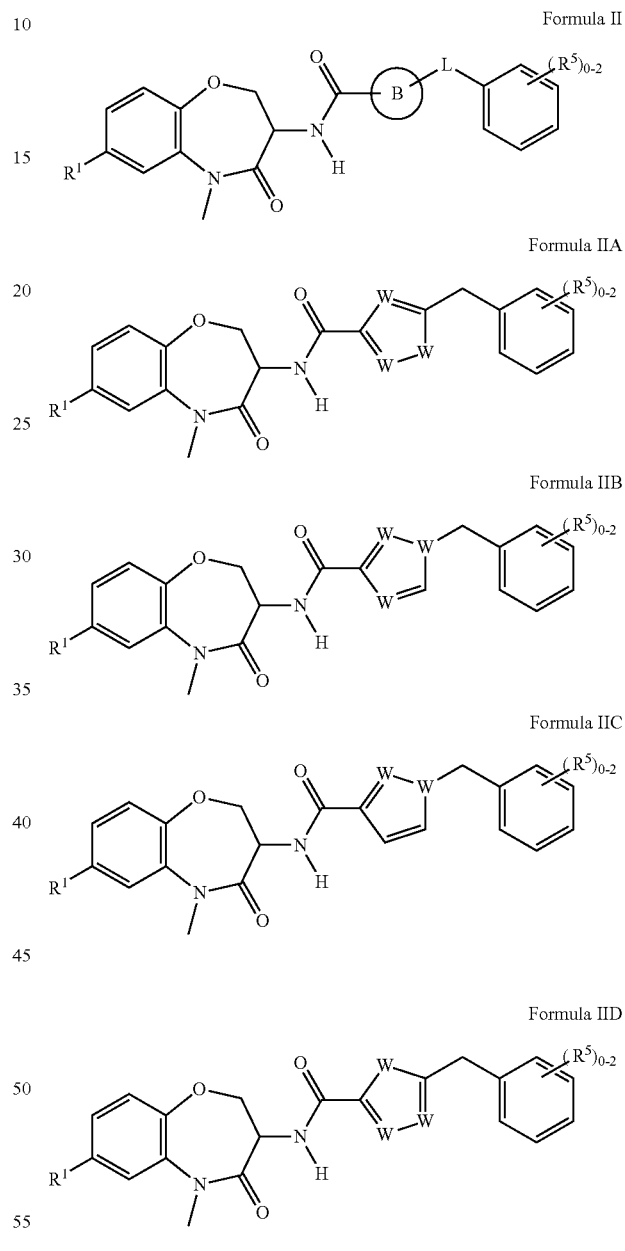

In some embodiments, each of $R^2$ and $R^3$ independently is $R^a$ wherein $R^a$ is independently in each occurrence hydrogen, methyl, ethyl, propyl, butyl, pentyl, or hexyl. In particular embodiments, each of $R^2$ and $R^3$ independently is $R^a$ which is independently for each occurrence hydrogen, methyl, or ethyl. In exemplary embodiments, $R^2$ is methyl and $R^3$ is hydrogen.

In some embodiments, each $R^4$ independently and/or each $R^5$ independently is $R^e$, wherein $R^e$ is alkyl, alkenyl, alkynyl, chloro, bromo, iodo, or fluoro. In particular embodiments, each $R^4$ and/or each $R^5$ independently is $R^e$ wherein $R^e$ is lower aliphatic (e.g., methyl), fluoro, or chloro.

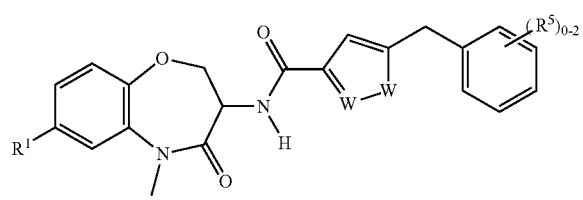

Formula IIF

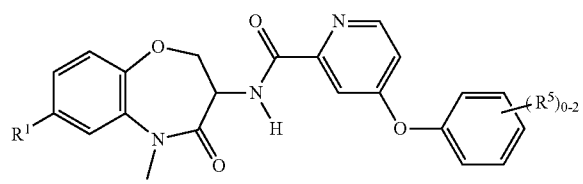

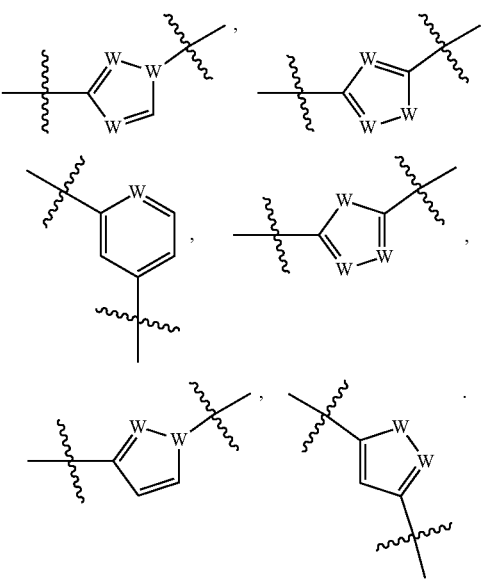

With reference to Formulas II and IIA-IIF, each of $R^1$ and $R^5$ are as recited above for Formulas I and/or IA. In particular embodiments, 0, 1, or 2 $R^5$ groups are present. $R^5$ can be $R^e$ wherein $R^e$ is fluoro or chloro. In other particular embodiments, $R^5$ is not present. With reference to Formulas IIA-IIF, each W independently is nitrogen or oxygen, and particularly nitrogen.

In some embodiments, the compounds of Formulas I or IA also can have structures satisfying any one or more of Formulas III-VI:

Formula III

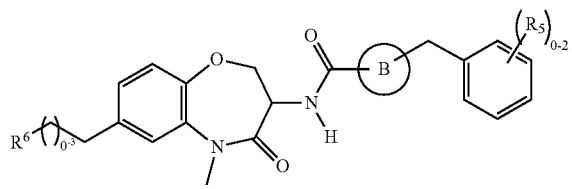

$R^6$ as illustrated in Formulas III-VI is as recited above and in some embodiments is selected from one of the following:

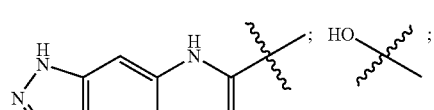

Formula IV

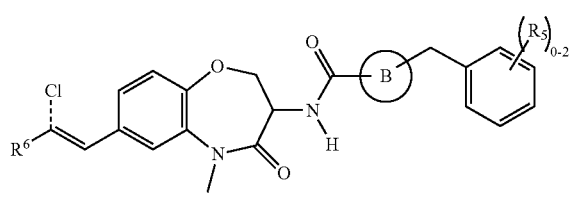

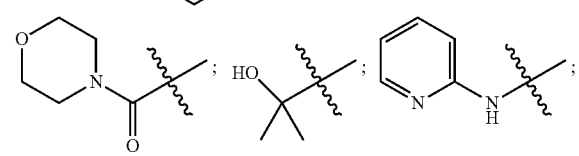

Formula V

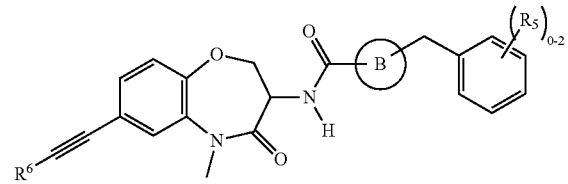

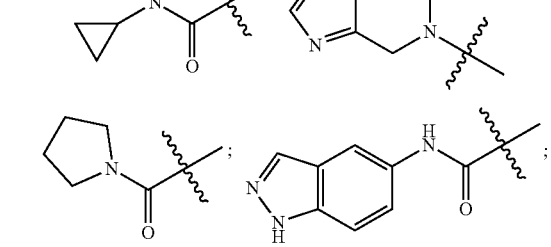

Formula VI

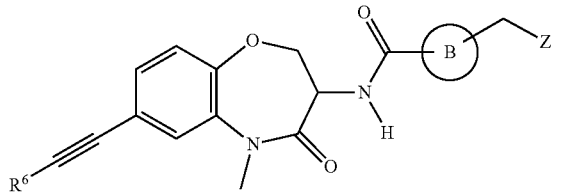

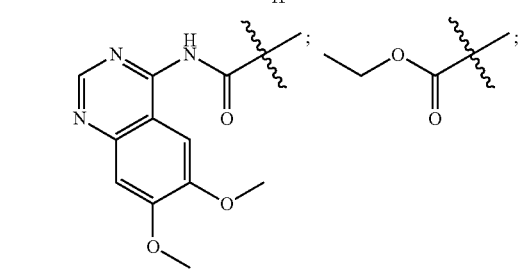

With reference to Formulas III-VI, each $R^5$ independently can be as recited above and in some particular embodiments is lower aliphatic (e.g., methyl) or halogen, such as chloro or fluoro. Also, ring B is as recited above and in some embodiments is selected from 33
-continued
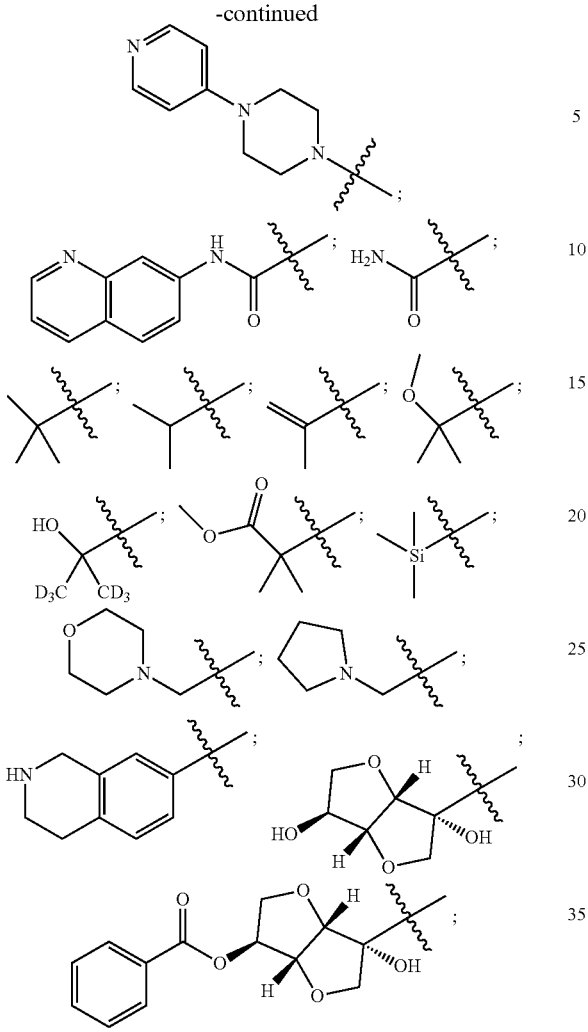
34
-continued
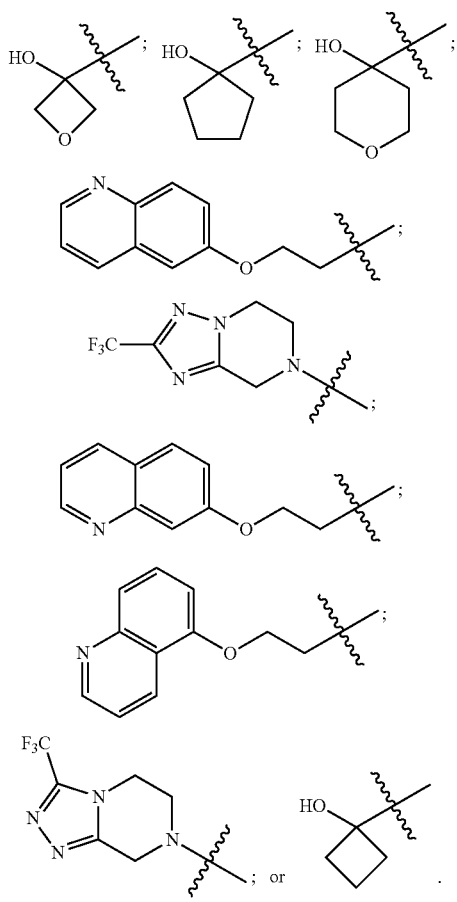
Certain disclosed exemplary compounds within the scope of one or more of Formulas I, IA, II, IIA-IIF, and III-VI include:
I-1
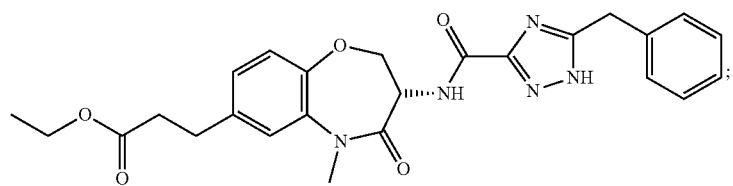
I-2
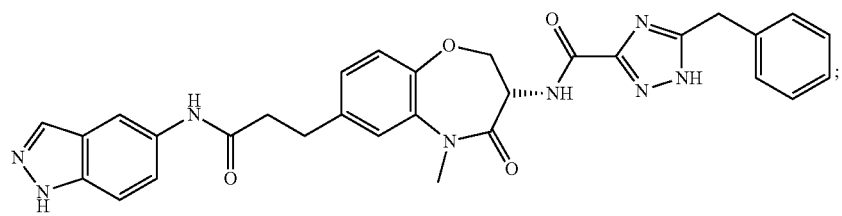

I-3
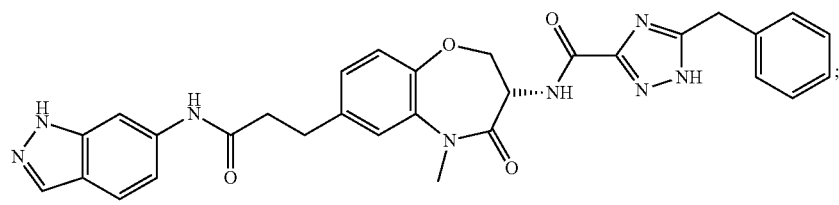
I-4
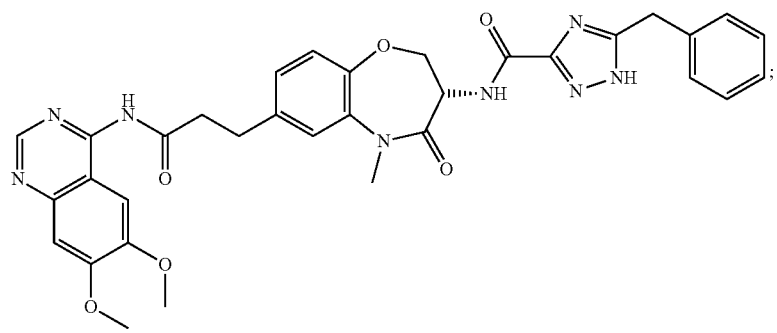
I-5
I-6
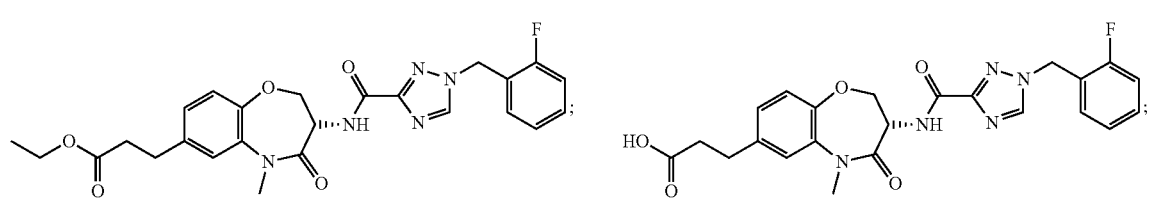
I-7
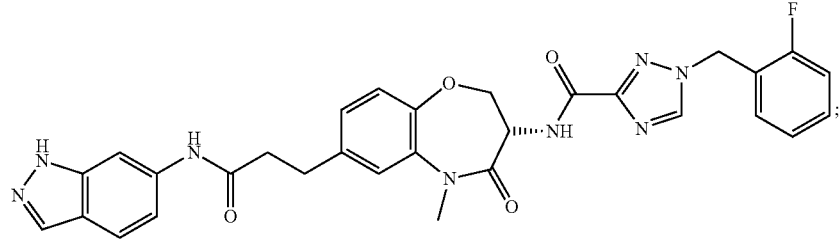
I-8
I-9
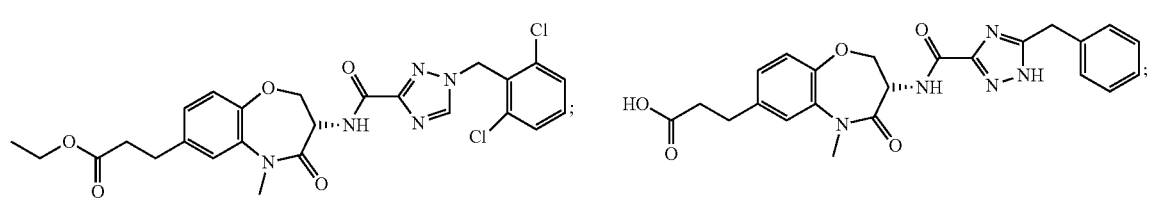
I-10
I-11
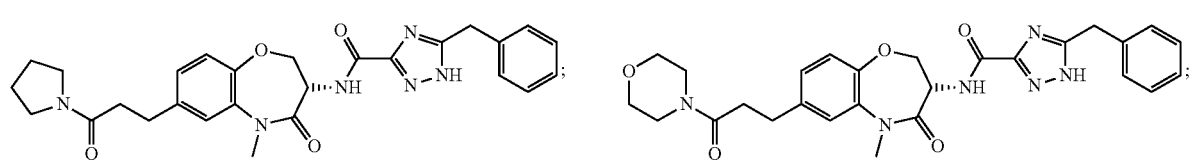
I-12
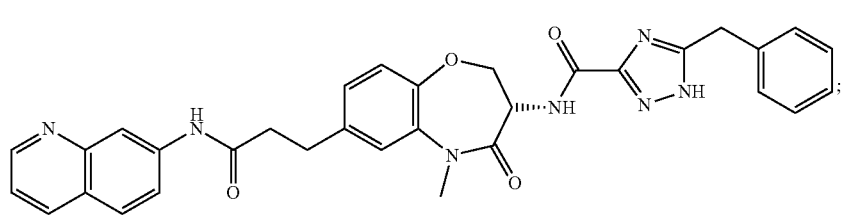

-continued
I-13
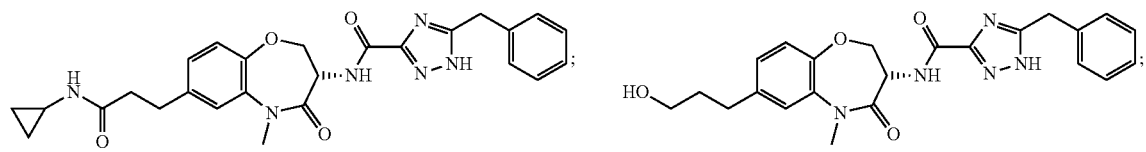
I-14
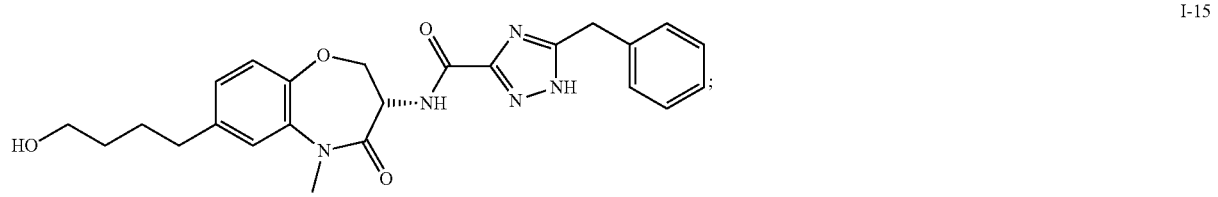
I-15
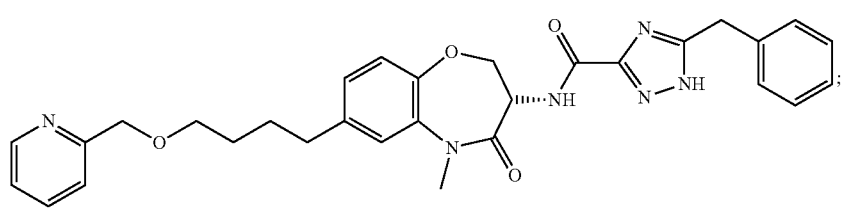
I-16
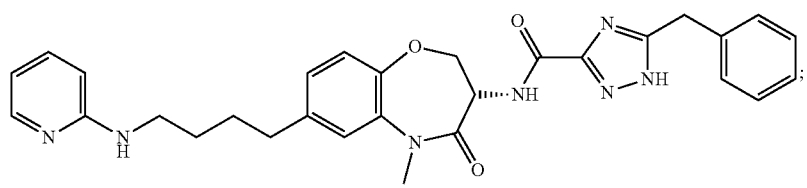
I-17
I-18
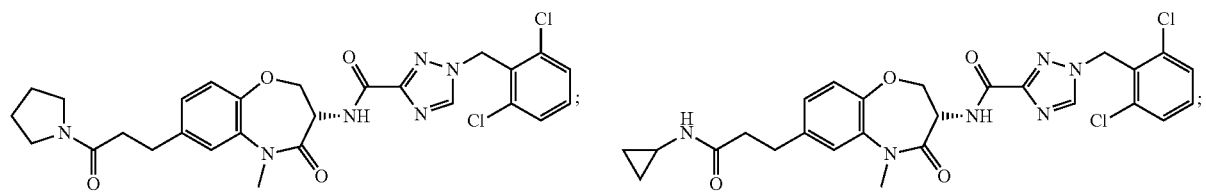
I-19
I-20
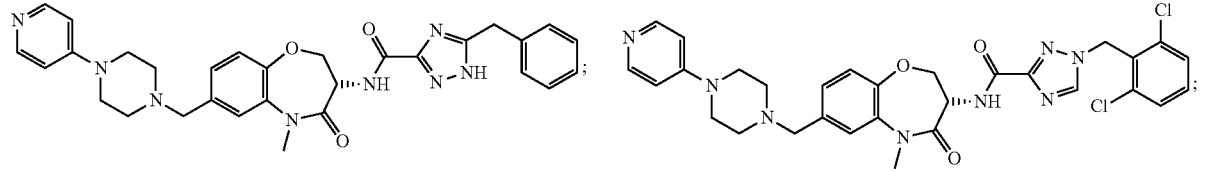
I-21
I-22
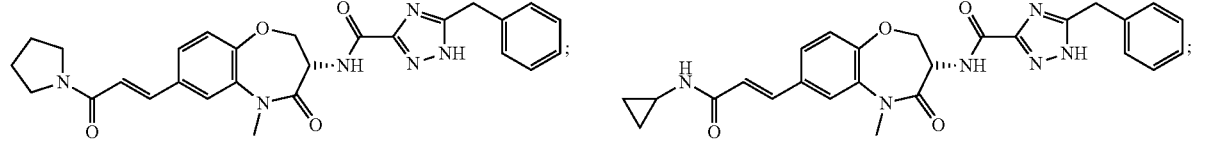
I-23
I-24
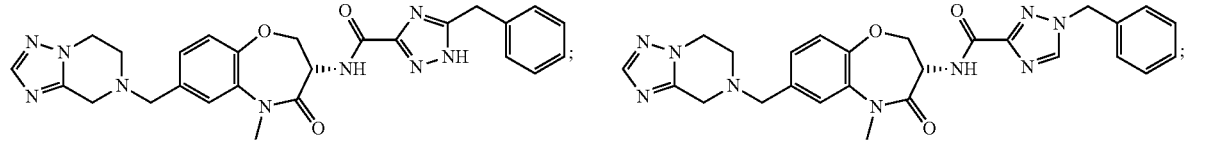
I-25

-continued
I-26
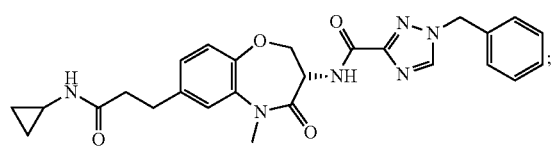
I-27
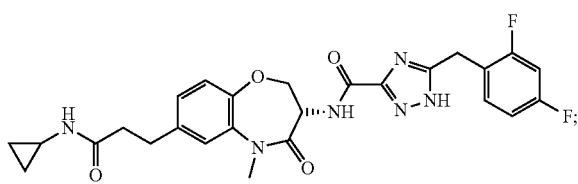
I-28
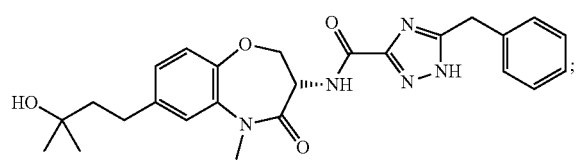
I-29
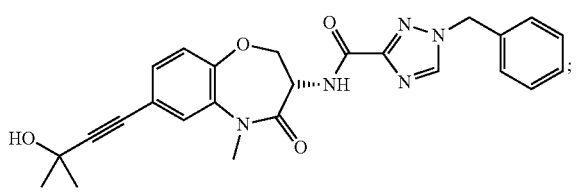
I-30
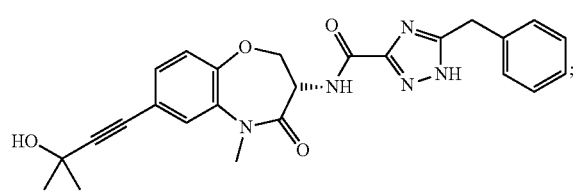
I-31
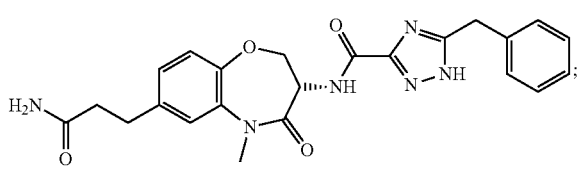
I-32
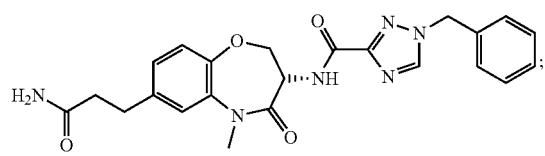
I-33
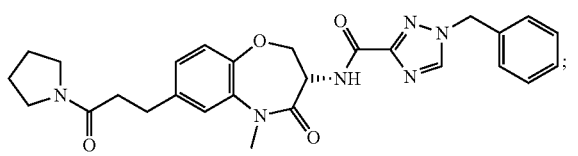
I-34
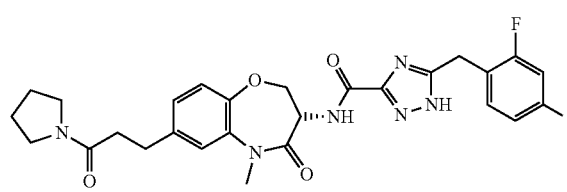
I-35
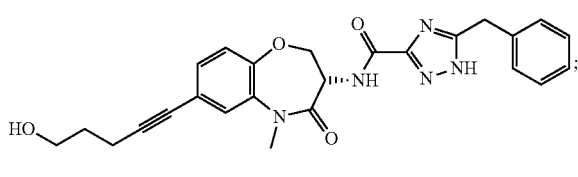
I-36
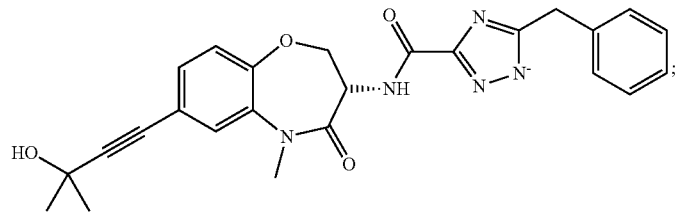
I-37
I-38
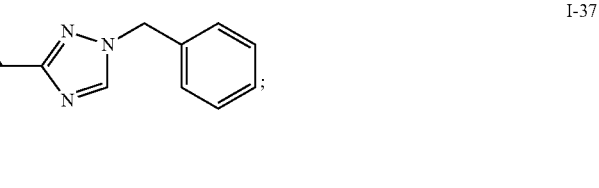
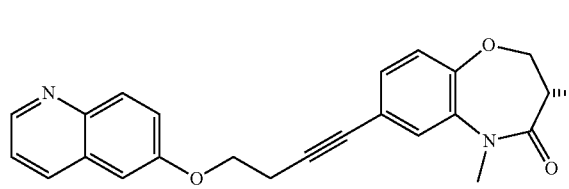

-continued
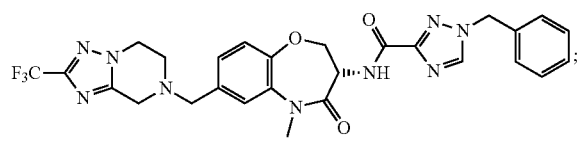
I-39
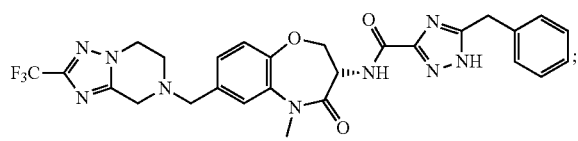
I-40
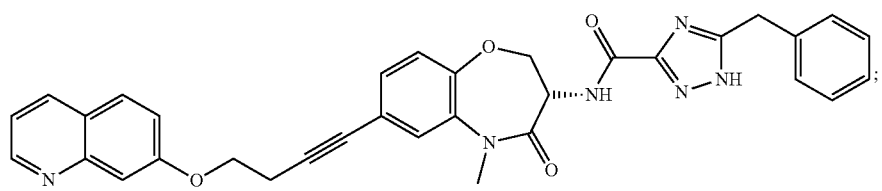
I-41
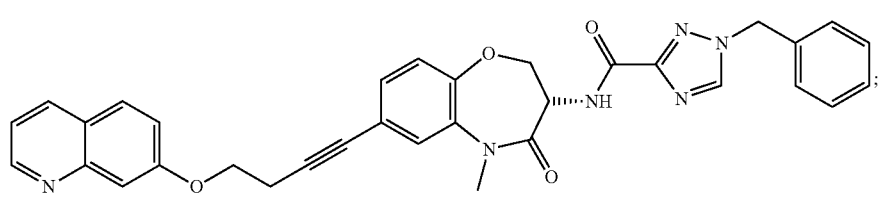
I-42
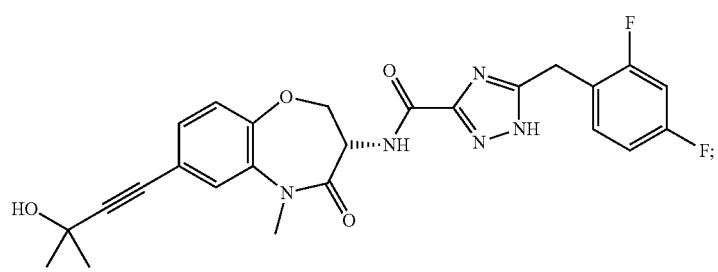
I-43
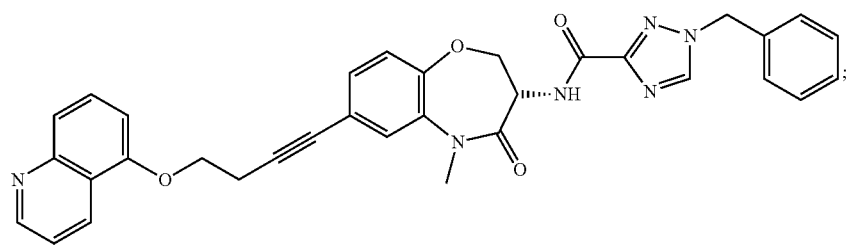
I-44
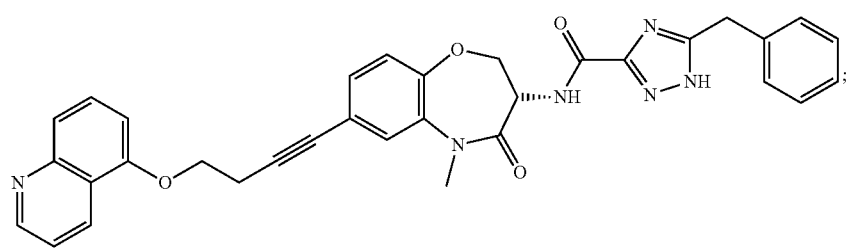
I-45
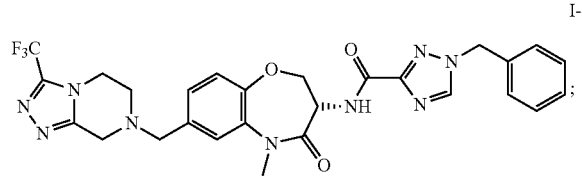
I-46
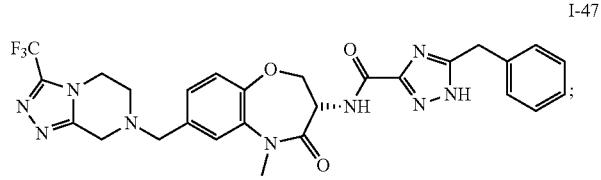
I-47

I-48
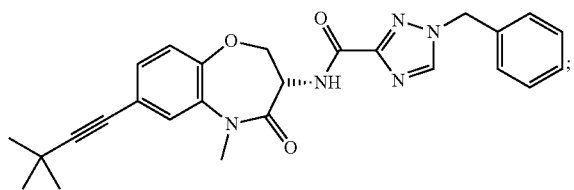
I-49
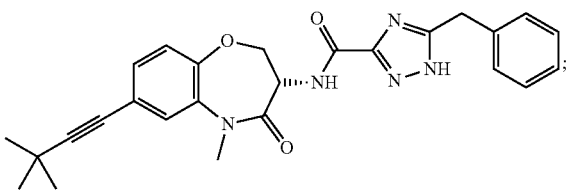
I-50
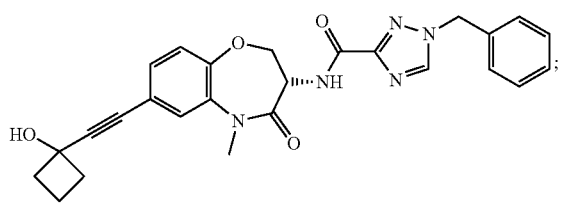
I-51
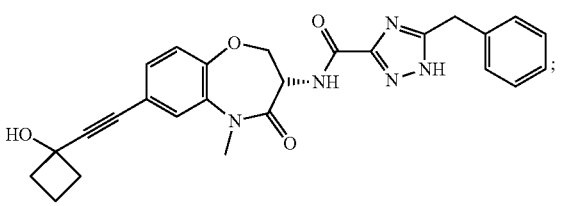
I-52
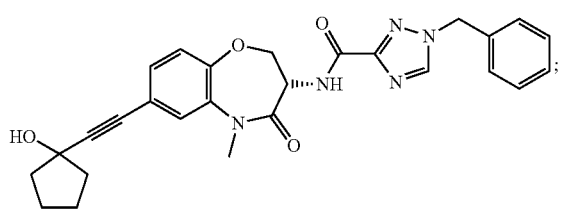
I-53
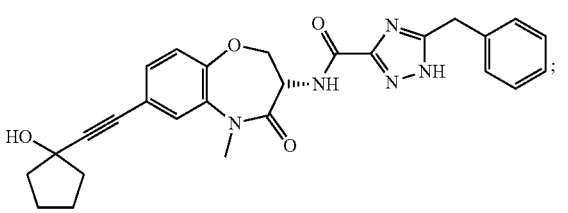
I-54
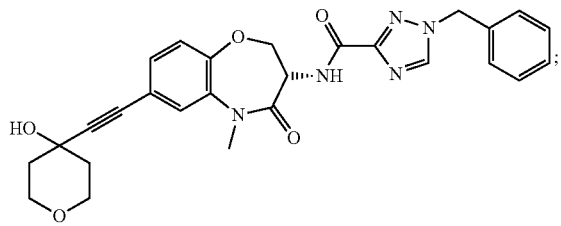
I-55
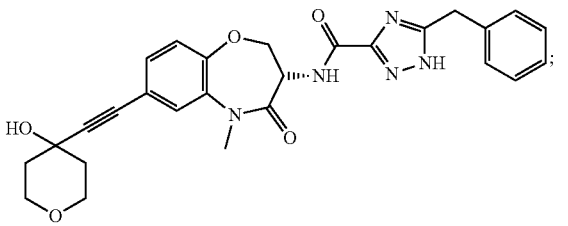
I-56
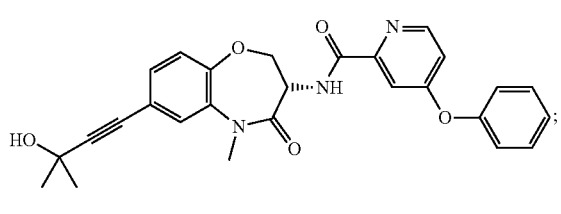
I-57
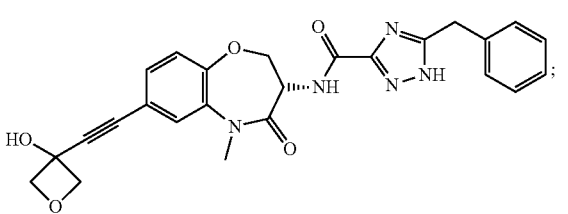
I-58
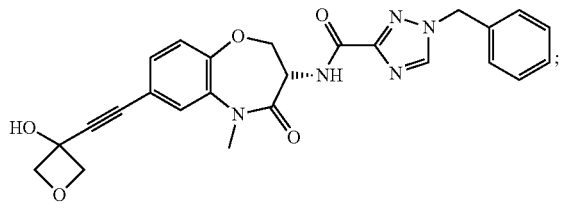
I-59
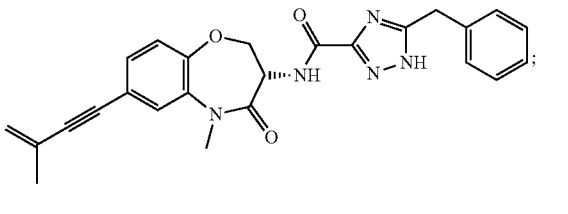
I-60
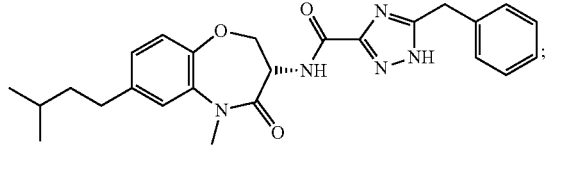
I-61
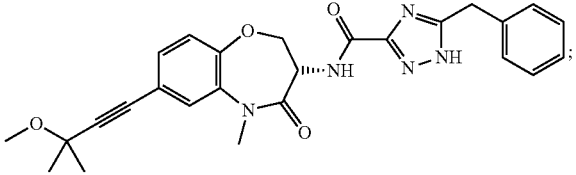

I-62
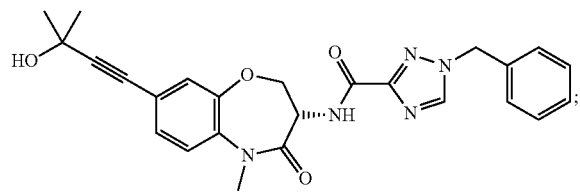
I-63
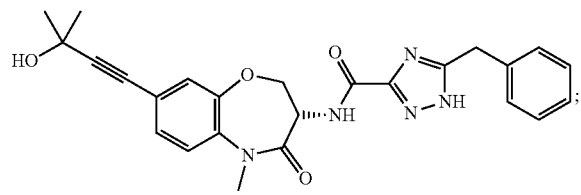
I-64
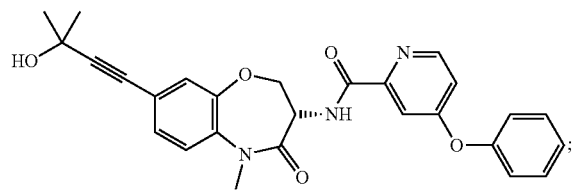
I-65
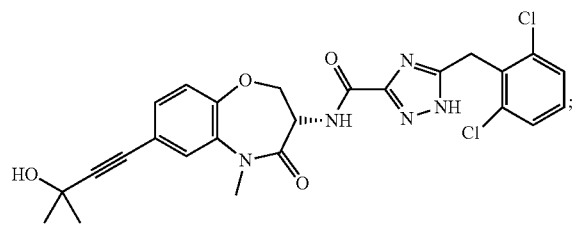
I-66
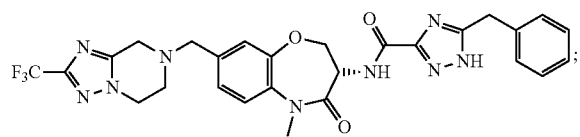
I-67
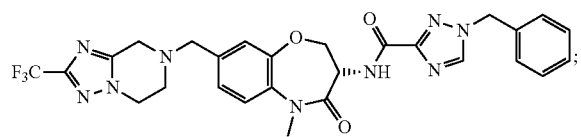
I-68
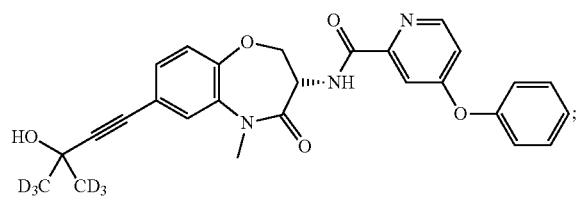
I-69
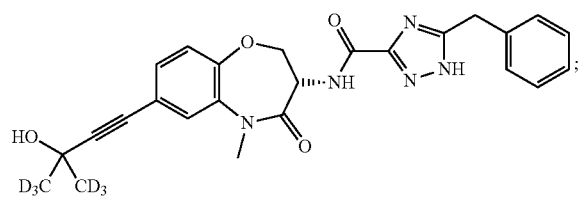
I-70
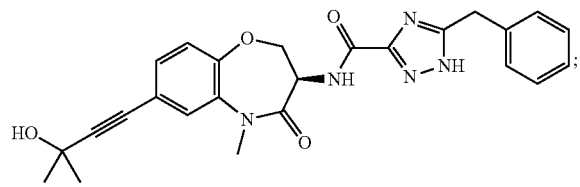
I-71
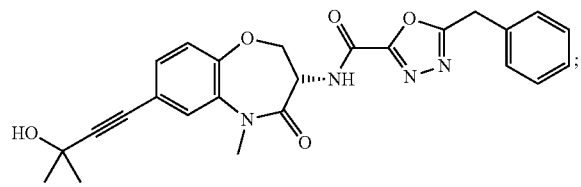
I-72
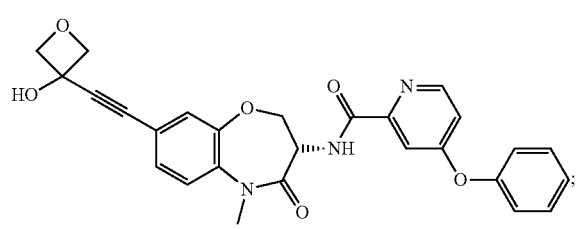
I-73
I-74
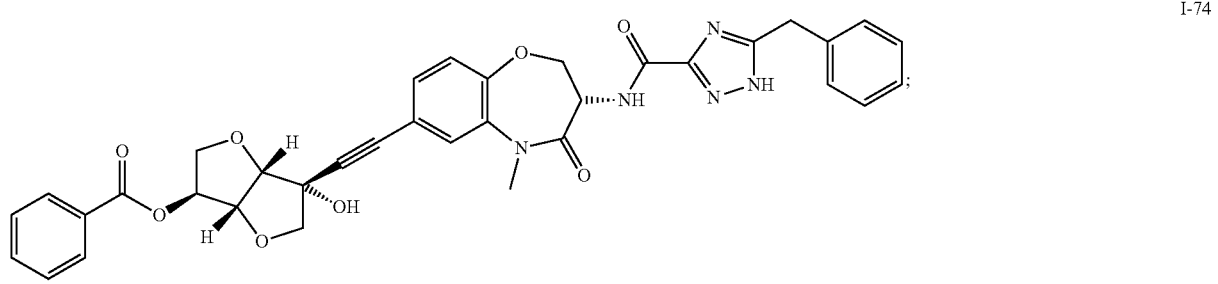

-continued
I-75
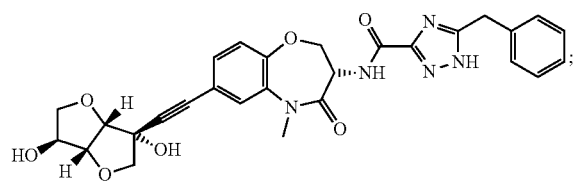
I-76
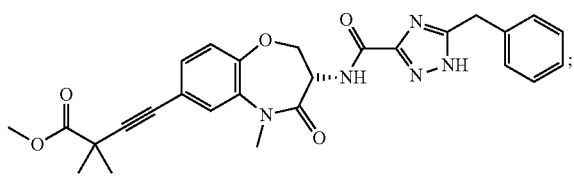
I-77
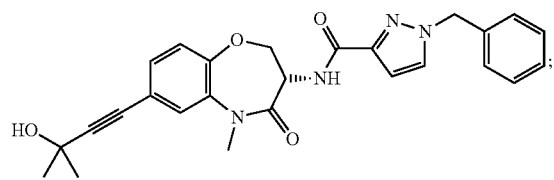
I-78
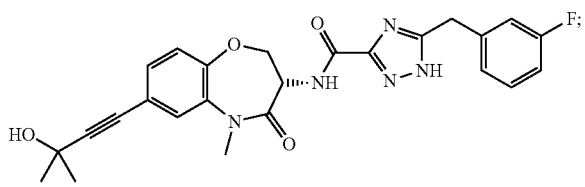
I-79
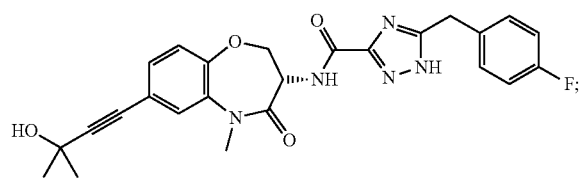
I-80
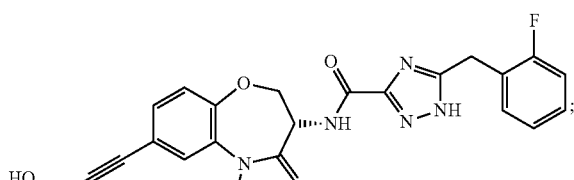
I-81
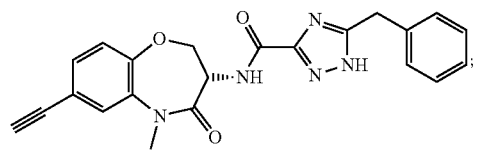
I-82
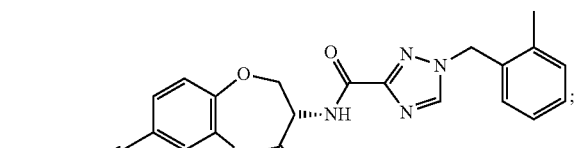
I-83
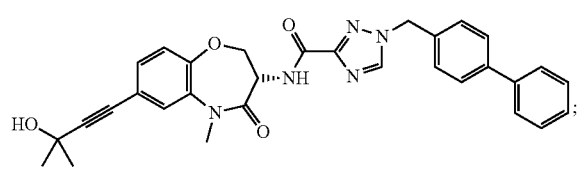
I-84
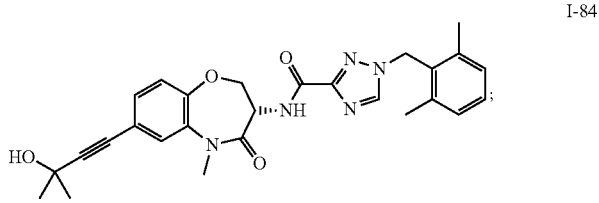
I-85
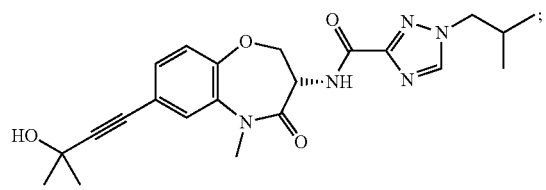
I-86
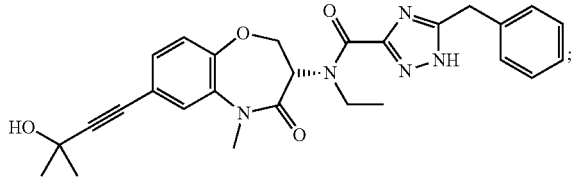
I-87
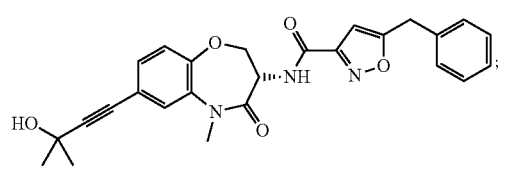
I-88
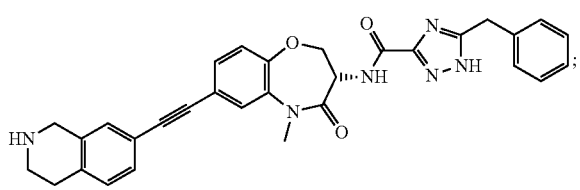

-continued

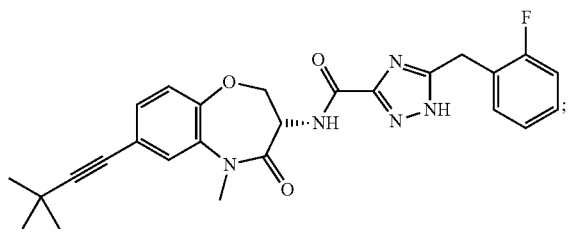

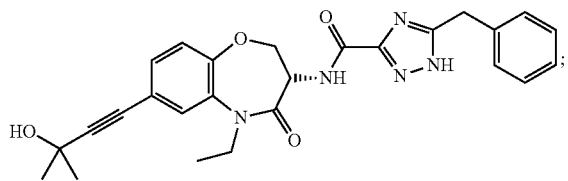

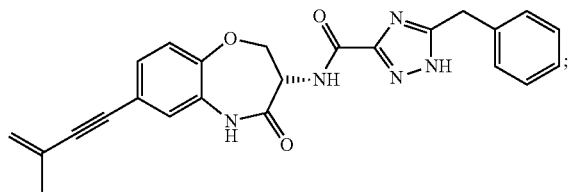

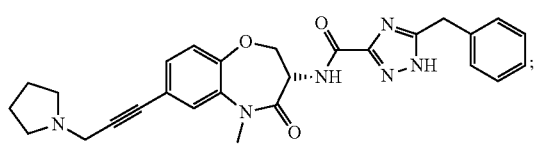

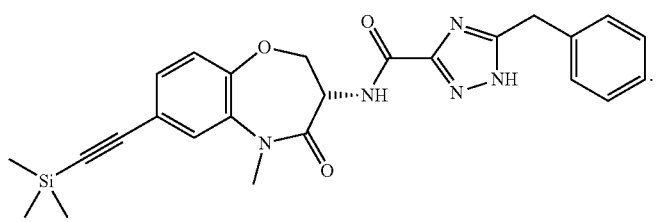

Exemplary compounds within the scope of one or more of Formulas I, IA, II, IIA-IIF, and III-VI include:

I-1: Ethyl (S)-3-(3-(5-benzyl-1H-1,2,4-triazole-3-carboxamido)-5-methyl-4-oxo-2,3,4,5-tetrahydrobenzo[b][1,4]oxazepin-7-yl)propanoate;

I-2: (S)—N-(7-(3-((1H-indazol-5-yl)amino)-3-oxopropyl)-5-methyl-4-oxo-2,3,4,5-tetrahydrobenzo[b][1,4]oxazepin-3-yl)-5-benzyl-1H-1,2,4-triazole-3-carboxamide;

I-3: (S)—N-(7-(3-((1H-indazol-6-yl)amino)-3-oxopropyl)-5-methyl-4-oxo-2,3,4,5-tetrahydrobenzo[b][1,4]oxazepin-3-yl)-5-benzyl-1H-1,2,4-triazole-3-carboxamide;

I-4: (S)-5-benzyl-N-(7-(3-((6,7-dimethoxyquinazolin-4-yl)amino)-3-oxopropyl)-5-methyl-4-oxo-2,3,4,5-tetrahydrobenzo[b][1,4]oxazepin-3-yl)-1H-1,2,4-triazole-3-carboxamide;

I-5: Ethyl (S)-3-(3-(1-(2-fluorobenzyl)-1H-1,2,4-triazole-3-carboxamido)-5-methyl-4-oxo-2,3,4,5-tetrahydrobenzo[b][1,4]oxazepin-7-yl)propanoate;

I-6: (S)-3-(3-(1-(2-fluorobenzyl)-1H-1,2,4-triazole-3-carboxamido)-5-methyl-4-oxo-2,3,4,5-tetrahydrobenzo[b][1,4]oxazepin-7-yl)propanoic acid;

I-7: (S)—N-(7-(3-((1H-indazol-6-yl)amino)-3-oxopropyl)-5-methyl-4-oxo-2,3,4,5-tetrahydrobenzo[b][1,4]oxazepin-3-yl)-1-(2-fluorobenzyl)-1H-1,2,4-triazole-3-carboxamide;

I-8: Ethyl (S)-3-(3-(1-(2,6-dichlorobenzyl)-1H-1,2,4-triazole-3-carboxamido)-5-methyl-4-oxo-2,3,4,5-tetrahydrobenzo[b][1,4]oxazepin-7-yl)propanoate;

I-9: (S)-3-(3-(5-benzyl-1H-1,2,4-triazole-3-carboxamido)-5-methyl-4-oxo-2,3,4,5-tetrahydrobenzo[b][1,4]oxazepin-7-yl)propanoic acid;

I-10: (S)-5-benzyl-N-(5-methyl-4-oxo-7-(3-oxo-3-(pyrrolidin-1-yl)propyl)-2,3,4,5-tetrahydrobenzo[b][1,4]oxazepin-3-yl)-1H-1,2,4-triazole-3-carboxamide;

I-11: (S)-5-benzyl-N-(5-methyl-7-(3-morpholino-3-oxopropyl)-4-oxo-2,3,4,5-tetrahydrobenzo[b][1,4]oxazepin-3-yl)-1H-1,2,4-triazole-3-carboxamide;

I-12: (S)-5-benzyl-N-(5-methyl-4-oxo-7-(3-oxo-3-(quinolin-7-ylamino)propyl)-2,3,4,5-tetrahydrobenzo[b][1,4]oxazepin-3-yl)-1H-1,2,4-triazole-3-carboxamide;

I-13: (S)-5-benzyl-N-(7-(3-(cyclopropylamino)-3-oxopropyl)-5-methyl-4-oxo-2,3,4,5-tetrahydrobenzo[b][1,4]oxazepin-3-yl)-1H-1,2,4-triazole-3-carboxamide;

I-14: (S)-5-benzyl-N-(7-(3-hydroxypropyl)-5-methyl-4-oxo-2,3,4,5-tetrahydrobenzo[b][1,4]oxazepin-3-yl)-1H-1,2,4-triazole-3-carboxamide;

I-15: (S)-5-benzyl-N-(7-(4-hydroxybutyl)-5-methyl-4-oxo-2,3,4,5-tetrahydrobenzo[b][1,4]oxazepin-3-yl)-1H-1,2,4-triazole-3-carboxamide;

I-16: (S)-5-benzyl-N-(5-methyl-4-oxo-7-(4-(pyridin-2-ylmethoxy)butyl)-2,3,4,5-tetrahydrobenzo[b][1,4]oxazepin-3-yl)-1H-1,2,4-triazole-3-carboxamide;

I-17: (S)-5-benzyl-N-(5-methyl-4-oxo-7-(4-(pyridin-2-ylamino)butyl)-2,3,4,5-tetrahydrobenzo[b][1,4]oxazepin-3-yl)-1H-1,2,4-triazole-3-carboxamide;

I-18: (S)-1-(2,6-dichlorobenzyl)-N-(5-methyl-4-oxo-3-(pyrrolidin-1-yl)propyl)-2,3,4,5-tetrahydrobenzo[b][1,4]oxazepin-3-yl)-1H-1,2,4-triazole-3-carboxamide;

I-19: (S)—N-(7-(3-(cyclopropylamino)-3-oxopropyl)-5-methyl-4-oxo-2,3,4,5-tetrahydrobenzo[b][1,4]oxazepin-3-yl)-1-(2,6-dichlorobenzyl)-1H-1,2,4-triazole-3-carboxamide;

I-20: (S)-5-benzyl-N-(5-methyl-4-oxo-7-((4-(pyridin-4-yl)piperazin-1-yl)methyl)-2,3,4,5-tetrahydrobenzo[b][1,4]oxazepin-3-yl)-1H-1,2,4-triazole-3-carboxamide;

I-21: (S)-1-(2,6-dichlorobenzyl)-N-(5-methyl-4-oxo-7-((4-(pyridin-4-yl)piperazin-1-yl)methyl)-2,3,4,5-tetrahydrobenzo[b][1,4]oxazepin-3-yl)-1H-1,2,4-triazole-3-carboxamide;

I-22: (S,E)-5-benzyl-N-(5-methyl-4-oxo-7-(3-oxo-3-(pyrrolidin-1-yl)prop-1-en-1-yl)-2,3,4,5-tetrahydrobenzo[b][1,4]oxazepin-3-yl)-1H-1,2,4-triazole-3-carboxamide;

I-23: (S,E)-5-benzyl-N-(7-(3-(cyclopropylamino)-3-oxoprop-1-en-1-yl)-5-methyl-4-oxo-2,3,4,5-tetrahydrobenzo[b][1,4]oxazepin-3-yl)-1H-1,2,4-triazole-3-carboxamide;

I-24: (S)-5-benzyl-N-(7-((5,6-dihydro-[1,2,4]triazolo[1,5-a]pyrazin-7(8H)-yl)methyl)-5-methyl-4-oxo-2,3,4,5-tetrahydrobenzo[b][1,4]oxazepin-3-yl)-1H-1,2,4-triazole-3-carboxamide;

I-25: (S)-1-benzyl-N-(7-((5,6-dihydro-[1,2,4]triazolo[1,5-a]pyrazin-7(8H)-yl)methyl)-5-methyl-4-oxo-2,3,4,5-tetrahydrobenzo[b][1,4]oxazepin-3-yl)-1H-1,2,4-triazole-3-carboxamide;

I-26: (S)-1-benzyl-N-(7-(3-(cyclopropylamino)-3-oxopropyl)-5-methyl-4-oxo-2,3,4,5-tetrahydrobenzo[b][1,4]oxazepin-3-yl)-1H-1,2,4-triazole-3-carboxamide;

I-27: (S)—N-(7-(3-(cyclopropylamino)-3-oxopropyl)-5-methyl-4-oxo-2,3,4,5-tetrahydrobenzo[b][1,4]oxazepin-3-yl)-5-(2,4-difluorobenzyl)-1H-1,2,4-triazole-3-carboxamide;

I-28: (S)-5-benzyl-N-(7-(3-hydroxy-3-methylbutyl)-5-methyl-4-oxo-2,3,4,5-tetrahydrobenzo[b][1,4]oxazepin-3-yl)-1H-1,2,4-triazole-3-carboxamide;

I-29: (S)-1-benzyl-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-30: (S)-5-benzyl-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-31: (S)—N-(7-(3-amino-3-oxopropyl)-5-methyl-4-oxo-2,3,4,5-tetrahydrobenzo[b][1,4]oxazepin-3-yl)-5-benzyl-1H-1,2,4-triazole-3-carboxamide;

I-32: (S)—N-(7-(3-amino-3-oxopropyl)-5-methyl-4-oxo-2,3,4,5-tetrahydrobenzo[b][1,4]oxazepin-3-yl)-1-benzyl-1H-1,2,4-triazole-3-carboxamide;

I-33: (S)-1-benzyl-N-(5-methyl-4-oxo-7-(3-oxo-3-(pyrrolidin-1-yl)propyl)-2,3,4,5-tetrahydrobenzo[b][1,4]oxazepin-3-yl)-1H-1,2,4-triazole-3-carboxamide;

I-34: (S)-5-(2,4-difluorobenzyl)-N-(5-methyl-4-oxo-7-(3-oxo-3-(pyrrolidin-1-yl)propyl)-2,3,4,5-tetrahydrobenzo[b][1,4]oxazepin-3-yl)-1H-1,2,4-triazole-3-carboxamide;

I-35: (S)-5-benzyl-N-(7-(5-hydroxypent-1-yn-1-yl)-5-methyl-4-oxo-2,3,4,5-tetrahydrobenzo[b][1,4]oxazepin-3-yl)-1H-1,2,4-triazole-3-carboxamide;

I-36: (S)-5-benzyl-3-((7-(3-hydroxy-3-methylbut-1-yn-1-yl)-5-methyl-4-oxo-2,3,4,5-tetrahydrobenzo[b][1,4]oxazepin-3-yl)carbamoyl)-1,2,4-triazol-1-ide;

I-37: (S)-1-benzyl-N-(5-methyl-4-oxo-7-(4-(quinolin-6-yloxy)but-1-yn-1-yl)-2,3,4,5-tetrahydrobenzo[b][1,4]oxazepin-3-yl)-1H-1,2,4-triazole-3-carboxamide;

I-38: (S)-5-benzyl-N-(5-methyl-4-oxo-7-(4-(quinolin-6-yloxy)but-1-yn-1-yl)-2,3,4,5-tetrahydrobenzo[b][1,4]oxazepin-3-yl)-1H-1,2,4-triazole-3-carboxamide;

I-39: (S)-1-benzyl-N-(5-methyl-4-oxo-7-((2-(trifluoromethyl)-5,6-dihydro-[1,2,4]triazolo[1,5-a]pyrazin-7(8H)-yl)methyl)-2,3,4,5-tetrahydrobenzo[b][1,4]oxazepin-3-yl)-1H-1,2,4-triazole-3-carboxamide;

I-40: (S)-5-benzyl-N-(5-methyl-4-oxo-7-((2-(trifluoromethyl)-5,6-dihydro-[1,2,4]triazolo[1,5-a]pyrazin-7(8H)-yl)methyl)-2,3,4,5-tetrahydrobenzo[b][1,4]oxazepin-3-yl)-1H-1,2,4-triazole-3-carboxamide;

I-41: (S)-5-benzyl-N-(5-methyl-4-oxo-7-(4-(quinolin-7-yloxy)but-1-yn-1-yl)-2,3,4,5-tetrahydrobenzo[b][1,4]oxazepin-3-yl)-1H-1,2,4-triazole-3-carboxamide;

I-42: (S)-1-benzyl-N-(5-methyl-4-oxo-7-(4-(quinolin-7-yloxy)but-1-yn-1-yl)-2,3,4,5-tetrahydrobenzo[b][1,4]oxazepin-3-yl)-1H-1,2,4-triazole-3-carboxamide;

I-43: (S)-5-(2,4-difluorobenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-44: (S)-1-benzyl-N-(5-methyl-4-oxo-7-(4-(quinolin-5-yloxy)but-1-yn-1-yl)-2,3,4,5-tetrahydrobenzo[b][1,4]oxazepin-3-yl)-1H-1,2,4-triazole-3-carboxamide;

I-45: (S)-5-benzyl-N-(5-methyl-4-oxo-7-(4-(quinolin-5-yloxy)but-1-yn-1-yl)-2,3,4,5-tetrahydrobenzo[b][1,4]oxazepin-3-yl)-1H-1,2,4-triazole-3-carboxamide;

I-46: (S)-1-benzyl-N-(5-methyl-4-oxo-7-((3-(trifluoromethyl)-5,6-dihydro-[1,2,4]triazolo[4,3-a]pyrazin-7(8H)-yl)methyl)-2,3,4,5-tetrahydrobenzo[b][1,4]oxazepin-3-yl)-1H-1,2,4-triazole-3-carboxamide;

I-47: (S)-5-benzyl-N-(5-methyl-4-oxo-7-((3-(trifluoromethyl)-5,6-dihydro-[1,2,4]triazolo[4,3-a]pyrazin-7(8H)-yl)methyl)-2,3,4,5-tetrahydrobenzo[b][1,4]oxazepin-3-yl)-1H-1,2,4-triazole-3-carboxamide;

I-48: (S)-1-benzyl-N-(7-(3,3-dimethylbut-1-yn-1-yl)-5-methyl-4-oxo-2,3,4,5-tetrahydrobenzo[b][1,4]oxazepin-3-yl)-1H-1,2,4-triazole-3-carboxamide;

I-49: (S)-5-benzyl-N-(7-(3,3-dimethylbut-1-yn-1-yl)-5-methyl-4-oxo-2,3,4,5-tetrahydrobenzo[b][1,4]oxazepin-3-yl)-1H-1,2,4-triazole-3-carboxamide;

I-50: (S)-1-benzyl-N-(7-((1-hydroxycyclobutyl)ethynyl)-5-methyl-4-oxo-2,3,4,5-tetrahydrobenzo[b][1,4]oxazepin-3-yl)-1H-1,2,4-triazole-3-carboxamide;

I-51: (S)-5-benzyl-N-(7-((1-hydroxycyclobutyl)ethynyl)-5-methyl-4-oxo-2,3,4,5-tetrahydrobenzo[b][1,4]oxazepin-3-yl)-1H-1,2,4-triazole-3-carboxamide;

I-52: (S)-1-benzyl-N-(7-((1-hydroxycyclopentyl)ethynyl)-5-methyl-4-oxo-2,3,4,5-tetrahydrobenzo[b][1,4]oxazepin-3-yl)-1H-1,2,4-triazole-3-carboxamide;

I-53: (S)-5-benzyl-N-(7-((1-hydroxycyclopentyl)ethynyl)-5-methyl-4-oxo-2,3,4,5-tetrahydrobenzo[b][1,4]oxazepin-3-yl)-1H-1,2,4-triazole-3-carboxamide;

I-54: (S)-1-benzyl-N-(7-((4-hydroxytetrahydro-2H-pyran-4-yl)ethynyl)-5-methyl-4-oxo-2,3,4,5-tetrahydrobenzo[b][1,4]oxazepin-3-yl)-1H-1,2,4-triazole-3-carboxamide;

I-55: (S)-5-benzyl-N-(7-((4-hydroxytetrahydro-2H-pyran-4-yl)ethynyl)-5-methyl-4-oxo-2,3,4,5-tetrahydrobenzo[b][1,4]oxazepin-3-yl)-1H-1,2,4-triazole-3-carboxamide;

I-56: (S)-i-(7-(3-hydroxy-3-methylbut-1-yn-1-yl)-5-methyl-4-oxo-2,3,4,5-tetrahydrobenzo[b][1,4]oxazepin-3-yl)-4-phenoxypicolinamide;

I-57: (S)-5-benzyl-N-(7-((3-hydroxyoxetan-3-yl)ethynyl)-5-methyl-4-oxo-2,3,4,5-tetrahydrobenzo[b][1,4]oxazepin-3-yl)-1H-1,2,4-triazole-3-carboxamide;

I-58: (S)-1-benzyl-N-(7-((3-hydroxyoxetan-3-yl)ethynyl)-5-methyl-4-oxo-2,3,4,5-tetrahydrobenzo[b][1,4]oxazepin-3-yl)-1H-1,2,4-triazole-3-carboxamide;

I-59: (S)-5-benzyl-N-(5-methyl-7-(3-methylbut-3-en-1-yn-1-yl)-4-oxo-2,3,4,5-tetrahydrobenzo[b][1,4]oxazepin-3-yl)-1H-1,2,4-triazole-3-carboxamide;

I-60: (S)-5-benzyl-N-(7-isopentyl-5-methyl-4-oxo-2,3,4,5-tetrahydrobenzo[b][1,4]oxazepin-3-yl)-1H-1,2,4-triazole-3-carboxamide;

I-61: (S)-5-benzyl-N-(7-(3-methoxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-62: (S)-1-benzyl-N-(8-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-63: (S)-5-benzyl-N-(8-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-64: (S)—N-(8-(3-hydroxy-3-methylbut-1-yn-1-yl)-5-methyl-4-oxo-2,3,4,5-tetrahydrobenzo[b][1,4]oxazepin-3-yl)-4-phenoxypicolinamide;

I-65: (S)-5-(2,6-dichlorobenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-66: (S)-5-benzyl-N-(5-methyl-4-oxo-8-((2-(trifluoromethyl)-5,6-dihydro-[1,2,4]triazolo[1,5-a]pyrazin-7(8H)-yl)methyl)-2,3,4,5-tetrahydrobenzo[b][1,4]oxazepin-3-yl)-1H-1,2,4-triazole-3-carboxamide;

I-67: (S)-1-benzyl-N-(5-methyl-4-oxo-8-((2-(trifluoromethyl)-5,6-dihydro-[1,2,4]triazolo[1,5-a]pyrazin-7(8H)-yl)methyl)-2,3,4,5-tetrahydrobenzo[b][1,4]oxazepin-3-yl)-1H-1,2,4-triazole-3-carboxamide;

I-68: (S)—N-(7-(3-hydroxy-3-(methyl-d3)but-1-yn-1-yl-4,4,4-d3)-5-methyl-4-oxo-2,3,4,5-tetrahydrobenzo[b][1,4]oxazepin-3-yl)-4-phenoxypicolinamide;

I-69: (S)-5-benzyl-N-(7-(3-hydroxy-3-(methyl-d3)but-1-yn-1-yl-4,4,4-d3)-5-methyl-4-oxo-2,3,4,5-tetrahydrobenzo[b][1,4]oxazepin-3-yl)-1H-1,2,4-triazole-3-carboxamide;

I-70: (R)-5-benzyl-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-71: (S)-5-benzyl-N-(7-(3-hydroxy-3-methylbut-1-yn-1-yl)-5-methyl-4-oxo-2,3,4,5-tetrahydrobenzo[b][1,4]oxazepin-3-yl)-1,3,4-oxadiazole-2-carboxamide;

I-72: (S)—N-(8-((3-hydroxyoxetan-3-yl)ethynyl)-5-methyl-4-oxo-2,3,4,5-tetrahydrobenzo[b][1,4]oxazepin-3-yl)-4-phenoxypicolinamide;

I-73: (S)-5-benzyl-N-(8-((3-hydroxyoxetan-3-yl)ethynyl)-5-methyl-4-oxo-2,3,4,5-tetrahydrobenzo[b][1,4]oxazepin-3-yl)-1H-1,2,4-triazole-3-carboxamide;

I-74: (3S,3aR,6R,6aS)-6-(((S)-3-(5-benzyl-1H-1,2,4-triazole-3-carboxamido)-5-methyl-4-oxo-2,3,4,5-tetrahydrobenzo[b][1,4]oxazepin-7-yl)ethynyl)-6-hydroxyhexahydrofuro[3,2-b]furan-3-yl benzoate;

I-75: 5-benzyl-N—((S)-7-(((3R,3aS,6S,6aR)-3,6-dihydroxyhexahydrofuro[3,2-b]furan-3-yl)ethynyl)-5-methyl-4-oxo-2,3,4,5-tetrahydrobenzo[b][1,4]oxazepin-3-yl)-1H-1,2,4-triazole-3-carboxamide;

I-76: methyl (S)-4-(3-(5-benzyl-1H-1,2,4-triazole-3-carboxamido)-5-methyl-4-oxo-2,3,4,5-tetrahydrobenzo[b][1,4]oxazepin-7-yl)-2,2-dimethylbut-3-ynoate;

I-77: (S)-1-benzyl-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-3-carboxamide;

I-78: (S)-5-(3-fluorobenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-79: (S)-5-(4-fluorobenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-80: (S)-5-(2-fluorobenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-81: (S)-5-benzyl-N-(7-ethynyl-5-methyl-4-oxo-2,3,4,5-tetrahydrobenzo[b][1,4]oxazepin-3-yl)-1H-1,2,4-triazole-3-carboxamide;

I-82: (S)—N-(7-(3-hydroxy-3-methylbut-1-yn-1-yl)-5-methyl-4-oxo-2,3,4,5-tetrahydrobenzo[b][1,4]oxazepin-3-yl)-1-(2-methylbenzyl)-1H-1,2,4-triazole-3-carboxamide;

I-83: (S)-1-([1,1'-biphenyl]-4-ylmethyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-84: (S)-1-(2,6-dimethylbenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-85: (S)—N-(7-(3-hydroxy-3-methylbut-1-yn-1-yl)-5-methyl-4-oxo-2,3,4,5-tetrahydrobenzo[b][1,4]oxazepin-3-yl)-1-isobutyl-1H-1,2,4-triazole-3-carboxamide;

I-86: (S)-5-benzyl-N-ethyl-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide;

I-87: (S)-5-benzyl-N-(7-(3-hydroxy-3-methylbut-1-yn-1-yl)-5-methyl-4-oxo-2,3,4,5-tetrahydrobenzo[b][1,4]oxazepin-3-yl)isoxazole-3-carboxamide;

I-88: (S)-5-benzyl-N-(5-methyl-4-oxo-7-((1,2,3,4-tetrahydroisoquinolin-7-yl)ethynyl)-2,3,4,5-tetrahydrobenzo[b][1,4]oxazepin-3-yl)-1H-1,2,4-triazole-3-carboxamide;

I-89: (S)—N-(7-(3,3-dimethylbut-1-yn-1-yl)-5-methyl-4-oxo-2,3,4,5-tetrahydrobenzo[b][1,4]oxazepin-3-yl)-5-(2-fluorobenzyl)-1H-1,2,4-triazole-3-carboxamide;

I-90: (S)-1-(2,6-dimethylbenzyl)-N-(7-(3,3-dimethylbut-1-yn-1-yl)-5-methyl-4-oxo-2,3,4,5-tetrahydrobenzo[b][1,4]oxazepin-3-yl)-1H-1,2,4-triazole-3-carboxamide;

I-91: (S)-5-benzyl-N-(5-ethyl-7-(3-hydroxy-3-methylbut-1-yn-1-yl)-4-oxo-2,3,4,5-tetrahydrobenzo[b][1,4]oxazepin-3-yl)-1H-1,2,4-triazole-3-carboxamide;

I-92: (S)—N-(5-ethyl-7-(3-hydroxy-3-methylbut-1-yn-1-yl)-4-oxo-2,3,4,5-tetrahydrobenzo[b][1,4]oxazepin-3-yl)-5-(3-fluorobenzyl)-1H-1,2,4-triazole-3-carboxamide;

I-93: (S)-5-benzyl-N-(7-(3-methylbut-3-en-1-yn-1-yl)-4-oxo-2,3,4,5-tetrahydrobenzo[b][1,4]oxazepin-3-yl)-1H-1,2,4-triazole-3-carboxamide;

I-94: (S,Z)-5-benzyl-N-(7-(2-chloro-3-hydroxy-3-methylbut-1-en-1-yl)-5-methyl-4-oxo-2,3,4,5-tetrahydrobenzo[b][1,4]oxazepin-3-yl)-1H-1,2,4-triazole-3-carboxamide;

I-95: (S)-5-benzyl-N-(5-methyl-4-oxo-7-(3-(pyrrolidin-1-yl)prop-1-yn-1-yl)-2,3,4,5-tetrahydrobenzo[b][1,4]oxazepin-3-yl)-1H-1,2,4-triazole-3-carboxamide;

I-96: (S)-5-benzyl-N-(5-methyl-7-(3-morpholinoprop-1-yn-1-yl)-4-oxo-2,3,4,5-tetrahydrobenzo[b][1,4]oxazepin-3-yl)-1H-1,2,4-triazole-3-carboxamide; or
I-97: (S)-5-benzyl-N-(5-methyl-4-oxo-7-((trimethylsilyl)ethynyl)-2,3,4,5-tetrahydrobenzo[b][1,4]oxazepin-3-yl)-1H-1,2,4-triazole-3-carboxamide.
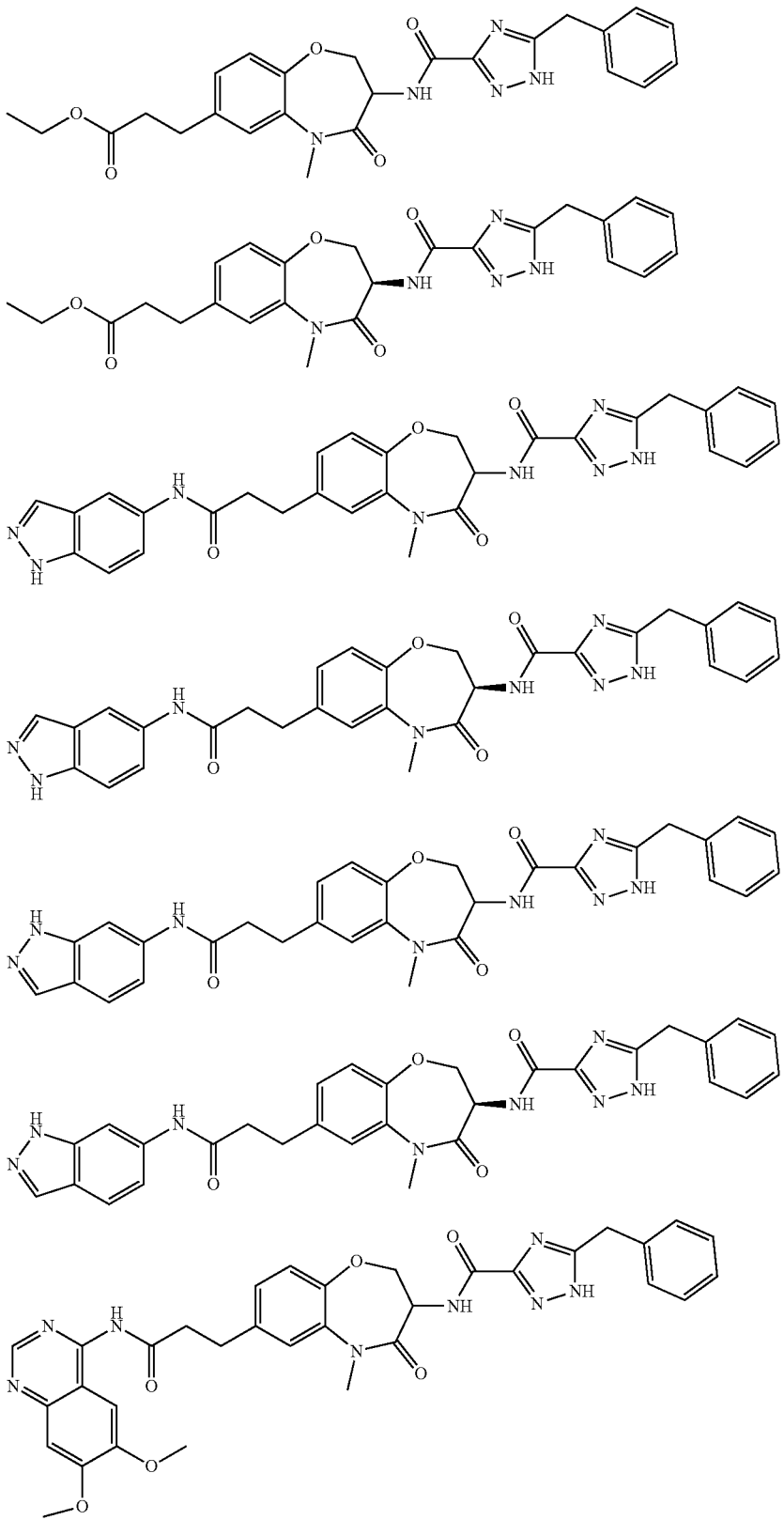

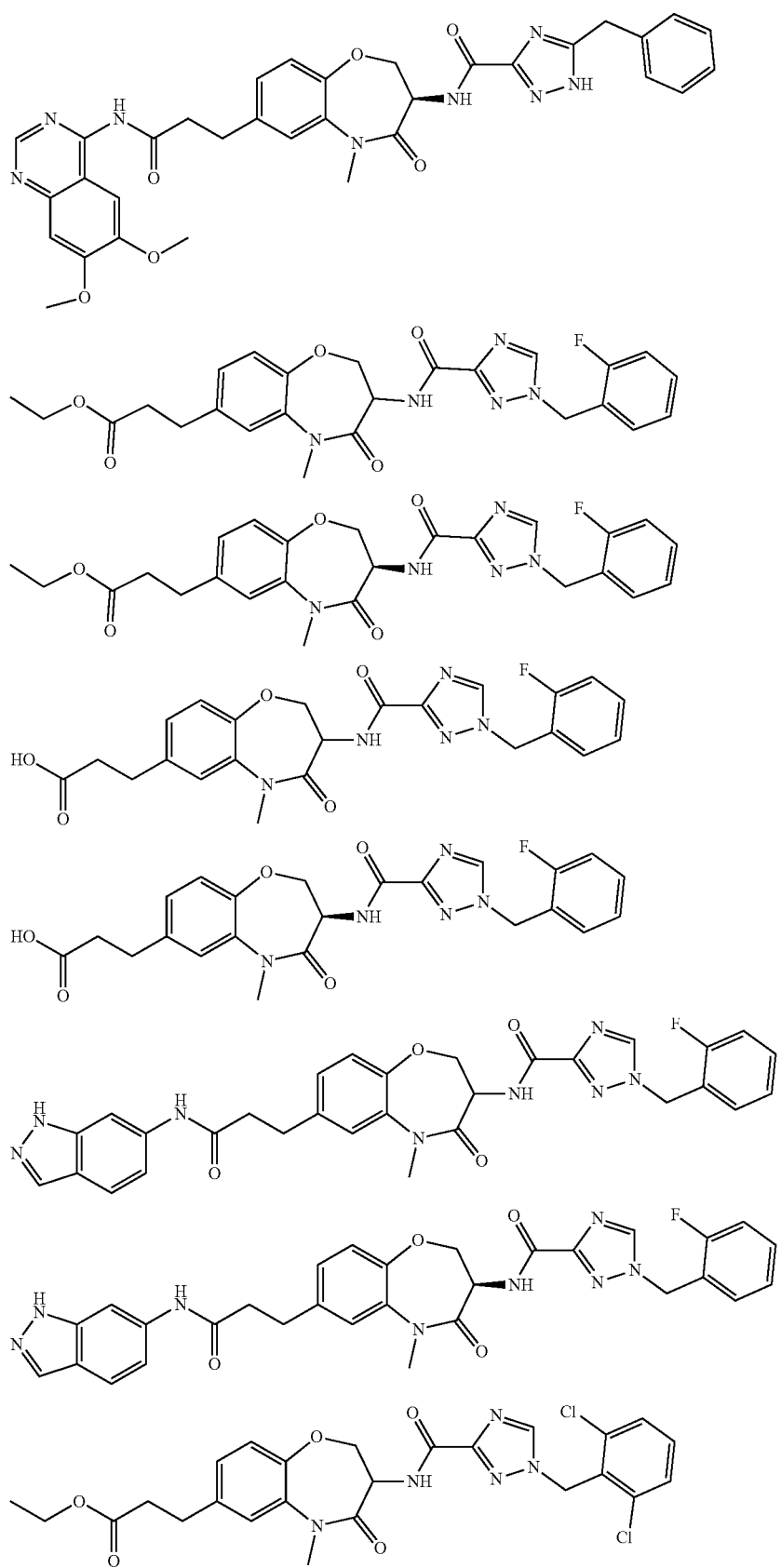

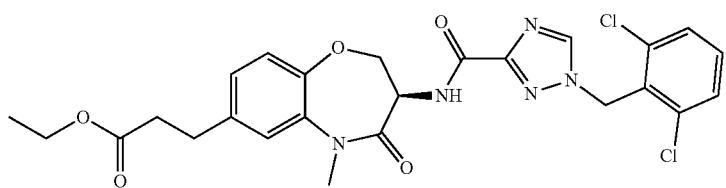
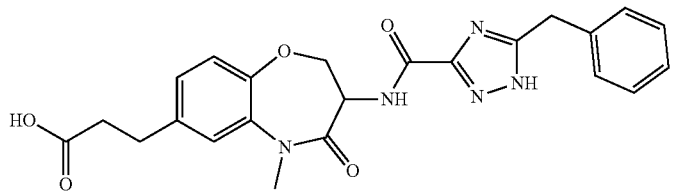
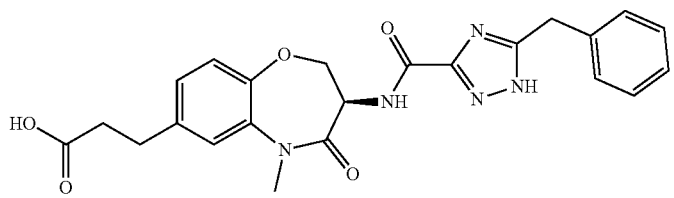
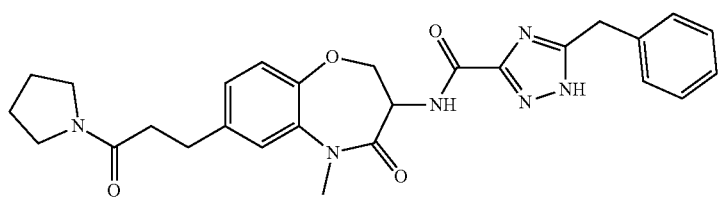
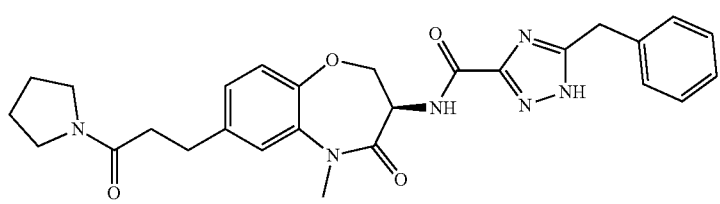
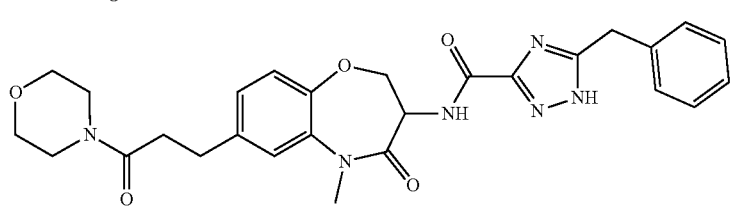
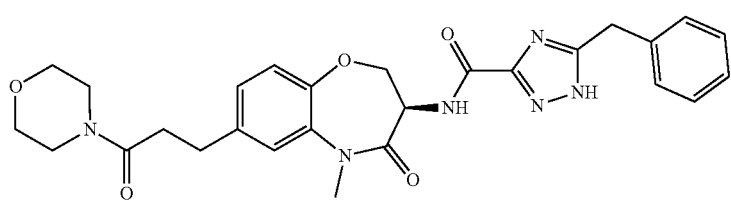
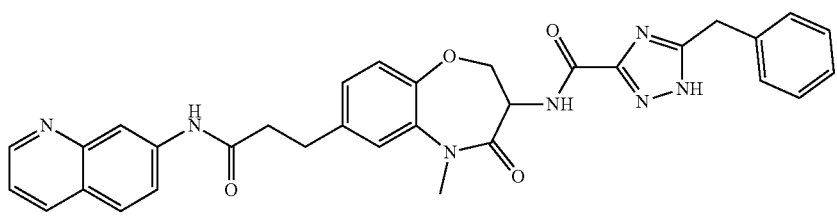

-continued
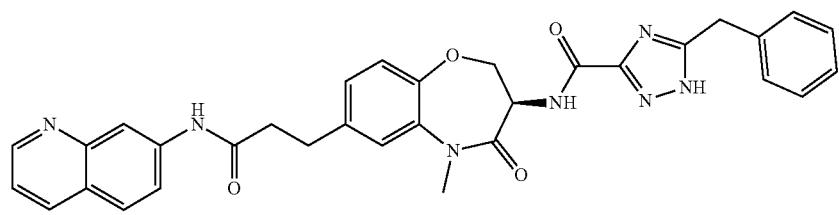
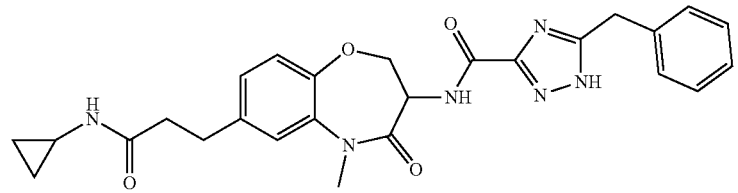
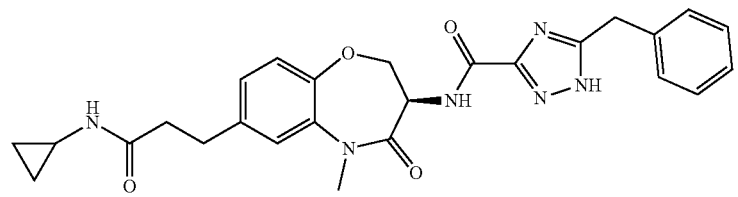
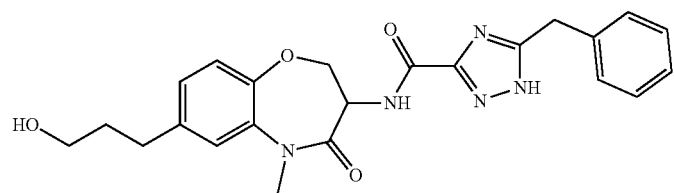
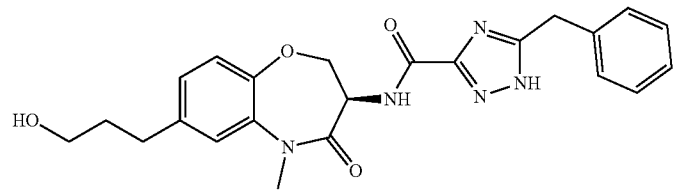
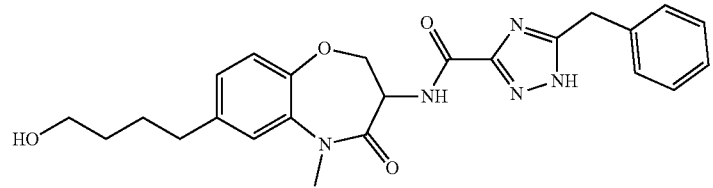
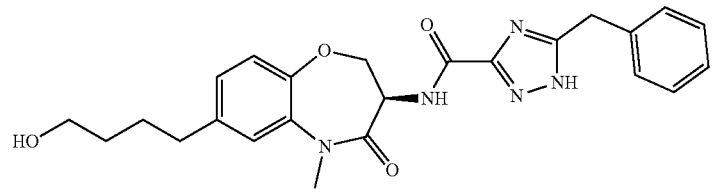
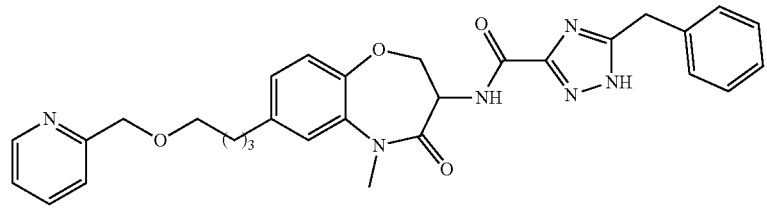

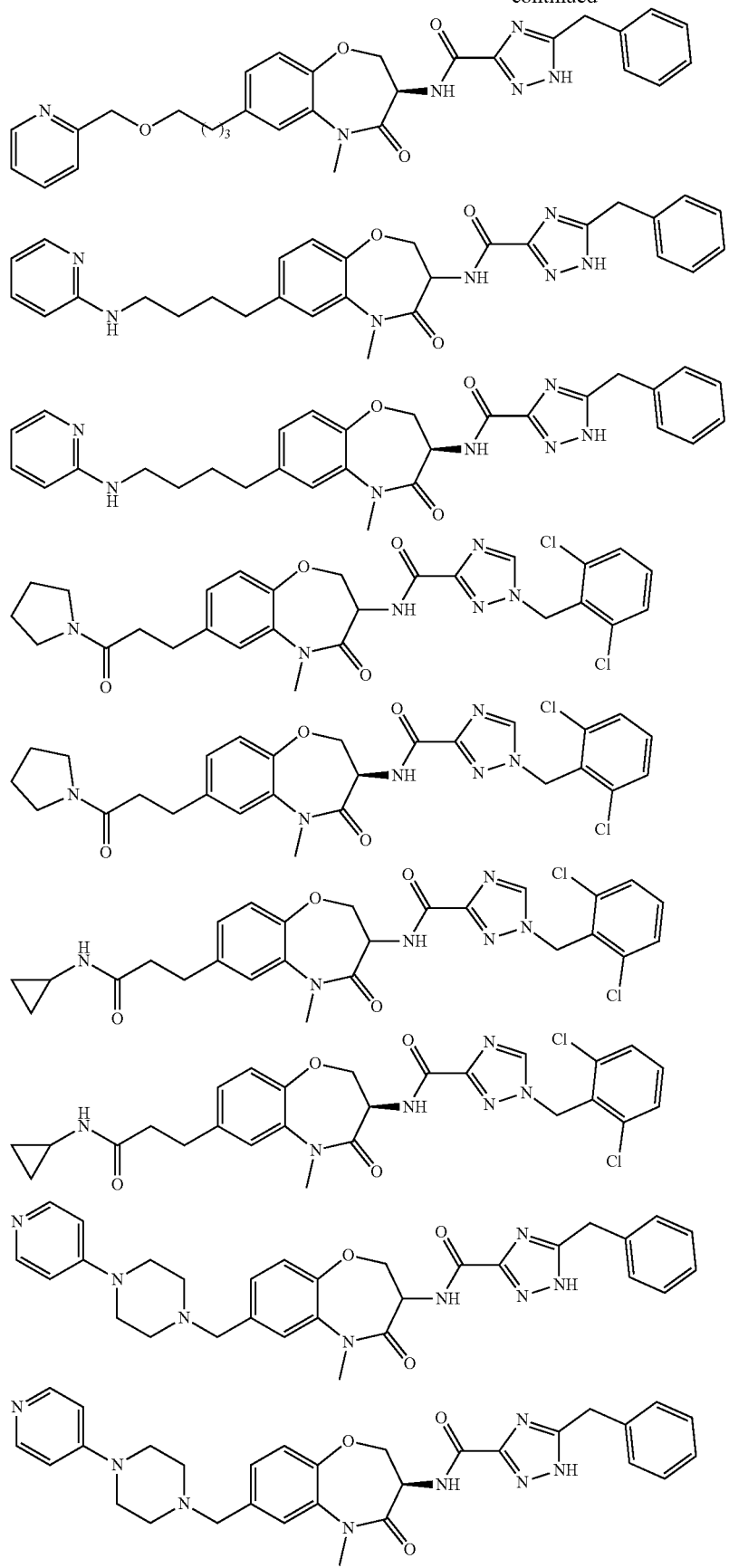

-continued
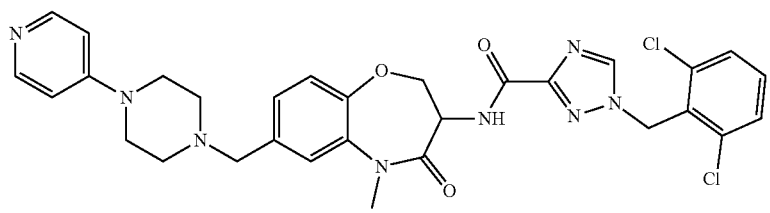
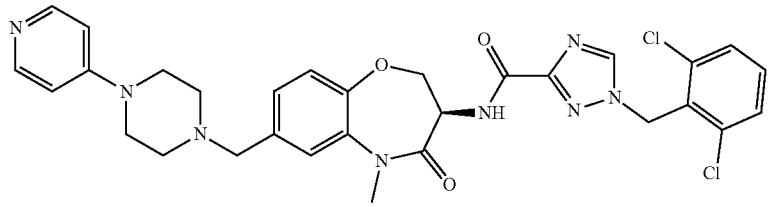
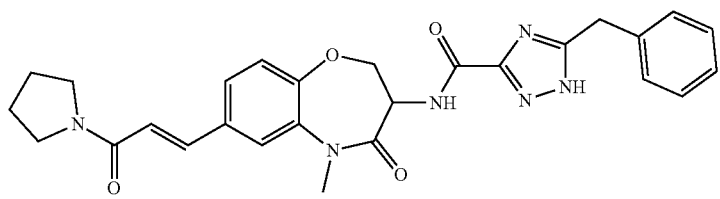
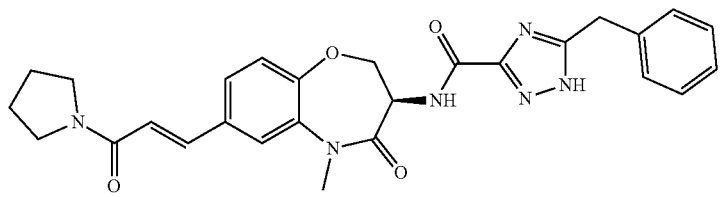
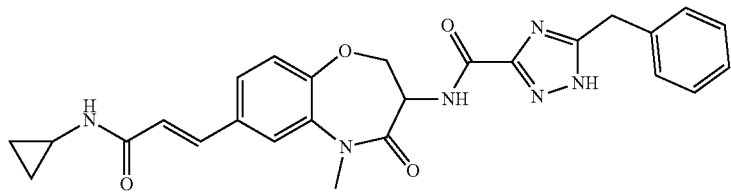
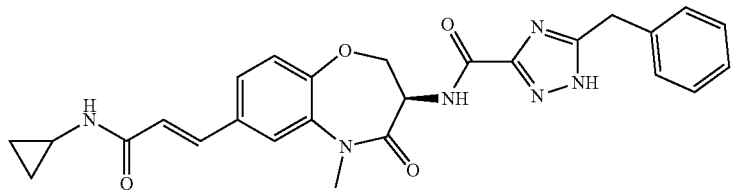
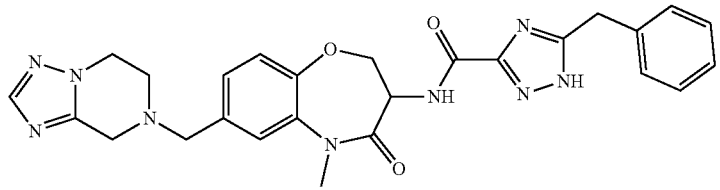
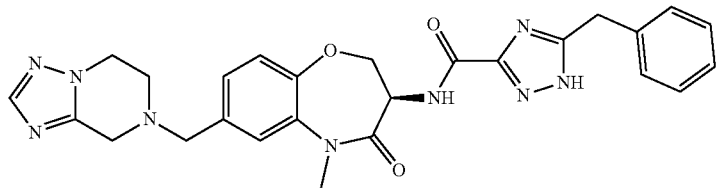

-continued
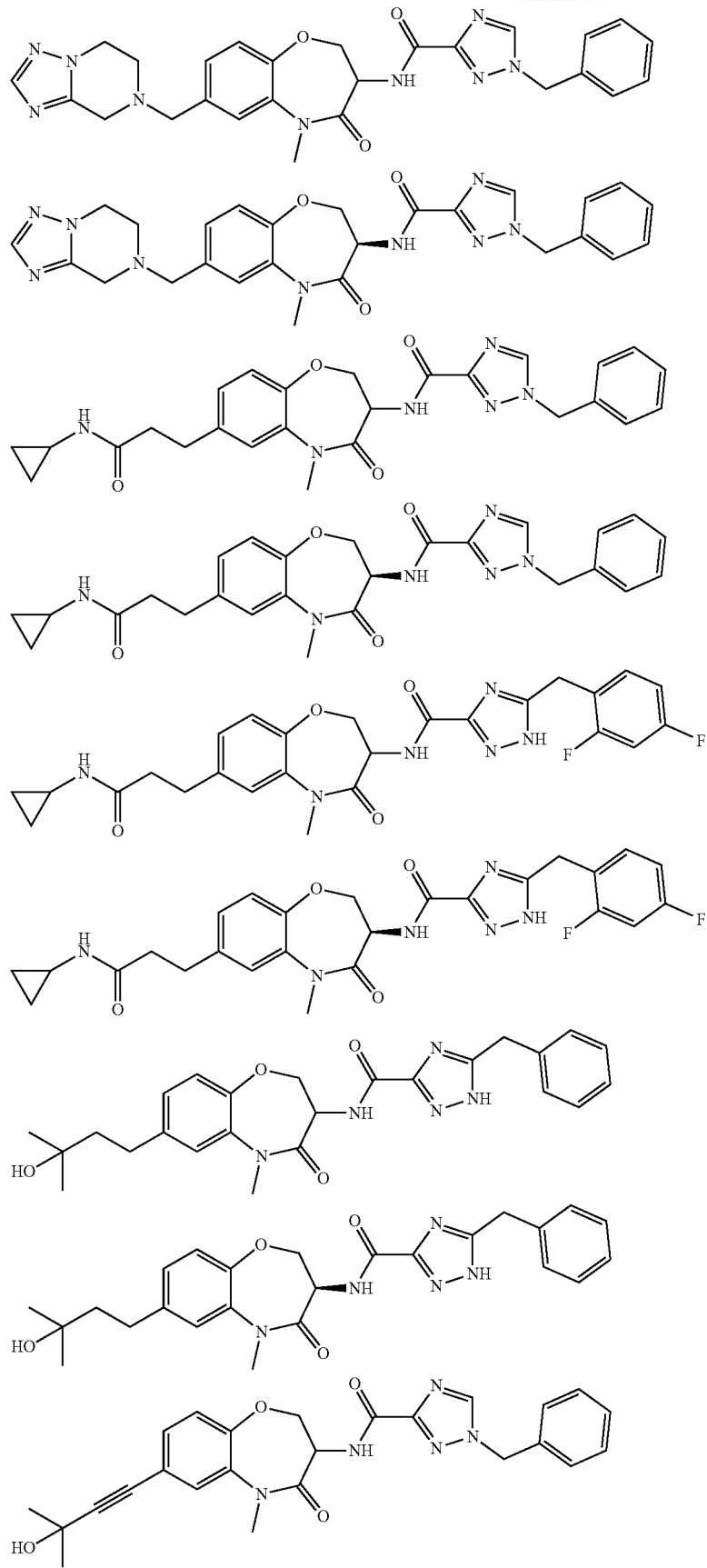

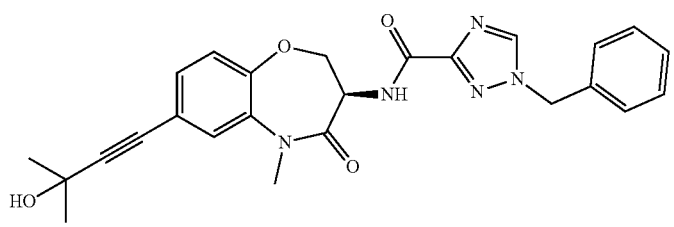
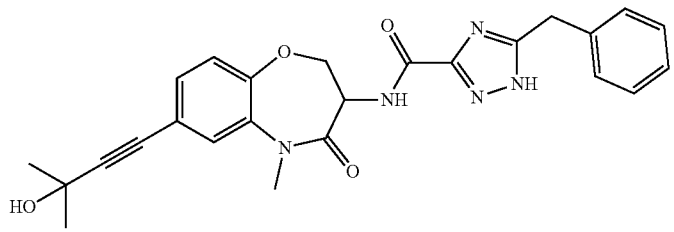
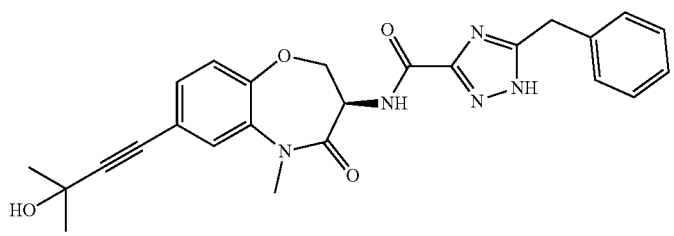
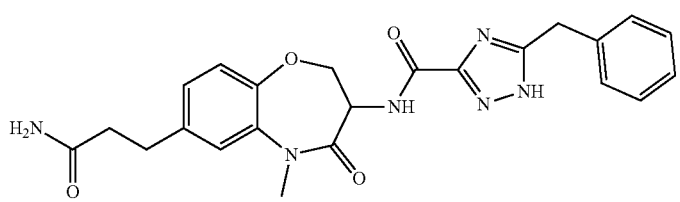
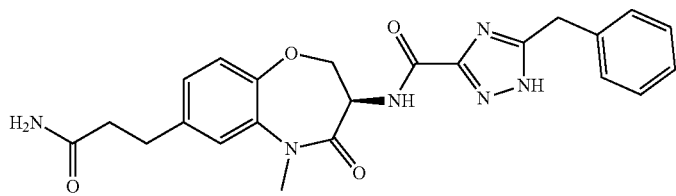
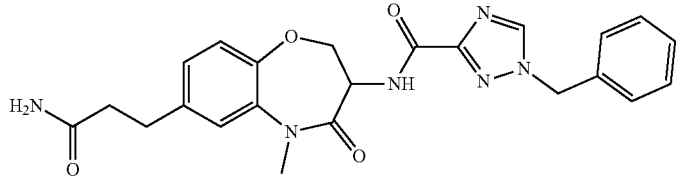
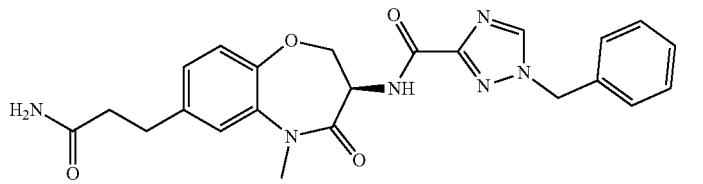
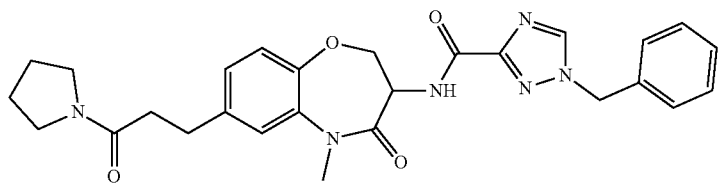

-continued
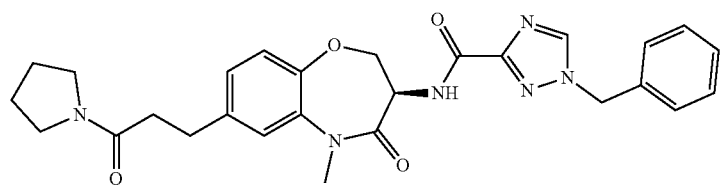
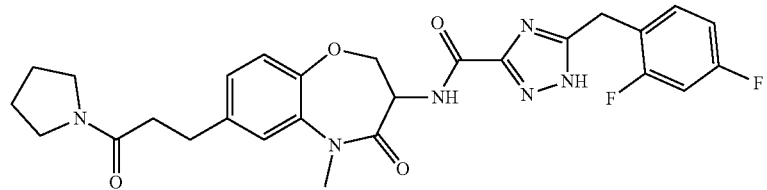
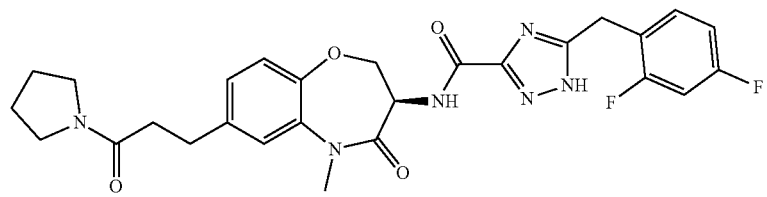
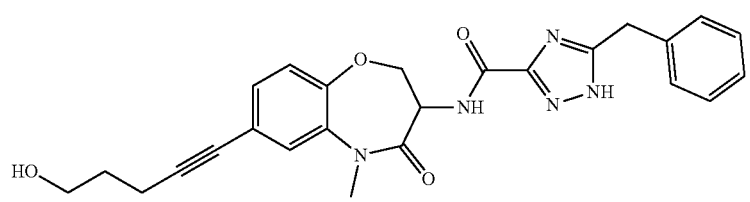
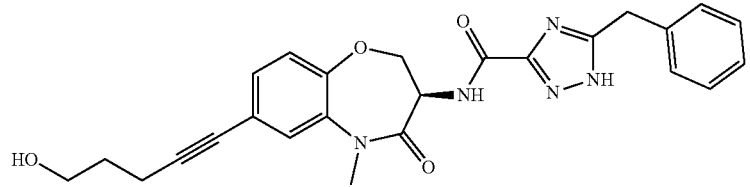
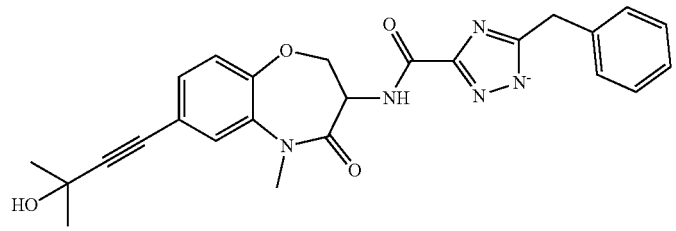
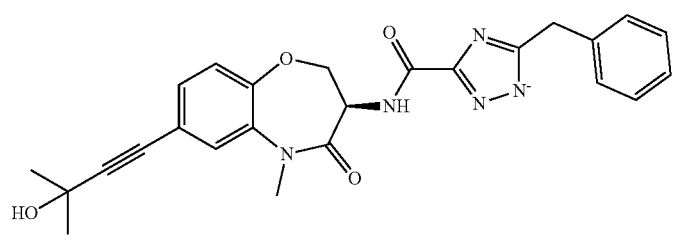
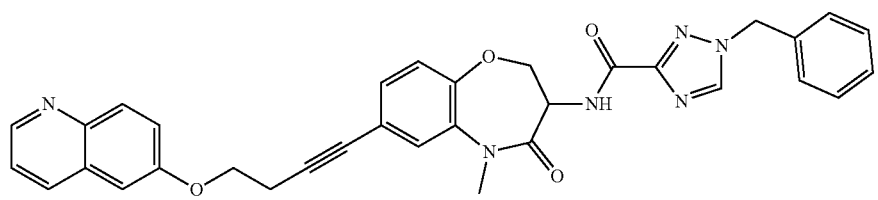

-continued
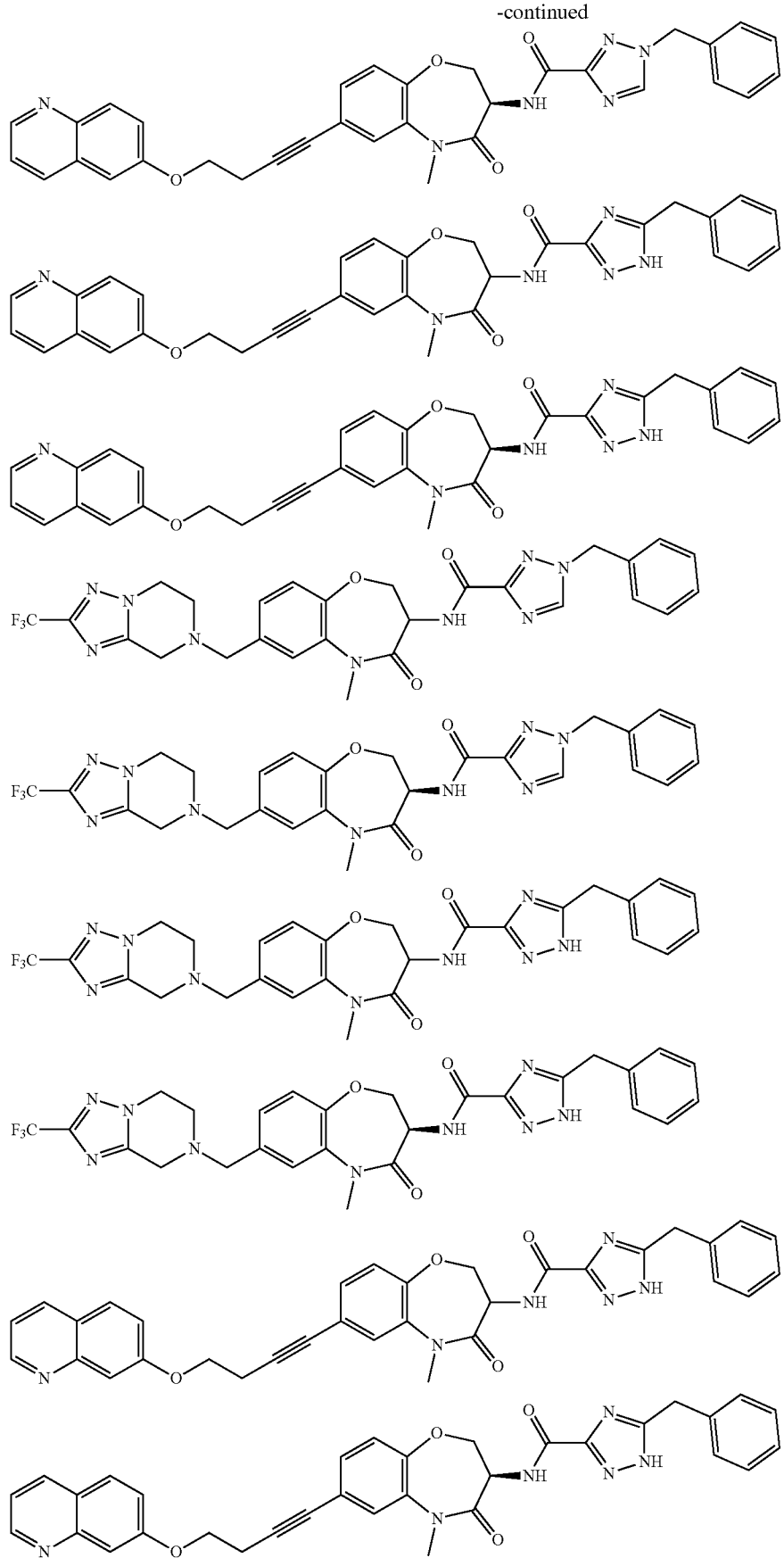

-continued
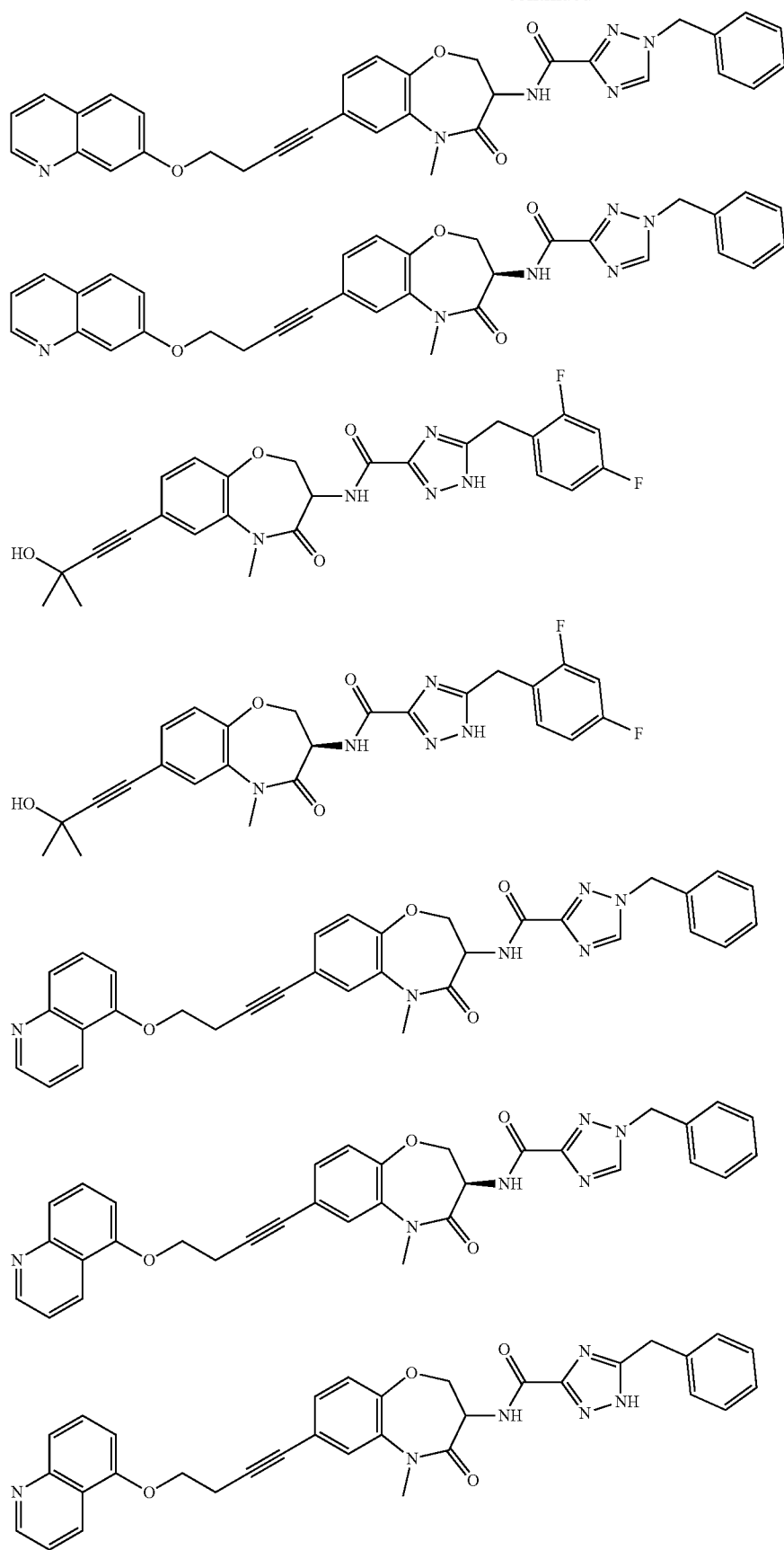

-continued
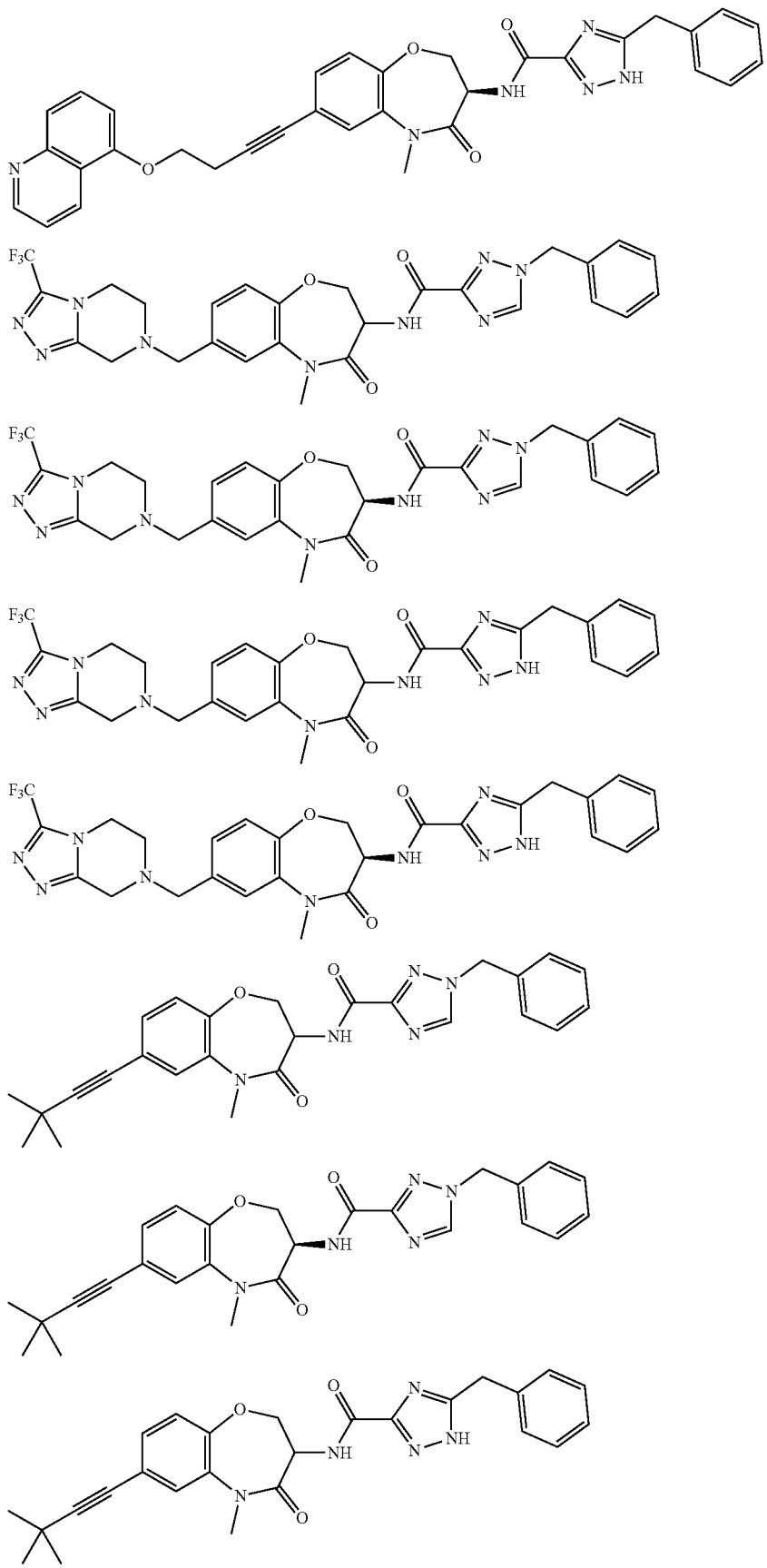

-continued
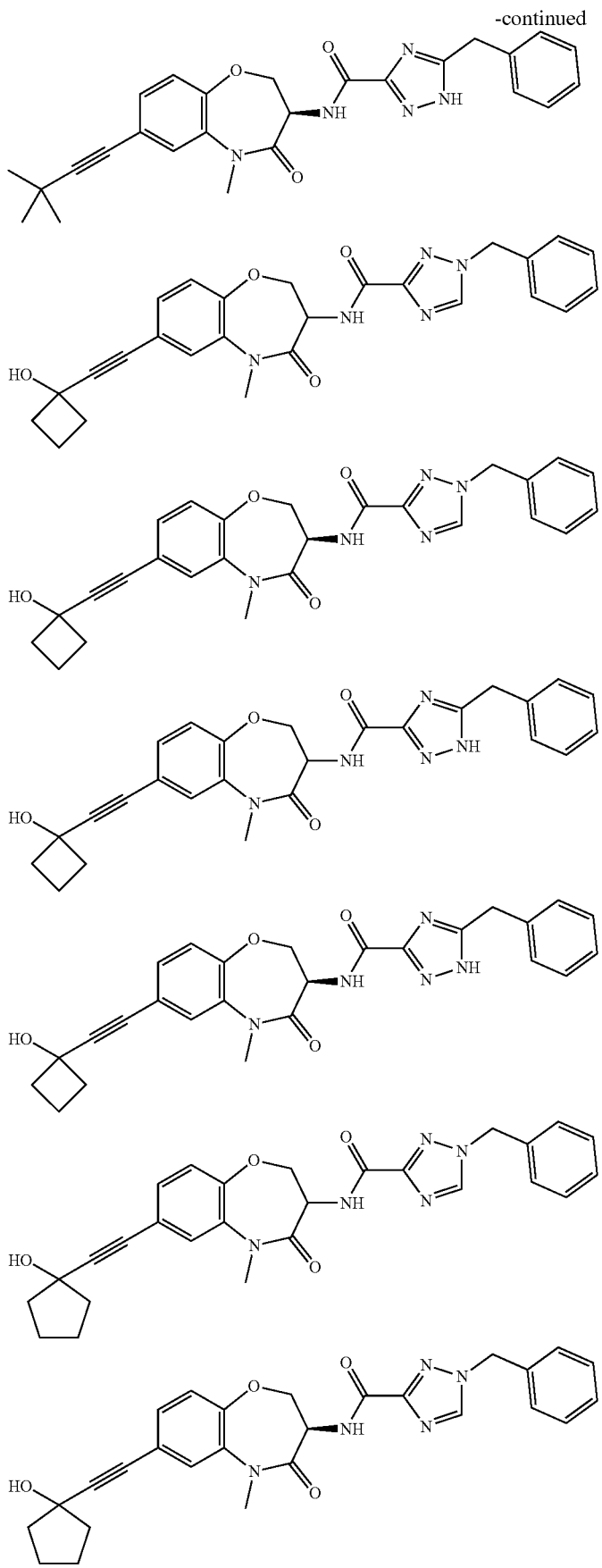

-continued
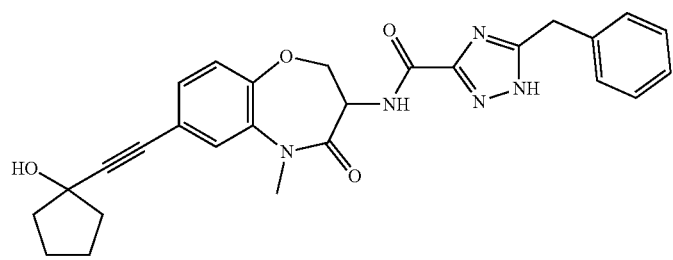
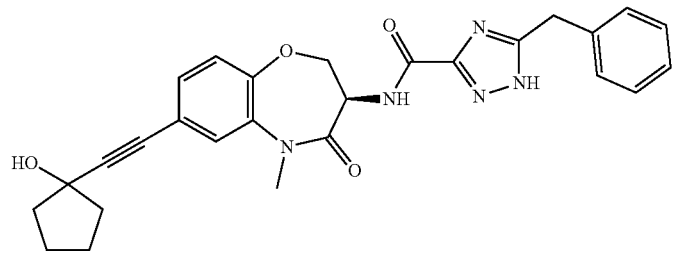
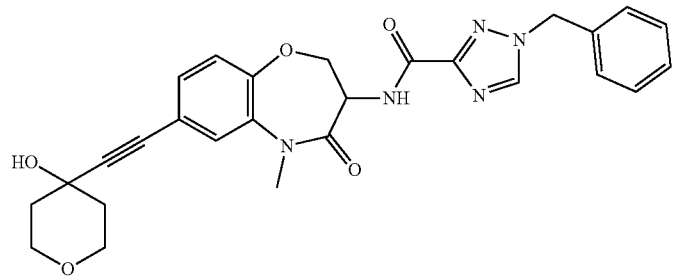
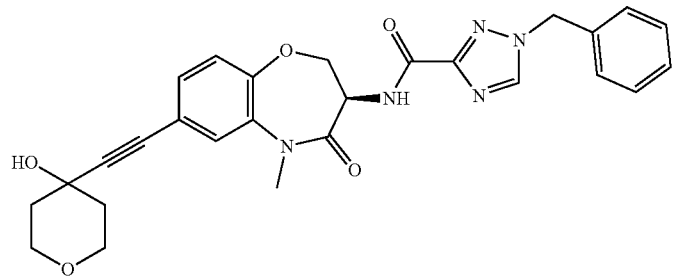
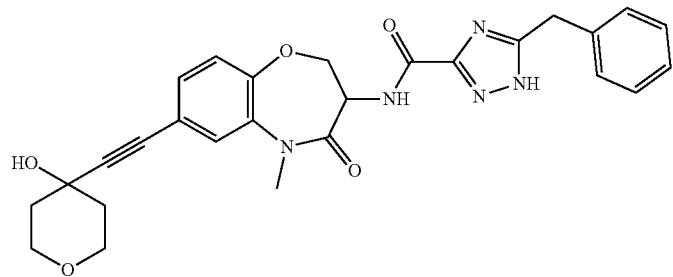
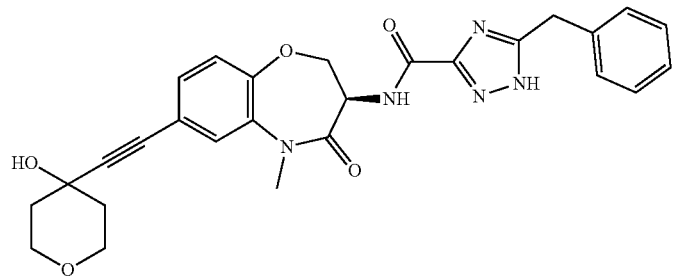

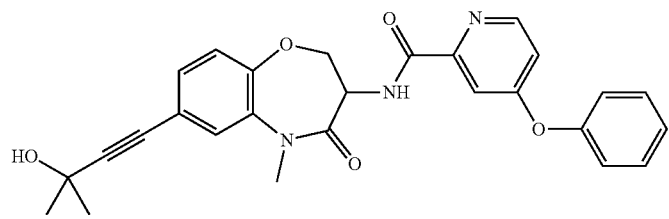
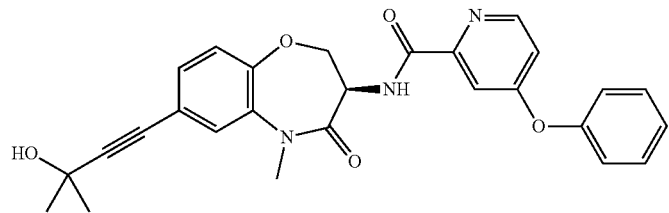
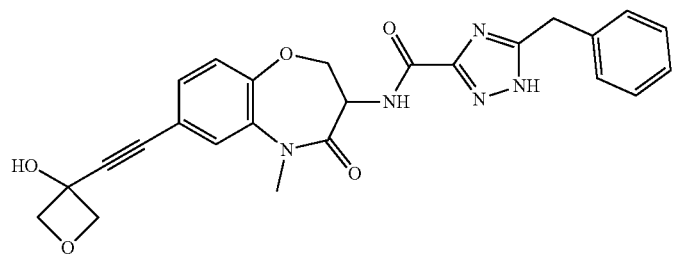
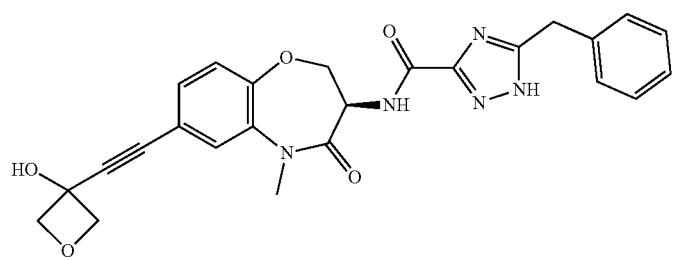
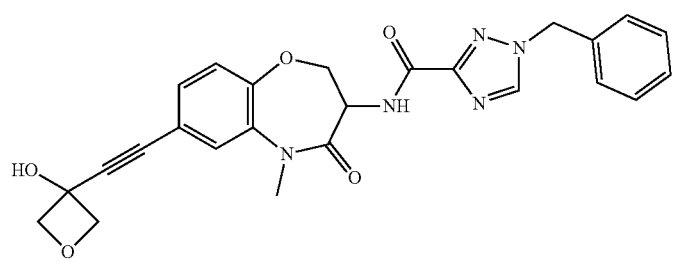
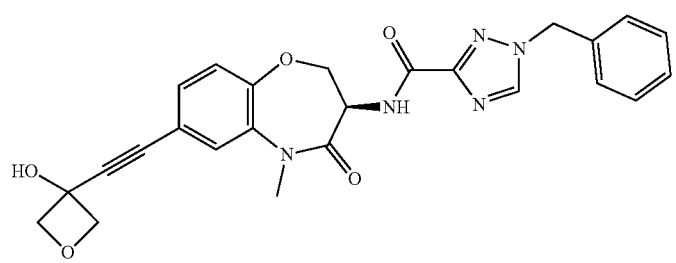
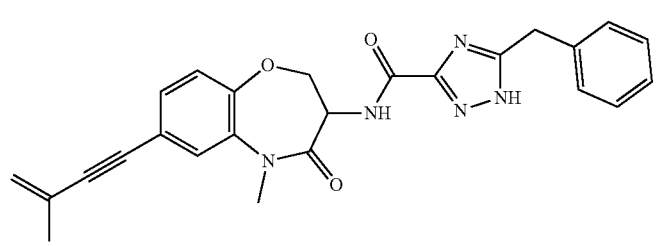

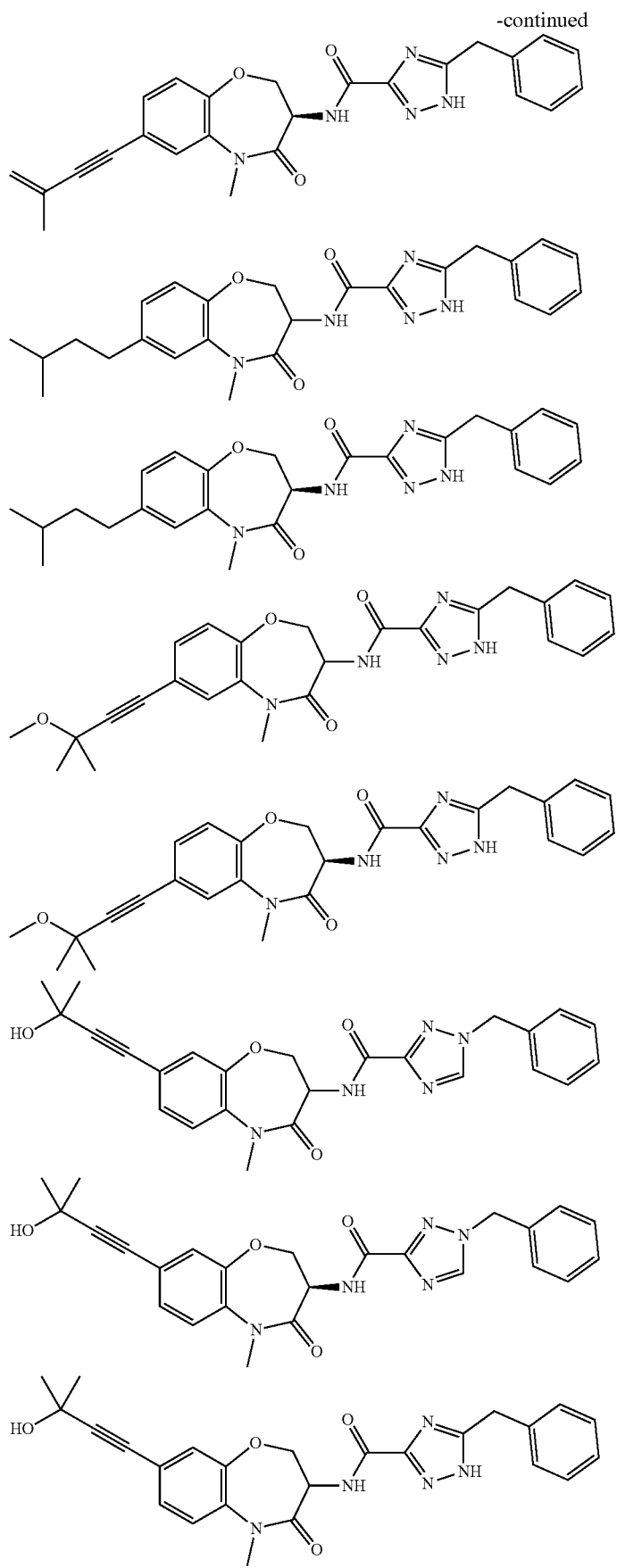

-continued
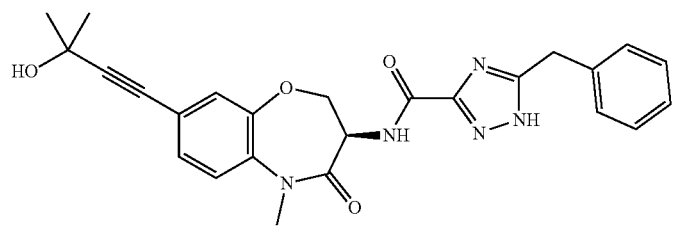
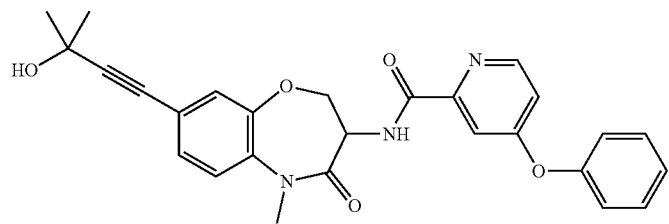
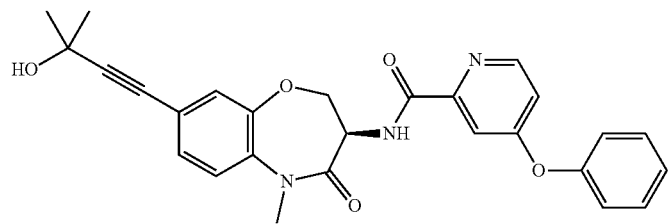
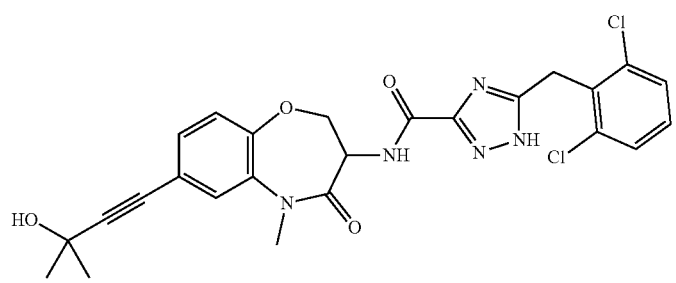
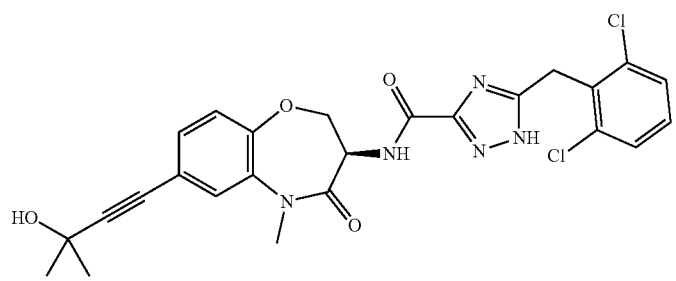
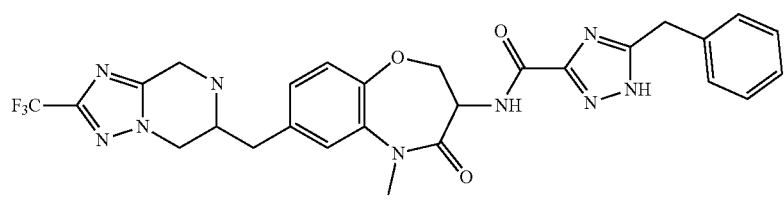
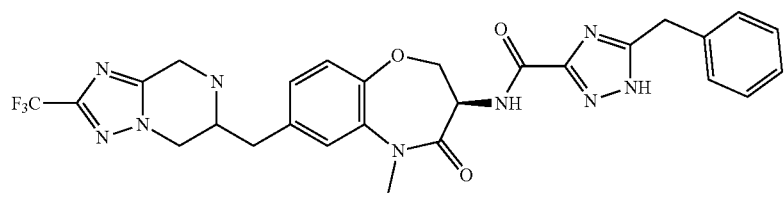

-continued
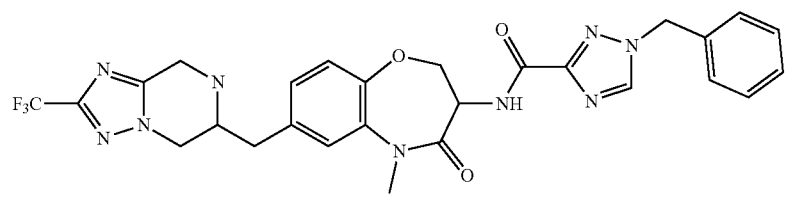
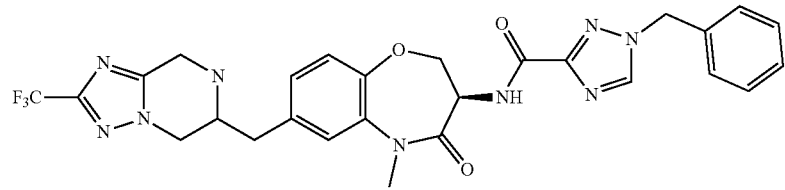
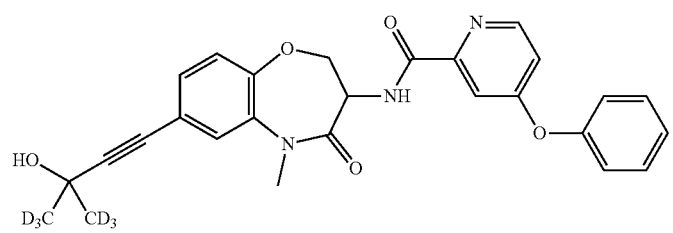
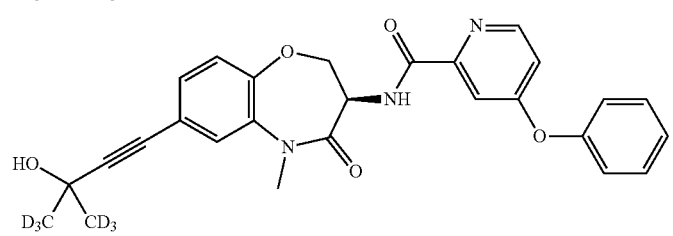
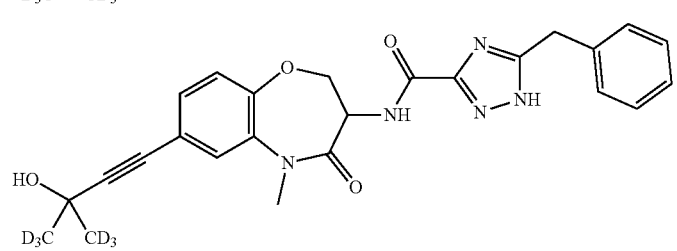
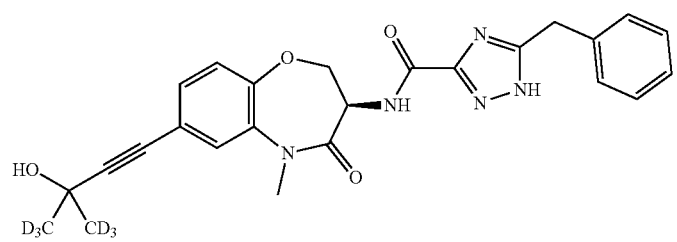
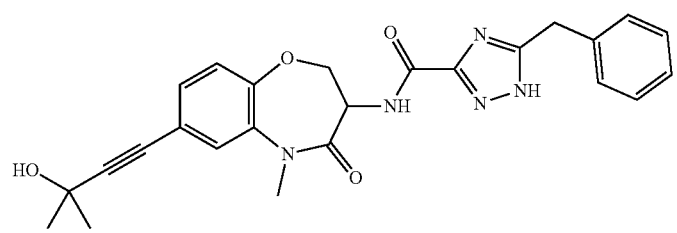

-continued
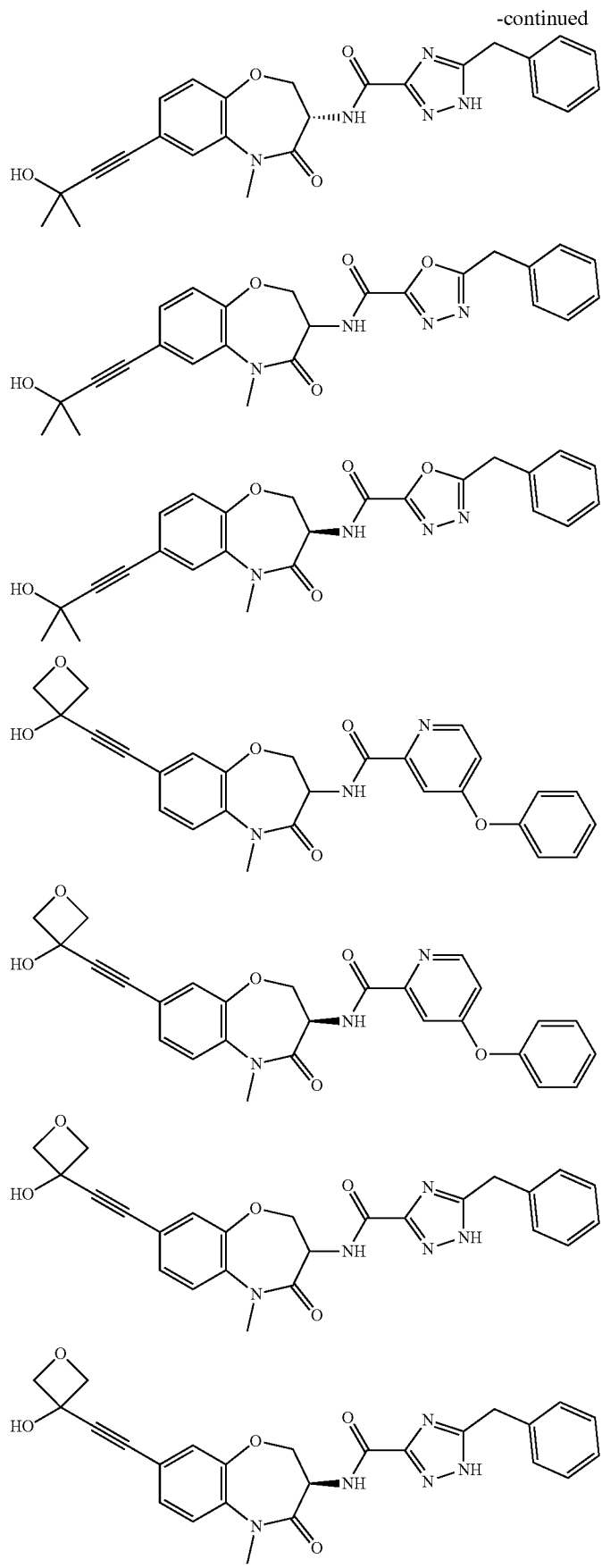

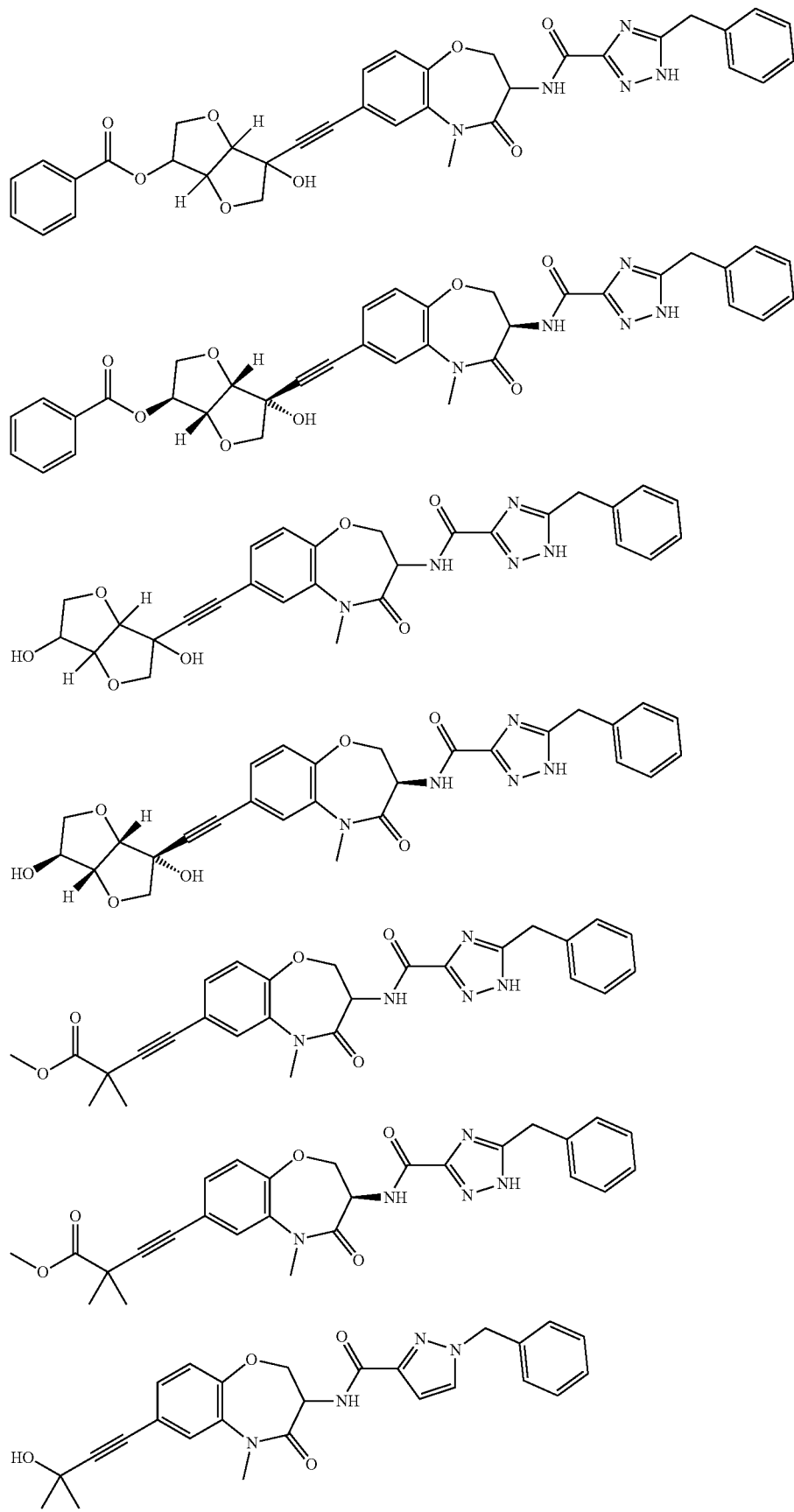

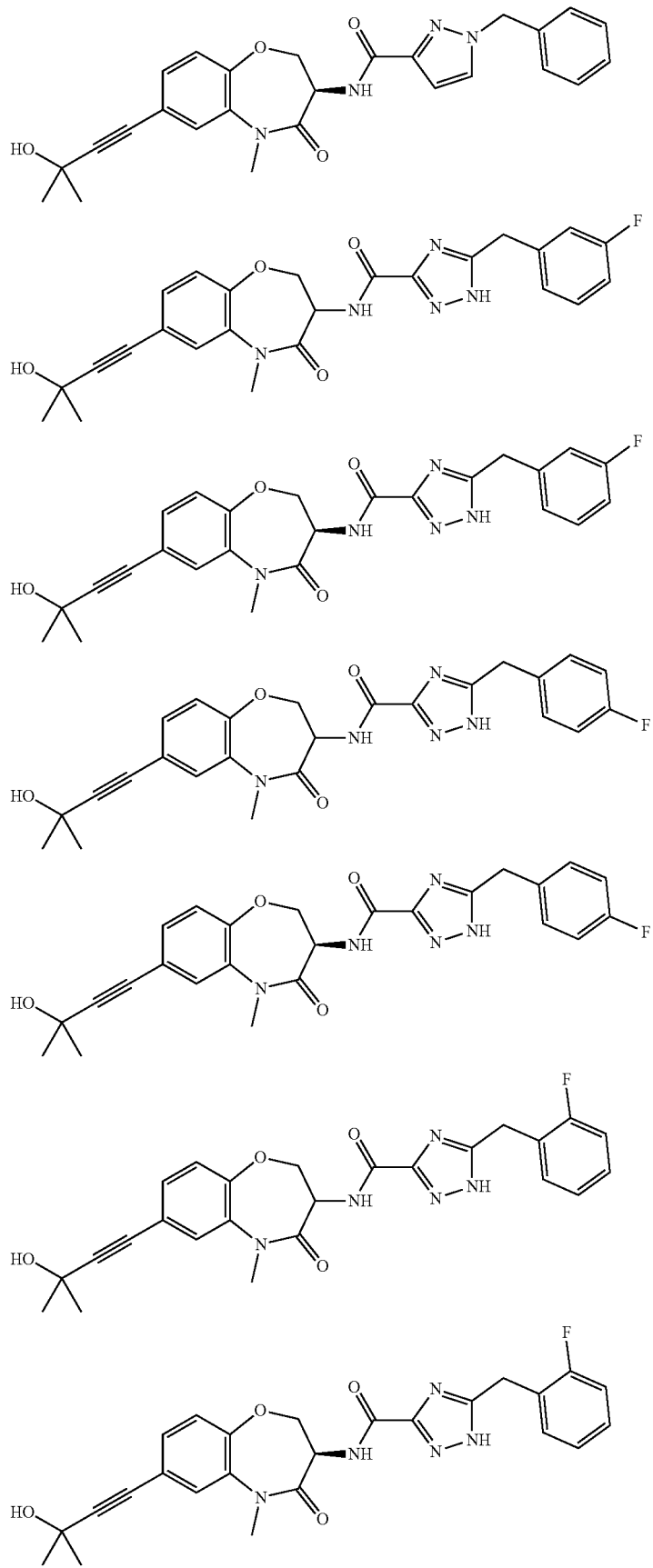

97 98
-continued
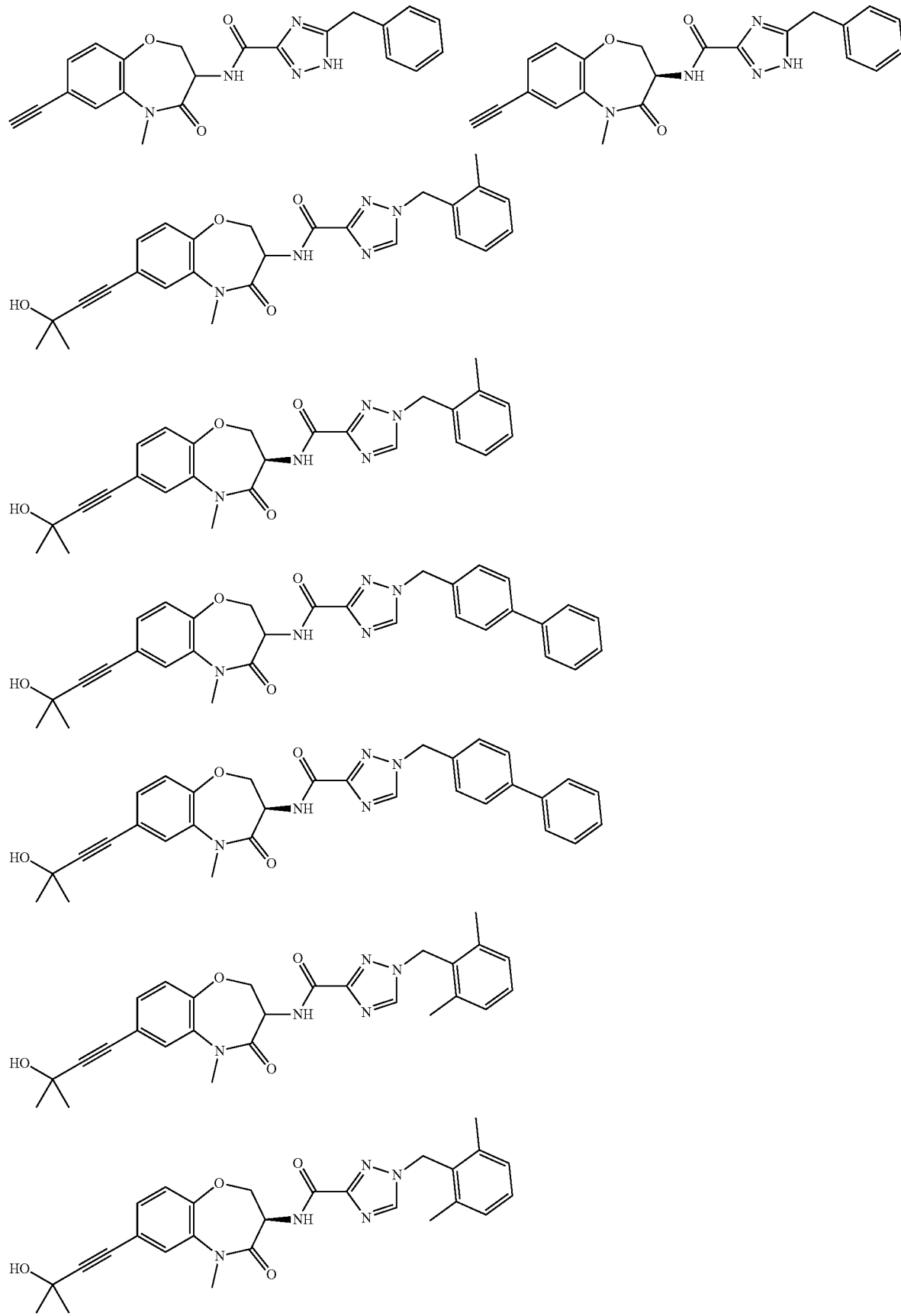

-continued
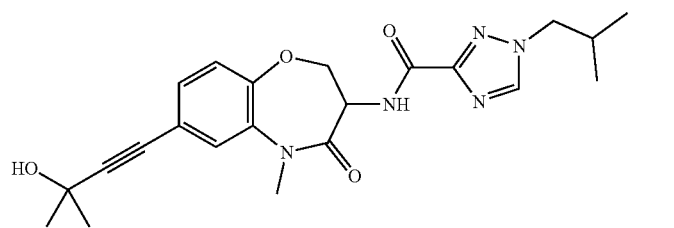
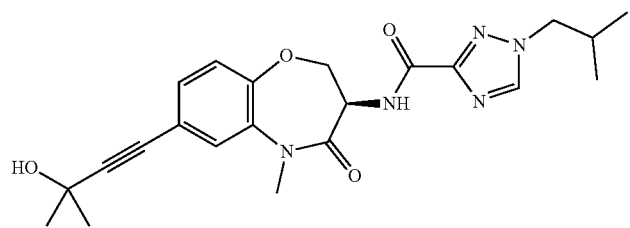
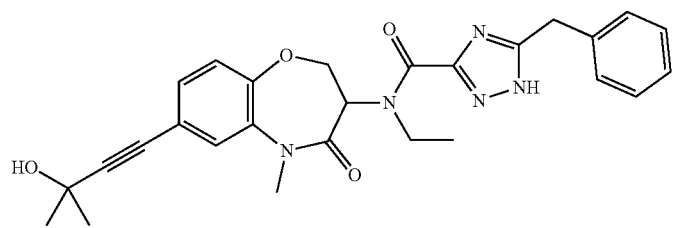
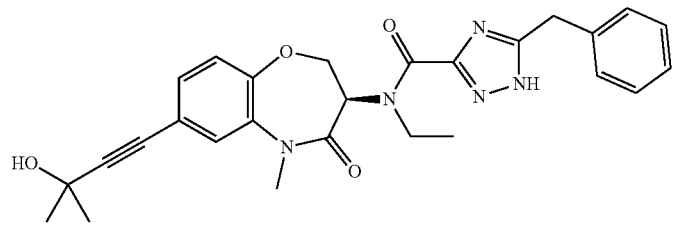
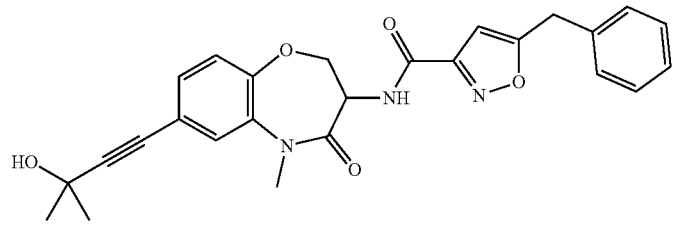
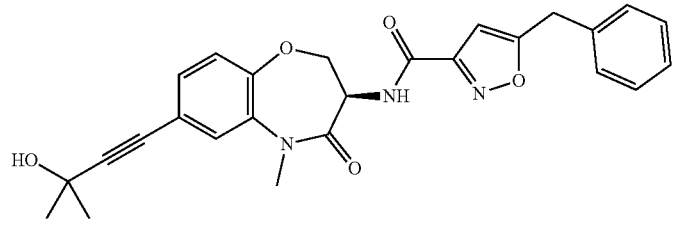
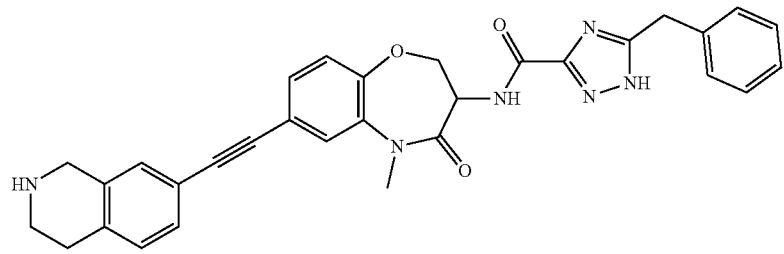

-continued
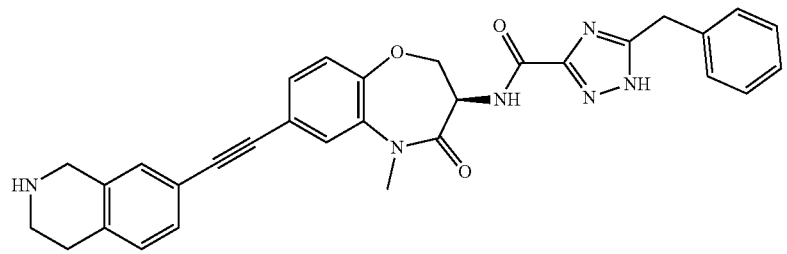
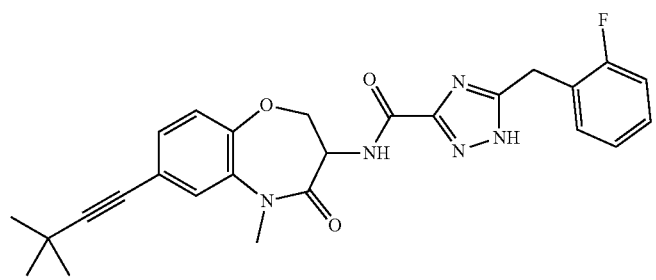
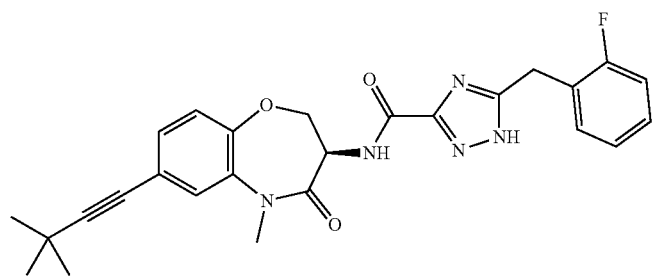
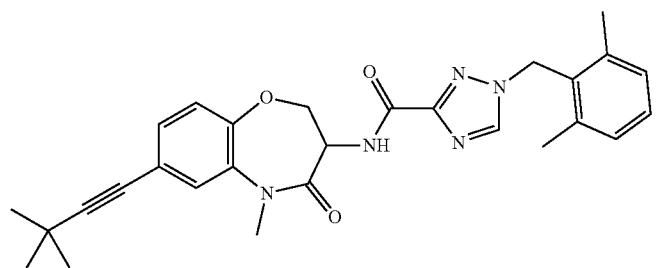
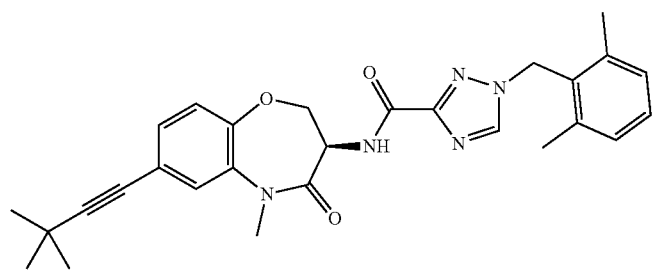
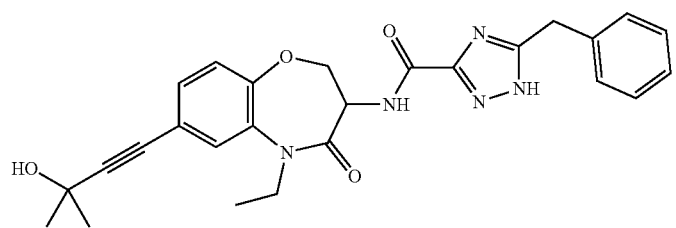

-continued
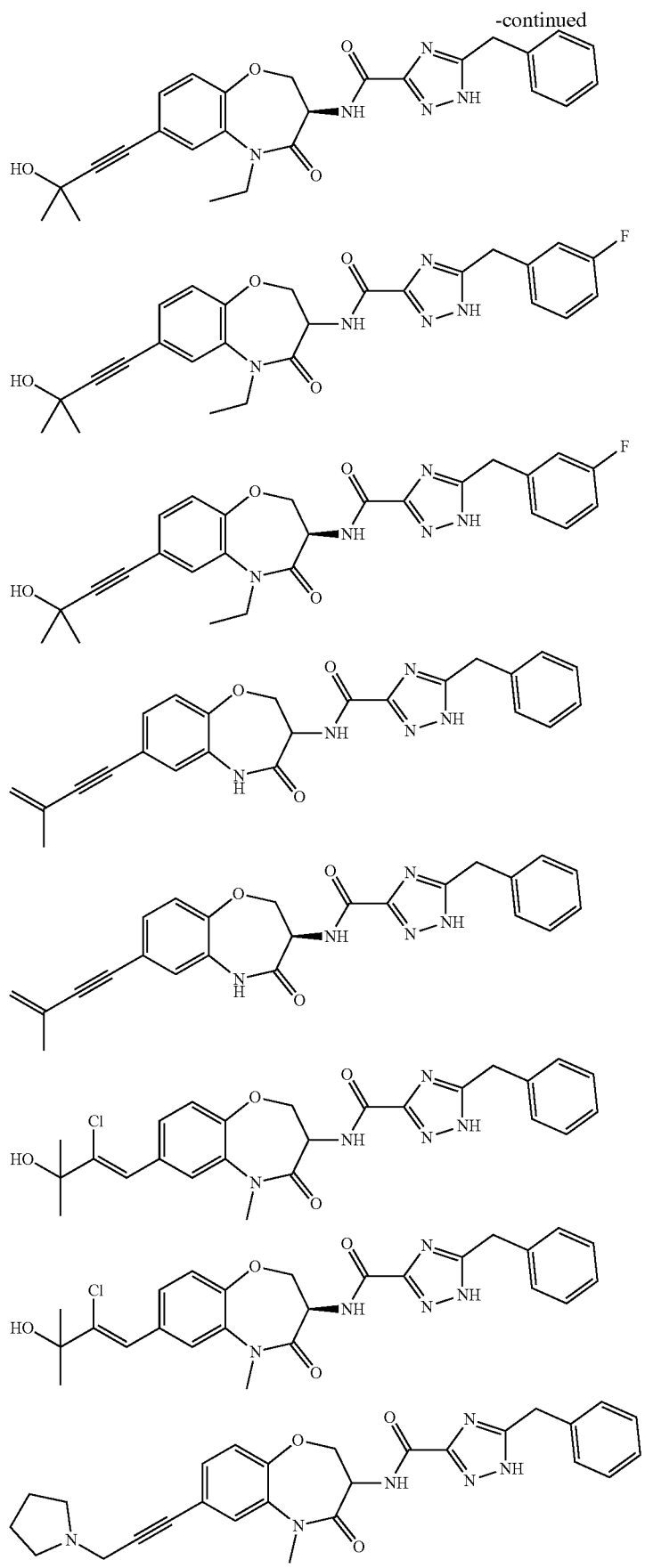

-continued

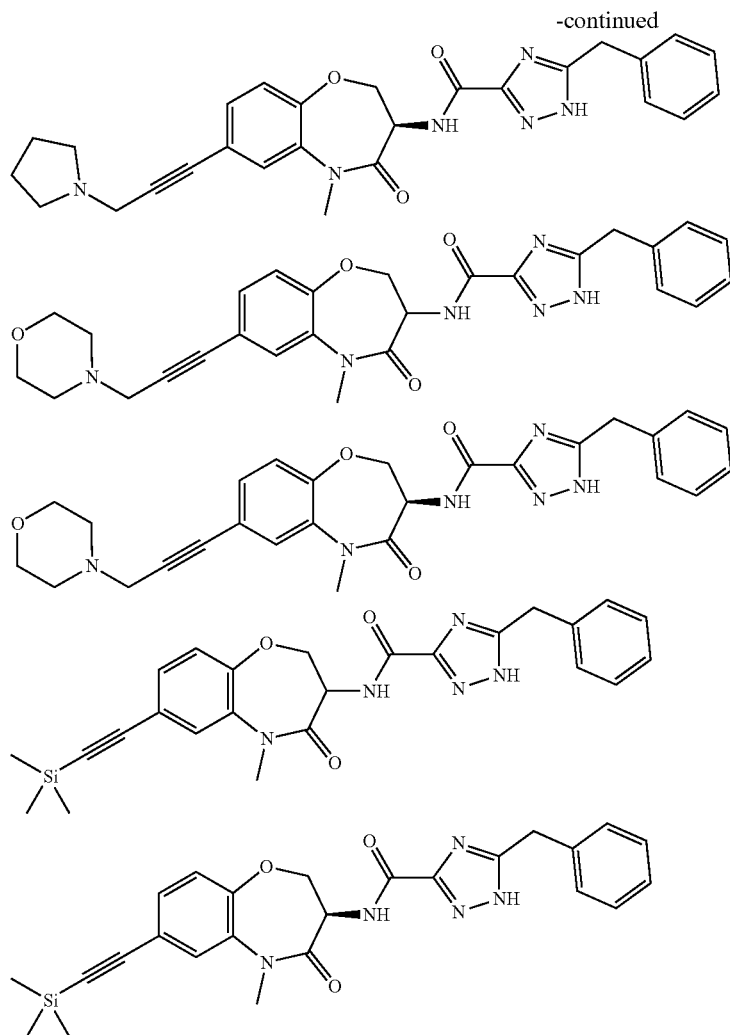

In some embodiments, one or more of the compounds can be included in a pharmaceutical composition or medicament, and in some embodiments the compound or compounds can be in the form of the parent compound or a pharmaceutically acceptable salt, a stereoisomer, an N-oxide, a tautomer, a hydrate, a solvate, an isotope, or a prodrug thereof. The pharmaceutical composition typically includes at least one additional component other than a disclosed compound or compounds, such as a pharmaceutically acceptable excipient, an adjuvant, an additional therapeutic agent (described in the following section), or any combination thereof.

Pharmaceutically acceptable excipients can be included in pharmaceutical compositions for a variety of purposes, such as to dilute a pharmaceutical composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. The pharmaceutically acceptable excipient(s) may include a pharmaceutically acceptable carrier(s). Exemplary excipients include, but are not limited to: mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose,), polysaccharides (such as starches, cellulose, microcrystalline cellulose, cellulose ethers (such as hydroxypropyl cellulose), gelatin, synthetic polymers (such as polyvinylpyrrolidone, polyalkylene glycols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben);

colorants; compression aids; emulsifying agents; encapsulation agents; gums; granulation agents; and combinations thereof.

B. Combinations of Therapeutic Agents

The compounds described herein may be used alone, in combination with one another, in separate pharmaceutical compositions, together in a single pharmaceutical composition, or as an adjunct to, or in combination with, other established therapies. The compound or compounds or composition comprising the compound (or compounds) may be administered once, or in plural administrations. In some embodiments, the compounds of the present invention may be used in combination with other therapeutic agents useful for the disorder or condition being treated. These other therapeutic agents may be administered simultaneously, sequentially in any order, by the same route of administration, or by a different route as the presently disclosed compounds. For sequential administration, the compound(s) and the therapeutic agent(s) may be administered such that an effective time period of at least one compound and the therapeutic agent overlaps with an effective time period of at least one other compound and/or therapeutic agent. In an exemplary embodiment of a combination comprising four components, the effective time period of the first component administered may overlap with the effective time periods of the second, third and fourth components, but the effective time periods of the second, third and fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. In some embodiments, the effective time periods of all compounds and/or therapeutic agents overlap with each other.

In some embodiments, the compounds are administered with another therapeutic agent, such as an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhbitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The presently disclosed compounds also may be used advantageously with CAR-T therapies. Example of currently available CAR-T therapies are axicabtagene ciloleucel and tisagenlecleucel.

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present compounds include proteasome inhibitors, such as bortezomib, carfilzomib, marizomib and the like.

Examples of kinase inhibitors that are useful in combination with the presently disclosed compounds, particularly in treating malignancies include: Btk inhibitors, such as ibrutinib; CDK inhibitors, such as palbociclib; EGFR inhibitors, such as afatinib, erlotinib, gefitinib, lapatinib, osimertinib and vandetinib; Mek inhibitors, such as trametinib; Raf inhibitors, such as dabrafenib, sorafenib and vemurafenib;

VEGFR inhibitors, such as axitinib, lenvatinib, nintedanib, pazopanib; BCR-Abl inhibitors, such as bosutinib, dasatinib, imatinib and nilotinib; FLT-3 inhibitors, such as gilteritinib and quizartinib, P3-kinase inhibitors, such as idelalisib, Syk inhibitors, such as fostamatinib; and JAK inhibitors, such as ruxolitinib and fedratinib.

In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab; anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents-steroids, e.g., budesonide, non-steroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues, for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

III. Methods of Making Compounds

The compounds can be prepared by any suitable method as will be understood by a person of ordinary skill in the art. One exemplary suitable method is provided below with reference to specific compounds in the examples, and can include the following first reaction step according to Scheme 1.

Scheme 1

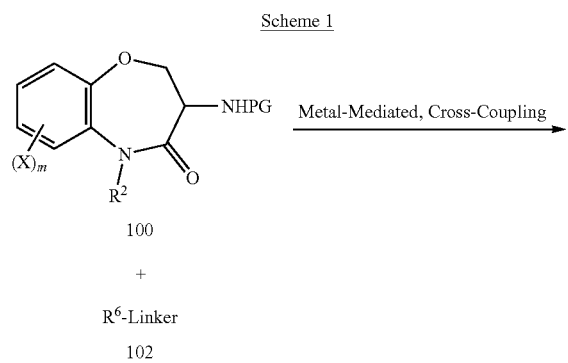

100

+

R⁶-Linker

102

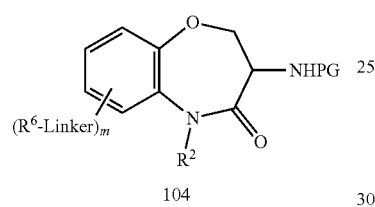

104

With reference to Scheme 1, protected amine precursor 100 can be coupled with $R^1$ group 102, which comprises an "$R^6$-linker" group as illustrated in Scheme 1, using a metal-mediated, cross-coupling reaction to provide the cross-coupled product 104. In some embodiments, the metal-mediated, cross-coupling reaction can be carried out using a transition metal catalyst, such as a palladium catalyst. Exemplary palladium catalysts include, but are not limited to, Pd(0) catalysts (e.g., $Pd_2(dba)_3$, $Pd(dba)_2$, $Pd(PPh_3)_4$, and the like) or Pd(II) catalyst (e.g., XPhos Pd generation 2 or generation 3, $PdCl_2$, $Pd(OAc)_2$, and the like). In some embodiments, the palladium catalyst can be used in combination with another co-catalyst, such as CuI, to promote the cross-coupling reaction, such as in a Sonogoshira reaction. The metal-mediated, cross-coupling also can comprise using a base, such as an amine base (e.g., $Et_3N$), or an inorganic base (e.g., $Cs_2CO_3$, $Na_2CO_3$, $K_2CO_3$ or the like), and a solvent (e.g., dimethylformamide). With reference to Scheme 1, X is a suitable group for metal-mediated, cross-coupling, such as a halogen or a triflate group and PG is an amine protecting group, which can be selected from, but is not limited to, a 9-fluorenylmethoxycarbonyl ("Fmoc") group, a t-butyloxycarbonyl ("Boc") group, a trityl ("Tr") group, an allyloxycarbonyl ("Alloc") group, a benzyloxycarbonyl ("Cbz") group, and the like.

Representative examples of the method steps shown in Scheme 1 are provided below in Schemes 2A-2F. A method similar to that illustrated in Scheme 2A can be used to make compounds I-14 to I-17 and I-35 by replacing the propargylic alcohol in Scheme 2A with the corresponding alkyne group that gives rise to each of compounds I-14 to I-17 and I-35; the further modifications that can be used to arrive at the final structure of compounds I-14 to I-17 are discussed below.

Scheme 2A

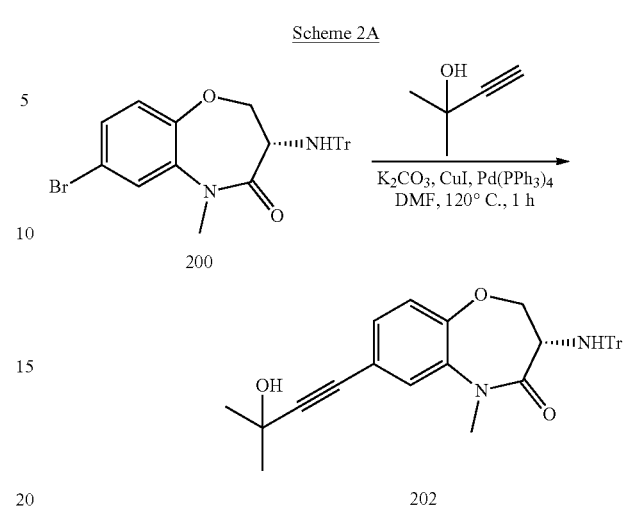

Scheme 2B

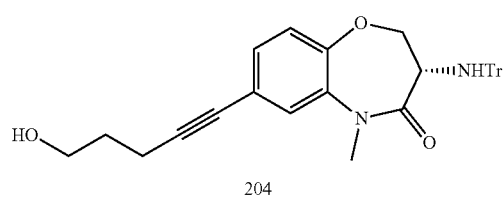

Scheme 2C

113

Scheme 2D

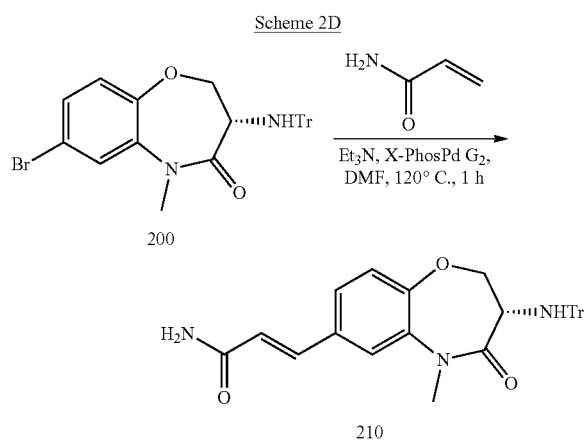

200

210

Scheme 2E

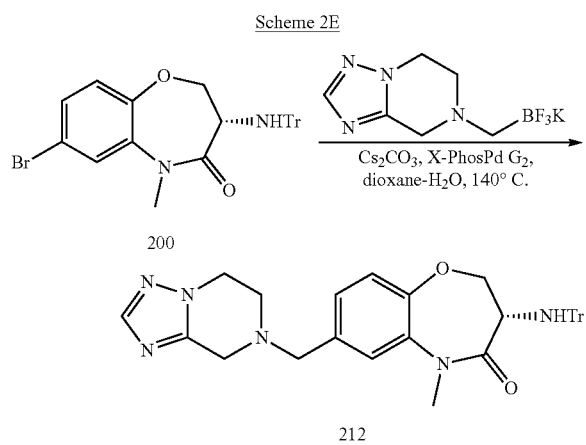

200

212

Scheme 2F

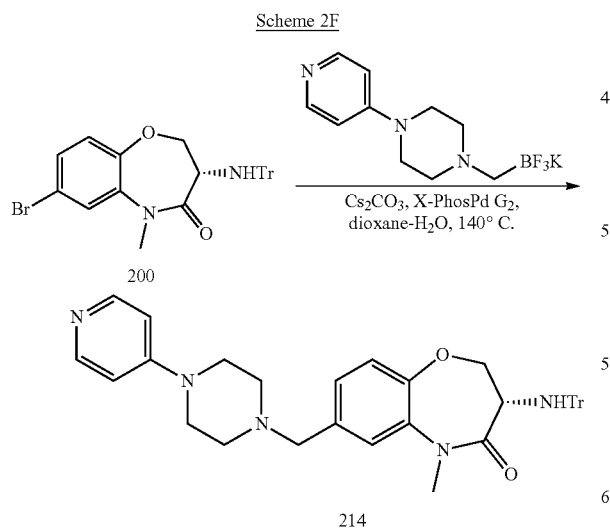

200

214

Once cross-coupled product 104 is made, it can be subjected to an optional linker group reduction step wherein linker groups comprising one or more sites of unsaturation can be reduced to saturated linker groups and/or linker

114 groups having fewer degrees of unsaturation. If a linker reduction group is used, it can then be followed by a deprotection step and then an amide formation step, as illustrated in Scheme 3. Alternatively, if a linker group reduction step is not used, then cross-coupled product 104 can be deprotected and converted to amide compound 302.

Scheme 3

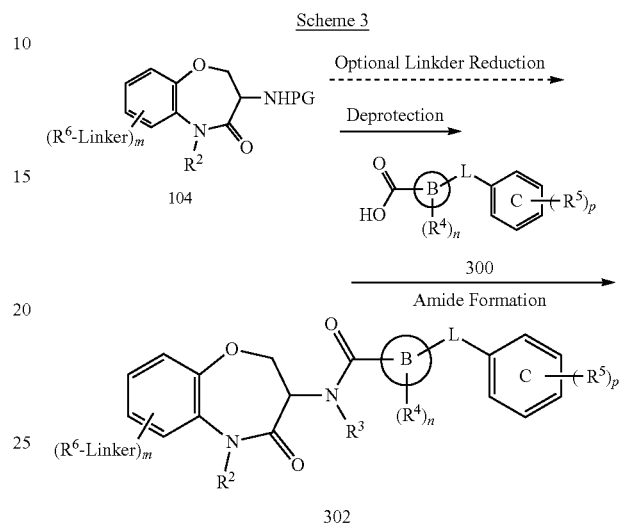

104

300

302

With reference to Scheme 3, an optional linker reduction step can be carried out. For example, if the linker comprises a site of unsaturation (e.g., a double or triple bond), the site of unsaturation can be reduced such that it becomes fully saturated (e.g., such as reducing a double bond and/or a triple bond to a single bond) or that it has few degrees of unsaturation (e.g., such as reducing a triple bond to a double bond). Suitable reagents for carrying out such an optional linker reduction step are recognized by those of ordinary skill in the art with the benefit of the present disclosure; however, one exemplary set of conditions includes exposing cross-coupled product 104 to H$_2$ in the presence of Pd on carbon. As these steps are optional, they need not be carried out in all embodiments. Instead, in some embodiments, cross-coupled product 104 can be deprotected to provide an amine that is then converted to amide compound 302 by reacting the amine with a suitable acid coupling partner 300, as illustrated in Scheme 3.

Representative examples of the method steps shown in Scheme 3 are provided below in Schemes 4A-4M. A method similar to that described in Scheme 4A can be used to make compounds I-14 to I-17. Compounds I-16 and I-17 can be further functionalized as discussed below.

Scheme 4A

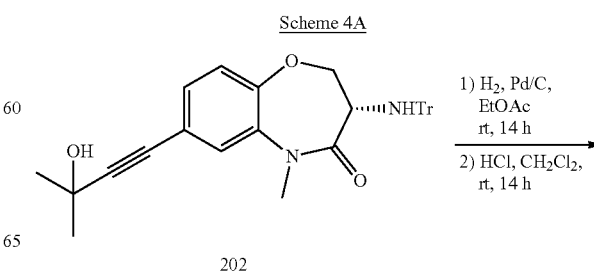

202

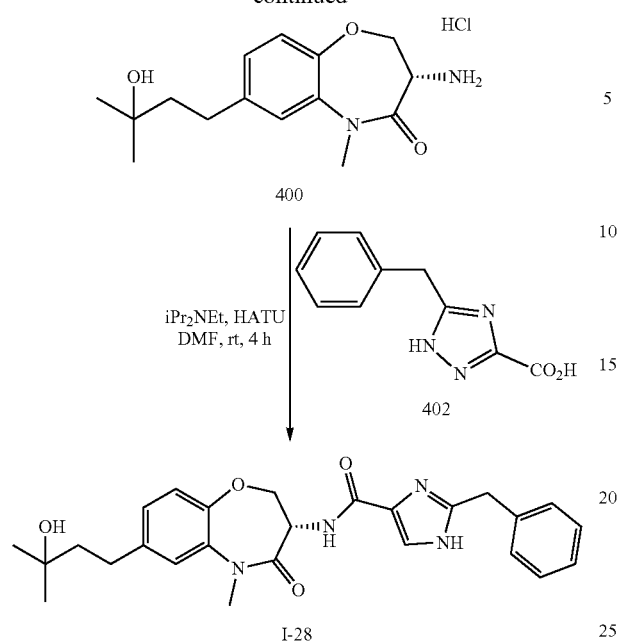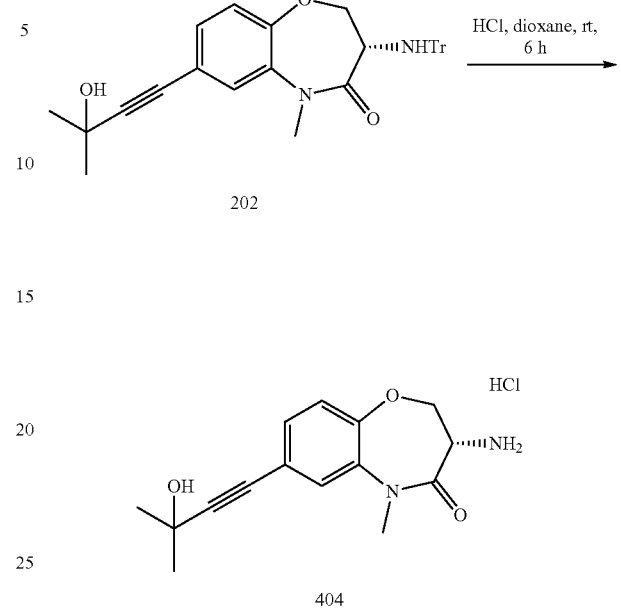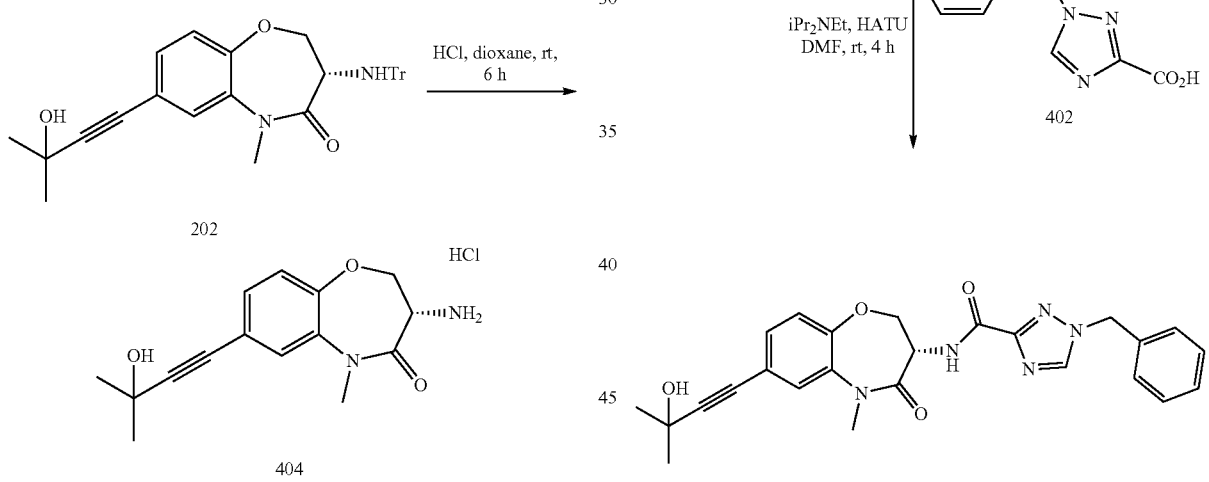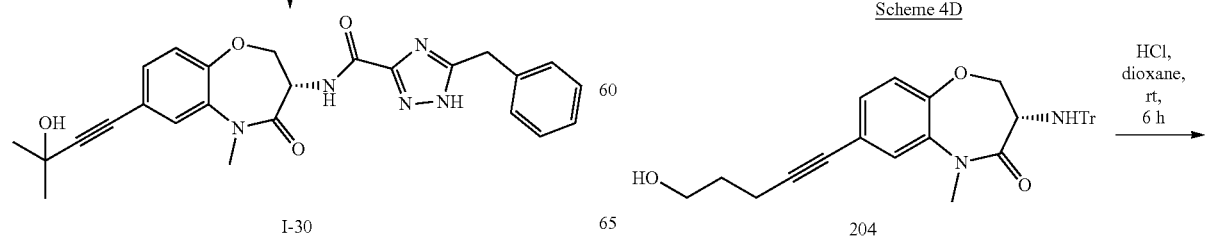

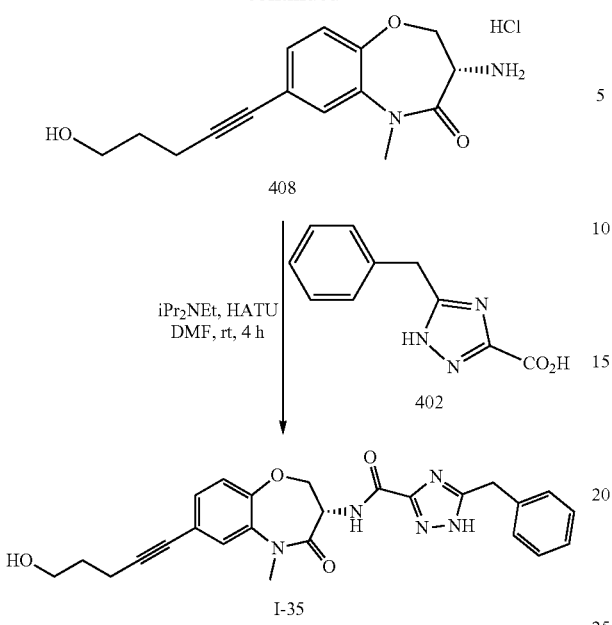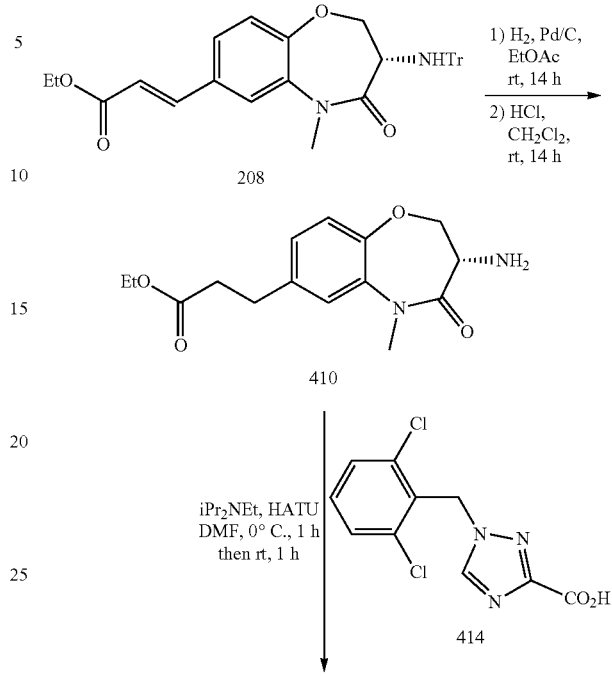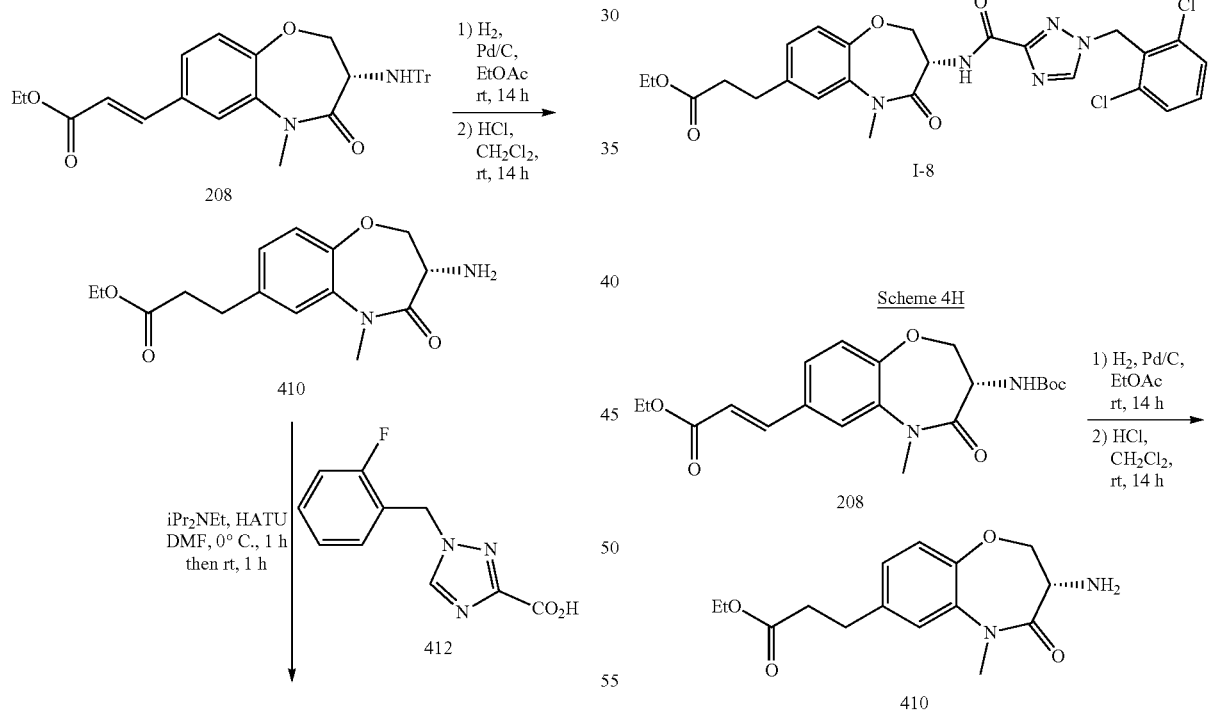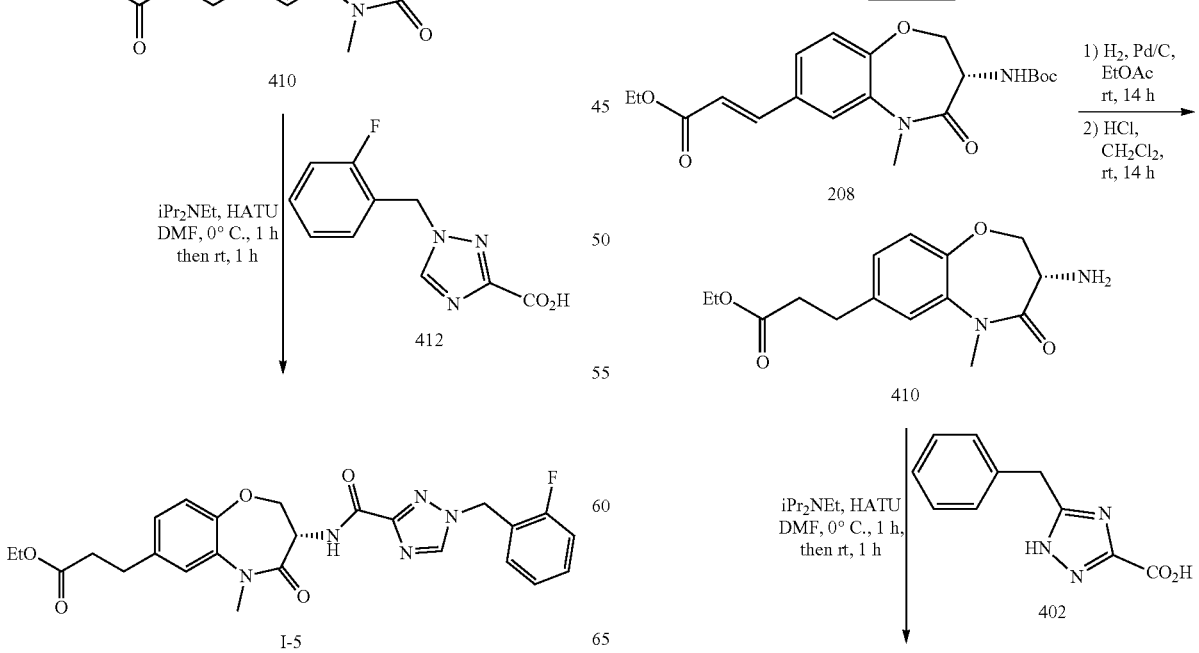

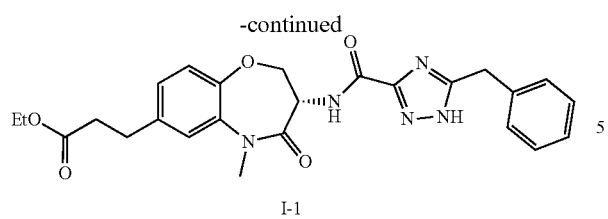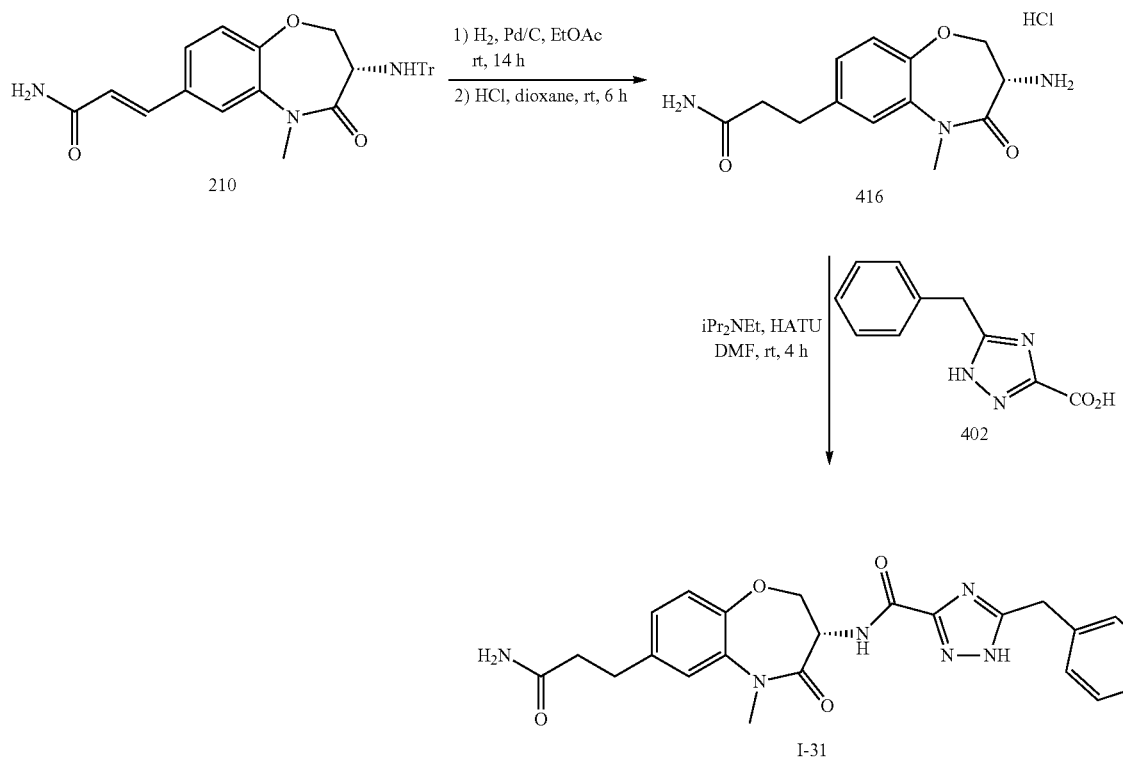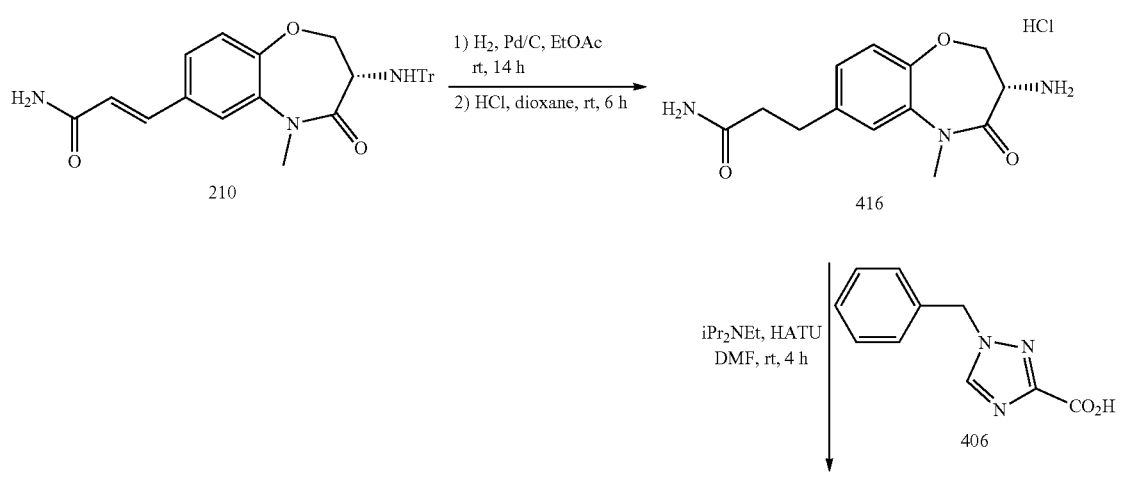

-continued
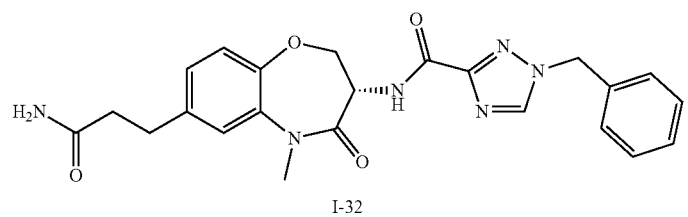
Scheme 4J
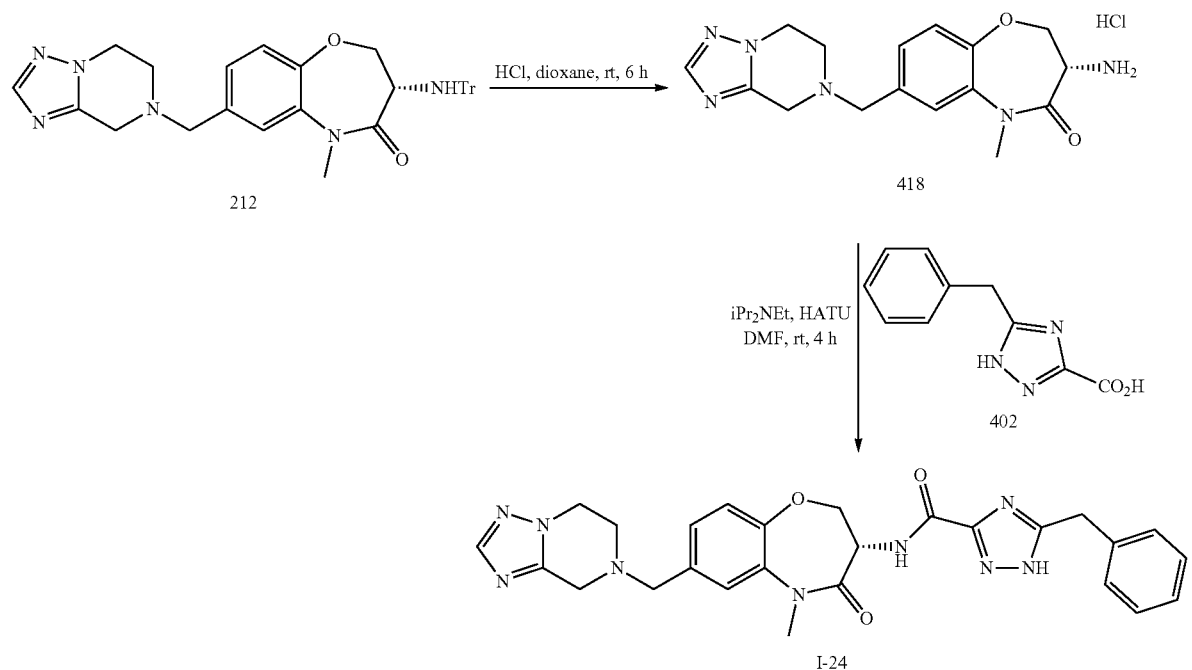
Scheme 4K
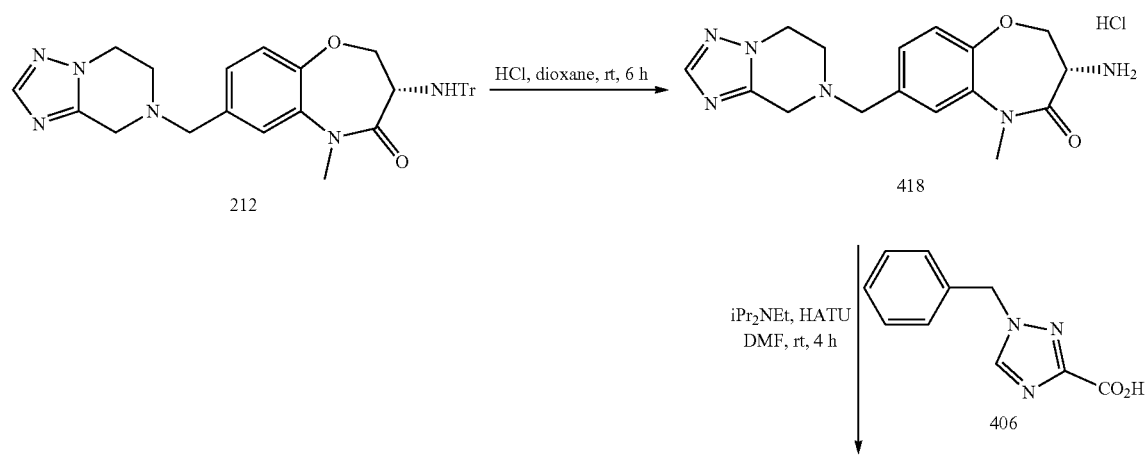

-continued
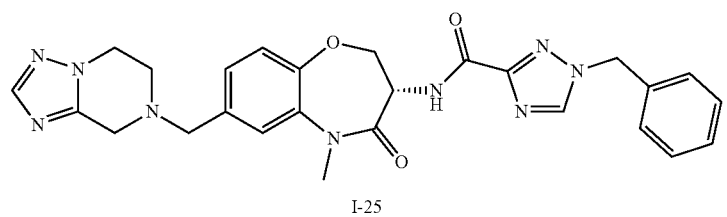
I-25
Scheme 4L
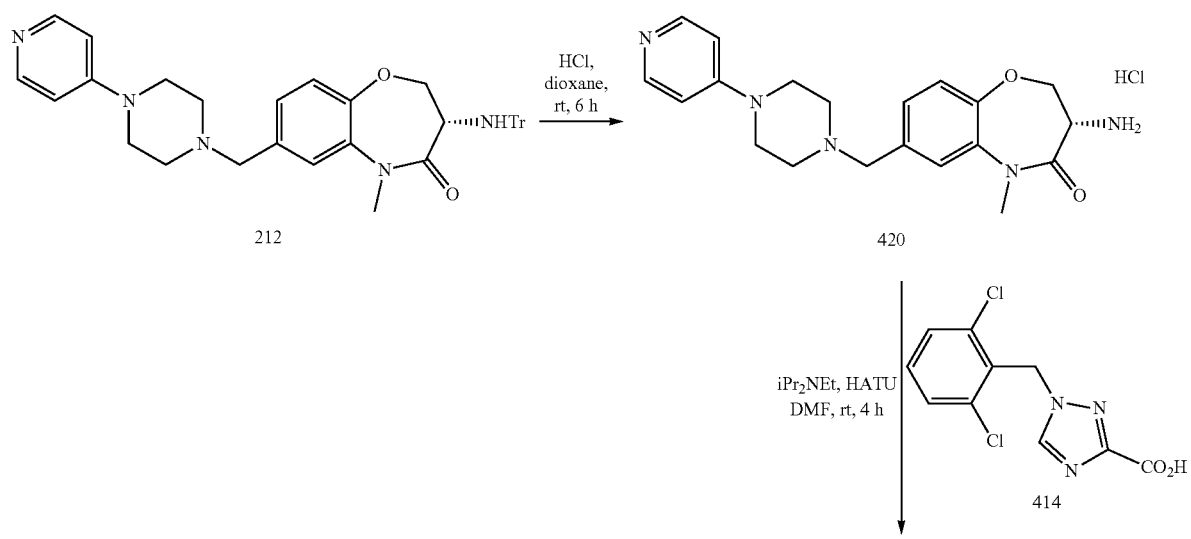
I-21

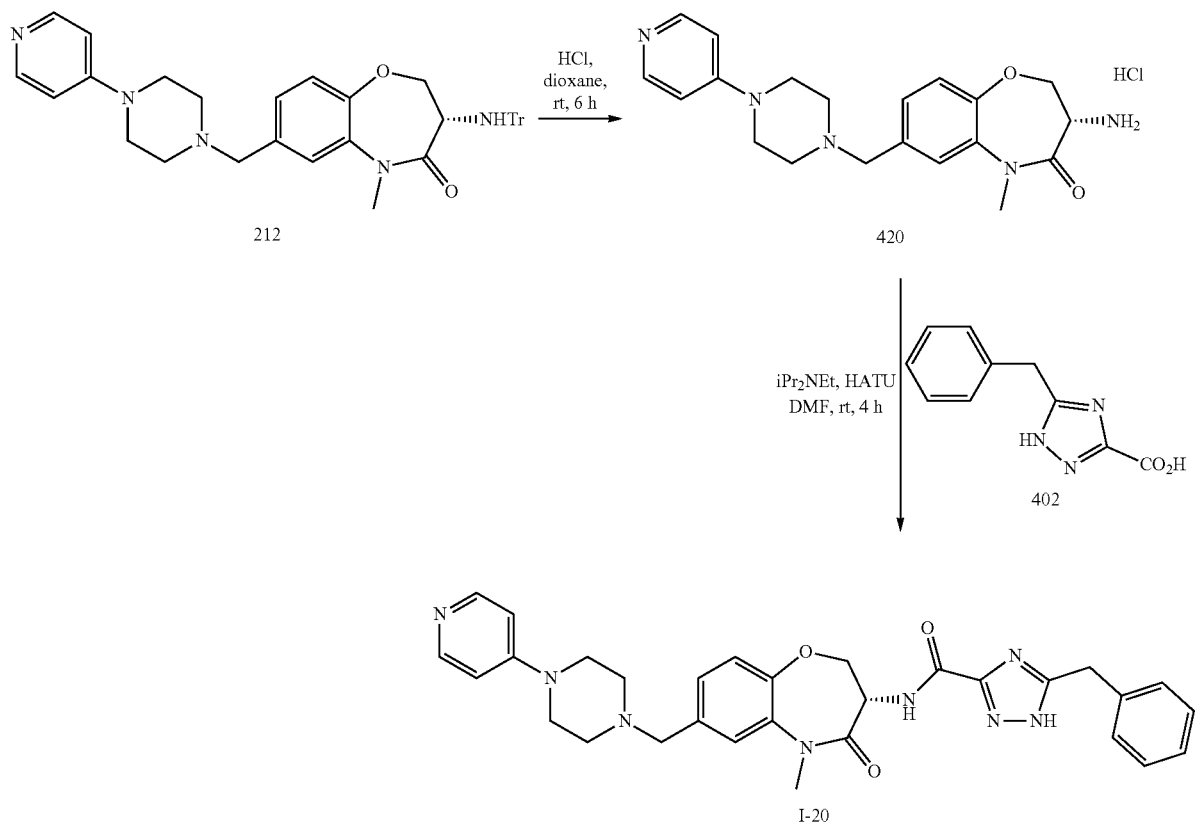

In some embodiments, the method can further comprise making one or more additional modifications to amide compound 302 to provide amide compound 500, such as modifying an $R^6$ group to form a different $R^6$ group, as illustrated in Scheme 5.

With reference to Scheme 5, one or more modifications to the $R^6$ group can be carried out. For example, if $R^6$ is an ester group, it can be converted to a carboxylic acid or to a primary alcohol. Suitable reagents for carrying out such an optional modification step are recognized by those of ordi-

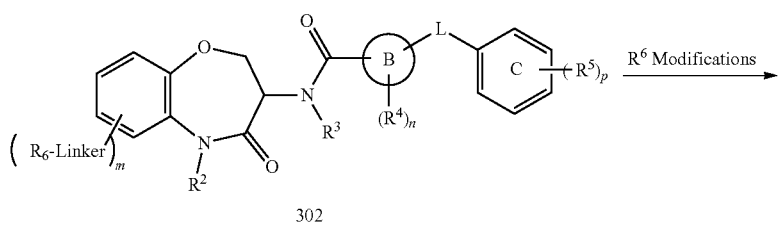

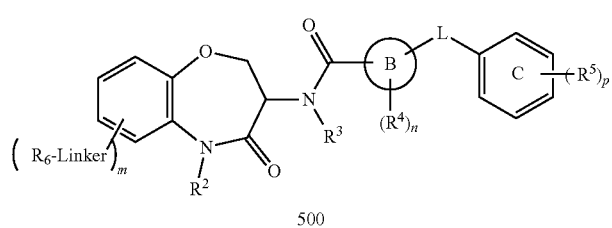

nary skill in the art with the benefit of the present disclosure; however, one exemplary set of conditions includes exposing an $R^6$ ester group to LiOH to provide the corresponding acid, such as is illustrated in Schemes 6A-6E below. The resulting acid can even be further modified to provide an amide-containing product by using suitable amide coupling conditions (such as those described above) in combination with an amine coupling partner, such as is illustrated in Schemes 6A-6E. Similar methods can be used to make compounds I-10, I-11, I-13, I-18, I-19, I-26, I-27, I-33, I-34, and I-22 and I-23 (wherein the double bond of the linker group is not first reduced prior to coupling). In yet additional embodiments, compounds I-16 and I-17 can be made by converting the terminal alcohol obtained in the above-described methods into a functionalized alcohol, such as for compound I-16, or to an amine, such as for compound I-17.

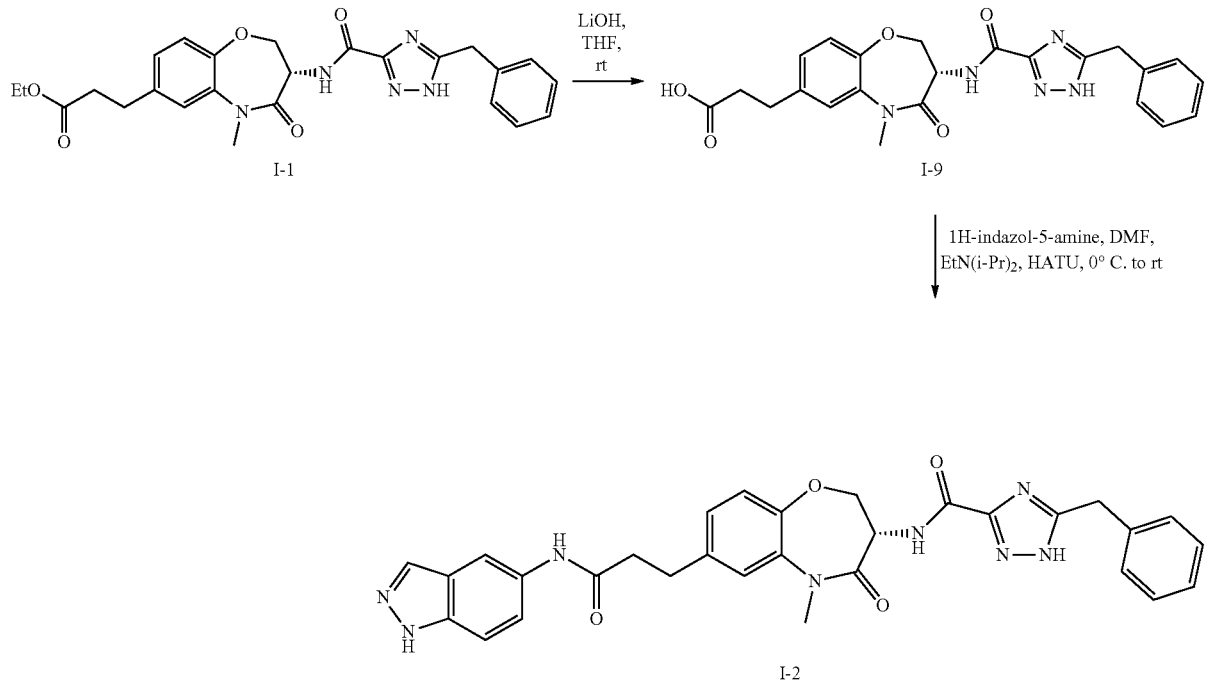

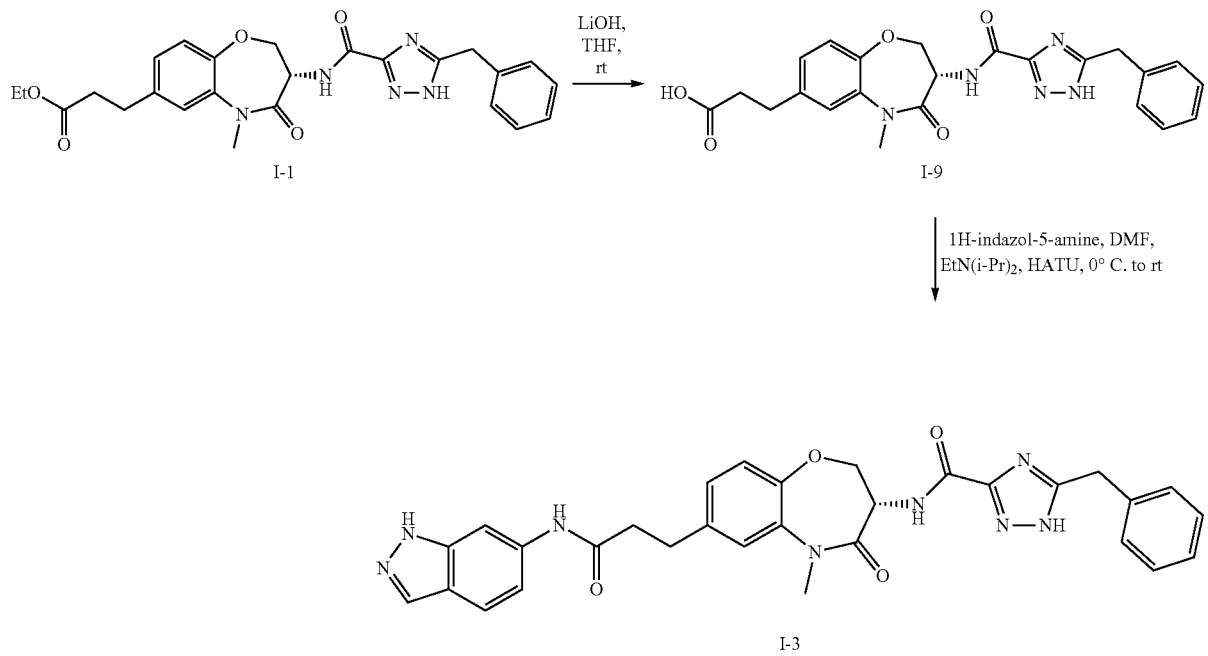

129 130
Scheme 6C
LiOH, THF, rt
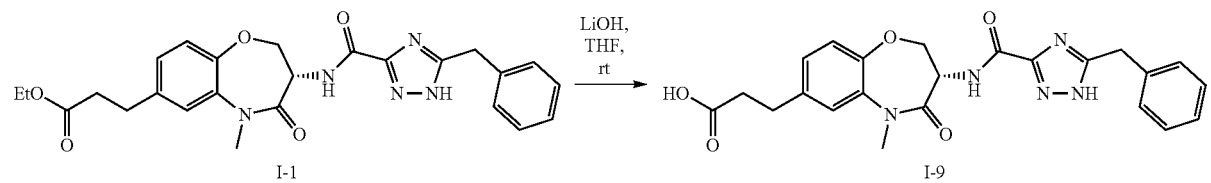
6,7-dimethoxyquinazolin-4-amine,
DMF, EtN(i-Pr)₂, HATU,
0° C. to rt
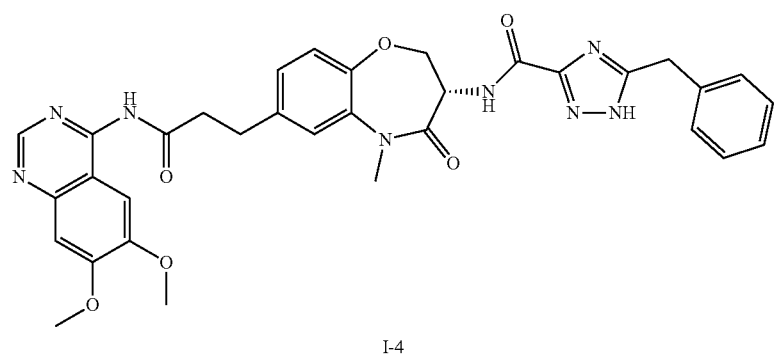
Scheme 6D
LiOH, THF, rt
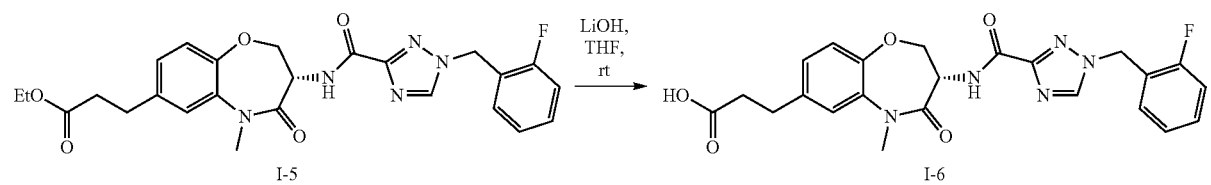
6-aminoindazole, DMF,
EtN(i-Pr)₂, HATU,
0° C. to rt
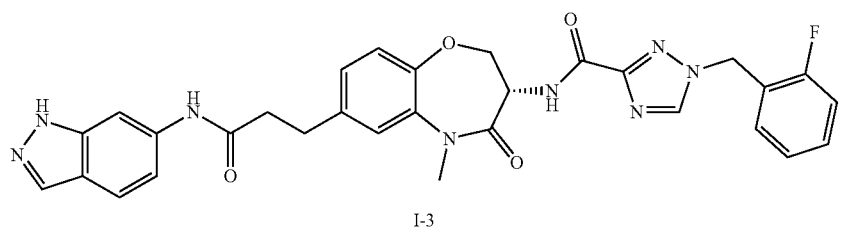

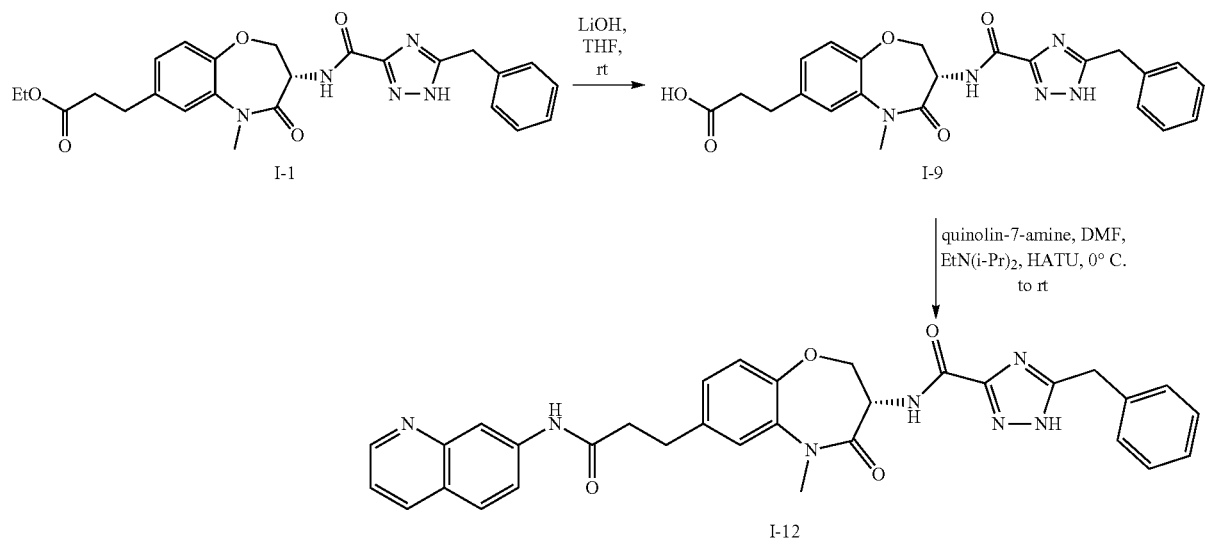

Scheme 6E

IV. Methods of Using Compounds

A. Diseases/Disorders

The disclosed compounds, as well as combinations and/or pharmaceutical compositions thereof, may be used to inhibit a RIP1 kinase by contacting the kinase either in vivo or ex vivo, with a compound or compounds of the present disclosure, or a composition comprising a compound or compounds of the present disclosure. Disclosed compound or compounds, or compositions comprising a disclosed compound or compounds also can be used to ameliorate, treat or prevent a variety of diseases and/or disorders. In particular embodiments, the disclosed compound, combinations of disclosed compounds, or pharmaceutical compositions thereof, may be useful for treating conditions in which inhibition of RIP1 or a pathway involving RIP1 is therapeutically useful. In some embodiments, the compounds directly inhibit RIP1 kinase activity. In certain embodiments, disclosed compounds are useful for treating autoimmune diseases, inflammatory disorders, cardiovascular diseases, nerve disorders, neurodegenerative disorders, allergic disorders, respiratory diseases, kidney diseases, cancers, ischemic conditions, erythrocyte deficiencies, lung and brain injuries (e.g., induced by ischemia-reperfusion or cisplatin and/or cerebrovascular accident), and bacterial and viral infections.

In some embodiments, the disclosed compound, combinations of disclosed compounds, or pharmaceutical compositions thereof, may be used to treat or prevent allergic diseases, amyotrophic lateral sclerosis (ALS), spinal muscular atrophy, systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmyopathy, or asthma.

The disclosed compound, combinations of disclosed compounds, or pharmaceutical compositions thereof, may also be useful for treating immune regulatory disorders related to bone marrow or organ transplant rejection or graft-versus-host disease. Examples of inflammatory and immune regulatory disorders that can be treated with the compounds (or pharmaceutical compositions or combinations thereof) include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, systemic inflammatory response syndrome, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, ischemia-reperfusion injuries, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis or myocardial infarction, scleroderma (including systemic scleroderma), anti-phospholipid syndrome, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, retinal degeneration, retinal detachment, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, alcoholic steatohepatitis, non-alcoholic steatohepatitis (NASH), autoimmune hepatobiliary diseases, acetaminophen toxicity, hepatotoxicity, hepatic failure, fulminant hepatic failure, late-onset hepatic failure, "acute-on-chronic" liver failure, chronic kidney diseases, kidney damage/injury (caused by, for example, nephritis, renal transplant, surgery, administration of nephrotoxic drugs, acute kidney injury), augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the compounds are useful for treating interleukin-1 converting enzyme-associated associated fever syndrome, tumor necrosis factor receptor-associated periodic syndrome, NEMO-deficiency syndrome, HOIL-1 deficiency, linear ubiquitin chain assembly complex deficiency syndrome, lysosomal storage diseases (e.g., Gaucher disease, GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sach disease, and Wolman disease).

In certain embodiments, the disclosed compound, combinations of disclosed compounds, or pharmaceutical compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), Alzheimer's disease, Huntington's disease, or Parkinson's disease.

Proliferative diseases that may be treated by the disclosed compound, combinations of disclosed compounds, or pharmaceutical compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Examples of allergic disorders that may be treated using the disclosed compound, combinations of disclosed compounds, or pharmaceutical compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, postnasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The disclosed compound, combinations of disclosed compounds, or pharmaceutical compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration

Pharmaceutical compositions comprising one or more active compounds of the invention may be manufactured by any suitable method, such as mixing, dissolving, granulating, dragee-making, levigating, emulsifying, encapsulating, entrapping or lyophilization processes. The pharmaceutical compositions may be formulated using one or more physiologically acceptable excipients (e.g., diluents, carriers, or auxiliaries), one or more adjuvants, or combinations thereof to provide preparations which can be used pharmaceutically.

The active compound(s) may be formulated in the pharmaceutical compositions per se, or in the form of a pharmaceutically acceptable salt, a stereoisomer, an N-oxide, a tautomer, a hydrate, a solvate, an isotope, or a prodrug thereof. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), pharmaceutically acceptable salt, stereoisomer, N-oxide, tautomer, hydrate, solvate, isotope, or prodrug may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The pharmaceutical compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable excipients such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound, as is well known.

For buccal administration, the pharmaceutical compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), pharmaceutically acceptable salt, stereoisomer, N-oxide, tautomer, hydrate, solvate, isotope, or prodrug can be conveniently delivered in the form of an aerosol spray from pressurized packs or a nebulizer with the use of a suitable propellant, e.g.,) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (1 15 mg/ml); phenylethanol (14 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL of the disclosed compound(s), 1% (v/v) polysorbate 80 (TWEEN® 80), 50 mM citrate and/or 0.9% sodium chloride.

For ocular administration, the active compound(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active compound(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The disclosed compound, pharmaceutical compositions, or combinations of disclosed compounds will generally be used in an amount effective to achieve the intended result, for example, in an amount effective to inhibit a RIP1 kinase and/or to treat, prevent or ameliorate a particular condition.

The disclosed compound(s), or pharmaceutical compositions thereof, can be administered therapeutically to achieve therapeutic benefit or prophylactically to achieve a prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of disclosed compounds may depend on various factors, including the age, weight, general health, and severity of the condition of the patient or subject being treated. Dosage also may need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, respiratory distress syndrome, chronic obstructive pulmonary disease, and respiratory infections. Dosage, and frequency of administration of the disclosed compound(s) or pharmaceutical compositions thereof, will also depend on whether the disclosed compound(s) are formulated for treatment of acute episodes of a condition or for the prophylactic treatment of a disorder. A person of ordinary skill in the art will be able to determine the optimal dose for a particular individual.

For prophylactic administration, the disclosed compound, combinations of disclosed compounds, or pharmaceutical compositions thereof, can be administered to a patient or subject at risk of developing one of the previously described conditions. For example, if it is unknown whether a patient or subject is allergic to a particular drug, the disclosed compound, combinations of disclosed compounds, or pharmaceutical compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a disclosed compound(s), or pharmaceutical composition thereof, can be administered to an allergy sufferer prior to expected exposure to the allergen. A disclosed compound, combinations of disclosed compounds, or pharmaceutical compositions thereof, can also be administered prophylactically to healthy individuals who are repeatedly exposed to agents known to one of the above-described maladies to prevent the onset of the disorder. For example, a disclosed compound, combinations of disclosed compounds, or pharmaceutical compositions thereof, can be administered to a healthy individual who is repeatedly exposed to an allergen known to induce allergies, such as latex, in an effort to prevent the individual from developing an allergy. Alternatively, a disclosed compound, combinations of disclosed compounds, or pharmaceutical compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 µM, such as from greater than 0 to 10 µM, from greater than 0 to 5 µM, from greater than 0 to 1 µM, from greater than 0 to 0.5 µM, from greater than 0 to 0.1 µM, or from greater than 0 to 0.05 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

In some embodiments, assays suitable for determining RIP1 activity can be used. Such assay methods can be used to evaluate the efficacy of compound embodiments disclosed herein and/or that can be used to determine amounts/dosages of the compound embodiments that can provide a desired efficacy. In some embodiments, the assay can be an ADP-Glo™ assay that assesses the ability of a compound embodiment to inhibit RIP1. In other embodiments, whole cell assays using mouse and/or human cells, such as U937 and/or L929 cell necroptosis assays, can be performed to determine safe and effective doses of compounds that can be used in human in vivo studies. Using these whole cell assays, the compound's activity against human and/or murine RIP1 can be assessed in an in vitro context, which then allows a person of ordinary skill in the art to determine safe and effective dosages for in vivo use. Yet another assay that can be used to evaluate the activity of compound embodiments described herein to treat a disease or condition involving RIP1 is an acute hypothermia mouse model, which assesses the compound's ability to inhibit TNF-alpha induced hypothermia. Each of these assays, and various results from using these assays, are described in detail in the Examples section of the present disclosure.

Dosage amounts of disclosed compounds will typically be in the range of from greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the disclosed compound, its bioavailability, the mode of administration, and various factors discussed above.

Dosage amount and dosage interval can be adjusted for individuals to provide plasma levels of the disclosed compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Pharmaceutical compositions comprising one or more of the disclosed compounds typically comprise from greater than 0 up to 99% of the disclosed compound, or compounds, and/or other therapeutic agent by total weight percent. More typically, pharmaceutical compositions comprising one or more of the disclosed compounds comprise from about 1 to about 20 total weight percent of the disclosed compound and other therapeutic agent, and from about 80 to about 99 weight percent of a pharmaceutically acceptable excipient. In some embodiments, the pharmaceutical composition can further comprise an adjuvant.

Preferably, the disclosed compound, combinations of disclosed compounds, or pharmaceutical compositions thereof, will provide therapeutic or prophylactic benefit without causing substantial toxicity. Toxicity of the disclosed compound can be determined using standard pharmaceutical procedures. The dose ratio between toxic and therapeutic (or prophylactic) effect is the therapeutic index. Disclosed compounds that exhibit high therapeutic indices are preferred.

V. Examples

Example 1

Compounds of the present disclosure can be made using a suitable starting compound, such as compound 200 or compound 206, illustrated in the schemes above. A representative method for making compound 200 is illustrated in Scheme 7A and a representative method for making compound 206 is illustrated in Scheme 7B.

Scheme 7A

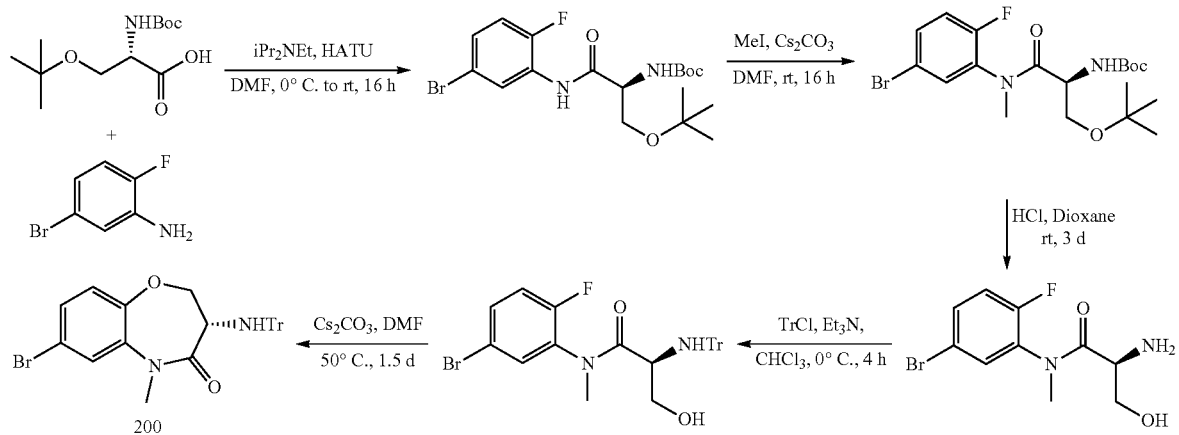

Scheme 7B

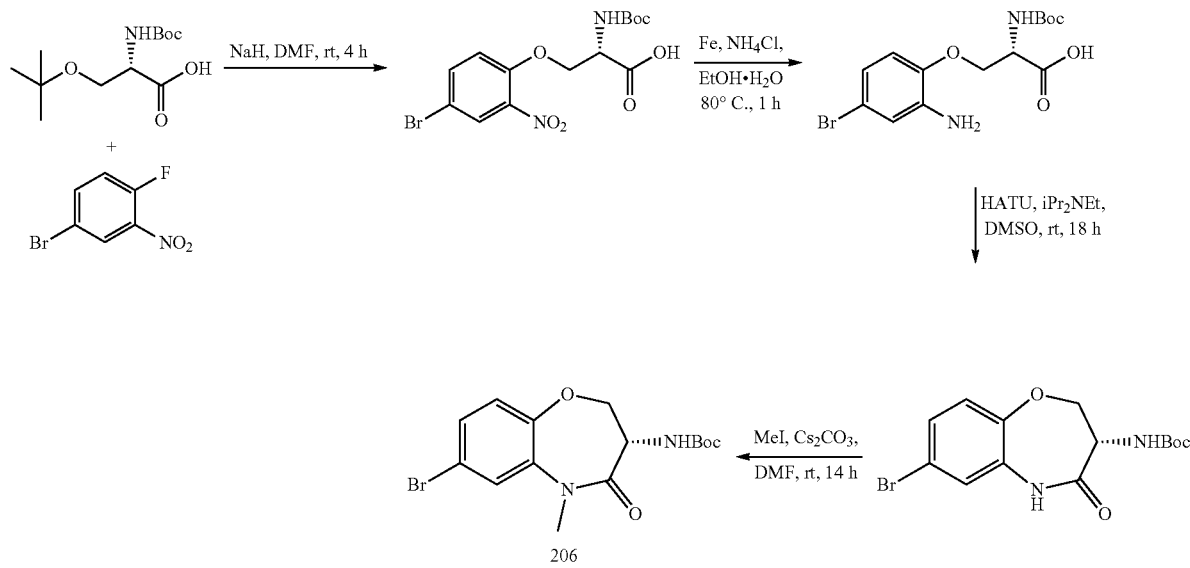

Spectral Characterization for 3-(S)—N-trityl-amino-7-bromo-5-methyl-4-oxobenzoxazapine (200)

¹H nmr (400 MHz, CDCl₃) δ 7.41-7.38 (6H, m, 6H of C(C₆H₅)₃), 7.25-7.15 (10H, m, oxobenzoxazapineH-8, 9H of C(C₆H₅)₃), 7.00 (1H, d, J 2.5 Hz, oxobenzoxazapineH-6), 6.91 (1H, d, J 8.5 Hz, oxobenzoxazapineH-9), 4.50 (1H, dd, J 10.0, 7.5 Hz, 1H of oxobenzoxazapineH-2), 4.37 (1H, dd, J 11.5, 10.0 Hz, 1H of oxobenzoxazapineH-2), 3.53 (1H, dd, J 11.5, 7.5 Hz, oxobenzoxazapineH-3), 3.30 (1H, br s, NH), 2.87 (3H, s, NCH₃).

Characterization data and particular methods of making representative compounds disclosed herein are provided below.

Example 2

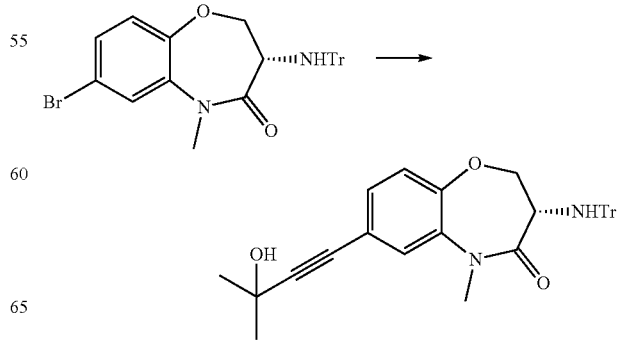

Synthesis of (S)-7-(3-hydroxy-3-methylbut-1-yn-1-yl)-5-methyl-3-(tritylamino)-2,3-dihydrobenzo[b][1,4]oxazepin-4(5H)-one A mixture of the bromooxazapine (0.210 g, 0.410 mmol, 1.0 eq) potassium carbonate (0.566 g, 4.101 mmol, 10.0 eq) and copper(I) iodide (0.008 g, 0.041 mmol, 0.1 eq) in dimethylformamide (3.0 mL) was degassed by bubbling argon through for five minutes. 2-Methyl-2-hydroxybut-3-yne (0.052 g, 0.060 mL, 0.615 mmol, 1.5 eq) and tetrakis(triphenylphosphine)palladium (0.024 g, 0.021 mmol, 0.05 eq) were added and the reaction sealed before heating in the microwave to 120° C. for 1 hour. The reaction was partitioned between EtOAc (80 mL) and water (80 mL). The organics were washed with brine (80 mL), water (80 mL) and brine (80 mL), dried (Na$_2$SO$_4$) and concentrated under reduced pressure. MPLC (10→80% EtOAc-hexane) yielded the starting material (0.091 g) and the title compound (0.079 g) as a colorless oil; $^1$H nmr (400 MHz, CDCl$_3$) δ 7.40-7.38 (6H, m, 6H of C(C$_6$H$_5$)$_3$), 7.24-7.7.14 (9H, m, 9H of C(C$_6$H$_5$)$_3$), 7.13 (1H, dd, J 8.0, 2.0 Hz, oxobenzoxazapineH-8), 6.96 (1H, d, J 8.0 Hz, oxobenzoxazapineH-9), 6.95 (1H, d, J 2.5 Hz, oxobenzoxazapineH-6), 4.48 (1H, dd, J 10.0, 7.5 Hz, 1H of oxobenzoxazapineH-2), 4.37 (1H, dd, J 11.5, 10.0 Hz, 1H of oxobenzoxazapineH-2), 3.55 (1H, dd, J 11.5, 7.5 Hz, oxobenzoxazapineH-3), 2.78 (3H, s, NCH$_3$), 1.62 (6H, s, C(CH$_3$)$_2$); m/z: 555 [M+K]$^+$, 243 [C(C$_6$H$_5$)$_3$]$^+$.

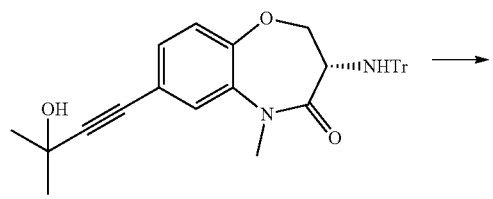

Deprotection of the Trityl Group

To a solution of the trityl protected amine (0.079 g, 0.153 g, 1.0 eq) in dioxane (2.0 mL) was added a solution of hydrogen chloride (0.15 mL of a 4M solution in dioxane, 0.614 mmol, 4.0 eq). The reaction was stirred at room temperature for 6 hours before concentrating to dryness to obtain a white solid, which was used without purification; m/z: 275 [M+H]$^+$.

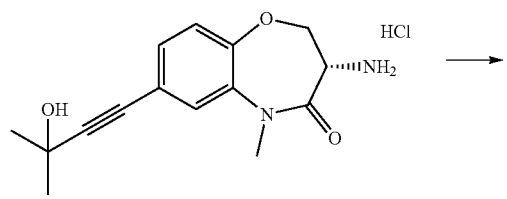

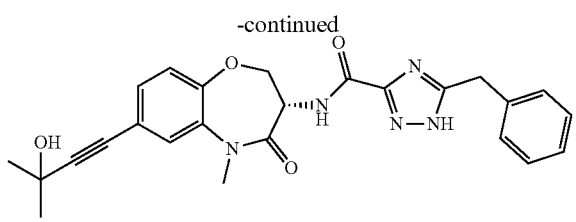

Synthesis of (S)-5-benzyl-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide To a solution of the aminooxobenzoxazapine hydrochloride (0.076 mmol, 1.0 eq) and benzyltriazole carboxylic acid (0.017 g, 0.084 mmol, 1.1 eq) in dimethylformamide (1.0 mL) was added diisopropylamine (0.025 g, 0.033 mL, 0.190 mmol, 2.5 eq) followed by HATU (0.032 g, 0.084 mmol, 1.1 eq). The reaction was stirred at room temperature for 4 hours and partitioned between EtOAc—CH$_2$Cl$_2$ (5:1, 60 mL) and NaHCO$_3$ (60 mL). The organics were washed with brine (50 mL), water (50 mL) and brine (50 mL), dried (Na$_2$SO$_4$) and concentrated under reduced pressure. MPLC (0→10% MeOH—CH$_2$Cl$_2$) yielded the title compound as a white solid; $^1$H nmr (400 MHz, CDCl$_3$) δ 8.08 (1H, d, J 7.5 Hz, NH), 7.30-7.22 (7H, m, 7×ArH), 7.11 (1H, d, J 9.0 Hz, oxobenzoxazapineH-9), 5.02 (1H, dt, J 11.0, 7.5 Hz, oxobenzoxazapineH-3), 4.68 (1H, dd, J 10.0, 7.5 Hz, 1H of oxobenzoxazapineH-2), 4.28 (1H, dd, J 11.0, 10.0 Hz, 1H of oxobenzoxazapineH-2), 4.14 (2H, s, CCH$_2$C$_6$H$_5$), 3.40 (3H, s, NCH$_3$), 1.63 (6H, s, C(CH$_3$)$_2$OH); m/z: 442 [M+H—H$_2$O]$^+$.

Similar steps as those above for Example 2 can be used to make compounds I-14, to I-17, and I-35.

Example 3

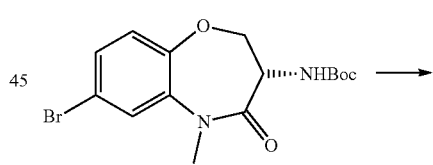

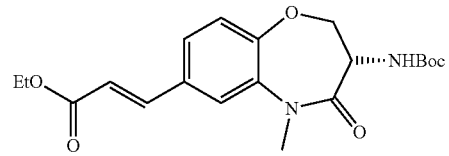

Synthesis of ethyl (S,E)-3-(3-((tert-butoxycarbonyl)amino)-5-methyl-4-oxo-2,3,4,5-tetrahydrobenzo[b][1,4]oxazepin-7-yl)acrylate To a suspension of tert-butyl (S)-(7-bromo-5-methyl-4-oxo-2,3,4,5-tetrahydrobenzo[b][1,4]oxazepin-3-yl)carbamate (0.500 g, 1.35 mmol, 1.0 eq) in dimethylformamide (8 mL) was degassed by bubbling argon through for five minutes. Ethyl acrylate (0.270 g, 0.29 mL, 2.70 mmol, 2.0 eq) and triethylamine (0.272 g, 0.37 mL, 2.0 eq) were added followed by tetrakis(triphenylphosphine (0.156 g, 0.14 mmol, 0.1 eq). The reaction was sealed and heated in the microwave to 100° C. for 1 hour and 120° C. for 1 hour. The reaction was partitioned between EtOAc (100 mL) and water (100 mL). The organics were washed with brine (70 mL), water (100 mL) and brine (70 mL), dried (Na$_2$SO$_4$) and concentrated under reduced pressure. Column chromatography (10→40% EtOAc-hexane) yielded the title compound (0.250 g, %) as a yellow foam; $^1$H nmr (400 MHz, CDCl$_3$) δ 7.62 (1H, d, J 16.0 Hz, ArCH=CHCO), 7.35 (1H, dd, J 8.0, 2.0 Hz, oxobenzoxazepineH-8), 7.33 (1H, d, J 2.0 Hz, oxobenzoxazepineH-6), 7.14 (1H, d, J 8.0 Hz, oxobenzoxazepineH-9), 6.37 (1H, d, J 16.0 Hz, ArCH=CHCO), 5.49 (1H, d, J 7.0 Hz, NH), 4.65 (1H, dt, J 11.0, 7.0 Hz, oxobenzoxazepineH-3), 4.57 (1H, dd, J 9.5, 7.0 Hz, 1H of oxobenzoxazepineH-2), 4.27 (2H, q, J 7.0 Hz, OCH$_2$CH$_3$), 4.19 (1H, dd, J 11.0, 9.5 Hz, 1H of oxobenzoxazepineH-2), 3.41 (3H, s, NCH$_3$), 1.39 (9H, s, C(CH$_3$)$_3$), 1.34 (3H, t, J 7.0 Hz, OCH$_2$CH$_3$); m/z: 291 [M+H—CO$_2$—C$_4$H]$^+$.

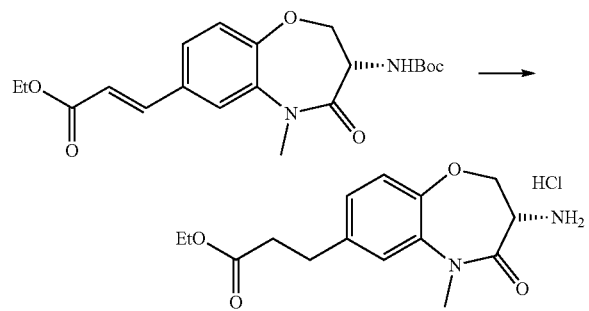

Synthesis of ethyl(S)-3-(3-amino-5-methyl-4-oxo-2,3,4,5-tetrahydrobenzo[b][1,4]oxazepin-7-yl)propanoate A solution of the α,β-unsaturated ester (0.25 g, 0.64 mmol, 1.0 eq) in ethyl acetate (20 mL) was added palladium on carbon (0.23 g). The reaction was purged with hydrogen and stirred under an atmosphere of hydrogen for 14 hours. The reaction was purged with nitrogen and filtered through Celite®, eluting with ethyl acetate (2×20 mL). The filtrate was concentrated under reduced pressure; $^1$H nmr (400 MHz, CDCl$_3$) δ 7.04-6.82 (3H, m, oxobenzoxazepineH-6, H-8, H-9), 5.50 (1H, d, J 7.5 Hz, NH), 4.61 (1H, dt, J 11.0, 7.5 Hz, oxobenzoxazepineH-3), 4.52 (1H, dd, J 9.5, 7.5 Hz, 1H of oxobenzoxazepineH-2), 4.14-4.07 (1H, m, 1H of oxobenzoxazepineH-2), 4.12 (2H, q, J 7.0 Hz, OCH$_2$CH$_3$), 3.36 (3H, s, NCH$_3$), 2.91 (2H, t, J 7.5 Hz, 2H of ArCH$_2$CH$_2$CO), 2.59 (2H, t, J 7.5 Hz, 2H of ArCH$_2$CH$_2$CO), 1.37 (9H, s, C(CH$_3$)$_3$), 1.23 (3H, t, J 7.0 Hz, OCH$_2$CH$_3$); m/z: 337 [M+H—C$_4$H$_8$]$^+$, 293 [M+H—CO$_2$—C$_4$H$_8$]$^+$. The crude material was dissolved in dichloromethane (10 mL). Hydrogen chloride (0.80 mL of a 4M solution in dioxane, 3.21 mmol, 5.0 eq). The reaction was stirred at room temperature for 14 hours before adding further hydrogen chloride solution (0.8 mL, 5.0 eq). After stirring for a further 2 hours the reaction was concentrated under reduced pressure and dried under vacuum to obtain a brown solid. The crude material was used without further purification; m/z: 293 [M+H]$^+$.

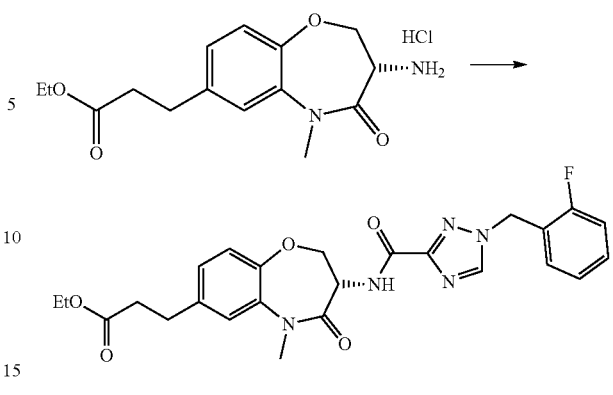

Synthesis of ethyl (S)-3-(3-(1-(2-fluorobenzyl)-1H-1,2,4-triazole-3-carboxamido)-5-methyl-4-oxo-2,3,4,5-tetrahydrobenzo[b][1,4]oxazepin-7-yl)propanoate Huorobenzyltriazole (0.116 g, 0.525 mmol, 1.1 eq) was added to a solution of the ethyl (S)-3-(3-(1-(2-fluorobenzyl)-1H-1,2,4-triazole-3-carboxamido)-5-methyl-4-oxo-2,3,4,5-tetrahydrobenzo[b][1,4]oxazepin-7-yl)propanoate (0.140 g, 0.477 mmol, 1.0 eq) and diisopropylethylamine (0.154 g, 0.21 mmol, 2.5 eq) in dimethylformamide (5.0 eq). HATU (0.199 g, 0.525 mmol, 1.1 eq) was added and the reaction stirred at 0° C. for 1 hour and room temperature for 1 hour. The reaction was partitioned between EtOAc (120 mL) and NaHCO$_3$-water (1:1, 120 mL). The organics were washed with brine (100 mL), water (100 mL) and brine (100 mL), dried (Na$_2$SO$_4$) and concentrated under reduced pressure. Column chromatography (40→80% EtOAc-hexane) yielded the title compound 0.138 mg) as a white solid; $^1$H nmr (400 MHz, CDCl$_3$) δ 8.11 (1H, s, triazoleH-5), 8.05 (1H, d, 7.0 Hz, NH), 7.38-7.30 (2H, m, 2H of C$_6$H$_4$F), 7.26-7.07 (6H, m, 2H of C$_6$H$_4$F, oxobenzoxazapineH-6, H-7, H-8, H-9), 5.42 (2H, s, CH$_2$C$_6$H$_4$F), 5.08 (1H, dt, J 11.0, 7.5 Hz, oxobenzoxazapineH-3), 4.75 (1H, dd, J 9.5, 7.5 Hz, 1H of oxobenzoxazapineH-2), 4.24 (1H, dd, J 11.0, 9.5 Hz, 1H of oxobenzoxazapineH-2), 3.42 (3H, s, NCH$_3$); $^{13}$C nmr (100 MHz, CDCl$_3$) δ 168.9, 160.6 (d, J 248.5 Hz), 158.3, 156.7, 150.1, 144.1 (d, J 2.0 Hz), 136.0, 131.1 (d, J 8.5 Hz), 130.9 (d, J 2.5 Hz), 127.6, 125.7, 124.9 (d, J Hz), 123.3, 123.1, 121.2 (d, J 14.0 Hz), 115.8 (d, J 21.5 Hz), 77.3, 49.2, 47.9 (d, J 4.0 Hz), 35.5; $^{19}$F nmr (380 MHz, CDCl$_3$) δ −118.1; m/z: 518 [M+Na]$^+$, 496 [M+H]$^+$ (found [M+H]$^+$, 496.1991, C$_{25}$H$_{26}$FN$_5$O$_5$ requires [M+H]$^+$ 496.1973).

Similar steps as those above for Example 3 and those below for Examples 4 and 5 can be used to make compounds I-10, I-11, I-13, I-18, I-19, I-26, I-27, I-33, I-34, and I-22 and I-23 (wherein the double bond of the linker group is not first reduced prior to coupling).

Example 4

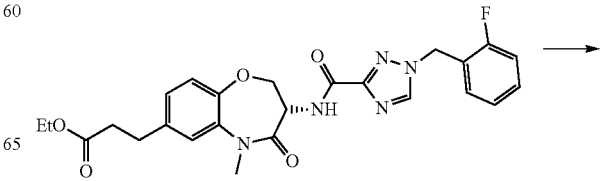

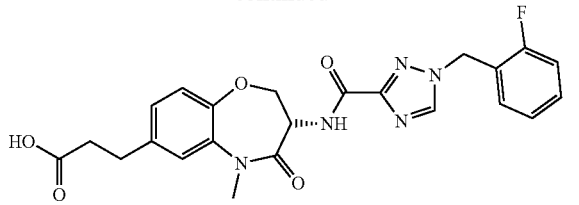

Synthesis of (S)-3-(3-(1-(2-fluorobenzyl)-1H-1,2,4-triazole-3-carboxamido)-5-methyl-4-oxo-2,3,4,5-tetrahydrobenzo[b][1,4]oxazepin-7-yl)propanoic Acid To a solution of the ethyl ester (0.103 g, 0.208 mmol, 1.0 eq) in tetrahydrofuran (3 mL) was added aqueous lithium hydroxide (0.017 g, 0.416 mmol, 2.0 eq in 1 mL of water). The reaction was stirred at room temperature for 3 hours before partitioning between EtOAc (80 mL) and NH$_4$Cl (80 mL). The aqueous phase was extracted with EtOAc (2×60 mL). The combined organics were washed with brine (80 mL), dried (Na$_2$SO$_4$) and concentrated under reduced pressure. Column chromatography (0→10% MeOH—CH$_2$C$_2$) yielded the title compound 0.054 g, %) was a white solid; $^1$H nmr (400 MHz, CDCl$_3$) δ 8.12 (1H, s, triazoleH-5), 8.04 (1H, d, J 7.5 Hz, NH), 7.40-7.30 (2H, m, 2×ArH), 7.16 (1H, dd, J 7.5, 1.0 Hz, 1×ArH), 7.14-7.10 (2H, m, 2×ArH), 7.07 (2H, m, 2×ArH), 5.43 (2H, s, NCH$_2$C$_6$H$_5$F), 5.07 (1H, dt, J 11.0, 7.5 Hz, oxobenzoxazepineH-3), 4.73 (1H, dd, J 9.5, 7.5 Hz, 1H of oxobenzoxazepineH-2), 4.22 (1H, dd, J 11.0, 9.5 Hz, 1H of oxobenzoxazepineH-2), 3.41 (3H, s, NCH$_3$), 2.96 (2H, t, J 7.5 Hz, 2H of ArCH$_2$CH$_2$CO), 2.70 (2H, t, J 7.5 Hz, 2H of ArCH$_2$CH$_2$CO); $^{19}$F nmr (CDCl$_3$) δ −118.1 (dd, J 16.5, 7.0 Hz); m/z: 468 [M+H]$^+$ (found [M+H]$^+$, 468.1688, C$_{23}$H$_{22}$FN$_5$O$_5$ requires [M+H]$^+$ 468.1678).

Example 5

Synthesis of(S)—N-(7-(3-((1H-indazol-6-yl)amino)-3-oxopropyl)-5-methyl-4-oxo-2,3,4,5-tetrahydrobenzo[b][1,4]oxazepin-3-yl)-1-(2-fluorobenzyl)-1H-1,2,4-triazole-3-carboxamide A solution of(S)-3-(3-(1-(2-fluorobenzyl)-1H-1,2,4-triazole-3-carboxamido)-5-methyl-4-oxo-2,3,4,5-tetrahydrobenzo[b][1,4]oxazepin-7-yl)propanoic acid (0.049 g, 0.105 mmol, 1.0 eq) and 6-aminoindazole (0.017 g, 0.126 mmol, 1.2 eq) in dimethylformamide (10 mL) was cooled to 0° C. Diisopropylethylamine (0.027 g, 0.036 mL, 0.210 mmol, 2.0 eq) was added followed by HATU (0.048 g, 0.126 mmol, 1.2 eq) and the reaction stirred at 0° C. for 1 hour and room temperature for 2 hours. The reaction was partitioned between EtOAc (50 mL) and NaHCO$_3$ (50 mL). The organics were washed with brine (50 mL). The combined aqueous phase was extracted with EtOAc (20 mL). The combined organics were washed with water (50 mL) and brine (50 mL), dried (Na$_2$SO$_4$) and concentrated under reduced pressure. Column chromatography (0→10% MeOH—CH$_2$Cl$_2$) yielded the title compound (0.xx g, %) yielded the title compound as a white solid; $^1$H nmr (400 MHz, CDCl$_3$) δ 8.12 (1H, s, triazoleH-5), 8.00 (1H, d, J 7.5 Hz, NH), 7.94 (1H, d, J 0.5 Hz, indazoleH-3), 7.90 (1H, s, NH), 7.83 (1H, m, indazoleH-7), 7.57 (1H, d, J 9.0 Hz, indazoleH-4), 7.37-7.30 (2H, m, 2H of C$_6$H$_4$F), 7.13 (1H, td, J 7.5, 1.0 Hz, 1H of C$_6$H$_4$F), 7.09-7.00 (5H, m, indazoleH-5, 1H of C$_6$H$_4$F, oxobenzoxazepineH-6, H-7, H-9), 5.40 (2H, s, NCH$_2$C$_6$H$_4$F), 5.02 (1H, td, J 11.5, 7.5 Hz, oxobenzoxazepineH-3), 4.63 (1H, dd, J 9.5, 7.5 Hz, 1H of oxobenzoxazepineH-2), 4.23 (1H, dd, J 11.5, 9.5 Hz, 1H of oxobenzoxazepineH-2), 3.29 (3H, s, NCH$_3$), 3.03 (2H, t, J 7.0 Hz, ArCH$_2$CH$_2$CON), 2.68 (2H, m, ArCH$_2$CH$_2$CON); $^{13}$C nmr (CDCl$_3$) δ 170.6, 168.7, 160.7 (d, J 248.5 Hz), 158.8, 156.4, 148.4, 144.4, 140.6, 138.5, 136.3, 135.9, 134.3, 131.2 (d, J 8.5 Hz), 131.0 (d, J 3.0 Hz), 127.5, 124.9 (d, J 4.0 Hz), 123.4, 122.9, 121.1, 121.0, 120.3, 115.8 (d, J 20.5 Hz), 115.3, 101.1, 77.2, 49.1, 48.0 (d, J 4.0 Hz), 39.3, 35.3, 31.1;

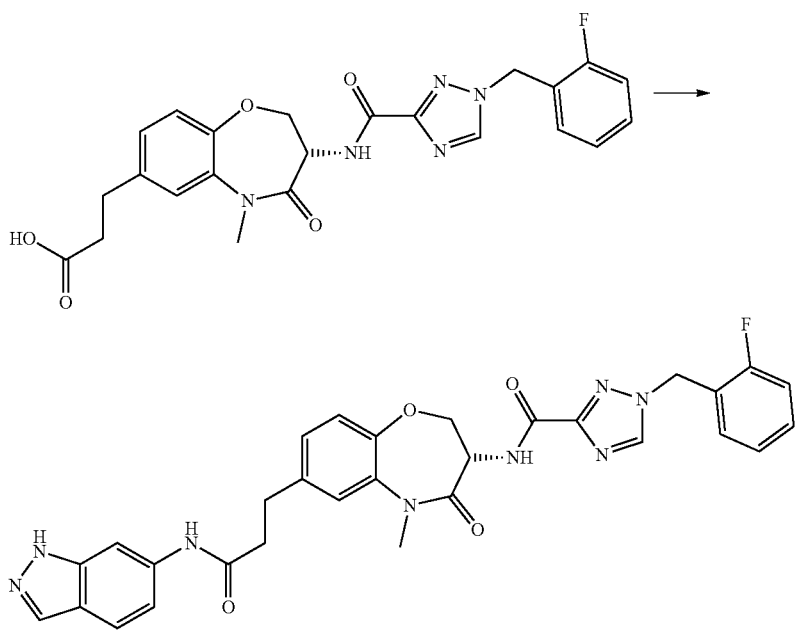

$^{19}$F nmr (CDCl$_3$) δ −118.0; m/z: 583 [M+H]$^+$ (found [M+H]$^+$, 583.2205, C$_{30}$H$_{27}$FN$_8$O$_4$ requires [M+H]$^+$ 583.2212).

Example 6

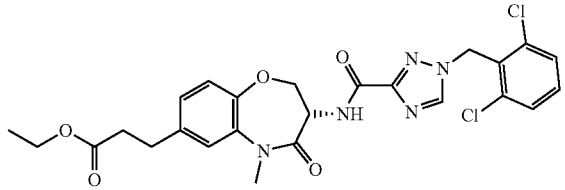

Ethyl (S)-3-(3-(1-(2,6-dichlorobenzyl)-1H-1,2,4-triazole-3-carboxamido)-5-methyl-4-oxo-2,3,4,5-tetrahydrobenzo[b][1,4]oxazepin-7-yl)propanoate $^1$H nmr (400 MHz, CDCl$_3$) δ 8.02 (1H, d, J 7.0 Hz, NH), 7.96 (1H, s, triazoleH-5), 7.42 (2H, m, 2×ArH), 7.32 (1H, dd, J 9.0, 7.0 Hz, 1×ArH), 7.10 (1H, m, 1×ArH), 7.06 (2H, dd, J 6.0, 2.0 Hz, 2×ArH), 5.70 (2H, s, CH$_2$C$_6$H$_3$Cl$_2$), 5.07 (1H, dt, J 11.0, 7.5 Hz, oxobenzoxazepineH-3), 4.74 (1H, dd, J 9.5, 7.5 Hz, 1H of oxobenzoxazepineH-2), 4.21 (1H, dd, J 11.0, 9.5 Hz, 1H of oxobenzoxazepineH-2), 4.14 (2H, q, J 7.0 Hz, OC<u>H</u>$_2$CH$_3$), 3.41 (3H, s, NCH$_3$), 2.95 (2H, t, J 7.5 Hz, 2H of ArCH$_2$CH$_2$CO), 2.63 (2H, t, J 7.5 Hz, 2H of ArCH$_2$CH$_2$CO), 1.24 (3H, t, J 7.0 Hz, OCH$_2$C<u>H</u>$_3$); $^{13}$C nmr (100 MHz, CDCl$_3$) δ 172.5, 168.9, 158.3, 156.5, 148.4, 143.9, 138.4, 136.9, 135.8, 131.4, 129.1, 128.9, 127.5, 123.2, 122.9, 77.2, 60.6, 49.4, 49.3, 35.7, 35.5, 30.3, 14.2; m/z: 548, 546 [M+H]+(found [M+H]$^+$, 546.1291, C$_{25}$H$_{25}$Cl$_2$N$_5$O$_5$ requires [M+H]$^+$ 546.1306).

Example 7

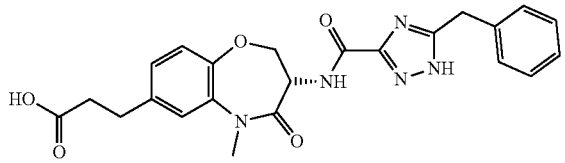

(S)-3-(3-(5-benzyl-1H-1,2,4-triazole-3-carboxamido)-5-methyl-4-oxo-2,3,4,5-tetrahydrobenzo[b][1,4]oxazepin-7-yl)propanoic Acid $^1$H nmr (400 MHz, CDCl$_3$) δ 8.13 (1H, d, J 7.5 Hz, NH), 7.32-7.22 (5H, m, 5×ArH), 7.08-7.06 (3H, m, 3×ArH), 4.97 (1H, dt, J 11.0, 7.5 Hz, oxobenzoxazapineH-3), 4.62 (1H, dd, J 9.5, 7.5 Hz, 1H of oxobenzoxazapineH-2), 4.24 (1H, dd, J 11.0, 9.5 Hz, 1H of oxobenzoxazapineH-2), 4.13 (2H, s, C<u>H</u>$_2$C$_6$H$_5$), 3.38 (3H, s, NCH$_3$), 2.94 (2H, m, 2H of ArC<u>H</u>$_2$CH$_2$CO$_2$H), 2.70 (2H, m, 2H of ArCH$_2$C<u>H</u>$_2$CO$_2$H); $^{19}$F nmr (CDCl$_3$) δ −118.1; m/z: 450 [M+H]$^+$ (found [M+H]$^+$, 450.1760, C$_{23}$H$_{23}$N$_5$O$_5$ requires [M+H]$^+$ 450.1772).

Example 8

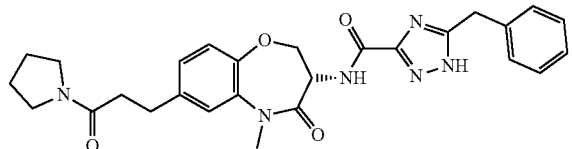

(S)-5-benzyl-N-(5-methyl-4-oxo-7-(3-oxo-3-(pyrrolidin-1-yl)propyl)-2,3,4,5-tetrahydrobenzo[b][1,4]oxazepin-3-yl)-1H-1,2,4-triazole-3-carboxamide $^1$H nmr (400 MHz, CDCl$_3$) δ 8.08 (1H, d, J 7.5 Hz, NH), 7.29-7.21 (5H, m, 5×ArH), 7.10-7.07 (3H, m, 3×ArH), 5.05 (1H, dt, J 11.0, 7.5 Hz, oxobenzoxazapineH-3), 4.66 (1H, dd, J 9.5, 7.5 Hz, 1H of oxobenzoxazapineH-2), 4.22 (1H, dd, J 11.0, 9.5 Hz, 1H of oxobenzoxazapineH-2), 4.15 (2H, s, CH$_2$Ph), 3.45 (2H, t, J 7.0 Hz, 2H of pyrrolidine), 3.38 (3H, s, NCH3), 3.35 (2H, m, 2H of pyrrolidine), 2.97 (2H, t, J 7.5 Hz, 2H of ArCH2CH2CO), 2.57 (2H, t, J 7.5 Hz, 2H of ArCH2CH2CO), 1.92 (2H, m, 2H of pyrrolidine), 1.83 (2H, m, 2H of pyrrolidine); $^{13}$C nmr (100 MHz, CDCl$_3$) δ 170.4, 168.9, 158.5, 148.2, 139.5, 135.9, 135.7, 128.9, 128.8, 127.6, 127.1, 123.5, 122.7, 77.1, 49.2, 46.6, 45.8, 36.6, 35.5, 33.2, 30.4, 26.0, 24.4; m/z: 503 [M+H]$^+$ (found [M+H]$^+$, 503.2403, C$_{27}$H$_{30}$N$_6$O$_4$ requires [M+H]$^+$ 503.2401).

Example 9

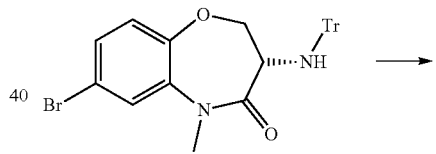

Synthesis of (S,E)-3-(5-methyl-4-oxo-3-(tritylamino)-2,3,4,5-tetrahydrobenzo[b][1,4]oxazepin-7-yl)acrylamide To a mixture of the bromooxobenzoxazapine (0.300 g, 0.586 mmol, 1.0 eq) and acrylamide (0.062 g, 0.879 mmol, 1.5 eq) was added dimethylformamide (5 mL) and the mixture degassed by bubbling argon through for five minutes. Triethylamine (0.178 g, 0.24 mL, 1.758 mmol, 3.0 eq) was added followed by X-PhosPd G2 (0.046 g, 0.059 mmol, 0.1 eq) and the reaction sealed and heated to 120° C. in the microwave for 1 hour. The reaction was partitioned between EtOAc (100 mL) and NaHCO$_3$ (100 mL). The organics were washed with brine (80 mL), water (100 mL) and brine (80 mL) dried (Na$_2$SO$_4$) and concentrated under reduced pressure. MPLC (0→10% MeOH—CH$_2$Cl$_2$) yielded the title compound (0.267 g, 91%) as a pale yellow solid; $^1$H nmr (400 MHz, CDCl₃) δ 7.55 (1H, d, J 15.5 Hz, ArCH=C$\underline{H}$CO), 7.39-7.36 (7H, m, 6H of C(C₆H₅)₃, oxobenzoxazapineH-8), 7.25-7.13 (9H, m, 9H of C(C₆H₅)₃), 7.01 (1H, d, J 8.5 Hz, oxobenzoxazepineH-9), 6.97 (1H, d, J 2.0 Hz, oxobenzoxazepineH-6), 6.39 (1H, d, J 15.5 Hz, ArC$\underline{H}$=CHCO), 5.95 (2H, br s, NH₂), 4.51 (1H, dd, J 9.5, 7.0 Hz, 1H of oxobenzoxazepineH-2), 4.39 (1H, dd, J 11.5, 9.5 Hz, 1H of oxobenzoxazepineH-2), 3.54 (1H, dt, J 11.5, 7.5 Hz, oxobenzoxazapineH-3), 3.31 (1H, d, J 8.5 Hz, NH), 2.94 (3H, s, NCH₃); m/z: 526 [M+Na]⁺, 243 [C(C₆H₅)₃]⁺.

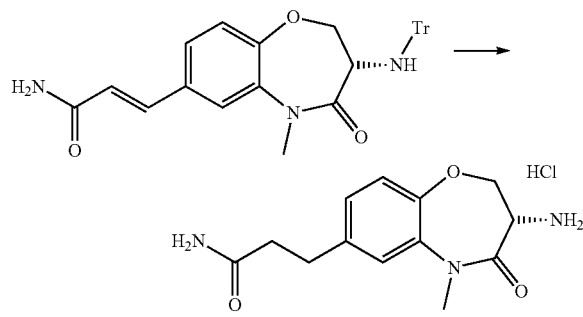

Synthesis of(S)-3-(3-amino-5-methyl-4-oxo-2,3,4,5-tetrahydrobenzo[b][1,4]oxazepin-7-yl)propanamide A solution of the α,β-unsaturated carboxamide (0.267 g, 0.532 mmol, 1.0 eq) in ethyl acetate-methanol (5:2, 7 mL) was purged with nitrogen and palladium on carbon (0.100 g) added. The reaction was purged with hydrogen and stirred under an atmosphere of hydrogen for 2 hours. The reaction was purged with nitrogen and filtered through celite, eluting with EtOAc (30 mL). The filtrate was concentrated under reduced pressure. The residue was dissolved in dioxane (5 mL) and hydrogen chloride (0.66 mL of a 4M solution in dioxane, 2.659 mmol, 5.0 eq) added. The reaction was stirred at room temperature for 6 hours, a white solid formed. The reaction was concentrated to dryness and used without purification; m/z: 265 [M+H]⁺.

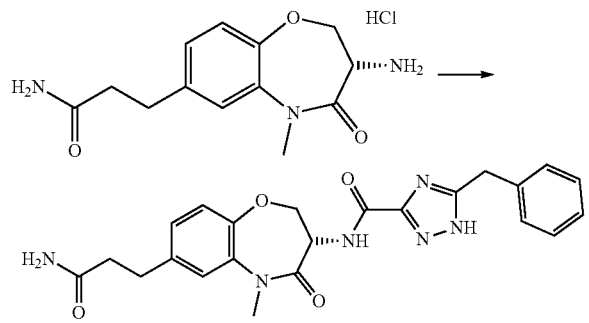

Synthesis of (S)—N-(7-(3-amino-3-oxopropyl)-5-methyl-4-oxo-2,3,4,5-tetrahydrobenzo[b][1,4]oxazepin-3-yl)-5-benzyl-1H-1,2,4-triazole-3-carboxamide To a mixture of the aminooxobenzoxazapine hydrochloride (0.134 mmol, 1.0 eq) and the benzyltriazole carboxylic acid (0.033 g, 0.161 mmol, 1.2 eq) in dimethylformamide (1.0 mL) was added diisopropylethylamine (0.043 g, 0.058 mL, 0.335 mmol, 2.5 eq) followed by HATU (0.102 g, 0.268 mmol, 2.0 eq). The reaction was stirred at room temperature for 4 hours and partitioned between EtOAc—CH₂Cl₂ (5:1, 60 mL) and water (60 mL). The organics were washed with brine (50 mL), water (60 mL) and brine (50 mL). The organics were dried (Na₂SO₄) and concentrated under reduced pressure. MPLC (0→10% MeOH—CH₂Cl₂) yielded the title compound as a white solid; ¹H nmr (400 MHz, CDCl₃) δ 8.05 (1H, d, J 7.5 Hz, NH), 7.36-7.28 (5H, m, 5×ArH), 7.11-7.06 (3H, m, 3×ArH), 5.44 (2H, br s, CONH₂), 5.02 (1H, dt, J 11.0, 7.5 Hz, oxobenzoxazapineH-3), 4.68 (1H, dd, J 9.5, 7.5 Hz, 1H of oxobenzoxazapineH-2), 4.24 (1H, dd, J 11.0, 9.5 Hz, 1H of oxobenzoxazapineH-2), 4.17 (2H, s, C$\underline{H}$₂C₆H₅), 3.41 (3H, s, NCH₃), 2.99 (2H, t, J 7.5 Hz, 2H of ArCH₂CH₂CO), 2.54 (2H, t, J 7.5 Hz, 2H of ArCH₂CH₂CO); m/z: 449 [M+H]⁺.

Example 10

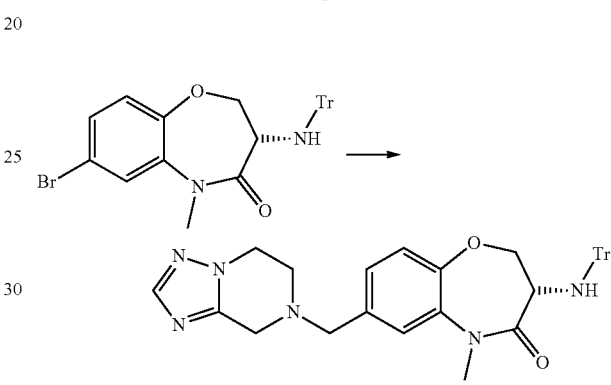

Formation of (S)-7-((5,6-dihydro-[1,2,4]triazolo[1,5-a]pyrazin-7(8H)-yl)methyl)-5-methyl-3-(tritylamino)-2,3-dihydrobenzo[b][1,4]oxazepin-4(5H)-one Dioxane (4 mL) and water (2 mL) were added to a mixture of the bromobenzoxazapine (0.270 g, 0.527 mmol, 1.0 eq), 7-((trifluoro-λ⁴-boraneyl)methyl)-5,6,7,8-tetrahydro-[1,2,4]triazolo[1,5-a]pyrazine, potassium salt (0.180 g, 0.738 mmol, 1.4 eq) and caesium carbonate (0.515 g, 1.581 mmol, 3.0 eq). The reaction was degassed by bubbling argon through for ten minutes. X-PhosPd G2 (0.021 g, 0.026 mmol, 0.05 eq) was added and the reaction sealed and heated in the microwave to 140° C. for 45 minutes. The reaction was partitioned between EtOAc (80 mL) and NaHCO₃ (80 mL). The organics were washed with brine (80 mL), dried (Na₂SO₄) and concentrated under reduced pressure. MPLC (0→10% MeOH [2M NH3]—CH₂Cl₂) yielded the title compound (0.255 g, %) as a yellow oil; ¹H nmr (400 MHz, CDCl₃) δ 7.88 (1H, s, triazoleH-3), 7.38-7.35 (6H, m, 6H of C(C₆H₅)₃), 7.21-7.11 (9H, m, 9H of C(C₆H₅)₃), 7.02 (1H, dd, J 8.0, 2.0 Hz, oxobenzoxazapineH-8), 6.97 (1H, d, J 8.0 Hz, oxobenzoxazapineH-9), 6.87 (1H, d, J 2.0 Hz, oxobenzoxazapineH-6), 4.50 (1H, dd, J 10.0, 7.5 Hz, 1H of oxobenzoxazapineH-2), 4.36 (1H, dd, J 11.5, 10.0 Hz, 1H of oxobenzoxazapineH-2), 4.16 (2H, t, J 5.5 Hz, 2H of NCH₂CH₂N), 3.82 (2H, s, ArCH₂N or NCH₂CN), 3.69 (2H, s, ArCH₂N or NCH₂CN), 3.51 (1H, dd, J 11.5, 7.5 Hz, oxobenzoxazapineH-3), 2.91 (2H, t, J 5.5 Hz, 2H of ArCH₂CH₂N), 2.88 (3H, s, NCH₃); m/z: 593 [M+Na]⁺, 243 [C(C₆H₅)₃]⁺.

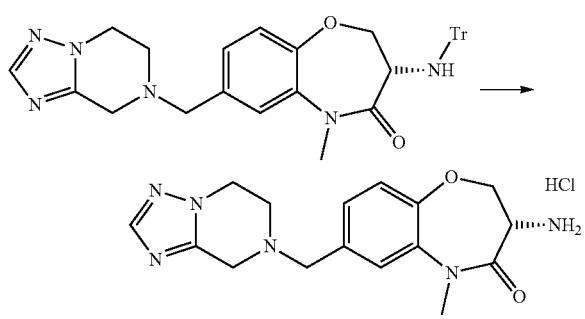

Deprotection of the Trityl Group

To a solution of the trityl protected amine (0.255 g, 0.447 mmol, 1.0 eq) in dioxazne (4.0 mL) was added hydrogen chloride (0.56 mL of a 4M solution in dioxane, 2.237 mmol, 5.0 eq). A white precipitate formed. The reaction was stirred at room temperature for 14 hours. The reaction was concentrated to dryness and used without purification; m/z: 329 [M+H]$^+$.

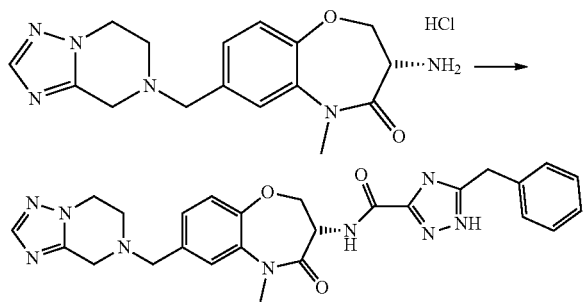

Formation of (S)-5-benzyl-N-(7-((5,6-dihydro-[1,2,4]triazolo[1,5-a]pyrazin-7(8H)-yl)methyl)-5-methyl-4-oxo-2,3,4,5-tetrahydrobenzo[b][1,4]oxazepin-3-yl)-1H-1,2,4-triazole-3-carboxamide To a solution of the aminooxobenzoxazapine hydrochloride (0.377 mmol, 1.0 eq) and benzyltriazole carboxylic acid (0.077 g, 0.377 mmol, 1.0 eq) in dimethylformamide (4.0 mL) was added diisopropylethylamine (0.122 g, 0.16 mL, 0.943 mmol, 2.5 eq). The reaction was cooled to 0° C. and HATU (0.143 g, 0.377 mmol, 1.0 eq) added. The reaction was stirred at 0° C. for 2 hours and room temperature for 18 hours. The reaction was partitioned between EtOAc—CH$_2$Cl$_2$ (9:1, 60 mL) and NaHCO$_3$-water (1:1, 60 mL). The organics were washed with brine (60 mL). The combined aqueous phase was back-extracted with EtOAc (30 mL). The combined organics were washed with water (90 mL) and brine (90 mL), dried (Na$_2$SO$_4$) and concentrated under reduced pressure. MPLC (0→8% MeOH—CH$_2$Cl$_2$) yielded the title compound as a white solid; $^1$H nmr (400 MHz, CDCl$_3$) δ 7.90 (1H, br m, NH), 7.75 (1H, s, triazoleH-3), 7.29-7.21 (7H, m, 7×ArH), 7.16 (1H, d, J 8.0 Hz, oxobenzoxazapineH-9), 5.10 (1H, oxobenzoxazapineH-3), 4.74 (1H, dd, J 9.5, 7.5 Hz, 1H of oxobenzoxazapineH-2), 4.28 (1H, t, 10.0 Hz, 1H of oxobenzoxazapineH-2), 4.21 (2H, t, J 5.5 Hz, 2H of NCH$_2$CH$_2$N), 4.15 (2H, s, NCH$_2$C$_6$H5), 3.84, 3.78 (2H, 2d AB system, J 15.5 Hz, ArCH$_2$N or NCH$_2$C), 3.77, 3.73 (2H, 2d AB system, J 13.5 Hz, ArCH$_2$N or NCH$_2$C), 3.40 (3H, s, NCH$_3$), 3.02 (2H, t, J 5.5 Hz, 2H of NCH$_2$CH$_2$N); m/z: 514 [M+H]$^+$ (found [M+H]$^+$, 514.2324, C$_{26}$H$_{27}$N$_9$O$_3$ requires [M+H]$^+$ 514.2310).

Additional exemplary compound embodiments are described below.

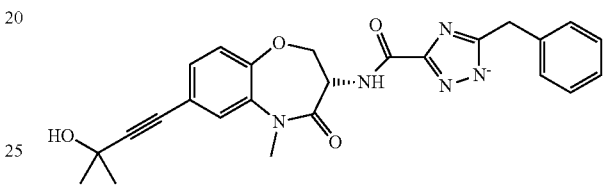

(S)-5-benzyl-3-((7-(3-hydroxy-3-methylbut-1-yn-1-yl)-5-methyl-4-oxo-2,3,4,5-tetrahydrobenzo[b][1,4]oxazepin-3-yl)carbamoyl)-1,2,4-triazol-1-ide $^1$H nmr (400 MHz, D$_6$DMSO) δ 7.83 (1H, d, J 8.0 Hz, NH), 7.45 (1H, d, J 2.0 Hz, oxobenzoxazapineH-6), 7.25 (1H, dd, J 8.0, 2.0 Hz, oxobenzoxazapineH-8), 7.20-7.15 (5H, m, oxobenzoxazapineH-9, 4H of C$_6$H$_5$), 7.09-7.04 (1H, m, 1H of C$_6$H$_5$), 5.47 (1H, br s, OH), 4.81-4.74 (1H, m, oxobenzoxazapineH-3), 4.39-4.36 (2H, m, 2H of oxobenzoxazapineH-2), 3.84 (2H, s, CH$_2$C$_6$H$_5$), 3.28 (3H, s, NCH$_3$), 1.44 (6H, s, C(CH$_3$)$_2$OH); m/z: 442 [M+H]$^+$.

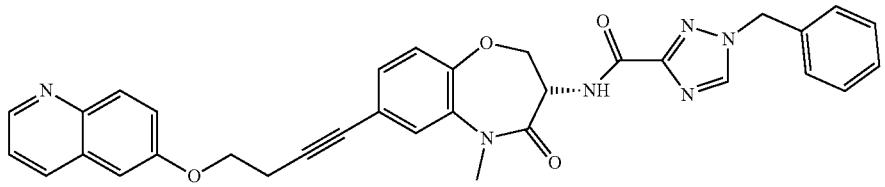

(S)-1-benzyl-N-(5-methyl-4-oxo-7-(4-(quinolin-6-yloxy)but-1-yn-1-yl)-2,3,4,5-tetrahydrobenzo[b][1,4]oxazepin-3-yl)-1H-1,2,4-triazole-3-carboxamide $^1$H nmr (400 MHz, CDCl$_3$) δ 8.76 (1H, dd, J 4.0, 1.5 Hz, quinolineH-2), 8.03 (2H, m, NH, quinolineH-4), 8.01 (1H, d, J 9.5 Hz, quinolineH-8), 7.99 (1H, s, triazoleH-5), 7.40 (1H, dd, J 9.0, 3.0 Hz, quinolineH-7), 7.37-7.7.33 (4H, m, 4H of C$_6$H$_5$, oxobenzoxazapineH-6, H-8), 7.28-7.24 (3H, m, 3H of C$_6$H$_5$, oxobenzoxazapineH-6, H-8), 7.12 (1H, d, J 2.5 Hz, quinolineH-5), 7.10 (1H, d, J 8.0 Hz, oxobenzoxazapineH-9), 5.36 (2H, s, NCH$_2$C$_6$H$_5$), 5.06 (1H, dt, J 11.0, 7.5 Hz, oxobenzoxazapineH-3), 4.75 (1H, dd, J 10.0, 7.5 Hz, 1H of oxobenzoxazapineH-2), 4.30 (2H, t, J 7.0 Hz, CCH$_2$CH$_2$O), 4.24 (1H, dd, J 11.0, 10.0 Hz, 1H of oxobenzoxazapineH-2), 3.39 (3H, s, NCH$_3$), 2.98 (2H, t, J 7.0 Hz, CCH$_2$CH$_2$O); m/z: 573 [M+H]$^+$ (found [M+H]$^+$, 573.2244, C$_{33}$H$_{28}$N$_6$O$_4$ requires [M+H]$^+$ 573.2245).

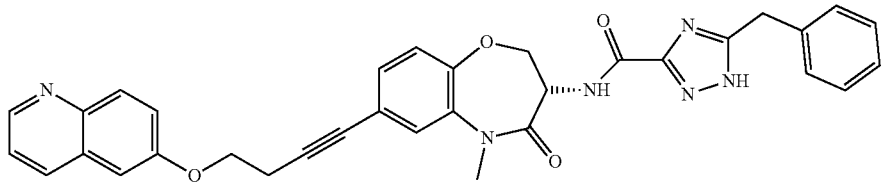

(S)-5-benzyl-N-(5-methyl-4-oxo-7-(4-(quinolin-6-yloxy)but-1-yn-1-yl)-2,3,4,5-tetrahydrobenzo[b][1,4]oxazepin-3-yl)-1H-1,2,4-triazole-3-carboxamide $^1$H nmr (400 MHz, CDCl$_3$) δ 8.73 (1H, dd, J 4.0, 1.5 Hz, quinolineH-2), 8.05 (2H, m, NH, quinolineH-4), 8.00 (1H, d, J 9.5 Hz, quinolineH-8), 7.40 (1H, dd, J 9.5, 3.0 Hz, quinolineH-7), 7.34 (1H, m, quinolineH-3), 7.25 (1H, dd, J 8.0, 2.0 Hz, oxobenzoxazapineH-8), 7.25-7.20 (6H, m, C$_6$H$_5$, oxobenzoxazapineH-7), 7.11 (1H, d, J 3.0 Hz, quinolineH-5), 7.09 (1H, d, J 8.0 Hz, oxobenzoxazapineH-9), (3H, s, NCH$_3$), 3.01 (2H, td, J 5.0, 1.5 Hz, 2H of NCH$_2$CH$_2$N); $^{13}$C nmr (100 MHz, CDCl$_3$) δ 168.8, 158.4, 156.6, 153.5 (q, J 39.5 Hz), 152.2, 149.6, 143.9, 136.4, 134.5, 133.7, 129.2, 129.0, 128.2, 127.8, 123.4, 123.3, 119.2 (q, J 270.5 Hz), 77.2, 60.6, 54.3, 50.7, 49.2, 48.4, 47.1, 35.6; $^{19}$F nmr (380 MHz, CDCl$_3$) δ −65.4 m/z: 582 [M+H]$^+$ (found [M+H]$^+$, 582.2188, C$_{27}$H$_{26}$F$_3$N$_9$O$_3$ requires [M+H]$^+$ 582.2183).

5.02 (1H, dt, J 11.0, 7.5 Hz, oxobenzoxazapineH-3), 4.67 (1H, dd, J 9.5, 7.5 Hz, 1H of oxobenzoxazapineH-2), 4.29 (2H, t, J 7.0 Hz, CCH$_2$CH$_2$O), 4.26 (1H, dd, J 11.0, 10.0 Hz, 1H of oxobenzoxazapineH-2), 4.14 (2H, s, CH$_2$C$_6$H$_5$), 3.37 (3H, s, NCH$_3$), 2.98 (2H, t, J 7.0 Hz, CCH$_2$CH$_2$O); $^{13}$C nmr (100 MHz, CDCl$_3$) δ 168.7, 156.6, 149.7, 148.0, 144.3, 136.0, 134.9, 131.0, 130.8, 129.2, 128.8 (2C), 128.6, 127.1, 126.5, 123.1, 122.4, 121.4, 121.0, 106.3, 86.6, 80.7, 77.2, 66.2, 49.1, 35.4, 33.4, 20.4; m/z: 573 [M+H]$^+$ (found [M+H]$^+$, 573.2262, C$_{33}$H$_{28}$N$_6$O$_4$ requires [M+H]$^+$ 573.2245).

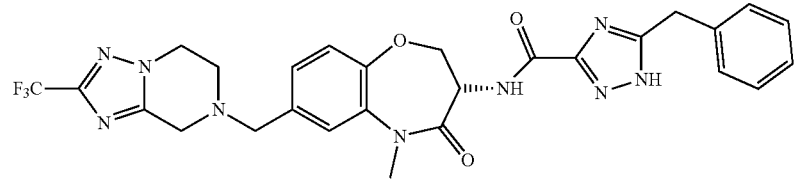

(S)-5-benzyl-N-(5-methyl-4-oxo-7-((2-(trifluoromethyl)-5,6-dihydro-[1,2,4]triazolo[1,5-a]pyrazin-7(8H)-yl)methyl)-2,3,4,5-tetrahydrobenzo[b][1,4]oxazepin-3-yl)-1H-1,2,4-triazole-3-carboxamide $^1$H nmr (400 MHz, CDCl$_3$) δ 8.02 (1H, d, J 7.5 Hz, NH), 7.27-7.21 (6H, m, C$_6$H$_5$, oxobenzoxazapineH-8), 7.21 (1H, dd, J 7.5, 2.0 Hz, oxobenzoxazapineH-8), 7.15 (1H, d, J 8.0 Hz, oxobenzoxazapineH-9), 5.07 (1H, dt, J 11.0, 7.5 Hz,

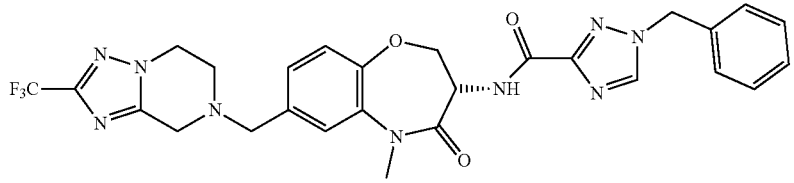

(S)-1-benzyl-N-(5-methyl-4-oxo-7-((2-(trifluoromethyl)-5,6-dihydro-[1,2,4]triazolo[1,5-a]pyrazin-7(8H)-yl)methyl)-2,3,4,5-tetrahydrobenzo[b][1,4]oxazepin-3-yl)-1H-1,2,4-triazole-3-carboxamide $^1$H nmr (400 MHz, CDCl$_3$) δ 8.04 (1H, d, J 7.5 Hz, NH), 8.00 (1H, s, triazoleH-5), 7.38-7.33 (3H, m, 3H of C$_6$H$_5$), 7.27-7.24 (2H, m, 2H of C$_6$H$_5$), 7.19 (2H, m, oxobenzoxazapineH-6, H-8), 7.15 (1H, d, J 8.0 Hz, oxobenzoxazapineH-9), 5.35 (2H, s, NCH$_2$C$_6$H$_5$), 5.09 (1H, dt, J 11.0, 7.5 Hz, oxobenzoxazapineH-3), 4.73 (1H, dd, J 9.5, 7.5 Hz, 1H of oxobenzoxazapineH-2), 4.26-4.21 (3H, m, 1H of oxobenzoxazapineH-2, 2H of NCH$_2$CH$_2$N), 3.87 (2H, s, 2H of ArCH$_2$NCH$_2$C), 3.75 (2H, s, 2H of ArCH$_2$NCH$_2$C), 3.40 oxobenzoxazapineH-3), 4.69 (1H, dd, J 9.5, 7.5 Hz, 1H of oxobenzoxazapineH-2), 4.29-4.23 (3H, m, 1H of oxobenzoxazapineH-2, 2H of NCH$_2$CH$_2$N), 4.12 (2H, s, CH$_2$C$_6$H$_5$), 3.86 (2H, s, 2H of ArCH$_2$NCH$_2$C), 3.76 (2H, s, 2H of ArCH$_2$NCH$_2$C), 3.39 (3H, s, NCH$_3$), 3.03 (2H, t, J 5.5 Hz, 2H of NCH$_2$CH$_2$N); $^{13}$C nmr (100 MHz, CDCl$_3$) δ 168.8, 158.7, 153.4 (q, J 39.5 Hz), 152.2, 149.6, 136.3, 135.7, 134.6, 128.8, 128.7, 127.9, 127.1, 123.4, 123.2, 123.1, 119.2 (q, J 269.5 Hz), 77.1, 60.7, 50.4, 49.4, 48.6, 47.1, 35.6, 33.0; $^{19}$F nmr (380 MHz, CDCl$_3$) δ −65.3 m/z: 582 [M+H]$^+$ (found [M+H]$^+$, 582.2167, C$_{27}$H$_{26}$F$_3$N$_9$O$_3$ requires [M+H]$^+$ 582.2183).

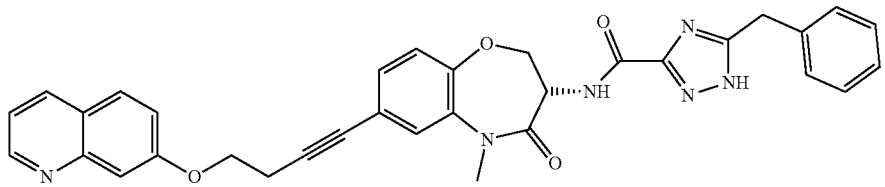

(S)-5-benzyl-N-(5-methyl-4-oxo-7-(4-(quinolin-7-yloxy)but-1-yn-1-yl)-2,3,4,5-tetrahydrobenzo[b][1,4]oxazepin-3-yl)-1H-1,2,4-triazole-3-carboxamide $^1$H nmr (400 MHz, CDCl$_3$) δ 8.75 (1H, dd, J 4.5, 2.0 Hz, quinolineH-2), 8.09-8.06 (2H, m, NH, quinolineH-4), 7.70 (1H, d, J 9.0 Hz, quinolineH-5), 7.50 (1H, d, J 2.5 Hz, quinolineH-8), 7.27-7.17 (9H, m, quinolineH-3, H-6, oxobenzoxazapineH-6, H-8, C$_6$H$_5$), 7.07 (1H, d, J 8.5 Hz, oxobenzoxazapineH-9), 5.00 (1H, dt, J 11.0, 7.5 Hz, oxobenzoxazapineH-3), 4.66 (1H, dd, J 9.5, 7.5 Hz, 1H of oxobenzoxazapineH-2), 4.31 (2H, td, J 7.0, 2.5 Hz, OCH$_2$CH$_2$C), 4.24 (1H, dd, J 11.0, 9.5 Hz, 1H of oxobenzoxazapineH-2), 4.13 (2H, s, CH$_2$C$_6$H$_5$), 3.36 (3H, s, NCH$_3$), 2.97 (2H, t, J 7.0 Hz, OCH$_2$CH$_2$C); $^{13}$C nmr (100 MHz, CDCl$_3$) δ 168.7, 159.6, 158.6, 150.3, 149.6, 149.5, 136.0 (2C), 135.9, 131.0, 128.9, 128.8, 128.7, 127.0, 126.5, 123.7, 123.0, 121.0, 120.1, 119.1, 107.9, 86.8, 80.6, 77.2, 66.1, 49.2, 35.5, 33.2, 20.3; m/z: 573 [M+H]$^+$ (found [M+H]$^+$, 573.2269, C$_{33}$H$_{28}$N$_6$O$_4$ requires [M+H]$^+$ 573.2245).

149.8, 149.7, 143.9, 135.9, 135.7, 133.7, 130.9, 129.2, 128.9, 128.2, 126.5, 123.7, 123.1, 121.0, 119.9, 119.1, 108.2, 86.6, 80.7, 77.1, 66.1, 54.3, 49.1, 38.6, 35.5, 20.3; m/z: 573 [M+H]$^+$ (found [M+H]$^+$, 573.2249, C$_{33}$H$_{28}$N$_6$O$_4$ requires [M+H]$^+$ 573.2245).

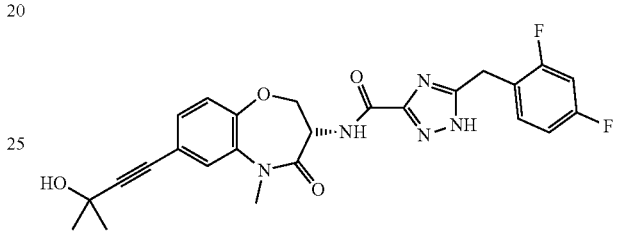

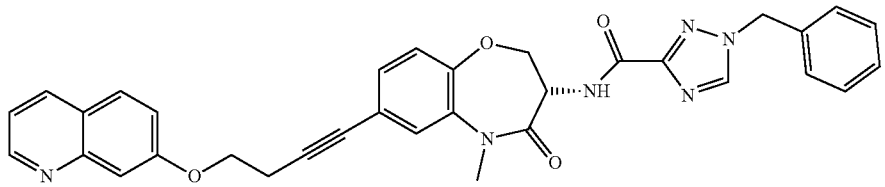

(S)-1-benzyl-N-(5-methyl-4-oxo-7-(4-(quinolin-7-yloxy)but-1-yn-1-yl)-2,3,4,5-tetrahydrobenzo[b][1,4]oxazepin-3-yl)-1H-1,2,4-triazole-3-carboxamide $^1$H nmr (400 MHz, CDCl$_3$) δ 8.20 (1H, dd, J 4.5, 2.0 Hz, quinolineH-2), 8.06 (1H, dd, J 8.0, 1.5 Hz, quinolineH-4), 8.03 (1H, d, J 7.0 Hz, NH), 7.99 (1H, s, triazoleH-5), 7.70 (1H, d, J 9.0 Hz, quinolineH-5), 7.45 (1H, d, J 2.5 Hz, quinolineH-8), 7.37-7.33 (3H, m, 3H of C$_6$H$_5$, oxobenzoxazapineH-6), 7.27-7.22 (6H, m, quinolineH-6, H-3, oxobenzoxazapineH-8, 3H of C$_6$H$_5$, oxobenzoxazapineH-6), 7.09 (1H, dd, J 8.0, 0.5 Hz, oxobenzoxazapineH-9), 5.35 (2H, s, NCH$_2$C$_6$H$_5$), 5.06 (1H, dt, J 11.0, 7.5 Hz, oxobenzoxazapineH-3), 4.75 (1H, dd, J 9.5, 7.5 Hz, 1H of oxobenzoxazapineH-2), 4.33 (2H, t, J 7.0 Hz, OCH$_2$CH$_2$C), 4.23 (1H, dd, J 9.5, 7.5 Hz, 1H of oxobenzoxazapineH-2), 3.39 (3H, s, NCH$_3$), 2.98 (2H, t, J 7.0 Hz, OCH$_2$CH$_2$C); $^{13}$C nmr (100 MHz, CDCl$_3$) δ 168.8, 159.4, 158.4, 156.6, 150.6,

(S)-5-(2,4-difluorobenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.05 (1H, d, J 7.5 Hz, NH), 7.27-7.20 (3H, m, oxobenzoxazapineH-6, H-8, 1H of C$_6$H$_3$F$_2$), 7.10 (1H, d, J 9.0 Hz, oxobenzoxazapineH-9), 6.82-6.74 (2H, m, 2H of C$_6$H$_3$F$_2$), 4.99 (1H, dt, J 11.0, 7.5 Hz, oxobenzoxazapineH-3), 4.66 (1H, dd, J 10.0, 7.5 Hz, 1H of oxobenzoxazapineH-2), 4.27 (1H, dd, J 11.0, 10.0 Hz, 1H of oxobenzoxazapineH-2), 4.12 (2H, s, CH$_2$C$_6$H$_3$F$_2$), 3.39 (3H, s, NCH$_3$), 1.61 (6H, s, C(CH$_3$)$_2$OH); $^{19}$F nmr (380 MHz, CDCl$_3$) δ -111.2; -113.2; m/z: 478 [M+H—H$_2$O]$^+$ (found [M+H]$^+$, 496.1795, C$_{25}$H$_{23}$F$_2$N$_5$O$_4$ requires [M+H]$^+$ 496.1791).

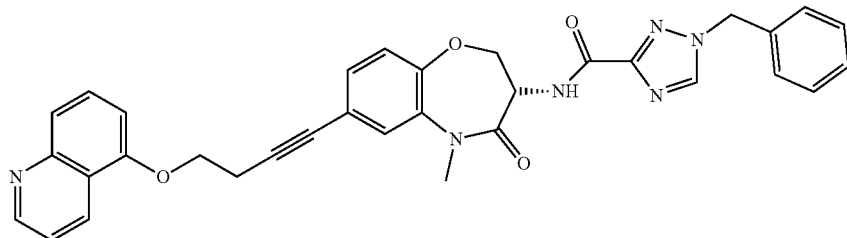

(S)-1-benzyl-N-(5-methyl-4-oxo-7-(4-(quinolin-5-yloxy)but-1-yn-1-yl)-2,3,4,5-tetrahydrobenzo[b][1,4]oxazepin-3-yl)-1H-1,2,4-triazole-3-carboxamide $^1$H nmr (400 MHz, CDCl$_3$) δ 8.89 (1H, dd, J 4.0, 2.0 Hz, quinolineH-2), 8.63 (1H, ddd, J 8.5, 2.0, 1.0 Hz, quinolineH-4), 8.02 (1H, d, J 7.5 Hz, NH), 7.99 (1H, s, triazoleH-5), 7.70 (1H, d, J 8.5 Hz, quinolineH-8), 7.59 (1H, dd, J 8.5, 7.5 Hz, quinolineH-7), 7.38-7.33 (4H, m, quinolineH-3, 3H of C$_6$H$_5$, oxobenzoxazapineH-6), 7.26-7.22 (4H, m, oxobenzoxazapineH-8, 3H of C$_6$H$_5$, oxobenzoxazapineH-6), 7.09 (1H, d, J 8.0 Hz, oxobenzoxazapineH-9), 6.89 (1H, dd, J 7.5, 0.5 Hz, quinolineH-6), 5.35 (2H, s, NCH$_2$C$_6$H$_5$), 5.06 (1H, dt, J 11.0, 7.5 Hz, oxobenzoxazapineH-3), 4.73 (1H, dd, J 10.0, 7.5 Hz, 1H of oxobenzoxazapineH-2), 4.35 (2H, t, J 7.0 Hz, OCH$_2$CH$_2$C), 4.24 (1H, dd, J 11.0, 10.0 Hz, 1H of oxobenzoxazapineH-2), 3.37 (3H, s, NCH$_3$), 3.03 (2H, t, J 7.0 Hz, OCH$_2$CH$_2$C); m/z: 573 [M+H]$^+$ (found [M+H]$^+$, 573.2251, C$_{33}$H$_{28}$N$_6$O$_4$ requires [M+H]$^+$ 573.2245).

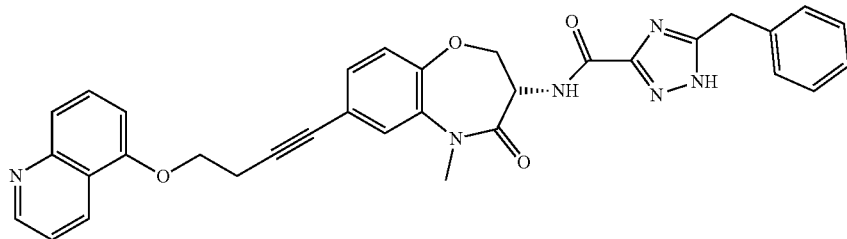

(S)-5-benzyl-N-(5-methyl-4-oxo-7-(4-(quinolin-5-yloxy)but-1-yn-1-yl)-2,3,4,5-tetrahydrobenzo[b][1,4]oxazepin-3-yl)-1H-1,2,4-triazole-3-carboxamide $^1$H nmr (400 MHz, CDCl$_3$) δ 8.85 (1H, dd, J 4.0, 2.0 Hz, quinolineH-2), 8.64 (1H, ddd, J 8.5, 2.0, 1.0 Hz, quinolineH-4), 8.07 (1H, d, J 7.5 Hz, NH), 7.69 (1H, d, J 8.5 Hz, quinolineH-8), 7.59 (1H, dd, J 8.5, 7.5 Hz, quinolineH-3), 7.26-7.17 (7H, m, C$_6$H$_5$, oxobenzoxazapineH-6, H-8), 7.08 (1H, d, J 8.0 Hz, oxobenzoxazapineH-9), 6.90 (1H, dd, J 8.0, 0.5 Hz, quinolineH-6), 5.02 (1H, dt, J 11.0, 7.5 Hz, oxobenzoxazapineH-3), 4.66 (1H, dd, J 9.5, 7.5 Hz, 1H of oxobenzoxazapineH-2), 4.36 (2H, t, J 7.0 Hz, OCH$_2$CH$_2$C), 4.25 (1H, dd, J 11.0, 10.0 Hz, 1H of oxobenzoxazapineH-2), 4.13 (2H, s, CH$_2$C$_6$H$_5$), 3.36 (3H, s, NCH$_3$), 3.04 (2H, t, J 7.0 Hz, OCH$_2$CH$_2$C); $^{13}$C nmr (100 MHz, CDCl$_3$) δ 168.7, 158.5, 153.9, 150.6, 149.7, 148.9, 136.0, 131.0, 130.9, 129.4, 128.8, 128.7, 127.0, 126.5, 123.1, 121.8, 121.0, 120.9, 120.3, 105.4, 86.7, 80.7, 77.2, 49.1, 35.5, 33.2, 20.5; m/z: 573 [M+H]$^+$ (found [M+H]$^+$, 573.2266, C$_{33}$H$_{28}$N$_6$O$_4$ requires [M+H]$^+$ 573.2245).

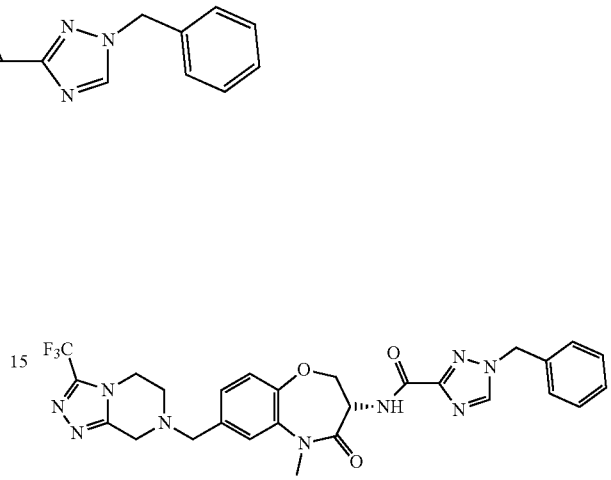

(S)-1-benzyl-N-(5-methyl-4-oxo-7-((3-(trifluoromethyl)-5,6-dihydro-[1,2,4]triazolo[4,3-a]pyrazin-7(8H)-yl)methyl)-2,3,4,5-tetrahydrobenzo[b][1,4]oxazepin-3-yl)-1H-1,2,4-triazole-3-carboxamide $^1$H nmr (400 MHz, CDCl$_3$) δ 8.06 (1H, d, J 7.5 Hz, NH), 8.02 (1H, s, triazoleH-5), 7.39-7.35 (3H, m, 3×ArH), 7.29-7.7.26 (2H, m, 2×ArH), 7.20 (2H, m, 2×ArH), 7.17 (1H, d, J 8.0 Hz, oxobenzoxazapineH-9), 5.38 (2H, s, NCH$_2$C$_6$H$_5$), 5.12 (1H, dt, J 11.0, 7.5 Hz, oxobenzoxazapineH-3), 4.76 (1H, dd, J 9.5, 7.5 Hz, 1H of oxobenzoxazapineH-2), 4.26 (1H, dd, J 11.0, 10.0 Hz, 1H of oxobenzoxazapineH-2), 4.15 (2H, t, J 5.5 Hz, 2H of NCH$_2$CH$_2$N), 3.98, 3.93 (2H, 2d AB system, J 15.5 Hz, 2H of ArCH$_2$NCH$_2$), 3.76 (2H, s, 2H of ArCH$_2$NCH$_2$), 3.42 (3H, s, NCH$_3$), 2.96 (2H, dt, J 4.0, 5.5 Hz, 2H of NCH$_2$CH$_2$N); $^{19}$F nmr (380 MHz, CDCl$_3$) δ −63.2; m/z: 582 [M+H]$^+$ (found [M+H]$^+$, 582.2173, C$_{27}$H$_{26}$F$_3$N$_9$O$_3$ requires [M+H]$^+$ 582.2183).

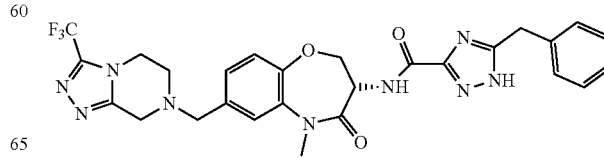

(S)-5-benzyl-N-(5-methyl-4-oxo-7-((3-(trifluoromethyl)-5,6-dihydro-[1,2,4]triazolo[4,3-a]pyrazin-7(8H)-yl)methyl)-2,3,4,5-tetrahydrobenzo[b][1,4]oxazepin-3-yl)-1H-1,2,4-triazole-3-carboxamide $^1$H nmr (400 MHz, CDCl$_3$) δ 8.01 (1H, d, J 7.0 Hz, NH), 7.27-7.19 (7H, m, C$_6$H$_5$, oxobenzoxazapineH-6, H-8), 7.16 (1H, d, J 8.0 Hz, oxobenzoxazapineH-9), 5.09 (1H, dt, J 10.5, 7.5 Hz, oxobenzoxazapineH-3), 4.70 (1H, dd, J 10.0, 7.5 Hz, 1H of oxobenzoxazapineH-2), 4.28 (1H, dd, J 10.5, 10.0 Hz, 1H of oxobenzoxazapineH-2), 4.14 (4H, m, 2H of NCH$_2$CH$_2$N), 2H of ArCH$_2$NCH$_2$ or C$\underline{H}_2$C$_6$H$_5$), 3.93 (2H, s, 2H of ArCH$_2$NCH$_2$ or C$\underline{H}_2$C$_6$H$_5$), 3.78, 3.74 (2H, 2d AB system, J 13.5 Hz, 2H of ArCH$_2$NCH$_2$), 3.40 (3H, s, NCH$_3$), 2.97 (2H, t, J 5.5 Hz, 2H of NCH$_2$CH$_2$N); $^{13}$C nmr (100 MHz, CDCl$_3$) δ 168.8, 158.6, 152.0, 149.6, 143.4 (q, J 40.0 Hz), 136.4, 135.8, 134.3, 128.8, 128.7, 127.9, 127.1, 126.9, 123.4, 123.2, 118.3 (q, J 270.5 Hz), 77.2, 60.8, 49.5, 49.4, 43.6, 35.6, 33.1; $^{19}$F nmr (380 MHz, CDCl$_3$) δ −63.2; m/z: 582 [M+H]$^+$ (found [M+H]$^+$, 582.2208, C$_{27}$H$_{26}$F$_3$N$_9$O$_3$ requires [M+H]$^+$ 582.2183).

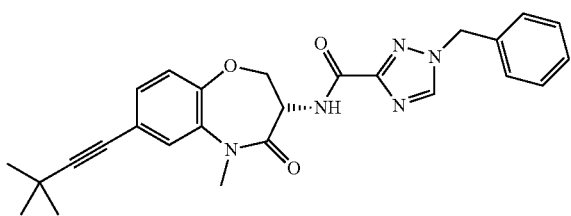

(S)-1-benzyl-N-(7-(3,3-dimethylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.04 (1H, d, J 7.0 Hz, NH), 8.01 (1H, s, triazoleH-5), 7.40-7.36 (3H, m, 3H of C$_6$H$_5$), 7.29-7.23 (4H, m, 2H of C$_6$H$_5$, oxobenzoxazapineH-6, H-8), 7.09 (1H, d, J 9.0 Hz, oxobenzoxazapineH-9), 5.38 (2H, s, NCH$_2$C$_6$H$_5$), 5.06 (1H, dt, J 11.0, 7.5 Hz, oxobenzoxazapineH-3), 4.76 (1H, dd, J 10.0, 7.5 Hz, 1H of oxobenzoxazapineH-2), 4.24 (1H, dd, J 11.0, 10.0 Hz, 1H of oxobenzoxazapineH-2), 3.40 (3H, s, NCH$_3$), 1.32 (9H, s, C(CH$_3$)$_3$); m/z: 458 [M+H]$^+$ (found [M+H]$^+$, 458.2205, C$_{26}$H$_{27}$N$_5$O$_3$ requires [M+H]$^+$ 458.2187).

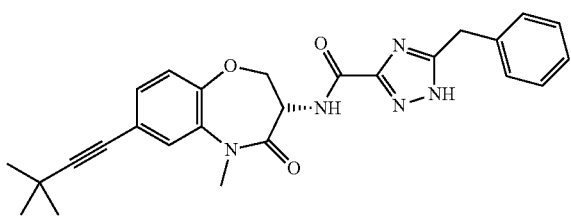

(S)-5-benzyl-N-(7-(3,3-dimethylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.08 (1H, d, J 7.5 Hz, NH), 7.26-7.21 (7H, m, C$_6$H$_5$, oxobenzoxazapineH-6, H-8), 7.07 (1H, d, J 9.0 Hz, oxobenzoxazapineH-9), 5.02 (1H, dt, J 11.0, 7.5 Hz, oxobenzoxazapineH-3), 4.66 (1H, dd, J 11.0, 10.0 Hz, 1H of oxobenzoxazapineH-2), 4.26 (1H, dd, J Hz, 1H of oxobenzoxazapineH-2), 4.15 (2H, s, C$\underline{H}_2$C$_6$H$_5$), 3.40 (3H, s, NCH$_3$), 1.32 (9H, s, C(CH$_3$)$_3$); $^{13}$C nmr (100 MHz, CDCl$_3$) δ 168.7, 158.5, 149.2, 135.9, 135.8, 130.9, 128.8, 128.7, 127.0, 126.4, 122.8, 121.8, 99.4, 77.6, 77.2, 49.1, 35.5, 33.2, 30.9, 27.9; m/z: 458 [M+H]$^+$ (found [M+H]$^+$, 458.2200, C$_{26}$H$_{27}$N$_5$O$_3$ requires [M+H]$^+$ 458.2187).

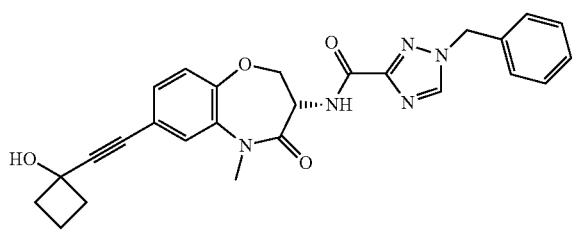

(S)-1-benzyl-N-(7-((1-hydroxycyclobutyl)ethynyl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.02 (1H, d, J 7.5 Hz, NH), 7.99 (1H, s, triazoleH-5), 7.38-7.34 (3H, m, 3H of C$_6$H$_5$), 7.29-7.25 (4H, m, 2H of C$_6$H$_5$, oxobenzoxazapineH-6, H-8), 7.11 (1H, d, J 9.0 Hz, oxobenzoxazapineH-9), 5.36 (2H, s, NCH$_2$C$_6$H$_5$), 5.06 (1H, dt, J 11.0, 7.5 Hz, oxobenzoxazapineH-3), 4.75 (1H, dd, J 9.5, 7.5 Hz, 1H of oxobenzoxazapineH-2), 4.25 (1H, dd, J 11.0, 9.5 Hz, 1H of oxobenzoxazapineH-2), 3.40 (3H, s, NCH$_3$), 2.55-2.49 (2H, m, 2H of cBuH-2, H-4), 2.33 (2H, m, 2H of cBuH-2, H-4), 1.87 (2H, m, cBuH-3); m/z: 472 [M+H]$^+$, 454 [M+H—H$_2$O]$^+$ (found [M+H]$^+$, 472.1994, C$_{26}$H$_{25}$N$_5$O$_4$ requires [M+H]$^+$ 472.1979).

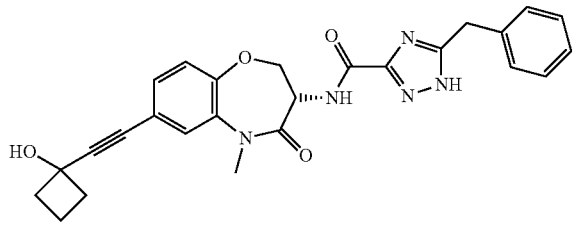

(S)-5-benzyl-N-(7-((1-hydroxycyclobutyl)ethynyl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.10 (1H, d, J 7.5 Hz, NH), 7.29-7.20 (7H, m, C$_6$H$_5$, 2H of oxobenzoxazapineH-6, H-8, H-9), 7.10 (1H, dd, J 7.5, 1.0 Hz, 1H of oxobenzoxazapineH-6, H-8, H-9), 5.01 (1H, dt, J 11.0, 7.5 Hz, oxobenzoxazapineH-3), 4.66 (1H, dd, J 9.5, 7.5 Hz, 1H of oxobenzoxazapineH-2), 4.28 (1H, dd, J 11.0, 9.5 Hz, 1H of oxobenzoxazapineH-2), 4.15, 4.11 (2H, 2d AB system, J 16.0 Hz, C$\underline{H}_2$C$_6$H$_5$), 3.39 (3H, s, NCH$_3$), 2.57-2.50 (2H, m, 2H of cBuH-2, H-4), 2.35 (2H, m, 2H of cBuH-2, H-4), 1.92-1.84 (2H, m, cBuH-3); $^{13}$C (100 MHz, CDCl$_3$) δ 168.7, 158.7, 149.9, 136.0, 135.8, 131.0, 128.8, 128.7, 127.0, 126.5, 123.0, 120.4, 93.4, 81.9, 76.9, 68.2, 49.1, 38.5, 35.5,

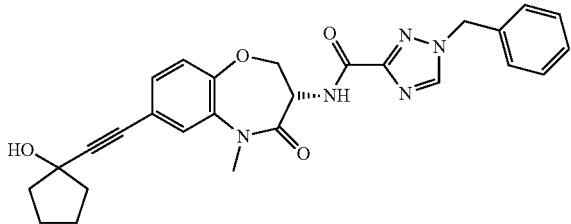

(S)-1-benzyl-N-(7-((1-hydroxycyclopentyl)ethynyl)-
5-methyl-4-oxo-2,3,4,5-tetrahydrobenzo[b][1,4]
oxazepin-3-yl)-1H-1,2,4-triazole-3-carboxamide $^1$H nmr (400 MHz, CDCl$_3$) δ 8.02 (1H, d, J 7.0 Hz, NH), 7.99 (1H, s, triazoleH-5), 7.38-7.34 (3H, m, 3H of C$_6$H$_5$), 7.28-7.26 (4H, m, 2H of C$_6$H$_5$, oxobenzoxazapineH-6, H-8), 7.10 (1H, d, J 9.0 Hz, oxobenzoxazapineH-9), 5.36 (2H, s, NCH$_2$C$_6$H$_5$), 5.06 (1H, dt, J 11.0, 7.5 Hz, oxobenzoxazapineH-3), 4.75 (1H, dd, J 9.5, 7.5 Hz, 1H of oxobenzoxazapineH-2), 4.24 (1H, dd, J 11.0, 9.5 Hz, 1H of oxobenzoxazapineH-2), 3.40 (3H, s, NCH$_3$), 2.08-1.99 (4H, m, cPentaneH-2, H-5), 1.90-1.84 (2H, m, 2H of cPentaneH-3, H-4), 1.83-1.76 (2H, m, 2H of cPentaneH-3, H-4); m/z: 486 [M+H]$^+$, 468 [M+H—H$_2$O]$^+$ (found [M+H]$^+$, 486.2122, C$_{27}$H$_{27}$N$_5$O$_4$ requires [M+H]$^+$ 486.2136).

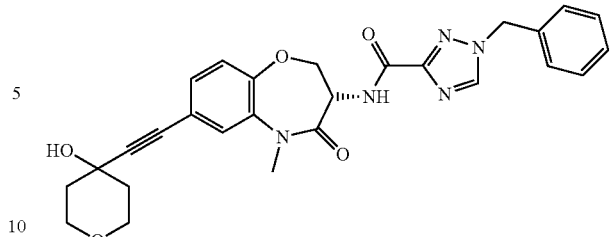

(S)-1-benzyl-N-(7-((4-hydroxytetrahydro-2H-pyran-
4-yl)ethynyl)-5-methyl-4-oxo-2,3,4,5-tetrahydrobenzo[b][1,4]oxazepin-3-yl)-1H-1,2,4-triazole-3-
carboxamide $^1$H nmr (400 MHz, CDCl$_3$) δ 8.03 (1H, d, J 7.0 Hz, NH), 8.02 (1H, s, triazoleH-5), 7.39-7.35 (3H, m, 3H of C$_6$H$_5$), 7.31-7.27 (4H, m, 2H of C$_6$H$_5$, oxobenzoxazapineH-6, H-8), 7.14 (1H, dd, J 8.0, 1.0 Hz, oxobenzoxazapineH-9), 5.37 (2H, s, NCH$_2$C$_6$H$_5$), 5.08 (1H, dt, J 11.5, 7.5 Hz, oxobenzoxazapineH-3), 4.76 (1H, dd, J 9.5, 7.5 Hz, 1H of oxobenzoxazapineH-2), 4.27 (1H, dd, J 11.0, 10.0 Hz, 1H of oxobenzoxazapineH-2), 3.95 (2H, dt, J 12.0, 4.5 Hz, 2H of pyranH-2, H-6), 3.72 (2H, ddd, J 12.0, 9.0, 3.0 Hz, 2H of pyranH-2, H-6), 3.42 (3H, s, NCH$_3$), 2.07-2.02 (2H, m, 2H of pyranH-3, H-5), 1.89 (2H, ddd, J 13.0, 9.0, 4.0 Hz, 2H of pyranH-3, H-5); m/z: 502 [M+H]$^+$, 484 [M+H—H$_2$O]$^+$ (found [M+H]$^+$, 502.2105, C$_{27}$H$_{27}$N$_5$O$_5$ requires [M+H]$^+$ 502.2085).

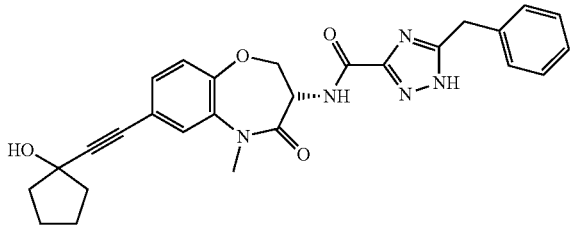

(S)-5-benzyl-N-(7-((1-hydroxycyclopentyl)ethynyl)-
5-methyl-4-oxo-2,3,4,5-tetrahydrobenzo[b][1,4]
oxazepin-3-yl)-1H-1,2,4-triazole-3-carboxamide $^1$H nmr (400 MHz, CDCl$_3$) δ 8.06 (1H, d, J 7.5 Hz, NH), 7.31-7.23 (7H, m, C$_6$H$_5$, oxobenzoxazapineH-6, H-7), 7.10 (1H, d, J 9.0 Hz, oxobenzoxazapineH-9), 5.01 (1H, dt, J 11.0, 7.5 Hz, oxobenzoxazapineH-3), 4.68 (1H, dd, J 9.5, 7.5 Hz, 1H of oxobenzoxazapineH-2), 4.26 (1H, dd, J 11.0, 9.5 Hz, 1H of oxobenzoxazapineH-2), 4.14 (2H, s, CH$_2$C$_6$H$_5$), 3.39 (3H, s, NCH$_3$), 2.08-1.97 (4H, m, cPentaneH-2, H-5), 1.90-1.85 (2H, m, 2H of cPentaneH-3, H-4), 1.82-1.76 (2H, m, 2H of cPentaneH-3, H-4); m/z: 468 [M+H—H$_2$O]$^+$ (found [M+H]$^+$, 486.2154, C$_{27}$H$_{27}$N$_5$O$_4$ requires [M+H]$^+$ 486.2136).

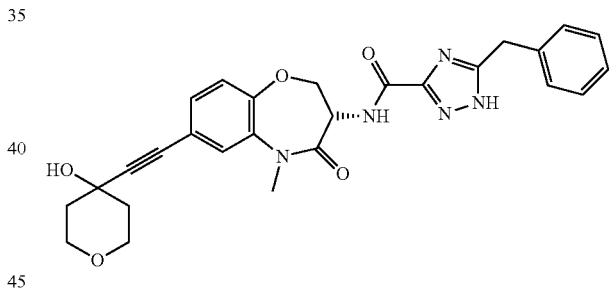

(S)-5-benzyl-N-(7-((4-hydroxytetrahydro-2H-pyran-
4-yl)ethynyl)-5-methyl-4-oxo-2,3,4,5-tetrahydrobenzo[b][1,4]oxazepin-3-yl)-1H-1,2,4-triazole-3-
carboxamide $^1$H nmr (400 MHz, CDCl$_3$) δ 8.07 (1H, d, J 6.5 Hz, NH), 7.28-7.19 (7H, m, C$_6$H$_5$, oxobenzoxazapineH-6, H-8), 7.09 (1H, d, J 8.0 Hz, oxobenzoxazapineH-9), 5.00 (1H, dt, J 11.5, 7.5 Hz, oxobenzoxazapineH-3), 4.64 (1H, dd, J 9.0, 7.5 Hz, 1H of oxobenzoxazapineH-2), 4.27 (1H, t, J 10.5 Hz, 1H of oxobenzoxazapineH-2), 4.12 (2H, s, CH$_2$C$_6$H$_5$), 3.93 (2H, dt, J 12.0, 4.5 Hz, 2H of pyranH-2, H-6), 3.70 (2H, ddd, J 11.5, 9.0, 2.5 Hz, 2H of pyranH-2, H-6), 3.37 (3H, s, NCH$_3$), 2.03 (2H, m, 2H of pyranH-3, H-5), 1.88 (2H, ddd, J 13.0, 9.0, 4.0 Hz, 2H of pyranH-3, H-5); $^{13}$C nmr (100 MHz, CDCl$_3$) δ 168.6, 158.7, 150.1, 136.1, 135.7, 131.1, 128.9, 128.8, 127.1, 126.6, 123.2, 120.0, 92.3, 83.4, 77.3, 66.1, 64.8, 49.1, 39.9, 35.6, 33.1; m/z: 484 [M+H—H$_2$O]$^+$ (found [M+H]$^+$, 502.2080, C$_{27}$H$_{27}$N$_5$O$_5$ requires [M+H]$^+$ 502.2085).

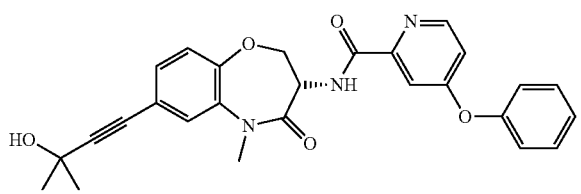

(S)-i-(7-(3-hydroxy-3-methylbut-1-yn-1-yl)-5-methyl-4-oxo-2,3,4,5-tetrahydrobenzo[b][1,4]oxazepin-3-yl)-4-phenoxypicolinamide ¹H nmr (400 MHz, CDCl₃) δ 8.85 (1H, d, J 7.5 Hz, NH), 8.42 (1H, d, J 5.5 Hz, pyH-6), 7.60 (1H, d, J 2.5 Hz, pyH-3), 7.40 (2H, m, 2H of C₆H₅), 7.27-7.22 (3H, m, oxobenzoxazapineH-6, H-8, 1H of C₆H₅), 7.10 (1H, d, J 9.0 Hz, oxobenzoxazapineH-9), 7.05 (2H, m, 2H of C₆H₅), 6.93 (1H, dd, J 5.5, 2.5 Hz, pyH-5), 5.01 (1H, dt, J 11.0, 7.5 Hz, oxobenzoxazapineH-3), 4.70 (1H, dd, J 9.5, 7.5 Hz, 1H of oxobenzoxazapineH-2), 4.28 (1H, dd, J 11.0, 9.5 Hz, 1H of oxobenzoxazapineH-2), 3.41 (3H, s, NCH₃), 1.61 (6H, s, C(CH₃)₂OH); ¹³C nmr (100 MHz, CDCl₃) δ 169.0, 166.1, 163.6, 153.7, 151.3, 150.1, 150.0, 136.2, 130.8, 130.3, 126.4, 125.6, 123.0, 120.7, 120.3, 114.4, 110.6, 94.4, 80.7, 77.2, 65.6, 49.3, 35.4, 31.4; m/z: 472 [M+H]+(found [M+H]⁺, 472.1891, C₂₇H₂₅N₃O₅ requires [M+H]⁺ 472.1867).

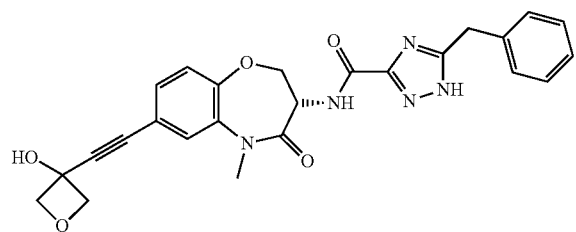

(S)-5-benzyl-N-(7-((3-hydroxyoxetan-3-yl)ethynyl)-5-methyl-4-oxo-2,3,4,5-tetrahydrobenzo[b][1,4]oxazepin-3-yl)-1H-1,2,4-triazole-3-carboxamide ¹H nmr (400 MHz, CDCl₃) δ 8.06 (1H, d, J 7.5 Hz, NH), 7.33-7.26 (7H, m, C₆H₅, oxobenzoxazapineH-6, H-8), 7.14 (1H, d, J 9.0 Hz, oxobenzoxazapineH-9), 5.03 (1H, dt, J 11.0, 7.5 Hz, oxobenzoxazapineH-3), 4.93 (2H, d, J 7.0 Hz, 2H of oxetaneH-2, H-4), 4.80 (2H, d, J 7.0 Hz, 2H of oxetaneH-2, H-4), 4.70 (1H, dd, J 10.0, 7.5 Hz, 1H of oxobenzoxazapineH-2), 4.30 (1H, dd, J 11.0, 9.5 Hz, 1H of oxobenzoxazapineH-2), 4.16 (2H, s, CH₂C₆H₅), 3.41 (3H, s, NCH₃), 2.98 (1H, br s, OH); m/z: 474 [M+H]⁺ (found [M+H]⁺, 474.1789, C₂₅H₂₃N₅O₅ requires [M+H]⁺ 474.1772).

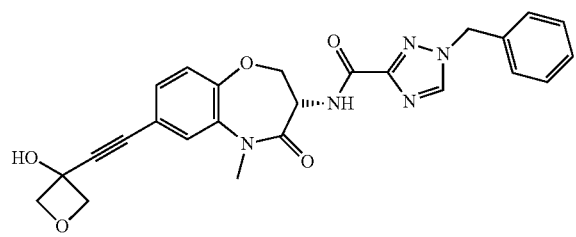

(S)-1-benzyl-N-(7-((3-hydroxyoxetan-3-yl)ethynyl)-5-methyl-4-oxo-2,3,4,5-tetrahydrobenzo[b][1,4]oxazepin-3-yl)-1H-1,2,4-triazole-3-carboxamide ¹H nmr (400 MHz, CDCl₃) δ 8.03 (1H, d, J 7.0 Hz, NH), 8.01 (1H, s, triazoleH-5), 7.37 (3H, m, 3H of C₆H₅), 7.28-7.25 (4H, m, 2H of C₆H₅, oxobenzoxazapineH-6, H-8), 7.12 (1H, d, J 8.5 Hz, oxobenzoxazapineH-9), 5.35 (2H, s, NCH₂C₆H₅), 5.04 (1H, dt, J 11.5, 7.5 Hz, oxobenzoxazapineH-3), 4.89 (2H, dd, J 7.0, 1.0 Hz, 2H of oxetaneH-2, H-4), 4.78 (2H, ddd, J 6.5, 2.0, 1.0 Hz, 2H of oxobenzoxazapineH-2, H-4), 4.72 (1H, dd, J 10.0, 7.5 Hz, 1H of oxobenzoxazapineH-2), 4.26 (1H, dd, J 11.5, 9.5 Hz, 1H of oxobenzoxazapineH-2), 3.53 (1H, s, OH), 3.38 (3H, s, NCH₃); ¹³C nmr (100 MHz, CDCl₃) δ 168.7, 158.4, 156.5, 150.4, 144.0, 136.1, 133.7, 130.9, 129.2, 129.0, 128.2, 126.6, 123.4, 119.5, 88.9, 84.5, 77.1, 67.3, 54.4, 53.4, 49.1, 35.5; m/z: 474 [M+H]⁺.

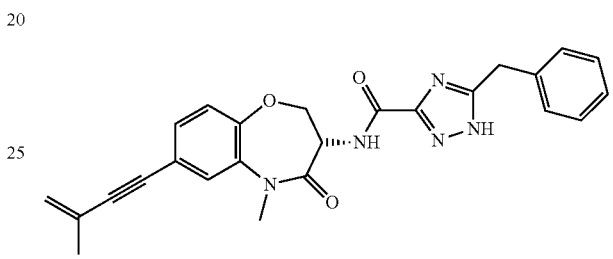

(S)-5-benzyl-N-(5-methyl-7-(3-methylbut-3-en-1-yn-1-yl)-4-oxo-2,3,4,5-tetrahydrobenzo[b][1,4]oxazepin-3-yl)-1H-1,2,4-triazole-3-carboxamide ¹H nmr (400 MHz, CDCl₃) δ 8.09 (1, d, J 7.5 Hz, NH), 7.27 (2H, t, J 7.0 Hz, 2H of C₆H₅), 7.20-7.15 (5H, m, 3H of C₆H₅, oxobenzoxazapineH-6, H-8), 7.09 (1H, d, J 9.0 Hz, oxobenzoxazapineH-9), 5.41 (1H, q, J 1.0 Hz, 1H of =CH₂), 5.32 (1H, m, 1H of =CH₂), 5.01 (1H, dt, J 11.0, 7.5 Hz, oxobenzoxazapineH-3), 4.63 (1H, dd, J 9.5, 7.5 Hz, 1H of oxobenzoxazapineH-2), 4.26 (1H, dd, J 11.0, 10.0 Hz, 1H of oxobenzoxazapineH-2), 4.12 (2H, s, CH₂C₆H₅), 3.38 (3H, s, NCH₃), 1.98 (3H, t, J Hz, C(CH₃)=CH₂); ¹³C nmr (100 MHz, CDCl₃) δ 168.7, 158.7, 154.6, 149.8, 136.0, 135.9, 130.9, 128.8, 128.7, 127.0, 126.4 (2C), 123.1, 122.6, 121.0, 91.3, 86.7, 77.2, 49.2, 35.5, 33.0, 23.3; m/z: 464 [M+Na]⁺, 442 [M+H]⁺ (found [M+H]⁺, 442.1869, C₂₅H₂₃N₅O₃ requires [M+H]⁺ 442.1874).

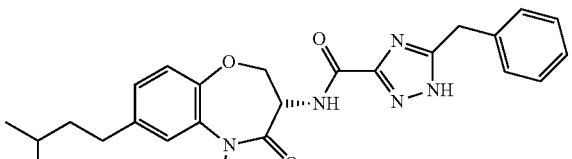

(S)-5-benzyl-N-(7-isopentyl-5-methyl-4-oxo-2,3,4,5-tetrahydrobenzo[b][1,4]oxazepin-3-yl)-1H-1,2,4-triazole-3-carboxamide ¹H nmr (400 MHz, CDCl₃) δ 8.09 (1H, d, J 7.5 Hz, NH), 7.29-7.19 (5H, m, C₆H₅), 7.06 (1H, d, J 8.0 Hz, oxobenzoxazapineH-9), 7.03 (1H, d, J 2.0 Hz, oxobenzoxazapineH- 6), 7.00 (1H, m, oxobenzoxazapineH-8), 5.04 (1H, dt, J 11.0, 7.5 Hz, oxobenzoxazapineH-3), 4.66 (1H, dd, J 9.5, 7.5 Hz, 1H of oxobenzoxazapineH-2), 4.22 (1H, dd, J 11.0, 10.0 Hz, 1H of oxobenzoxazapineH-2), 4.14 (2H, s, C$\underline{H}_2$C$_6$H$_5$), 3.39 (3H, s, NCH$_3$), 2.60 (2H, m, C$\underline{H}_2$CH$_2$CH(CH$_3$)$_2$), 1.60 (1H, m, CH$_2$CH$_2$C$\underline{H}$(CH$_3$)$_2$), 1.52-1.46 (2H, m, CH$_2$C$\underline{H}_2$CH(CH$_3$)$_2$), 0.94 (6H, d, J 6.5 Hz, CH$_2$CH$_2$CH(C$\underline{H}_3$)$_2$); m/z: 448 [M+H]$^+$ (found [M+H]$^+$, 448.2335, C$_{25}$H$_{29}$N$_5$O$_3$ requires [M+H]$^+$ 448.2343).

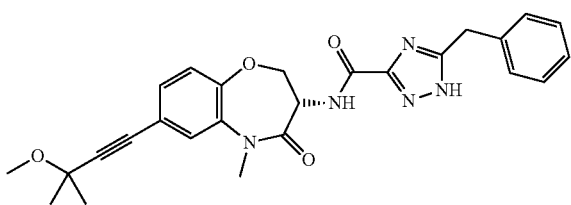

(S)-5-benzyl-N-(7-(3-methoxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.09 (1H, d, J 7.5 Hz, NH), 7.28-7.25 (2H, m, 2H of C$_6$H$_5$), 7.19 (5H, m, 3H of C$_6$H$_5$, oxobenzoxazapineH-6, H-8), 7.09 (1H, d, J 8.0 Hz, oxobenzoxazapineH-9), 5.01 (1H, dt, J 11.0, 7.5 Hz, oxobenzoxazapineH-3), 4.63 (1H, dd, J 9.0, 8.0 Hz, 1H of oxobenzoxazapineH-2), 4.26 (1H, dd, J 10.5, 9.5 Hz, 1H of oxobenzoxazapineH-2), 4.12 (2H, s, C$\underline{H}_2$C$_6$H$_5$), 3.43 (3H, s, NCH$_3$ or OCH$_3$), 3.39 (3H, s, NCH$_3$ or OCH$_3$), 1.54 (6H, s, C(C$\underline{H}_3$)$_2$OCH$_3$); m/z: 474 [M+H]$^+$, 442 [M+H—CH$_3$OH]$^+$ (found [M+H]$^+$, 474.2138, C$_{26}$H$_{27}$N$_5$O$_4$ requires [M+H]$^+$ 474.2136).

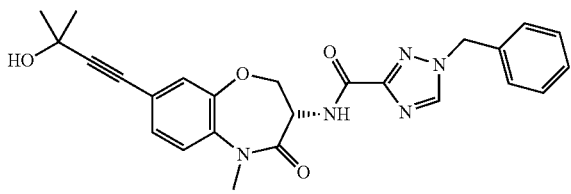

(S)-1-benzyl-N-(8-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.01 (1H, d, J 7.5 Hz, NH), 8.00 (1H, s, triazoleH-5), 7.39-7.34 (3H, m, 3H of C$_6$H$_5$), 7.27-7.23 (4H, m, 2H of C$_6$H$_5$, oxobenzoxazapineH-8, H-9), 7.12 (1H, d, J 8.0 Hz, oxobenzoxazapineH-6), 5.36 (2H, s, NC$\underline{H}_2$C$_6$H$_5$), 5.05 (1H, dt, J 11.0, 7.5 Hz, oxobenzoxazapineH-3), 4.73 (1H, dd, J 9.5, 7.5 Hz, 1H of oxobenzoxazapineH-2), 4.23 (1H, dd, J 11.0, 10.0 Hz, 1H of oxobenzoxazapineH-2), 3.39 (3H, s, NCH$_3$), 1.61 (6H, s, C(C$\underline{H}_3$)$_2$OH); m/z: 460 [M+H]$^+$, 442 [M+H—H$_2$O]$^+$ (found [M+H]$^+$, 460.1968, C$_{25}$H$_{25}$N$_5$O$_4$ requires [M+H]$^+$ 460.1979).

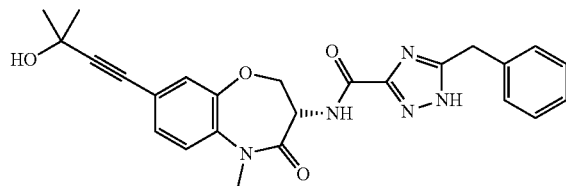

(S)-5-benzyl-N-(8-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.08 (1H, d, J 7.5 Hz, NH), 7.26-7.18 (7H, m, C$_6$H$_5$, oxobenzoxazapineH-7, H-9), 7.11 (1H, d, J 8.0 Hz, oxobenzoxazapineH-6), 5.00 (1H, dt, J 11.0, 7.5 Hz, oxobenzoxazapineH-3), 4.62 (1H, dd, J 9.5, 7.5 Hz, 1H of oxobenzoxazapineH-2), 4.24 (1H, dd, J 11.5, 9.5 Hz, 1H of oxobenzoxazapineH-2), 4.14, 4.10 (2H, 2d, J 16.0 Hz, C$\underline{H}_2$C$_6$H$_5$), 3.37 (3H, s, NCH$_3$), 1.61 (6H, s, C(C$\underline{H}_3$)$_2$OH); $^{13}$C nmr (100 MHz, CDCl$_3$) δ 168.7, 158.7, 149.5, 136.1, 135.9, 129.0, 128.8, 128.7, 127.0, 126.0, 123.1, 122.2, 95.1, 80.6, 76.9, 65.5, 49.2, 35.4, 33.0, 31.4 (2C); m/z: 442 [M+H—H$_2$O]$^+$ (found [M+H]$^+$, 460.1972, C$_{25}$H$_{25}$N$_5$O$_4$ requires [M+H]$^+$ 460.1979).

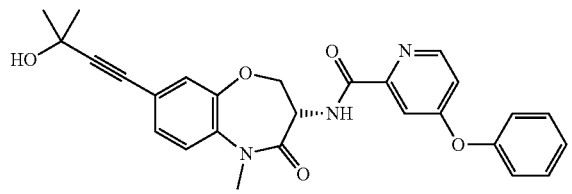

(S)—N-(8-(3-hydroxy-3-methylbut-1-yn-1-yl)-5-methyl-4-oxo-2,3,4,5-tetrahydrobenzo[b][1,4]oxazepin-3-yl)-4-phenoxypicolinamide $^1$H nmr (400 MHz, CDCl$_3$) δ 8.83 (1H, d, J 7.5 Hz, NH), 8.42 (1H, d, J 5.5 Hz, pyridineH-3), 7.60 (1H, d, J 2.5 Hz, pyridineH-6), 7.42-7.38 (2H, m, 2H of C$_6$H$_5$), 7.28-7.22 (3H, m, 1H of C$_6$H$_5$, oxobenzoxazapineH-7, H-9), 7.13 (1H, d, J 8.0 Hz, oxobenzoxazapineH-6), 7.07-7.04 (2H, m, 2H of C$_6$H$_5$), 6.93 (1H, dd, J 5.5, 2.5 Hz, pyridineH-4), 5.01 (1H, dt, J 11.0, 7.5 Hz, oxobenzoxazapineH-3), 4.68 (1H, dd, J 9.5, 7.5 Hz, 1H of oxobenzoxazapineH-2), 4.27 (1H, dd, J 11.0, 9.5 Hz, 1H of oxobenzoxazapineH-2), 3.40 (3H, s, NCH$_3$), 1.61 (6H, s, C(C$\underline{H}_3$)$_2$OH); $^{13}$C nmr (100 MHz, CDCl$_3$) δ 169.0, 166.1, 163.6, 153.7, 151.3, 150.1, 149.6, 136.4, 130.3, 128.9, 126.0, 125.7, 123.0, 122.0, 120.7, 114.4, 110.6, 94.9, 80.6, 77.2, 65.6, 49.4, 35.3, 31.4; m/z: 472 [M+H]$^+$ (found [M+H]$^+$, 472.1873, C$_{27}$H$_{25}$N$_3$O$_5$ requires [M+H]$^+$ 472.1867).

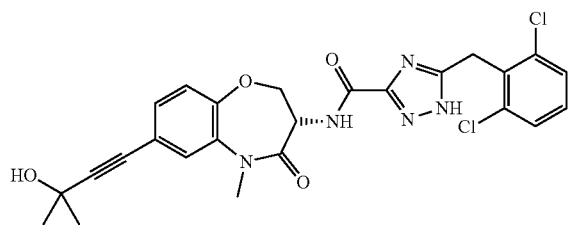

(S)-5-(2,6-dichlorobenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.05 (1H, d, J 7.5 Hz, NH), 7.33-7.29 (3H, m, 3H of C$_6$H$_3$Cl$_2$, oxobenzoxazapineH-6), 7.226-7.24 (1H, m, 1H of C$_6$H$_3$Cl$_2$, oxobenzoxazapineH-6), 7.18-7.15 (1H, m, oxobenzoxazapineH-8)), 7.10 (1H, d, J 8.5 Hz, oxobenzoxazapineH-9), 5.00 (1H, dt, J 11.5, 7.5 Hz, oxobenzoxazapineH-3), 4.67 (1H, dd, J 10.0, 7.5 Hz, 1H of oxobenzoxazapineH-2), 4.48 (2H, s, C$\underline{H}_2$C$_6$H$_3$Cl$_2$), 4.27 (1H, dd, J 11.0, 10.0 Hz, 1H of oxobenzoxazapineH-2), 3.39 (3H, s, NCH$_3$), 1.61 (6H, s, C(CH$_3$)$_2$); m/z: 532, 530, 528 [M+H]$^+$ 514, 512, 510 [M+H—H$_2$O]$^+$ (found [M+H]$^+$, 528.1201, C$_{25}$H$_{23}$Cl$_2$N$_5$O$_4$ requires [M+H]$^+$ 528.1200).

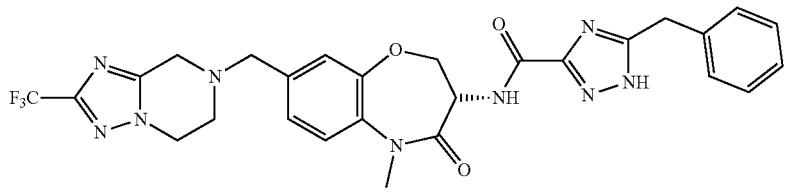

(S)-5-benzyl-N-(5-methyl-4-oxo-8-((2-(trifluoromethyl)-5,6-dihydro-[1,2,4]triazolo[1,5-a]pyrazin-7(8H)-yl)methyl)-2,3,4,5-tetrahydrobenzo[b][1,4]oxazepin-3-yl)-1H-1,2,4-triazole-3-carboxamide $^1$H nmr (400 MHz, CDCl$_3$) δ 8.04 (1H, d, J 7.5 Hz, NH), 7.30-7.17 (8H, m, C$_6$H$_5$, oxobenzoxazapineH-6, H-7, H-9), 5.08 (1H, dt, J 11.0, 7.5 Hz, oxobenzoxazapineH-3), 4.70 (1H, dd, J 10.0, 7.5 Hz, 1H of oxobenzoxazapineH-2), 4.30-4.25 (3H, m, 1H of oxobenzoxazapineH-2, NCH$_2$CH$_2$N), 4.14 (2H, s, CH$_2$C$_6$H$_5$), 3.88, 3.83 (2H, 2d AB system, J 16.0 Hz, 2H of ArCH$_2$NCH$_2$), 3.76 (2H, s, ArCH$_2$NCH$_2$), 3.40 (3H, s, NCH$_3$), 3.09-3.02 (2H, m, NCH$_2$CH$_2$N); $^{19}$F nmr (380 MHz, CDCl$_3$) δ −65.3; m/z: 604 [M+Na]$^+$ 582 [M+H]$^+$.

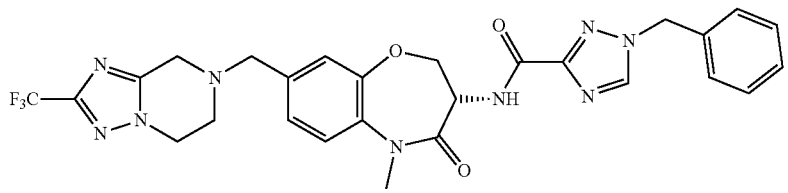

(S)-1-benzyl-N-(5-methyl-4-oxo-8-((2-(trifluoromethyl)-5,6-dihydro-[1,2,4]triazolo[1,5-a]pyrazin-7(8H)-yl)methyl)-2,3,4,5-tetrahydrobenzo[b][1,4]oxazepin-3-yl)-1H-1,2,4-triazole-3-carboxamide $^1$H nmr (400 MHz, CDCl$_3$) δ 8.05 (1H, d, J 7.0 Hz, NH), 8.00 (1H, s, triazoleH-5), 7.39-7.35 (3H, m, 3H of C$_6$H$_5$, oxobenzoxazapineH-6, H-7, H-9), 7.28-7.25 (2H, m, 2H of C$_6$H$_5$, oxobenzoxazapineH-6, H-7, H-9), 7.23-7.17 (3H, m, 3H of C$_6$H$_5$, oxobenzoxazapineH-6, H-7, H-9), 5.37 (2H, s, NC$\underline{H}_2$C$_6$H$_5$), 5.11 (1H, dt, J 11.0, 7.5 Hz, oxobenzoxazapineH-3), 4.76 (1H, dd, J 9.5, 7.5 Hz, 1H of oxobenzoxazapineH-2), 4.28-4.23 (3H, m, 1H of oxobenzoxazapineH-2, 2H of NCH$_2$CH$_2$N), 3.90, 3.86 (2H, 2d AB system, J 16.0 Hz, 2H of ArCH$_2$NCH$_2$), 3.79, 3.75 (2H, 2d AB system, J 13.5 Hz, 2H of ArCH$_2$NCH$_2$), 3.42 (3H, s, NCH$_3$), 3.10-3.02 (2H, m, 2H of NCH$_2$CH$_2$N); $^{19}$F nmr (380 MHz, CDCl$_3$) δ −65.4; m/z: 604 [M+Na]$^+$, 582 [M+H]$^+$.

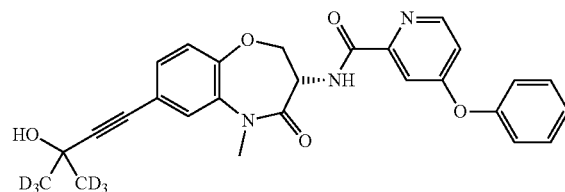

(S)—N-(7-(3-hydroxy-3-(methyl-d$_3$)but-1-yn-1-yl-4,4,4-d$_3$)-5-methyl-4-oxo-2,3,4,5-tetrahydrobenzo[b][1,4]oxazepin-3-yl)-4-phenoxypicolinamide $^1$H nmr (400 MHz, CDCl$_3$) δ 8.85 (1H, d, J 7.5 Hz, NH), 8.43 (1H, d, J 5.5 Hz, pyH-3), 7.60 (1H, d, J 2.5 Hz, pyH-4), 7.42-7.38 (2H, m, 2H of C$_6$H$_5$), 7.27-7.22 (3H, m, 3H of C$_6$H$_5$, oxobenzoxazapineH-6, H-8), 7.11 (1H, d, J 9.0 Hz, oxobenzoxazapineH-9), 7.10-7.05 (2H, m, 2H of C$_6$H$_5$, oxobenzoxazapineH-6, H-8), 6.93 (1H, dd, J 5.5, 2.5 Hz, pyH-6), 5.01 (1H, dt, J 11.5, 7.5 Hz, oxobenzoxazapineH-3), 4.70 (1H, dd, J 10.0, 7.5 Hz, 1H of oxobenzoxazapineH-2), 4.28 (1H, dd, J 11.5, 10.0 Hz, 1H of oxobenzoxazapineH-2), 3.41 (3H, s, NCH$_3$); m/z: 478 [M+H]$^+$, 460 [M+H—H$_2$O]$^+$ (found [M+H]$^+$, 478.2255, C$_{27}$H$_{19}$D$_6$N$_3$O$_4$ requires [M+H]$^+$ 478.2244).

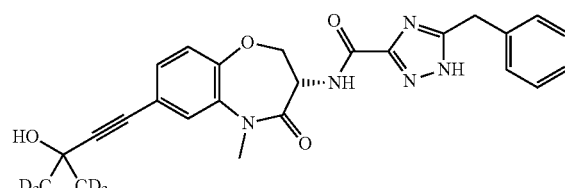

(S)-5-benzyl-N-(7-(3-hydroxy-3-(methyl-d₃)but-1-yn-1-yl-4,4,4-d₃)-5-methyl-4-oxo-2,3,4,5-tetrahydrobenzo[b][1,4]oxazepin-3-yl)-1H-1,2,4-triazole-3-carboxamide ¹H nmr (400 MHz, CDCl₃) δ 8.09 (1H, d, J 7.5 Hz, NH), 7.28-7.21 (7H, m, C₆H₅, oxobenzoxazapineH-6, H-8), 7.10 (1H, d, J 9.0 Hz, oxobenzoxazapineH-9), 5.01 (1H, dt, J 11.0, 7.5 Hz, oxobenzoxazapineH-3), 4.66 (1H, dd, J 9.5, 7.5 Hz, 1H of oxobenzoxazapineH-2), 4.27 (1H, dd, J 11.0, 9.5 Hz, 1H of oxobenzoxazapineH-2), 4.14 (2H, s, CH₂C₆H₅), 3.39 (3H, s, NCH₃); ¹³C nmr (100 MHz, CDCl₃) δ 168.6, 158.5, 149.9, 136.0, 135.8, 131.0, 128.8 (2C), 127.1 (2C), 126.5, 123.1, 120.5, 94.6, 80.6, 77.2, 65.3, 49.1, 35.5, 33.2, 30.5 (m); m/z: 466 [M+H]⁺, 448 [M+H—H₂O]⁺ (found [M+H]⁺, 466.2356, C₂₅H₁₉D₆N₅O₄ requires [M+H]⁺ 466.2356).

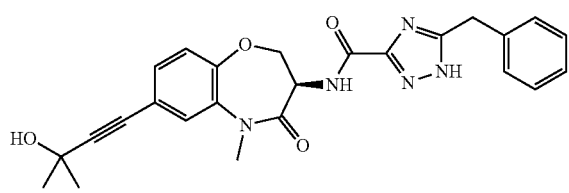 [SMILES: CN1C(=O)[C@H](NC(=O)c2n[nH]c(Cc3ccccc3)n2)COc2ccc(C#CC(C)(C)O)cc21]

(R)-5-benzyl-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide

[α]₅₈₂²⁰·²+135.9 (CHCl₃, c 0.54); ¹H nmr (400 MHz, CDCl₃) δ 8.08 (1H, d, J 7.5 Hz, NH), 7.30-7.23 (7H, m, C₆H₅, oxobenzoxazapineH-6, H-8), 7.11 (1H, d, J 9.0 Hz, oxobenzoxazapineH-9), 5.02 (1H, dt, J 11.0, 7.5 Hz, oxobenzoxazapineH-3), 4.68 (1H, dd, J 9.5, 7.5 Hz, 1H of oxobenzoxazapineH-2), 4.28 (1H, dd, J 11.0, 9.5 Hz, 1H of oxobenzoxazapineH-2), 4.15 (2H, s, CH₂C₆H₅), 3.40 (3H, s, NCH₃), 1.63 (6H, s, C(CH₃)₂OH); m/z: 460 [M+H]⁺, 442 [M+H—H₂O]⁺ (found [M+H]⁺, 460.1985, C₂₅H₂₅N₅O₄ requires [M+H]⁺ 460.1979).

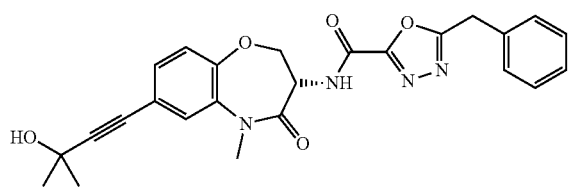

(S)-5-benzyl-N-(7-(3-hydroxy-3-methylbut-1-yn-1-yl)-5-methyl-4-oxo-2,3,4,5-tetrahydrobenzo[b][1,4]oxazepin-3-yl)-1,3,4-oxadiazole-2-carboxamide ¹H nmr (400 MHz, CDCl₃) δ 7.99 (1H, d, J 6.5 Hz, NH), 7.36-7.29 (7H, m, C₆H₅, oxobenzoxazapineH-6, H-8), 7.13 (1H, d, J 9.0 Hz, oxobenzoxazapineH-9), 4.97 (1H, ddd, J 11.0, 7.5, 7.0 Hz, oxobenzoxazapineH-3), 4.72 (1H, dd, J 9.5, 7.5 Hz, 1H of oxobenzoxazapineH-2), 4.27 (1H, m, 1H of oxobenzoxazapineH-2), 4.26 (2H, s, CH₂C₆H₅), 3.43 (3H, s, NCH₃), 1.63 (6H, s, C(CH₃)₂); m/z: 484 [M+Na]⁺, 443 [M+H—H₂O]⁺ (found [M+H]⁺, 443.1727, C₂₅H₂₄N₄O₅ requires [M+H—H₂O]⁺ 443.1714).

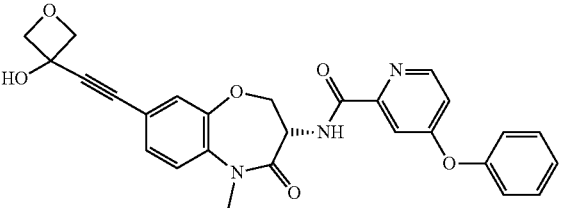

(S)—N-(8-((3-hydroxyoxetan-3-yl)ethynyl)-5-methyl-4-oxo-2,3,4,5-tetrahydrobenzo[b][1,4]oxazepin-3-yl)-4-phenoxypicolinamide ¹H nmr (400 MHz, CDCl₃) δ 8.84 (1H, d, J 7.5 Hz, NH), 8.43 (1H, d, J 5.5 Hz, pyH-6), 7.60 (1H, d, J 2.5 Hz, pyH-3), 7.42-7.39 (2H, m, 2H of C₆H₅), 7.31 (1H, dd, J 8.0, 2.0 Hz, oxobenzoxazapineH-7), 7.27-7.22 (2H, m, 1H of C₆H₅, oxobenzoxazapineH-9), 7.17 (1H, d, J 8.0 Hz, oxobenzoxazapineH-6), 7.07-7.05 (2H, m, 2H of C₆H₅), 6.93 (1H, dd, J 5.5, 2.5 Hz, pyH-5), 5.02 (1H, dt, J 11.0, 7.5 Hz, oxobenzoxazapineH-3), 4.93 (2H, d, J 7.0 Hz, 2H of oxetaneH-2, H-4), 4.79 (2H, d, J 7.0 Hz, 2H of oxetaneH-2, H-4), 4.69 (1H, dd, J 9.5, 7.5 Hz, 1H of oxobenzoxazapineH-2), 4.29 (1H, dd, J 11.0, 9.5 Hz, 1H of oxobenzoxazapineH-2), 3.42 (3H, s, NCH₃); m/z: 486 [M+H]⁺, (found [M+H]⁺, 486.1674, C₂₈H₂₃N₃O₆ requires [M+H]⁺ 486.1660).

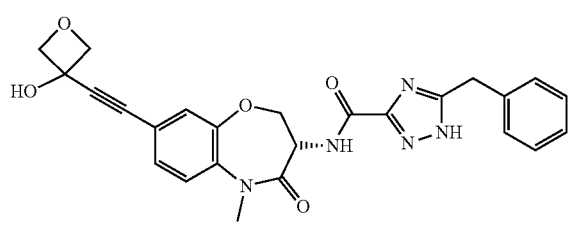

(S)-5-benzyl-N-(8-((3-hydroxyoxetan-3-yl)ethynyl)-5-methyl-4-oxo-2,3,4,5-tetrahydrobenzo[b][1,4]oxazepin-3-yl)-1H-1,2,4-triazole-3-carboxamide ¹H nmr (400 MHz, CDCl₃) δ 8.07 (1H, d, J 7.5 Hz, NH), 7.97 (1H, s, OH), 7.32-7.22 (6H, m, C₆H₅, oxobenzoxazapineH-7), 7.20 (1H, d, J 2.0 Hz, oxobenzoxazapineH-9), 7.14 (1H, d, J 8.5 Hz, 1H of oxobenzoxazapineH-6), 4.99 (1H, dt, J 11.0, 7.5 Hz, oxobenzoxazapineH-3), 4.92 (2H, d, J 7.0 Hz, 2H of oxetaneH-2, H-4), 4.79 (2H, d, J 6.5 Hz, 2H of oxetaneH-2, H-4), 4.64 (1H, dd, J 9.5, 7.5 Hz, 1H of oxobenzoxazapineH-2), 4.25 (1H, dd, J 11.0, 9.5 Hz, 1H of oxobenzoxazapineH-2), 4.14 (2H, s, CH₂C₆H₅), 3.40 (3H, s, NCH₃); m/z: 474 [M+H]⁺, 456 [M+H—H₂O]⁺ (found [M+H]⁺, 474.1784, C₂₅H₂₃N₅O₅ requires [M+H]⁺ 474.1772).

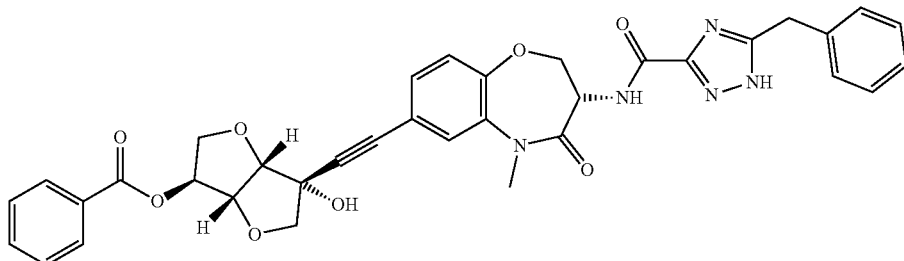

(3S,3aR,6R,6aS)-6-(((S)-3-(5-benzyl-1H-1,2,4-triazole-3-carboxamido)-5-methyl-4-oxo-2,3,4,5-tetrahydrobenzo[b][1,4]oxazepin-7-yl)ethynyl)-6-hydroxyhexahydrofuro[3,2-b]furan-3-ylbenzoate $^1$H nmr (400 MHz, CDCl$_3$) δ 8.07 (1H, d, J 7.5 Hz, NH), 8.03 (2H, m, 2H of COC$_6$H$_5$), 7.59 (1H, tt, J 7.5, 1.0 Hz, 1H of COC$_6$H$_5$), 7.45 (2H, t, J 7.5 Hz, 2H of COC$_6$H$_5$), 7.32-7.23 (7H, m, CH$_2$C$_6$H$_5$, oxobenzoxazapineH-6, H-8), 7.12 (1H, d, J 8.5 Hz, oxobenzoxazapineH-9), 5.23 (1H, d, J 3.0 Hz, isosorbateH-6), 5.02 (1H, dt, J 11.0, 7.5 Hz, oxobenzoxazapineH-3), 4.87, 4.83 (2H, 2d AB system, J 4.5 Hz, isosorbateH-3a, H-6a), 4.69 (1H, dd, J 9.5, 7.5 Hz, 1H of oxobenzoxazapineH-2), 4.28 (1H, dd, J 11.0, 10.0 Hz, 1H of oxobenzoxazapineH-2), 4.25-4.20 (2H, m, isosorbateH-5), 4.15 (2H, s, CH$_2$C$_6$H$_5$), 4.04, 3.95 (2H, 2d AB system, J 9.5 Hz, isosorbateH-2), 3.40 (3H, s, NCH$_3$); m/z: 650 [M+H]$^+$ (found [M+H]$^+$, 650.2283, C$_{35}$H$_{31}$N$_5$O$_8$ requires [M+H]$^+$ 650.2245).

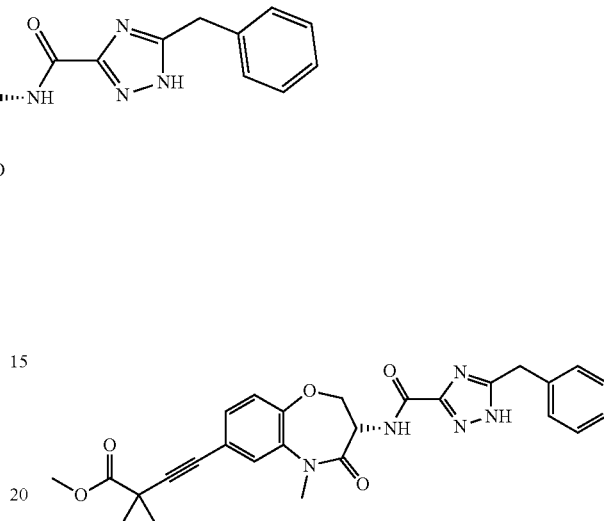

methyl (S)-4-(3-(5-benzyl-1H-1,2,4-triazole-3-carboxamido)-5-methyl-4-oxo-2,3,4,5-tetrahydrobenzo[b][1,4]oxazepin-7-yl)-2,2-dimethylbut-3-ynoate $^1$H nmr (400 MHz, CDCl$_3$) δ 8.06 (1H, d, J 7.5 Hz, NH), 7.31-7.23 (7H, m, C$_6$H$_5$, oxobenzoxazapineH-6, H-8), 7.10 (1H, d, J 9.0 Hz, oxobenzoxazapineH-9), 5.02 (1H, dt, J 11.0, 7.5 Hz, oxobenzoxazapineH-3), 4.68 (1H, dd, J 10.0, 7.5 Hz, 1H of oxobenzoxazapineH-2), 4.26 (1H, dd, J 11.0, 10.0 Hz, 1H of oxobenzoxazapineH-2), 4.16 (2H, s, CH$_2$C$_6$H$_5$), 3.78 (3H, s, OCH$_3$), 3.41 (3H, s, NCH$_3$), 1.58 (6H, s, C(CH$_3$)$_2$); m/z: 502 [M+H]$^+$ (found [M+H]$^+$, 502.2107, C$_{27}$H$_{27}$N$_5$O$_4$ requires [M+H]$^+$ 502.2085).

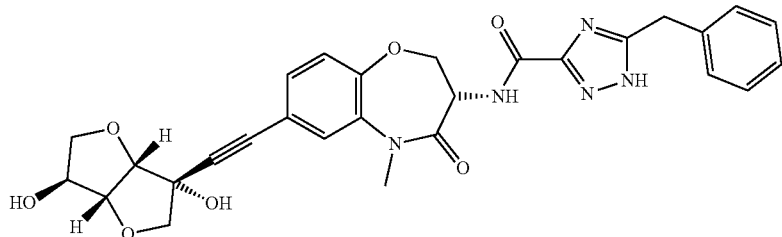

5-benzyl-N-((S)-7-(((3R,3aS,6S,6aR)-3,6-dihydroxyhexahydrofuro[3,2-b]furan-3-yl)ethynyl)-5-methyl-4-oxo-2,3,4,5-tetrahydrobenzo[b][1,4]oxazepin-3-yl)-1H-1,2,4-triazole-3-carboxamide $^1$H nmr (400 MHz, CD$_3$OD) δ 7.51 (1H, d, J 2.0 Hz, oxobenzoxazapineH-6), 7.36 (1H, dd, J 8.0, 2.0 Hz, oxobenzoxazapineH-8), 7.33-7.23 (5H, m, C$_6$H$_5$), 7.19 (1H, d, J 8.0 Hz, oxobenzoxazapineH-9), 5.01 (1H, dd, J 11.5, 7.5 Hz, oxobenzoxazapineH-3), 4.65, 4.54 (2H, 2d AB system, J 4.5 Hz, isosorbateH-3a, H-6a), 4.60 (1H, dd, J 10.0, 7.5 Hz, 1H of oxobenzoxazapineH-2), 4.41 (1H, dd, J 11.5, 10.0 Hz, 1H of oxobenzoxazapineH-2), 4.24 (1H, d, J 2.5 Hz, isosorbateH-6), 4.15 (2H, s, CH$_2$C$_6$H$_5$), 3.99-3.91 (2H, m, 2H of isosorbateH-5), 3.93, 3.71 (2H, 2d AB system, J 8.5 Hz, isosorbateH-2), 3.40 (3H, s, NCH$_3$); $^{13}$C nmr (100 MHz, CD$_3$OD) δ 169.1, 150.3, 136.5, 130.7, 128.4, 128.3, 126.8, 126.6, 122.7, 119.9, 110.0, 89.5, 88.6, 87.1, 83.7, 78.1, 77.8, 77.5, 74.4, 49.1, 34.4, 33.2; m/z: 546 [M+H]$^+$ (found [M+H]$^+$, 546.2007, C$_{28}$H$_{27}$N$_5$O$_7$ requires [M+H]$^+$ 546.1983).

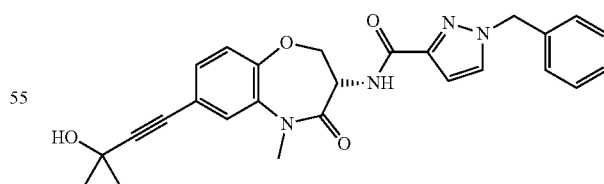

(S)-1-benzyl-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-3-carboxamide $^1$H nmr (400 MHz, CDCl$_3$) δ 7.79 (1H, d, J 7.0 Hz, NH), 7.38-7.32 (4H, m, 4H or C$_6$H$_5$, pyrazoleH-4 or H-5, oxobenzoxazapineH-6, H-8), 7.28-7.21 (4H, m, 4H of C$_6$H$_5$, pyrazoleH-4 or H-5, oxobenzoxazapineH-6 or H-8), 7.12 (1H, d, J 9.0 Hz, oxobenzoxazapineH-9), 6.74 (1H, d, J 2.5 Hz, pyrazoleH-4 or H-5), 5.31 (2H, s, NC$\underline{H}_2$C$_6$H$_5$), 5.05 (1H, dt, J 11.0, 7.0 Hz, oxobenzoxazapineH-3), 4.73 (1H, dd, J 9.5, 7.5 Hz, 1H of oxobenzoxazapineH-2), 4.28 (1H, dd, J 11.0, 9.5 Hz, 1H of oxobenzoxazapineH-2), 3.42 (3H, s, NCH$_3$), 1.62 (6H, s, C(C$\underline{H}_3$)$_2$OH); m/z: 459 [M+H]$^+$, 441 [M+H—H$_2$O]$^+$ (found [M+H]$^+$, 459.2040, C$_{26}$H$_{26}$N$_4$O$_4$ requires [M+H]$^+$ 459.2027).

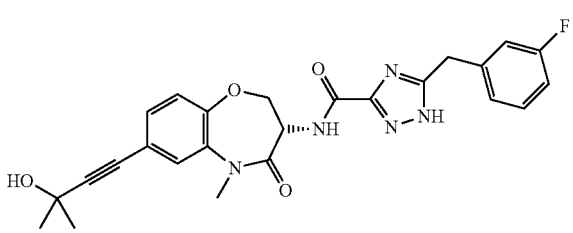

(S)-5-(3-fluorobenzyl)-N-(7-(3-hydroxy-3-methyl-but-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.10 (1H, d, J 7.0 Hz, NH), 7.28 (2H, m, oxobenzoxazapineH-6, H-8), 7.21 (1H, m, 1H of C$_6$H$_4$F), 7.10 (1H, d, J 9.0 Hz, oxobenzoxazapineH-9), 7.01 (1H, br d, J 8.0 Hz, 1H of C$_6$H$_4$F), 6.96 (1H, br d, J 9.5 Hz, 1H of C$_6$H$_4$F), 6.90 (1H, td, J 8.5, 2.5 Hz, 1H of C$_6$H$_4$F), 5.00 (1H, dt, J 11.0, 7.5 Hz, oxobenzoxazapineH-3), 4.66 (1H, dd, J 10.0, 7.5 Hz, 1H of oxobenzoxazapineH-2), 4.29 (1H, dd, J 11.0, 10.0 Hz, 1H of oxobenzoxazapineH-2), 4.15 (2H, s, C$\underline{H}_2$C$_6$H$_4$F), 3.40 (3H, s, NCH$_3$), 1.62 (6H, s, C(C$\underline{H}_3$)$_2$OH); $^{13}$C nmr (100 MHz, CD$_3$OD) δ 168.5, 164.0, 161.6, 149.9, 138.5, 135.9, 131.0, 130.2 (d, J 8.5 Hz), 128.8, 126.5, 124.5 (d, J 2.5 Hz), 123.0, 120.5, 115.8 (d, J 22.0 Hz), 113.9 (d, J 21.5 Hz), 94.6, 80.6, 76.9, 65.6, 49.2, 35.5, 32.9, 31.4; $^{19}$F nmr (380 MHz, CDCl$_3$) δ −112.6; m/z: 460 [M+H—H$_2$O]$^+$ (found [M+H]$^+$, 478.1901, C$_{25}$H$_{24}$FN$_5$O$_4$ requires [M+H]$^+$ 478.1885).

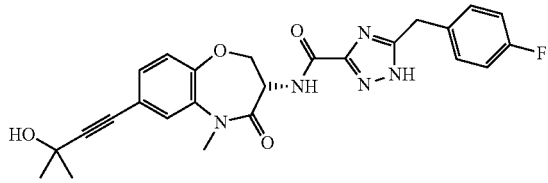

(S)-5-(4-fluorobenzyl)-N-(7-(3-hydroxy-3-methyl-but-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.11 (1H, d, J 7.5 Hz, NH), 7.27-7.25 (2H, m, oxobenzoxazapineH-6, H-8), 7.17 (2H, dd, J 8.5, 5.5 Hz, 2H of C$_6$H$_4$F), 7.09 (1H, d, J 9.0 Hz, oxobenzoxazapineH-9), 6.90 (2H, t, J 8.5 Hz, 2H of C$_6$H$_4$F), 4.99 (1H, dt, J 11.5, 7.5 Hz, oxobenzoxazapineH-3), 4.64 (1H, dd, J 10.0, 7.5 Hz, 1H of oxobenzoxazapineH-2), 4.29 (1H, dd, J 11.5, 10.0 Hz, 1H of oxobenzoxazapineH-2), 4.09 (2H, s, C$\underline{H}_2$C$_6$H$_4$F), 3.39 (3H, s, NCH$_3$), 1.62 (6H, s, C(C$\underline{H}_3$)$_2$OH); $^{19}$F nmr (380 MHz, CDCl$_3$) δ −115.6; m/z: 478 [M+H]$^+$ 460 [M+H—H$_2$O]$^+$ (found [M+H]$^+$, 478.1902, C$_{25}$H$_{24}$FN$_5$O$_4$ requires [M+H]$^+$ 478.1885).

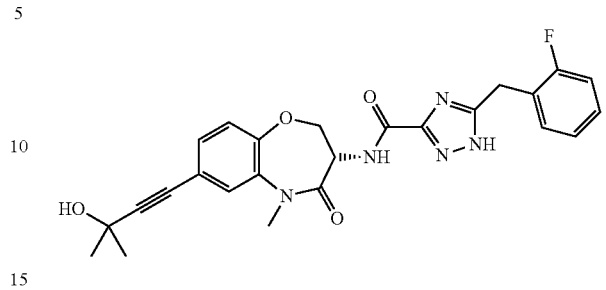

(S)-5-(2-fluorobenzyl)-N-(7-(3-hydroxy-3-methyl-but-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.08 (1H, d, J 7.5 Hz, NH), 7.26-7.16 (3H, m, oxobenzoxazapineH-6, H-8, 1H of C$_6$H$_4$F), 7.09 (1H, d, J 9.0 Hz, oxobenzoxazapineH-9), 7.01 (1H, td, J 7.5, 1.0 Hz, 1H of C$_6$H$_4$F), 7.00-6.96 (1H, m, 1H of C$_6$H$_4$F), 5.00 (1H, dt, J 11.0, 7.5 Hz, oxobenzoxazapineH-3), 4.65 (1H, dd, J 9.5, 7.5 Hz, 1H of oxobenzoxazapineH-2), 4.27 (1H, dd, J 11.0, 9.5 Hz, 1H of oxobenzoxazapineH-2), 4.17 (2H, s, C$\underline{H}_2$C$_6$H$_4$F), 3.38 (3H, s, NCH$_3$), 1.62 (6H, s, C(C$\underline{H}_3$)$_2$OH); $^{13}$C nmr (100 MHz, CDCl$_3$) δ 168.7, 160.7 (d, J 246.3 Hz), 158.5, 149.9, 136.0, 131.0 (d, J 4.0 Hz), 131.0, 129.1, 129.0 (d, J 8.5 Hz), 126.5, 126.3, 124.4 (d, J 4.0 Hz), 123.1, 120.4, 115.4 (d, J 12.0 Hz), 94.6, 80.6, 76.9, 65.6, 49.1, 35.5, 31.4, 26.3; $^{19}$F nmr (380 MHz, CDCl$_3$) δ −117.5; m/z: 460 [M+H—H$_2$O]$^+$ (found [M+H]$^+$, 478.1895, C$_{25}$H$_{24}$FN$_5$O$_4$ requires [M+H]$^+$ 478.1885).

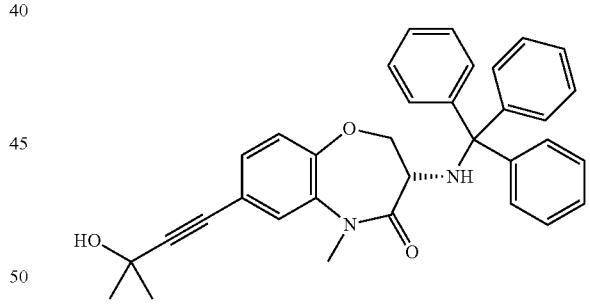

(S)-7-(3-hydroxy-3-methylbut-1-yn-1-yl)-5-methyl-3-(tritylamino)-2,3-dihydrobenzo[b][1,4]oxazepin-4(5H)-one $^1$H nmr (400 MHz, CDCl$_3$) δ 7.40-7.38 (6H, m, 3×2H of C$_6$H$_5$), 7.24-7.20 (6H, m, 3×2H of C$_6$H$_5$), 7.18-7.12 (4H, m, 3×1H of C$_6$H$_5$, 1H of oxbenzoxazapineH-6, H-8, H-9), 6.97-6.95 (2H, m, 2H of oxobenzoxazapineH-6, H-8, H-9), 4.48 (1H, dd, J 9.5, 7.5 Hz, 1H of oxobenzoxazapineH-2), 4.37 (1H, dd, J 11.5, 9.5 Hz, 1H of oxobenzoxazapineH-2), 3.55 (1H, dt, J 11.5, 7.5 Hz, oxobenzoxazapineH-3), 3.28 (1H, d, J 8.5 Hz, NH), 2.88 (3H, s, NCH$_3$), 1.63 (6H, s, C(C$\underline{H}_3$)$_2$OH); m/z: 561 [M−H+HCO$_2$H]$^−$.

177

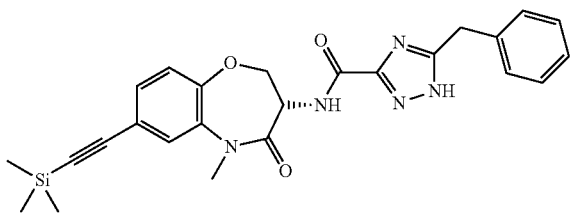

(S)-5-benzyl-N-(5-methyl-4-oxo-7-((trimethylsilyl)ethynyl)-2,3,4,5-tetrahydrobenzo[b][1,4]oxazepin-3-yl)-1H-1,2,4-triazole-3-carboxamide $^1$H nmr (400 MHz, CDCl$_3$) δ 8.09 (1H, d, J 7.5 Hz, NH), 7.33-7.31 (2H, m, oxobenzoxazapineH-8, H-9), 7.25-7.20 (5H, m, C$_6$H$_5$), 7.09 (1H, d, J 9.0 Hz, oxobenzoxazapineH-9), 5.01 (1H, dt, J 11.0, 7.5 Hz, oxobenzoxazapineH-3), 4.66 (1H, dd, J 9.5, 7.5 Hz, 1H of oxobenzoxazapineH-2), 4.27 (1H, dd, J 11.0, 10.0 Hz, 1H of oxobenzoxazapineH-2), 4.15 (2H, s, CH$_2$C$_6$H$_5$), 3.40 (3H, s, NCH$_3$), 0.26 (9H, s, Si(CH$_3$)$_3$); m/z: 474 [M+H]$^+$ (found [M+H]$^+$, 474.1981, C$_{25}$H$_{27}$N$_5$O$_3$Si requires [M+H]$^+$ 474.1956).

178

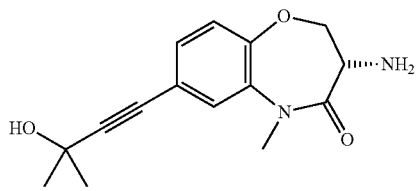

(S)-3-amino-7-(3-hydroxy-3-methylbut-1-yn-1-yl)-5-methyl-2,3-dihydrobenzo[b][1,4]oxazepin-4(5H)-one $^1$H nmr (400 MHz, CDCl$_3$) δ 7.24 (1H, d, J 2.0 Hz, oxobenzoxazapineH-6), 7.22 (1H, dd, J 8.0, 2.0 Hz, oxobenzoxazapineH-8), 7.06 (1H, d, J 8.0 Hz, oxobenzoxazapineH-9), 4.41 (1H, dd, J 10.0, 7.5 Hz, 1H of oxobenzoxazapineH-2), 4.12 (1H, dd, J 11.5, 10.0 Hz, 1H of oxobenzoxazapineH-2), 3.72 (1H, dd, J 11.5, 7.5 Hz, oxobenzoxazapineH-3); m/z: 275 [M+H]$^+$ (found [M+H]$^+$, 275.1390, C$_{15}$H$_{18}$N$_2$O$_3$ requires [M+H]$^+$ 275.1404).

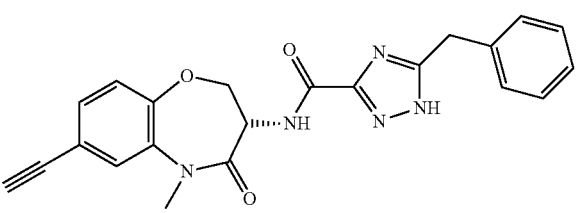

(S)-5-benzyl-N-(7-ethynyl-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.06 (1H, d, J Hz, NH), 7.36 (1H, dd, J Hz, oxobenzoxazapineH-8), 7.35-7.26 (6H, m, C$_6$H$_5$, oxobenzoxazapineH-6), 7.14 (1H, d, J 8.5 Hz, oxobenzoxazapineH-9), 5.04 (1H, dt, J 11.0, 7.5 Hz, oxobenzoxazapineH-3), 4.71 (1H, dd, J 9.5, 7.5 Hz, 1H of oxobenzoxazapineH-2), 4.29 (1H, dd, J 11.0, 9.5 Hz, 1H of oxobenzoxazapineH-2), 4.17 (2H, s, CH$_2$C$_6$H$_5$), 3.42 (3H, s, NCH$_3$), 3.12 (1H, s, HCC); $^{13}$C nmr (100 MHz, CDCl$_3$) δ 168.6, 150.4, 136.1, 131.5, 128.9 (2C), 127.3, 127.0, 123.3, 119.8, 82.0, 78.1, 77.2, 49.1, 35.5, 33.5; m/z: 402 [M+H]$^+$ (found [M+H]$^+$, 402.1561, C$_{22}$H$_{19}$N$_5$O$_3$ requires [M+H]$^+$ 402.1576).

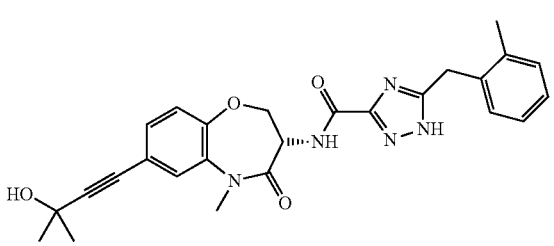

(S)—N-(7-(3-hydroxy-3-methylbut-1-yn-1-yl)-5-methyl-4-oxo-2,3,4,5-tetrahydrobenzo[b][1,4]oxazepin-3-yl)-1-(2-methylbenzyl)-1H-1,2,4-triazole-3-carboxamide $^1$H nmr (400 MHz, CDCl$_3$) δ 8.03 (1H, d, J 7.0 Hz, NH), 7.83 (1H, s, triazoleH-5), 7.32-7.21 (5H, m, 5H of C$_6$H$_4$, oxobenzoxazapineH-6), 7.16 (1H, dd, J 9.0, 2.0 Hz, oxobenzoxazapineH-8), 7.12 (1H, d, J 9.0 Hz, oxobenzoxazapineH-9), 5.37 (2H, s, NCH$_2$C$_6$H$_4$CH$_3$), 5.07 (1H, dt, J 11.0, 7.5 Hz, oxobenzoxazapineH-3), 4.76 (1H, dd, J 9.5, 7.5 Hz, 1H of oxobenzoxazapineH-2), 4.26 (1H, dd, J 11.0, 9.5 Hz, 1H of oxobenzoxazapineH-2), 3.41 (3H, s, NCH$_3$), 2.27 (3H, s, C$_6$H$_4$CH$_3$), 1.62 (6H, s, C(CH$_3$)$_2$OH); $^{13}$C nmr (100 MHz, CDCl$_3$) δ 168.8, 158.4, 156.5, 149.9, 143.8, 136.8, 136.0, 131.4, 131.1, 130.9, 129.7, 129.4, 126.8, 126.5, 123.2, 120.4, 94.5, 80.6, 77.1, 65.5, 52.6, 49.1, 35.5, 31.4, 19.0; m/z: 474 [M+H]$^+$, 456 [M+H—H$_2$O]$^+$

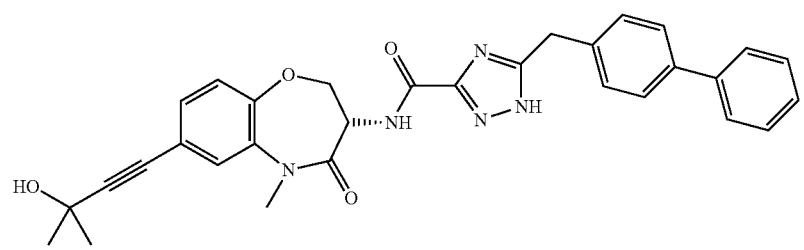

(S)-1-([1,1'-biphenyl]-4-ylmethyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.07 (1H, s, traizoleH-5), 8.06 (1H, d, J 7.0 Hz, NH), 7.60-7.55 (4H, m, 4H of C$_6$H$_4$C$_6$H$_5$), 7.45-7.42 (2H, m, 2H of C$_6$H$_4$C$_6$H$_5$), 7.38-7.34 (3H, m, 3H of C$_6$H$_4$C$_6$H$_5$), 7.28-7.26 (2H, m, oxobenzoxazapineH-6, H-8), 7.11 (1H, d, J 9.0 Hz, oxobenzoxazapineH-9), 5.41 (2H, s, NCH$_2$C$_6$H$_4$Ph), 5.07 (1H, dt, J 11.0, 7.5 Hz, oxobenzoxazapineH-3), 4.76 (1H, dd, J 9.5, 7.5 Hz, 1H of oxobenzoxazapineH-2), 4.27 (1H, dd, J 11.0, 10.0 Hz, 1H of oxobenzoxazapineH-2), 3.41 (3H, s, NCH$_3$), 1.62 (6H, s, C(CH$_3$)$_2$OH); $^{13}$C nmr (100 MHz, CDCl$_3$) δ 169.1, 158.7, 157.0, 150.3, 144.3, 142.3, 140.4, 136.3, 132.9, 131.2, 129.2, 129.0, 128.2, 128.0, 127.4, 126.8, 123.5, 120.7, 94.9, 80.9, 77.5, 65.9, 54.4, 49.4, 35.8, 31.7; m/z: 536 [M+H]$^+$, 518 [M+H—H$_2$O]$^+$

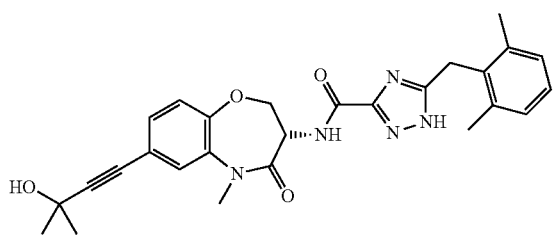

(S)-1-(2,6-dimethylbenzyl)-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.02 (1H, d, J 7.0 Hz, NH), 7.59 (1H, s, triazoleH-5), 7.28-7.21 (3H, m, 3H of oxobenzoxazapineH-6, H-8, H-9, C$_6$H$_3$(CH$_3$)$_2$), 7.13-7.10 (3H, m, 3H of oxobenzoxazapineH-6, H-8, H-9, C$_6$H$_3$(CH$_3$)$_2$), 5.41 (2H, s, NCH$_2$C$_6$H$_3$(CH$_3$)$_2$), 5.06 (1H, dt, J 11.0, 7.5 Hz, oxobenzoxazapineH-3), 4.76 (1H, dd, J 9.5, 7.5 Hz, 1H of oxobenzoxazapineH-2), 4.26 (1H, dd, J 11.0, 9.5 Hz, 1H of oxobenzoxazapineH-2), 3.41 (3H, s, NCH$_3$), 2.30 (6H, s, C$_6$H$_3$(CH$_3$)$_2$), 1.62 (6H, s, C(CH$_3$)$_2$OH); $^{13}$C nmr (100 MHz, CDCl$_3$) δ 168.8, 158.5, 156.5, 149.9, 143.1, 138.1, 136.0, 130.9, 129.6, 129.0 (2C), 126.5, 123.2, 120.4, 94.5, 80.6, 77.1, 65.5, 49.1, 49.0, 35.5, 31.4, 19.6; m/z: 488 [M+H]$^+$, 470 [M+H—H$_2$O]$^+$ (found [M+H]$^+$, 488.2292, C$_{27}$H$_{29}$N$_5$O$_4$ requires [M+H]$^+$ 488.2292).

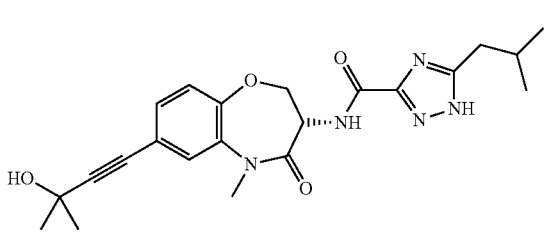

(S)—N-(7-(3-hydroxy-3-methylbut-1-yn-1-yl)-5-methyl-4-oxo-2,3,4,5-tetrahydrobenzo[b][1,4]oxazepin-3-yl)-1-isobutyl-1H-1,2,4-triazole-3-carboxamide $^1$H nmr (400 MHz, CDCl$_3$) δ 8.04 (1H, s, triazoleH-5), 8.03 (1H, d, J 7.0 Hz, NH), 7.29-7.26 (2H, m, oxobenzoxazapineH-6, H-8), 7.12 (1H, d, J 9.0 Hz, oxobenzoxazapineH-9), 5.06 (1H, ddd, J 11.0, 7.5, 7.0 Hz, oxobenzoxazapineH-3), 4.75 (1H, dd, J 9.5, 7.5 Hz, 1H of oxobenzoxazapineH-2), 4.26 (1H, dd, J 11.0, 10.0 Hz, 1H of oxobenzoxazapineH-2), 3.98 (2H, d, J 7.0 Hz, NCH$_2$CH(CH$_3$)$_2$), 3.41 (3H, s, NCH$_3$), 2.30-2.23 (1H, m, CH(CH$_3$)$_2$), 1.62 (6H, s, C(CH$_3$)$_2$OH), 0.91 (6H, dd, J 6.5, 1.0 Hz, CH(CH$_3$)$_2$); $^{13}$C nmr (100 MHz, CDCl$_3$) δ 168.9, 158.5, 156.5, 149.9, 144.3, 136.0, 130.9, 126.5, 123.2, 120.4, 94.5, 80.6, 77.1, 65.5, 57.6, 49.1, 35.5, 31.4, 29.0, 19.7; m/z: 426 [M+H]$^+$, 408 [M+H—H$_2$O]$^+$ (found [M+H]$^+$, 426.2126, C$_{22}$H$_{27}$N$_5$O$_4$ requires [M+H]$^+$ 426.2136).

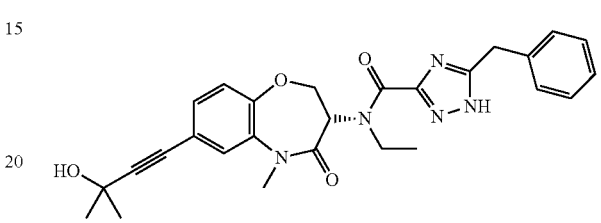

(S)-5-benzyl-N-ethyl-N-(7-(3-hydroxy-3-methylbut-1-yn-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 7.30-7.18 (5H, m, 5H of C$_6$H$_5$, oxobenzoxazapineH-6, H-8, H-9), 7.13-7.06 (3H, m, 3H of C$_6$H$_5$, oxobenzoxazapineH-6, H-8, H-9), 6.85-6.77 (0.66H, m, oxobenzoxazapineH-3major), 5.34-5.27 (0.33H, m, oxobenzoxazapineH-3minor), 4.94 (0.33H, dd, J 12.0, 10.5 Hz, oxobenzoxazapineH-3minor), 4.84 (0.66H, dd, J 12.0, 9.5 Hz, oxobenzoxazapineH-3major), 4.55 (0.66H, dd, J 9.5, 7.5 Hz, 1H of oxobenzoxazapineH-2major), 4.50 (0.33H, m, 1H of oxobenzoxazapineH-2minor), 4.11 (0.66H, s, CH$_2$C$_6$H$_5$minor), 4.05 (1.32H, q, J 7.0 Hz, NCH$_2$CH$_3$major), 3.91, 3.84 (1.32H, 2d AB system, J 15.5 Hz, CH$_2$C$_6$H$_5$major), 3.50 (0.66H, q, J 7.0 Hz, NCH$_2$CH$_3$minor), 3.28 (1H, s, NCH$_3$minor), 3.25 (2H, s, NCH$_3$major), 1.61 (2H, s, C(CH$_3$)$_2$OHminor), 1.57 (4H, s, C(CH$_3$)$_2$OHmajor), 1.20 (3H, t, J 7.0 Hz, NCH$_2$CH$_3$); m/z: 488 [M+H]$^+$, 470 [M+H—H$_2$O]$^+$ (found [M+H]$^+$, 488.2291, C$_{27}$H$_{29}$N$_5$O$_4$ requires [M+H]$^+$ 488.2292).

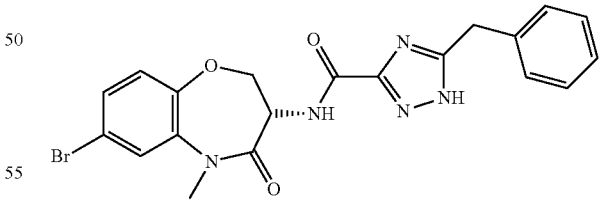

(S)-5-benzyl-N-(7-bromo-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.10 (1H, d, J Hz, NH), 7.33 (1H, m, oxobenzoxazapineH-6), 7.31 (1H, dd, J 8.0, 2.5 Hz, oxobenzoxazapineH-8), 7.15 (5H, br s, C$_6$H$_5$), 7.02 (1H, dd, J 8.0, 1.0 Hz, oxobenzoxazapineH-9), 4.10 (2H, s, CH$_2$C$_6$H$_5$), 3.36 (3H, s, NCH$_3$); $^{13}$C (100 MHz, 100 MHz) δ

168.7, 158.9, 149.1, 137.4, 135.8, 130.6, 128.8, 128.7, 127.1, 126.4, 118.1, 77.2, 49.2, 35.5, 32.9; m/z: 458, 456 [M+H]⁺ (found [M+H]⁺, 458.0651, C$_{20}$H$_{18}$BrN$_5$O$_3$ requires [M+H]⁺ 458.0645).

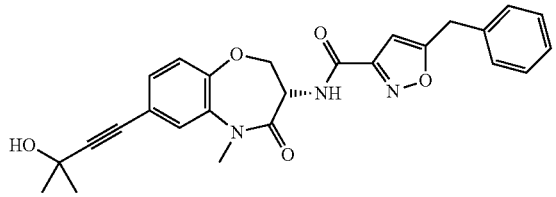

(S)-5-benzyl-N-(7-(3-hydroxy-3-methylbut-1-yn-1-yl)-5-methyl-4-oxo-2,3,4,5-tetrahydrobenzo[b][1,4]oxazepin-3-yl)isoxazole-3-carboxamide ¹H nmr (400 MHz, CDCl$_3$) δ 7.72 (1H, d, J 7.0 Hz, NH), 7.36-7.21 (7H, m, C$_6$H$_5$, oxobenzoxazapineH-6, H-8), 7.11 (1H, d, J 9.0 Hz, oxobenzoxazapineH-9), 6.30 (1H, br s, isoxazoleH-5), 4.99 (1H, dt, J 11.0, 7.0 Hz, oxobenzoxazapineH-3), 4.70 (1H, dd, J 9.5, 7.5 Hz, 1H of oxobenzoxazapineH-2), 4.26 (1H, dd, J 11.0, 10.0 Hz, 1H of oxobenzoxazapineH-2), 4.10 (2H, s, CH$_2$C$_6$H$_5$), 3.41 (3H, s, NCH$_3$), 1.62 (6H, s, C(CH$_3$)$_2$OH); ¹³C nmr (100 MHz, CDCl$_3$) δ 174.1, 168.4, 158.5, 157.9, 149.9, 136.0, 135.2, 130.9, 128.9, 128.7, 127.4, 126.5, 123.1, 120.4, 101.6, 94.6, 80.6, 76.9, 65.6, 49.2, 35.5, 33.2, 31.4; m/z: 460 [M+H]⁺, 442 [M+H—H$_2$O]⁺ (found [M+H]⁺, 460.1884, C$_{26}$H$_{25}$N$_3$O$_5$ requires [M+H]⁺ 460.1867).

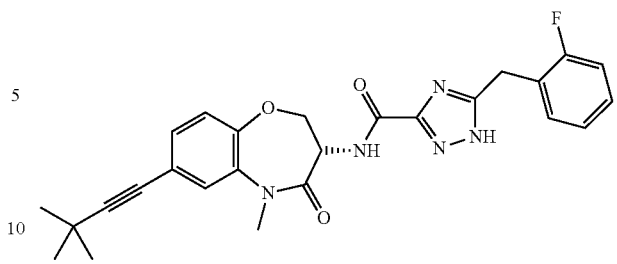

(S)—N-(7-(3,3-dimethylbut-1-yn-1-yl)-5-methyl-4-oxo-2,3,4,5-tetrahydrobenzo[b][1,4]oxazepin-3-yl)-5-(2-fluorobenzyl)-1H-1,2,4-triazole-3-carboxamide ¹H nmr (400 MHz, CDCl$_3$) δ 8.07 (1H, d, J 7.0 Hz, NH), 7.26-7.19 (4H, m, oxobenzoxazapineH-6, H-7, 2H of C$_6$H$_4$F), 7.08 (1H, d, J 9.0 Hz, oxobenzoxazapineH-9), 7.06-7.02 (1H, m, 1H of C$_6$H$_4$F), 7.03-6.99 (1H, m, 1H of C$_6$H$_4$F), 5.01 (1H, dt, J 11.0, 7.5 Hz, oxobenzoxazapineH-3), 4.66 (1H, dd, J 10.0, 7.5 Hz, 1H of oxobenzoxazapineH-2), 4.25 (1H, dd, J 11.0, 10.0 Hz, 1H of oxobenzoxazapineH-2), 4.19 (2H, s, CH$_2$C$_6$H$_4$F), 3.40 (3H, s, NCH$_3$), 1.32 (9H, s, C(CH$_3$)$_3$); ¹³C nmr (100 MHz, CDCl$_3$) δ 168.8, 160.7 (d, J 245.5 Hz), 158.5, 149.2, 135.8, 131.0 (d, J 4.0 Hz), 130.9, 128.9 (d, J 8.5 Hz), 126.4, 124.3 (d, J 4.0 Hz), 123.1 (d, J 15.0 Hz), 122.8, 121.8, 115.3 (d, J 21.5 Hz), 99.4, 77.6, 77.0, 49.2, 35.5, 30.9, 27.9, 26.3; m/z: 476 [M+H]⁺ (found [M+H]⁺, 476.2100, C$_{25}$H$_{26}$FN$_5$O$_3$ requires [M+H]⁺ 476.2092).

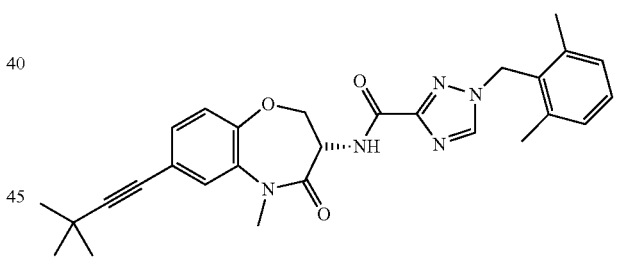

(S)-5-benzyl-N-(5-methyl-4-oxo-7-((1,2,3,4-tetrahydroisoquinolin-7-yl)ethynyl)-2,3,4,5-tetrahydrobenzo[b][1,4]oxazepin-3-yl)-1H-1,2,4-triazole-3-carboxamide ¹H nmr (400 MHz, CD$_3$OD) δ 7.71 (1H, dd, J 5.5, 3.0 Hz, 1×ArH), 7.20 (1H, dd, J 5.5, 3.0 Hz, 1×ArH), 7.59 (1H, d, J 2.0 Hz, 1×ArH), 7.44 (1H, td, J 8.5, 2.0 Hz, 1×ArH), 7.41 (1H, br s, 1×ArH), 7.33-7.23 (6H, m, 6×ArH), 5.03 (1H, dd, J 11.5, 7.5 Hz, oxobenzoxazapineH-3), 4.60 (1H, dd, J 9.5, 7.5 Hz, 1H of oxobenzoxazapineH-2), 4.45 (1H, dd, J 11.5, 9.5 Hz, 1H of oxobenzoxazapineH-2), 4.35 (2H, s, isoquinolineH-1), 4.16 (2H, s CH2C6H5), 3.50 (2H, t, J 6.5 Hz, isoquinolineH-3 or H-4), 3.42 (3H, s, NCH$_3$), 3.13 (2H, dd, J 7.0, 6.0 Hz, isoquinolineH-3 or H-4); m/z: 533 [M+H]⁺ (found [M+H]⁺, 533.2296, C$_{31}$H$_{28}$N$_6$O$_3$ requires [M+H]⁺ 533.2296).

(S)-1-(2,6-dimethylbenzyl)-N-(7-(3,3-dimethylbut-1-yn-1-yl)-5-methyl-4-oxo-2,3,4,5-tetrahydrobenzo[b][1,4]oxazepin-3-yl)-1H-1,2,4-triazole-3-carboxamide ¹H nmr (400 MHz, CDCl$_3$) δ 8.02 (1H, d, J 7.5 Hz, NH), 7.59 (1H, s, triazoleH-5), 7.26-7.22 (3H, m, oxobenzoxazapineH-6, H-8, C$_6$H$_3$(CH$_3$)$_2$H-4), 7.12 (2H, d, J 7.5 Hz, C$_6$H$_3$(CH$_3$)$_2$H-3, H-5), 7.09 (1H, d, J 9.0 Hz, oxobenzoxazapineH-9), 5.42 (2H, s, NCH$_2$C$_6$H$_3$(CH$_3$)$_2$), 5.06 (1H, dt, J 11.0, 7.5 Hz, oxobenzoxazapineH-3), 4.76 (1H, dd, J 9.5, 7.5 Hz, 1H of oxobenzoxazapineH-2), 4.24 (1H, dd, J 11.0, 10.0 Hz, 1H of oxobenzoxazapineH-2), 3.42 (3H, s, NCH$_3$), 2.31 (6H, s, C$_6$H$_3$(CH$_3$)$_2$, 1.32 (9H, s, C(CH$_3$)$_3$); m/z: 486 [M+H]⁺ (found [M+H]⁺, 486.2506, C$_{28}$H$_{31}$N$_5$O$_3$ requires [M+H]⁺ 486.2500).

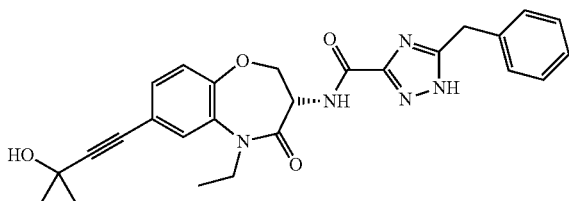

(S)-5-benzyl-N-(5-ethyl-7-(3-hydroxy-3-methylbut-1-yn-1-yl)-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.08 (1H, d, J 7.5 Hz, NH), 7.33-7.26 (7H, m, C$_6$H$_5$, oxobenzoxazapineH-6, H-8), 7.12 (1H, d, J 9.0 Hz, oxobenzoxazapineH-9), 4.99 (1H, dt, J 11.0, 7.5 Hz, oxobenzoxazapineH-3), 4.66 (1H, dd, J 9.5, 7.5 Hz, 1H of oxobenzoxazapineH-2), 4.26 (1H, dd, J 11.0, 10.0 Hz, 1H of oxobenzoxazapineH-2), 4.21-4.11 (1H, m, 1H of NCH$_2$CH$_3$), 4.16 (2H, s, NCH$_2$C$_6$H$_5$), 3.66 (1H, heptet, J 7.0 Hz, 1H of NCH$_2$CH$_3$), 1.63 (6H, s, C(CH$_3$)$_2$OH), 1.19 (3H, t, J 7.0 Hz, NCH$_2$CH$_3$); m/z: 456 [M+H—H$_2$O]$^+$ (found [M+H]$^+$, 474.2143, C$_{26}$H$_{27}$N$_5$O$_4$ requires [M+H]$^+$ 474.2136).

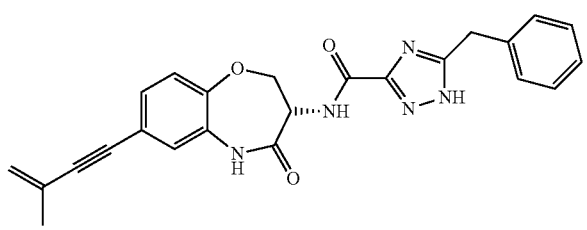

(S)—N-(5-ethyl-7-(3-hydroxy-3-methylbut-1-yn-1-yl)-4-oxo-2,3,4,5-tetrahydrobenzo[b][1,4]oxazepin-3-yl)-5-(3-fluorobenzyl)-1H-1,2,4-triazole-3-carboxamide $^1$H nmr (400 MHz, CDCl$_3$) δ 8.09 (1H, d, J 7.5 Hz, NH), 7.30-7.28 (2H, m, oxobenzoxazapineH-6, H-8), 7.26-7.21 (1H, m, 1H of C$_6$H$_4$F), 7.12 (1H, d, J 8.5 Hz, oxobenzoxazapineH-9), 7.03 (1H, br d, J 7.5 Hz, 1H of C$_6$H$_4$F), 6.98 (1H, br d, J 9.5 Hz, 1H of C$_6$H$_4$F), 6.92 (1H, td, J 8.5, 2.5 Hz, 1H of C$_6$H$_4$F), 4.97 (1H, dt, J 11.0, 7.5 Hz, oxobenzoxazapineH-3), 4.65 (1H, dd, J 9.5, 7.5 Hz, 1H of oxobenzoxazapineH-2), 4.27 (1H, dd, J 11.0, 10.5 Hz, 1H of oxobenzoxazapineH-2), 4.22-4.10 (1H, m, 1H of NCH$_2$CH$_3$), 4.14 (2H, s, CH$_2$C$_6$H$_4$F), 3.66 (1H, heptet, J 7.0 Hz, 1H of NCH$_2$CH$_3$), 1.63 (6H, s, C(CH$_3$)$_2$OH), 1.19 (3H, t, J 7.0 Hz, NCH$_2$CH$_3$); $^{19}$F nmr (380 MHz, CDCl$_3$) δ −112.6; m/z: 474 [M+H—H$_2$O]$^+$ (found [M+H]$^+$, 492.2047, C$_{26}$H$_{26}$FN$_5$O$_4$ requires [M+H]$^+$ 492.2042).

(S)-5-benzyl-N-(7-(3-methylbut-3-en-1-yn-1-yl)-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.01 (1H, d, J 7.0 Hz, 1×NH), 7.54 (1H, s, 1×NH), 7.35-7.24 (6H, m, C$_5$H$_5$, oxobenzoxazapineH-8), 7.10 (1H, d, J 8.5 Hz, oxobenzoxazapineH-9), 7.09 (1H, m, oxobenzoxazapineH-6), 5.40 (1H, br s, 1H of C=CH$_2$), 5.32 (1H, br s, 1H of C=CH$_2$), 5.08 (1H, m, oxobenzoxazapineH-3), 4.76 (1H, dd, J 10.0, 6.0 Hz, 1H of oxobenzoxazapineH-2), 4.33 (1H, t, J 10.5 Hz, 1H of oxobenzoxazapineH-2), 4.18 (2H, s, CH$_2$C$_6$H$_5$), 1.98 (3H, s, CCH$_3$); m/z: 428 [M+H]$^+$ (found [M+H]$^+$, 428.1709, C$_{24}$H$_{21}$N$_5$O$_3$ requires [M+H]$^+$ 428.1717).

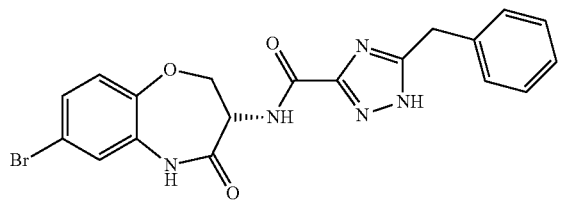

(S)-5-benzyl-N-(7-bromo-4-oxo-2,3,4,5-tetrahydrobenzo[b][1,4]oxazepin-3-yl)-1H-1,2,4-triazole-3-carboxamide $^1$H nmr (400 MHz, CD$_3$OD) δ 7.32-7.21 (7H, m, C$_6$H$_5$, oxobenzoxazapineH-6, H-8), 7.06 (1H, d, J 8.0 Hz, oxobenzoxazapineH-9), 5.00 (1H, dd, J 10.5, 6.5 Hz, oxobenzoxazapineH-3), 4.61 (1H, dd, J 10.5, 6.5 Hz, 1H of oxobenzoxazapineH-2), 4.40 (1H, t, J 9.5 Hz, 1H of oxobenzoxazapineH-2), 4.15 (2H, s, CH$_2$C$_6$H$_5$); m/z: 444, 442 [M+H]$^+$ (found [M+H]$^+$, 444.0492, C$_{19}$H$_{16}$BrN$_5$O$_3$ requires [M+H]$^+$ 444.0489).

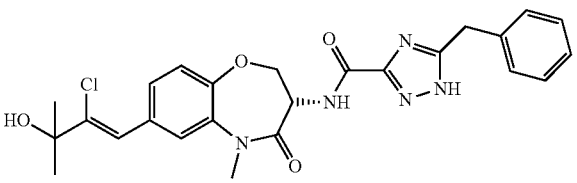

(S,Z)-5-benzyl-N-(7-(2-chloro-3-hydroxy-3-methylbut-1-en-1-yl)-5-methyl-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.09 (1H, d, J 7.5 Hz, NH), 7.41-7.39 (2H, m, oxobenzoxazapineH-6, H-8), 7.29-7.22 (5H, m, C$_6$H$_5$), 7.15 (1H, d, J 9.0 Hz, oxobenzoxazapineH-9), 6.31 (1H, s, CH=CC), 5.05 (1H, dt, J 11.5, 7.5 Hz, oxobenzoxazapineH-3), 4.67 (1H, dd, J 9.5, 7.5 Hz, 1H of oxobenzoxazapineH-2), 4.28 (1H, dd, J 11.0, 10.0 Hz, 1H of oxobenzoxazapineH-2), 4.14 (2H, s, CH$_2$C$_6$H$_5$), 3.43 (3H, s, NCH$_3$), 1.57 (6H, s, C(CH$_3$)$_2$OH); $^{13}$C nmr (100 MHz, CDCl$_3$) δ 168.7, 158.9, 158.4, 154.3, 150.2, 136.5, 135.9, 135.7, 135.7, 130.1, 128.9, 128.8, 127.2, 125.8, 122.8, 121.8, 77.2, 71.2, 49.1, 35.6, 33.2, 29.4; m/z: 480, 478 [M+H—H$_2$O]$^+$; m/z: 496, 494 [M−H]$^−$ (found [M+H]$^+$, 496.1743, C$_{25}$H$_{26}$ClN$_5$O$_4$ requires [M+H]$^+$ 496.1746).

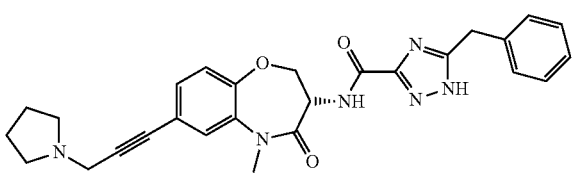

(S)-5-benzyl-N-(5-methyl-4-oxo-7-(3-(pyrrolidin-1-yl)prop-1-yn-1-yl)-2,3,4,5-tetrahydrobenzo[b][1,4]oxazepin-3-yl)-1H-1,2,4-triazole-3-carboxamide $^1$H nmr (400 MHz, CDCl$_3$) δ 8.07 (1H, d, J 7.5 Hz, NH), 7.28-7.20 (7H, m, oxobenzoxazapineH-6, H-8, C$_6$H$_5$), 7.09 (1H, d, J 9.0 Hz, oxobenzoxazapineH-9), 5.02 (1H, dt, J 11.0, 7.5 Hz, oxobenzoxazapineH-3), 4.66 (1H, dd, J 9.5, 7.5 Hz, 1H of oxobenzoxazapineH-2), 4.26 (1H, dd, J 11.0, 10.0 Hz, 1H of oxobenzoxazapineH-2), 4.14 (2H, s, C$\underline{H}_2$C$_6$H$_5$), 3.62 (2H, s, CCH$_2$N), 3.38 (3H, s, NCH$_3$), 2.73-2.70 (4H, m, 4H of pyrrolidine), 1.86-1.82 (4H, m, 4H of pyrrolidine); m/z: 485 [M+H]$^+$ (found [M+H]$^+$, 485.2322, C$_{27}$H$_{28}$N$_6$O$_3$ requires [M+H]$^+$ 485.2296).

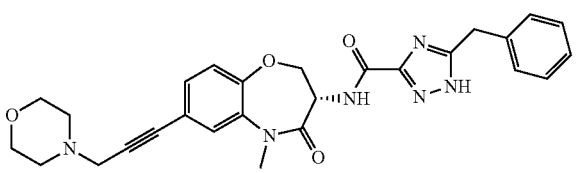 [SMILES: CN1C(=O)[C@@H](NC(=O)c2n[nH]c(Cc3ccccc3)n2)COc2ccc(C#CCN3CCOCC3)cc21]

(S)-5-benzyl-N-(5-methyl-7-(3-morpholinoprop-1-yn-1-yl)-4-oxo-2,3,4,5-tetrahydrobenzo[b][1,4]oxazepin-3-yl)-1H-1,2,4-triazole-3-carboxamide $^1$H nmr (400 MHz, CDCl$_3$) δ 8.08 (1H, d, J 7.0 Hz, NH), 7.29-7.7.27 (2H, m, oxobenzoxazapineH-6, H-8), 7.25-7.18 (5H, m, C$_6$H$_5$), 7.10 (1H, d, J 9.0 Hz, oxobenzoxazapineH-9), 5.02 (1H, dt, J 11.0, 7.0 Hz, oxobenzoxazapineH-3), 4.65 (1H, dd, J 9.5, 7.5 Hz, 1H of oxobenzoxazapineH-2), 4.27 (1H, t, J 10.5 Hz, 1H of oxobenzoxazapineH-2), 4.13 (2H, s, C$\underline{H}_2$C$_6$H$_5$), 3.78, 3.76 (4H, 2d AB system, J 4.5 Hz, 4H of morpholine), 3.50 (2H, s, CCH$_2$N), 3.39 (3H, s, NCH$_3$), 2.65, 2.63 (4H, 2d AB system, J 4.5 Hz, 4H of morpholine); m/z: 501 [M+H]$^+$ (found [M+H]$^+$, 501.2245, C$_{27}$H$_{28}$N$_6$O$_4$ requires [M+H]$^+$ 501.2245).

Example 11

In this example, compounds of the disclosure were evaluated using a biochemical assay using the ADP-Glo™ technology.

ADP-Glo™ (Promega, Madison, Wis., USA) reagents were thawed at ambient temperature. Kinase Detection Reagent was prepared by mixing kinase detection buffer with the lyophilized kinase detection substrate.

A 500 ml stock volume of 5× Reaction Kinase Buffer was made by mixing 1000 μl of 1M MgCl$_2$, 500 μl of 1M Tris-HCL pH7.4, 0.5 mg/ml (25 mg) of BSA, and 3475 μl of distilled H$_2$O. A 3 ml 2× working stock volume of Reaction Kinase Buffer was made containing a final concentration of 100 μM DTT and 4 mM MnCl$_2$.

Components of RIPK1 enzyme (Rigel Pharmaceuticals, South San Francisco, Calif., USA) were thawed on ice. Diluted RIPK1 was prepared in 1× Kinase Reaction Buffer (diluted from 2× buffer) to 31 ng/well. A 166 M working stock ATP assay solution was prepared in 1× Kinase Reaction Buffer (diluted from 2× buffer).

Compounds were serially diluted in DMSO from 250 uM in 4-fold dilutions then diluted 1:5 in 2× Reaction Buffer in a 96 well plate. 1.0 ul of diluted compound was added to a 384 well plate in duplicate. 2 μl of diluted Active RIPK1 was added to 384 well plate (do not add to column1) add 2× rxn buffer to column 1. AKT (Anaspec, Fremont, Calif., USA) at 150 nM was combined with ATP working stock at equal volume and 2 ul/well were added to the 384 well plate. The final reaction volume was 5.0 μl.

The plate was quickly centrifuged and the reaction was incubated at 30° C. for 30 minutes. Adding 5 μl of ADP-Glo™ terminated the reaction. The plate was quickly centrifuged and the reaction was incubated at room temperature for 40 minutes. Kinase Detection Reagent was then added and incubated at room temperature for 30 minutes. The relative light unit (RLU) of kinase reaction was determined by luminescent (Luminescence 0.1 s) using a Wallac Victor2 Luminometer (PerkinElmer, Waltham, Mass., USA). IC$_{50}$ values obtained from this example are provided by Table 1.

TABLE 1

| Compound | RIPK1 ADP-Glo Kinase (IC$_{50}$) |
| --- | --- |
| I-1 | 0.019 |
| I-2 | 0.0157 |
| I-3 | 0.0402 |
| I-4 | 0.0568 |
| I-5 | 0.0197 |
| I-6 | 0.0724 |
| I-7 | 0.021 |
| I-8 | 0.0529 |
| I-9 | 0.1892 |
| I-10 | 0.0429 |
| I-11 | 0.0571 |
| I-12 | 0.052 |
| I-13 | 0.0539 |
| I-14 | 0.073 |
| I-15 | 0.1359 |
| I-16 | 1.633 |
| I-17 | 0.4906 |
| I-18 | 0.1645 |
| I-19 | 0.1455 |
| I-20 | 0.1528 |
| I-21 | 0.077 |
| I-22 | 0.048 |
| I-23 | 0.0352 |
| I-24 | 0.0592 |
| I-25 | 0.051 |
| I-26 | 0.0656 |
| I-27 | 0.1583 |
| I-28 | 0.0375 |
| I-29 | 0.0124 |
| I-30 | 0.0402 |
| I-31 | 0.0334 |
| I-32 | 0.0219 |
| I-33 | 0.0145 |
| I-34 | 0.0492 |
| I-35 | 0.0223 |
| I-36 | 0.0338 |
| I-37 | 0.0565 |
| I-38 | 0.068 |
| I-39 | 0.0364 |
| I-40 | 0.0887 |
| I-41 | 0.08 |
| I-42 | 0.0477 |
| I-43 | 0.0854 |
| I-44 | 0.034 |
| I-45 | 0.0825 |
| I-46 | 0.0437 |
| I-47 | 0.0683 |
| I-48 | 0.0624 |

TABLE 1-continued

| Compound | RIPK1 ADP-Glo Kinase (IC$_{50}$) |
|---|---|
| I-49 | 0.0604 |
| I-50 | 0.0234 |
| I-51 | 0.0317 |
| I-52 | 0.0249 |
| I-53 | 0.034 |
| I-54 | 0.0269 |
| I-55 | 0.0337 |
| I-57 | 0.0215 |
| I-58 | 0.011 |
| I-59 | 0.0579 |
| I-60 | 0.0644 |
| I-61 | 0.0654 |
| I-62 | 0.0355 |
| I-63 | 0.0303 |
| I-64 | 0.019 |
| I-65 | 0.0639 |
| I-66 | 0.0794 |
| I-67 | 0.0415 |
| I-68 | 0.0222 |
| I-69 | 0.0286 |
| I-70 | 1.155 |
| I-71 | 0.0217 |
| I-73 | 0.0429 |
| I-74 | 0.0518 |
| I-75 | 0.0546 |
| I-76 | 0.0449 |
| I-77 | 0.0327 |
| I-78 | 0.0334 |
| I-79 | 0.0347 |
| I-80 | 0.0206 |
| I-81 | 0.019 |
| I-82 | 0.0255 |
| I-83 | 0.0664 |
| I-84 | 0.0441 |
| I-85 | 0.0423 |
| I-86 | 0.6161 |
| I-87 | 0.0187 |
| I-88 | 0.0738 |
| I-89 | 0.0527 |
| I-90 | 0.3649 |
| I-91 | 0.3879 |
| I-92 | 0.9325 |
| I-93 | 0.0641 |
| I-94 | 0.0333 |
| I-95 | 0.0271 |
| I-96 | 0.0317 |
| I-97 | 0.0858 |

Example 12

In this example, U937 and L929 cells were exposed to compounds of the present disclosure and a cell necroptosis assay was conducted to evaluate the compounds' activity against human RIP1 and murine RIP1.

U937 and L929 cells were obtained from the American Type Culture Collection (Manassa, Va., USA). Both cells were maintained in logarithmic growth phase in complete RPMI 1640 media (Sigma, ST Louis, Mo., USA) supplemented with 10% fetal bovine serum (Sigma, ST Louis, Mo., USA) at 37° C. with 5% $CO_2$. For necroptosis assay, L929 cells were plated for 18 h in 100 μL/well medium at 10K cells/well in Costar 96-well black clear-bottom plates (Fisher Scientific, Hampton, N.H., USA); U937 cells were plated on the day of the assay in 50 μL/well medium containing 60 uM zVAD-fmk (Lonza, Basel, Switzerland) at 50K cells/well. Medium from L929 cells were removed from the 96-well plates and replaced with 50 μL/well new medium containing 40 uM zVAD-fmk. Each compound of the present disclosure evaluated in this example was serially diluted in DMSO from 2.5 mM in 4-fold dilutions, and then diluted 1:125 in complete medium. 50 μL/well 2× of the compound was then added to the cells in the plates. The cells were pre-incubated with the compound for 1 hour at 37° C. with 5% $CO_2$ and before addition of 10 μL/well 11×TNFa (Peprotech, Rocky Hill, N.J., USA) to give a final concentration of 2 ng/mL for TNFa. The relative amount of necroptosis cells was determined by luminescent using a Wallac Victor2 Luminometer (PerkinElmer, Waltham, Mass., USA) and a CellTiter-Glo® Luminescent Cell Viability Reagent Assay (Promega, Madison, Wis., USA) added per manufacturer instructions after 18 hours of TNFa stimulation at 37° C. with 5% $CO_2$. Results from this example are summarized in Table 2. This example establishes that embodiments of the compounds described herein have unexpectedly potent activity against human RIP1 and murine RIP1, which allows their assessment in in vivo mouse models of disease. These results are useful in determining safe and effective doses for humans.

TABLE 2

| Compound | L929-CTG-recovery, L929, TNFa + zVAD (IC$_{50}$) | U937 Zvad TNF CTG Recovery, U937, TNFa + zVAD (IC$_{50}$) |
|---|---|---|
| I-1 | 2.356 | 0.0027 |
| I-2 |  | 0.0319 |
| I-3 | 0.4278 | 0.0049 |
| I-4 |  | 0.0293 |
| I-5 | 0.0188 | 0.0005 |
| I-6 | 97.54 | 0.0438 |
| I-7 | 1.959 | 0.0009 |
| I-8 | 0.0092 | 0.0014 |
| I-9 |  | 0.3623 |
| I-10 | 11.23 | 0.0079 |
| I-11 | 14.1 | 0.0081 |
| I-12 | 41.95 | 0.0053 |
| I-13 |  | 0.0138 |
| I-14 | 5.878 | 0.0114 |
| I-15 | 2.2 | 0.0048 |
| I-16 | 5.669 | 0.0517 |
| I-17 | 0.3683 | 0.0024 |
| I-18 | 0.2797 | 0.0013 |
| I-19 | 1.302 | 0.0027 |
| I-20 | 53.37 | 0.0136 |
| I-21 | 1.306 | 0.0025 |
| I-22 | 3.383 | 0.0048 |
| I-23 | 14.5 | 0.0067 |
| I-24 | 4.608 | 0.0036 |
| I-25 | 0.4895 | 0.0027 |
| I-26 | 0.6131 | 0.0044 |
| I-27 |  | 0.0697 |
| I-28 | 0.6735 | 0.0054 |
| I-29 | 0.0088 | 0.0023 |
| I-30 | 0.0723 | 0.0036 |
| I-31 |  | 0.0337 |
| I-32 | 17.74 | 0.0027 |
| I-33 | 1.227 | 0.0015 |
| I-34 | 9.592 | 0.0222 |
| I-35 | 0.0178 | 0.0031 |
| I-36 | 0.0014 | 0.0022 |
| I-37 | 0.0002 | 0.001 |
| I-38 | 0.0005 | 0.0036 |
| I-39 | 0.0004 | 0.0027 |
| I-40 | 0.0003 | 0.0023 |
| I-41 | 0.0016 | 0.0052 |
| I-42 | 0.0012 | 0.0033 |
| I-43 | 0.0009 | 0.0038 |
| I-44 | 0.0002 | 0.0011 |
| I-45 | 0.0003 | 0.0014 |
| I-46 | 0.0004 | 0.0012 |
| I-47 | 0.0015 | 0.0046 |
| I-48 | 0.0005 | 0.0016 |
| I-49 | 0.0012 | 0.005 |
| I-50 | 0.0003 | 0.0011 |
| I-51 | 0.0005 | 0.0017 |
| I-52 | 0.0003 | 0.0009 |

TABLE 2-continued

| Compound | L929-CTG-recovery, L929, TNFa + zVAD (IC$_{50}$) | U937 Zvad TNF CTG Recovery, U937, TNFa + zVAD (IC$_{50}$) |
|---|---|---|
| I-53 | 0.0005 | 0.0018 |
| I-54 | 0.0003 | 0.0009 |
| I-55 | 0.0006 | 0.002 |
| I-57 | 0.0009 | 0.003 |
| I-58 | 0.0002 | 0.0008 |
| I-59 | 0.0007 | 0.0019 |
| I-60 | 0.0024 | 0.0048 |
| I-61 | 0.0013 | 0.0034 |
| I-62 | 0.0007 | 0.002 |
| I-63 | 0.0003 | 0.001 |
| I-64 | 0.0001 | 0.0005 |
| I-65 | 0.0415 | 0.042 |
| I-66 | 0.0949 | 0.1886 |
| I-67 | 0.0085 | 0.0152 |
| I-68 | 0.0003 | 0.0007 |
| I-69 | 0.0009 | 0.0022 |
| I-70 | 0.0195 | 0.1876 |
| I-71 | 0.0002 | 0.0009 |
| I-73 | 0.0027 | 0.0117 |
| I-74 | 0.0002 | 0.0014 |
| I-75 | 0.0014 | 0.0083 |
| I-76 | 0.0024 | 0.0181 |
| I-77 | 0.0003 | 0.0028 |
| I-78 | 0.0009 | 0.0025 |
| I-79 | 0.0008 | 0.0051 |
| I-80 | 0.0007 | 0.0027 |
| I-81 | 0.0012 | 0.0042 |
| I-82 | 0.0003 | 0.0019 |
| I-83 | 0.0001 | 0.001 |
| I-84 | 0.0122 | 0.0563 |
| I-85 | 0.0006 | 0.0033 |
| I-86 | 0.0006 | 0.0041 |
| I-87 | 0.0292 | 0.1385 |
| I-88 | 0.00009757 | 0.0007 |
| I-89 | 0.0007 | 0.0045 |
| I-90 | 0.0046 | 0.0091 |
| I-91 | 0.0037 | 0.0198 |
| I-92 | 0.4305 | 4.835 |
| I-93 | 0.9207 | 3.238 |
| I-94 | 0.0046 | 0.022 |
| I-95 | 0.0005 | 0.0014 |
| I-96 | 0.0008 | 0.0031 |
| I-97 | 0.0009 | 0.0017 |

Example 13

In this example, an acute hypothermia mouse model assay was used to evaluate the ability of compounds disclosed herein to inhibit TNF-alpha induced hypothermia.

Female C57BL/6 mice are randomly grouped and weighed on Day −1. On the day of the study (Day 0), mice are administered vehicle or test article by oral gavage. Fifteen minutes after oral administration of test agents, each mouse is administered an intraperitoneal (IP) injection of solution containing recombinant human tumor necrosis factor alpha (TNF-a, 25.0 µg) and zVAD-FMK (200 µg). Body temperature is measured at 0 hours (before IP injections) and every hour via rectal probe temperature measuring device. Three (3) hours after IP injections of TNF-a and zVAD/FMK, mice are euthanized by CO$_2$ asphyxiation and blood is collected via cardiac puncture. Serum and plasma are harvested for determination of cytokine and compound levels, respectively. Separate groups of mice (satellite mice) are included for the determination of compound levels in plasma at the time of administration of TNFa/zVAD-FMK.

(S)-5-benzyl-N-(5-methyl-4-oxo-2,3,4,5-tetrahydrobenzo [b][1,4]oxazepin-3-yl)-4H-1,2,4-triazole-3-carboxamide (WO 2014/125444), having a structure as illustrated below, was used as a comparative compound and was examined using a similar protocol as described by WO 2014/125444. This comparative compound exhibited 93% inhibition at a dose of 30 mg/kg according to WO 2014/125444; however, in the inventors hands, the compound inhibited only 70% at 30 mg/kg. In comparison, compound I-30 of the present disclosure achieved greater than 85% inhibition at a dose of just 5 mg/kg using the similar assay protocol described above.

Comparative Compound

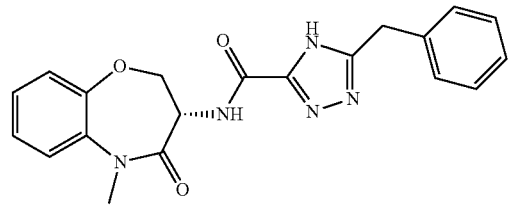

In view of the many possible embodiments to which the principles of the present disclosure may be applied, it should be recognized that the illustrated embodiments are only preferred examples and should not be taken as limiting. Rather, the scope of the present disclosure is defined by the following claims. We therefore claim as our invention all that comes within the scope and spirit of these claims.

We claim:

1. A compound, having a formula

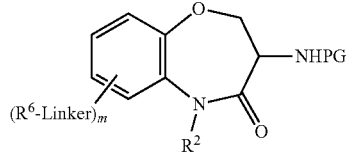

wherein $R^2$ is $R^a$;

$R^a$ is independently for each occurrence H, D, C$_1$alkyl, substituted or non-substituted C$_{2-10}$aliphatic, substituted or non-substituted C$_{1-10}$haloaliphatic, substituted or non-substituted C$_{5-10}$aromatic, or substituted or non-substituted C$_{3-6}$heterocyclic;

linker is CH$_2$ or $R^a$, provided that $R^a$ is not H or D;

$R^6$ is $R^b$, —C(R$^f$)$_3$, or —C(R$^f$)=C(R$^f$)$_2$;

$R^b$ is independently for each occurrence —OH, —SH, —OR$^c$, —SR$^c$, —NR$^d$R$^d$, —Si(R$^a$)$_3$, —C(O)OH, —C(O)OR$^c$, or —C(O)NR$^d$R$^d$;

$R^c$ is independently for each occurrence substituted or non-substituted C$_{1-10}$alkyl, substituted or non-substituted C$_{2-10}$alkenyl, substituted or non-substituted C$_{2-10}$alkynyl, or substituted or non-substituted C$_{3-6}$cycloalkyl;

$R^d$ is independently for each occurrence H; substituted or non-substituted C$_{1-6}$alkyl; substituted or non-substituted C$_{3-6}$cycloalkyl; substituted or non-substituted C$_{3-6}$heterocyclic; substituted or non-substituted C$_{5-10}$aryl; substituted or non-substituted C$_{5-10}$heteroaryl; or two R$^d$ groups together with the nitrogen bound thereto provide a substituted or non-substituted C$_{3-9}$heterocyclic group, or a substituted or non-substituted C$_{5-10}$heteroaryl;

$R^e$ is independently for each occurrence halogen, substituted or non-substituted C$_{1-6}$alkyl, substituted or non-substituted C$_{2-10}$alkenyl, substituted or non-substituted C$_{2-10}$alkynyl, substituted or non-substituted C$_{1-6}$haloalkyl, substituted or non-substituted C$_{3-6}$cycloalkyl, substituted or non-substituted C$_{5-10}$heteroaryl, or —OR$^a$;

R$^f$ is independently for each occurrence R$^a$, R$^b$, or R$^c$, or two R$^f$ groups together with the carbon atom bound thereto provide a substituted or non-substituted C$_{3-6}$cycloalkyl group or a substituted or non-substituted C$_{3-10}$heterocyclic group;

m is 1 to 4; and

PG is an amine protecting group.

2. The compound of claim 1, wherein PG is a 9-fluorenylmethoxycarbonyl group, a t-butyloxycarbonyl group, a trityl group, an allyloxycarbonyl group, or a benzyloxycarbonyl group.

3. The compound of claim 1, wherein the linker is CH$_2$ or a substituted or non-substituted C$_2$, C$_3$, or C$_4$ aliphatic group.

4. The compound of claim 3, wherein the substituted or non-substituted C$_2$ aliphatic group comprises a substituted or non-substituted alkyne and wherein R$^6$ is —C(R$^f$)$_3$, wherein one R$^f$ is R$^e$ and each other R$^f$ independently for each occurrence is substituted or non-substituted C$_{1-4}$alkyl.

5. The compound of claim 4, wherein R$^e$ is —OR$^a$, wherein R$^a$ is H.

6. The compound of claim 4, wherein the substituted or non-substituted C$_{1-4}$alkyl is methyl.

7. The compound of claim 1, wherein the linker is a substituted or non-substituted alkyne and wherein R$^6$ is —C(R$^f$)$_3$, wherein one R$^f$ is OR$^a$ wherein R$^a$ is H, and the remaining two R$^f$ groups together with the carbon atom bound thereto provide an oxetane.

8. The compound of claim 1, wherein the linker is a substituted or non-substituted alkyne and wherein R$^6$ is —C(R$^f$)$_3$, wherein one R$^f$ is OR$^a$ wherein R$^a$ is H, and the remaining two R$^f$ groups together with the carbon atom bound thereto provide a tetrahydropyran.

9. The compound of claim 1, wherein the linker-R$^6$ group is selected from

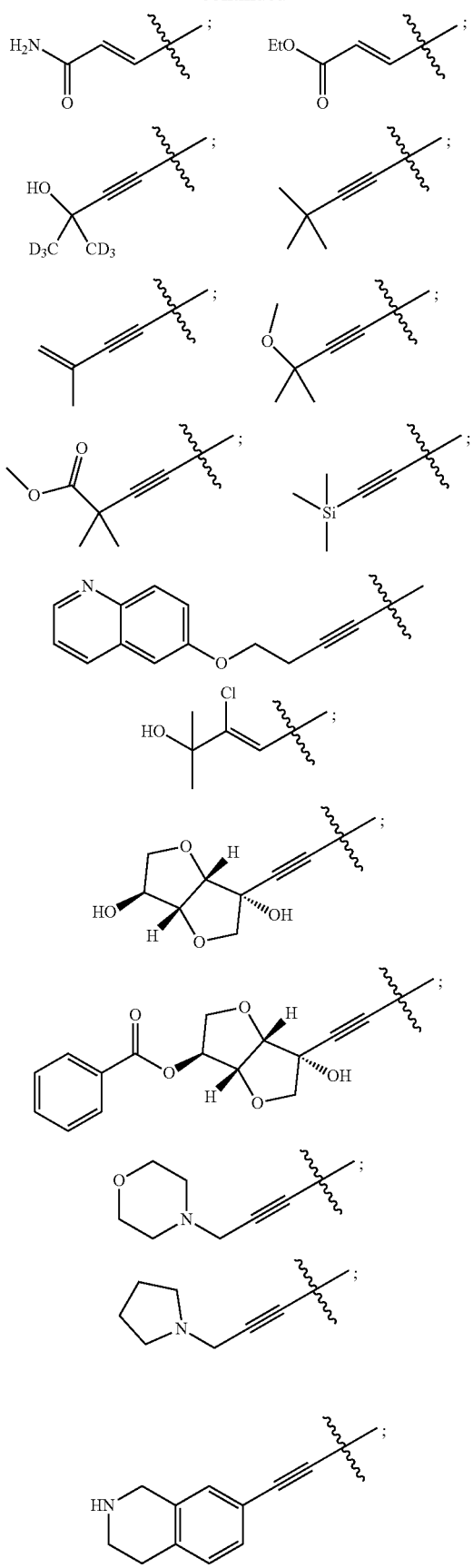

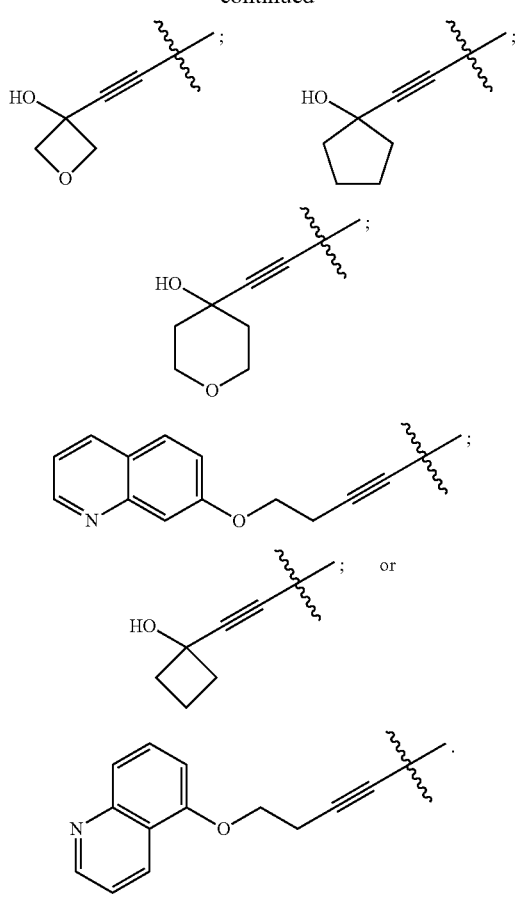
10. The compound of claim 1, wherein the compound is
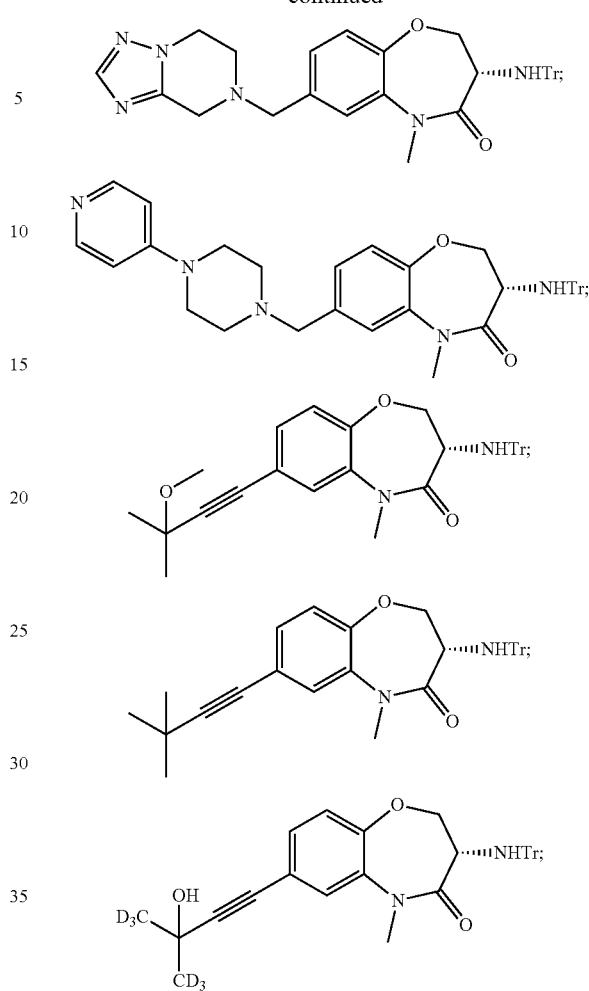
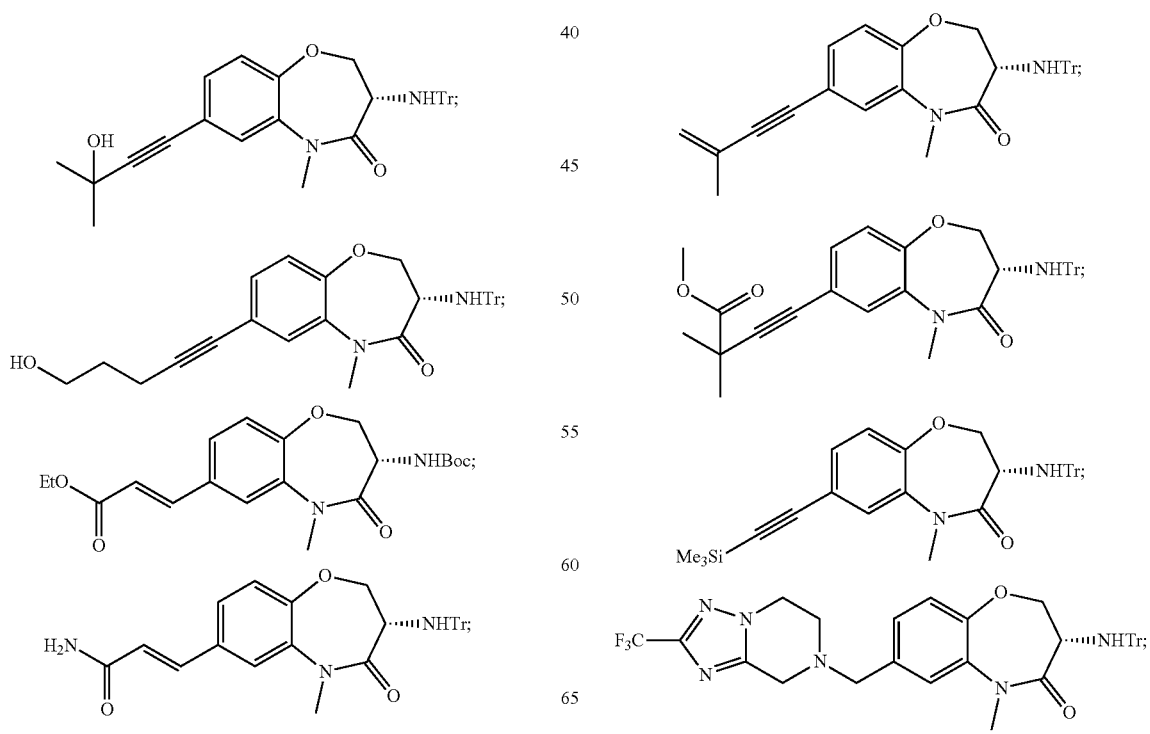

195
-continued

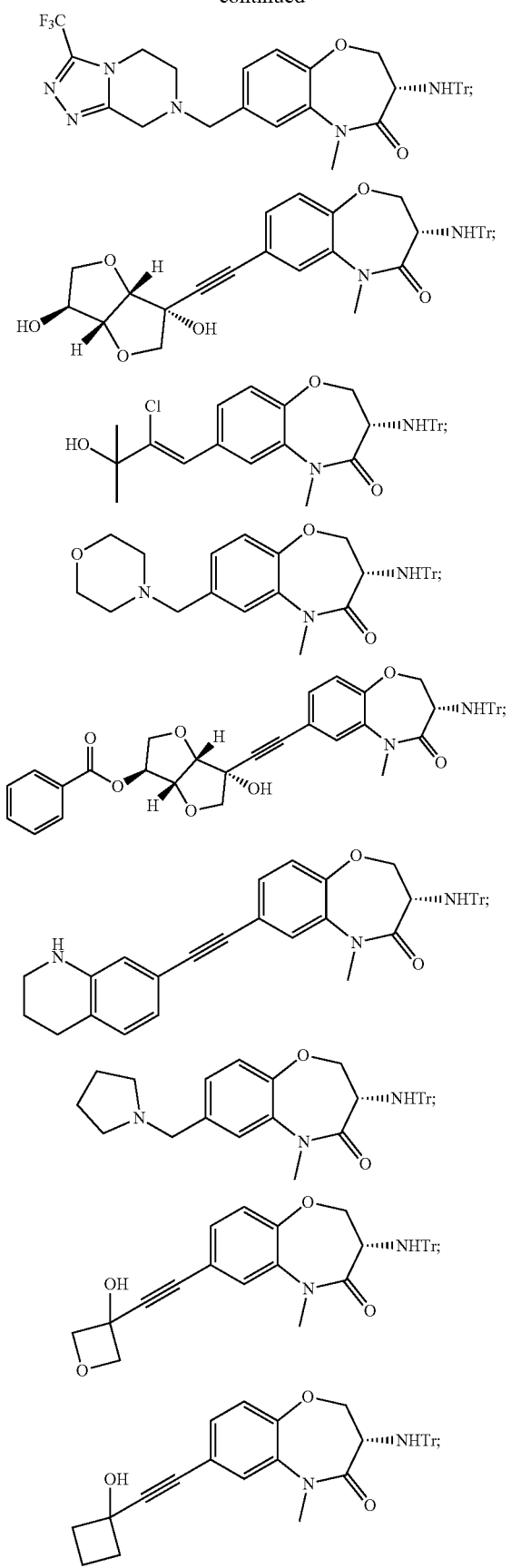

196
-continued

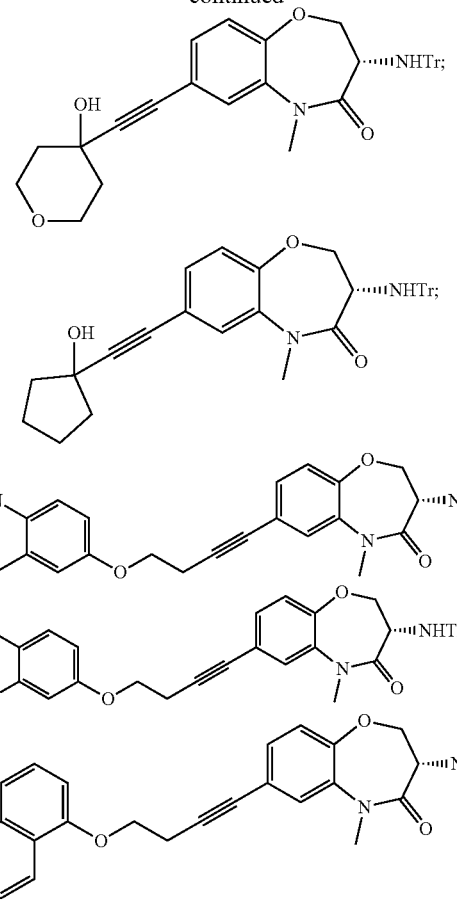

11. A compound, having a formula

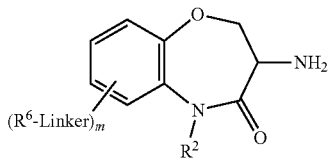

or a salt thereof, wherein:
$R^2$ is $R^a$;
$R^a$ is independently for each occurrence H, D, $C_1$alkyl, substituted or non-substituted $C_{2-10}$aliphatic, substituted or non-substituted $C_{1-10}$haloaliphatic, or substituted or non-substituted $C_{3-6}$heterocyclic;
linker is $CH_2$ or $R^a$, provided that $R^a$ is not H or D;
$R^6$ is $R^b$, —$C(R^f)_3$, or —$C(R^f)$=$C(R^f)_2$;
$R^b$ is independently for each occurrence —OH, —SH, —$OR^c$, —$SR^c$, —$NR^dR^d$, —$Si(R^a)_3$, —C(O)OH, —$C(O)OR^c$, or —$C(O)NR^dR^d$;
$R^c$ is independently for each occurrence substituted or non-substituted $C_{1-10}$alkyl, substituted or non-substituted $C_{2-10}$alkenyl, substituted or non-substituted $C_{2-10}$alkynyl, or substituted or non-substituted $C_{3-6}$cycloalkyl;
$R^d$ is independently for each occurrence H; substituted or non-substituted $C_{1-6}$alkyl; substituted or non-substituted $C_{3-6}$cycloalkyl; substituted or non-substituted $C_{3-6}$heterocyclic; substituted or non-substituted $C_{5-10}$aryl; substituted or non-substituted $C_{5-10}$heteroaryl; or two $R^d$ groups together with the nitrogen bound thereto provide a substituted or non-substituted $C_{3-9}$heterocyclic group, or a substituted or non-substituted $C_{5-10}$heteroaryl;

$R^e$ is independently for each occurrence halogen, substituted or non-substituted $C_{1-6}$alkyl, substituted or non-substituted $C_{2-10}$alkenyl, substituted or non-substituted $C_{2-10}$alkynyl, substituted or non-substituted $C_{1-6}$haloalkyl, substituted or non-substituted $C_{3-6}$cycloalkyl, substituted or non-substituted $C_{5-10}$heteroaryl, or —$OR^a$;

$R^f$ is independently for each occurrence $R^a$, $R^b$, or $R^c$, or two $R^f$ groups together with the carbon atom bound thereto provide a substituted or non-substituted $C_{3-6}$cycloalkyl group or a substituted or non-substituted $C_{3-10}$heterocyclic group;

m is 1 to 4.

12. The compound of claim 11, wherein the linker is $CH_2$, or a substituted or non-substituted $C_2$, $C_3$, or $C_4$ aliphatic group.

13. The compound of claim 12, wherein the substituted or non-substituted $C_2$ aliphatic group comprises a substituted or non-substituted alkyne and wherein $R^6$ is —$C(R^f)_3$, wherein one $R^f$ is $R^e$ and each other $R^f$ independently for each occurrence is $C_{1-4}$alkyl.

14. The compound of claim 13, wherein $R^e$ is —$OR^a$, wherein $R^a$ is H.

15. The compound of claim 13, wherein the $C_{1-4}$alkyl is methyl.

16. The compound of claim 11, wherein the linker-$R^6$ group is selected from

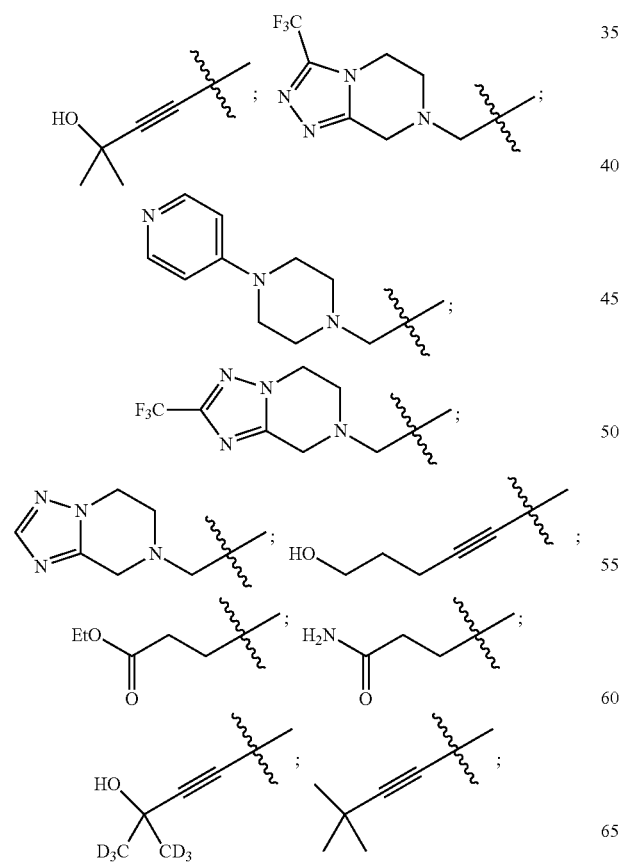

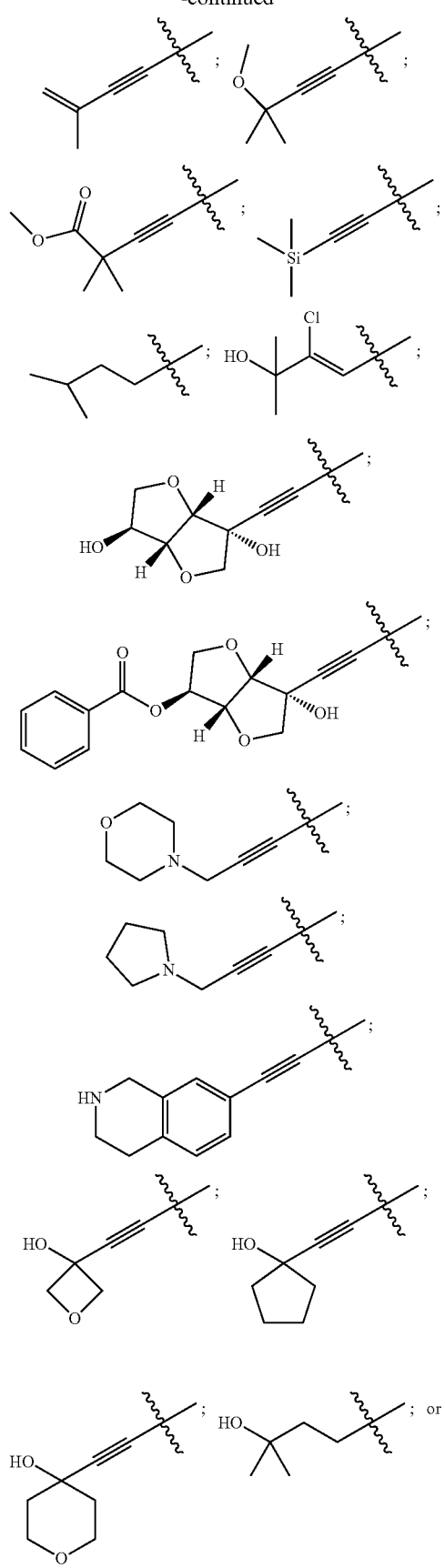

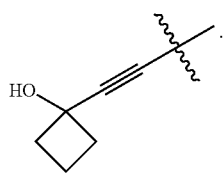
17. The compound of claim 11, wherein the compound is selected from
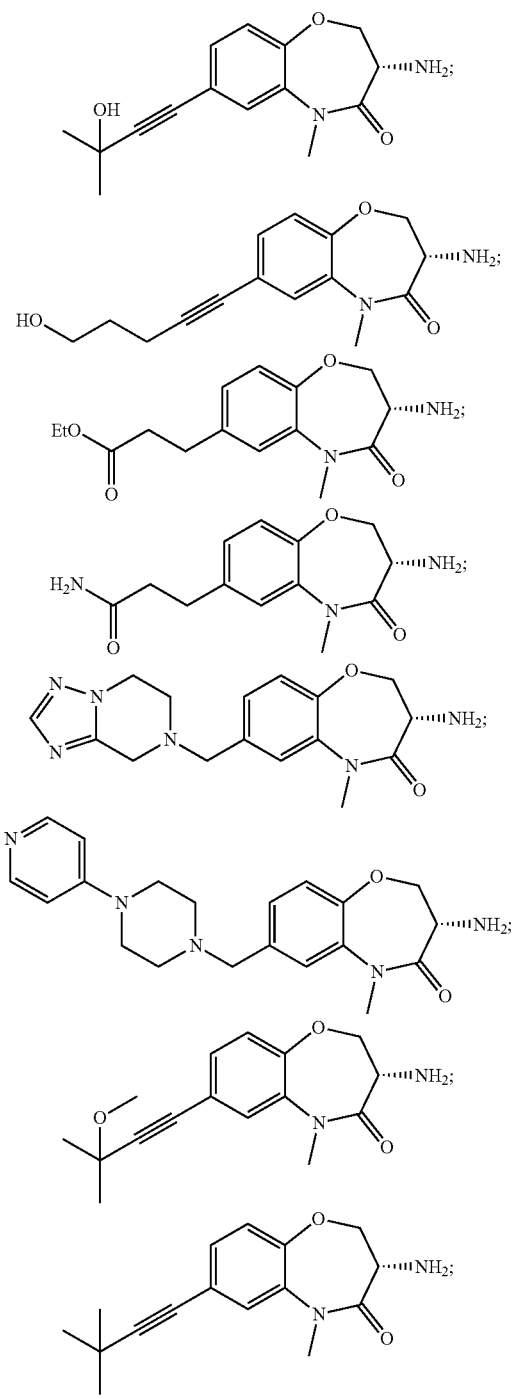
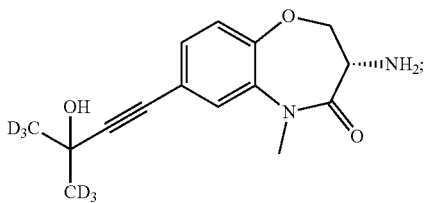
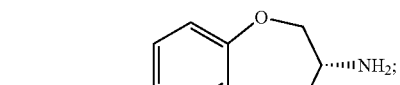
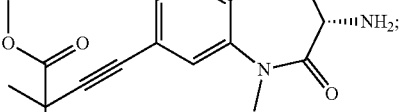
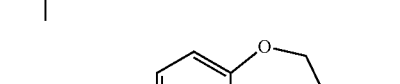
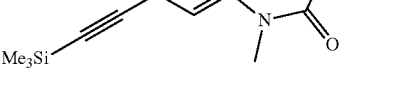
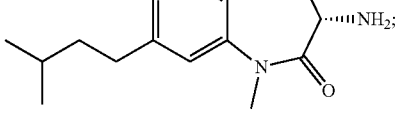
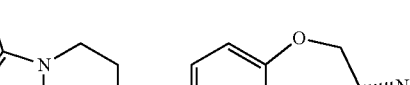
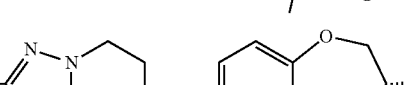
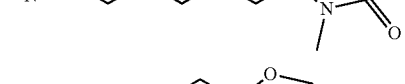
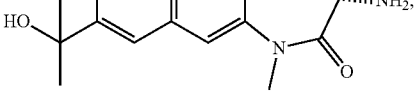
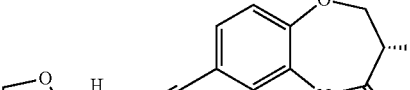
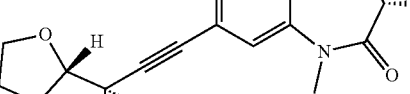

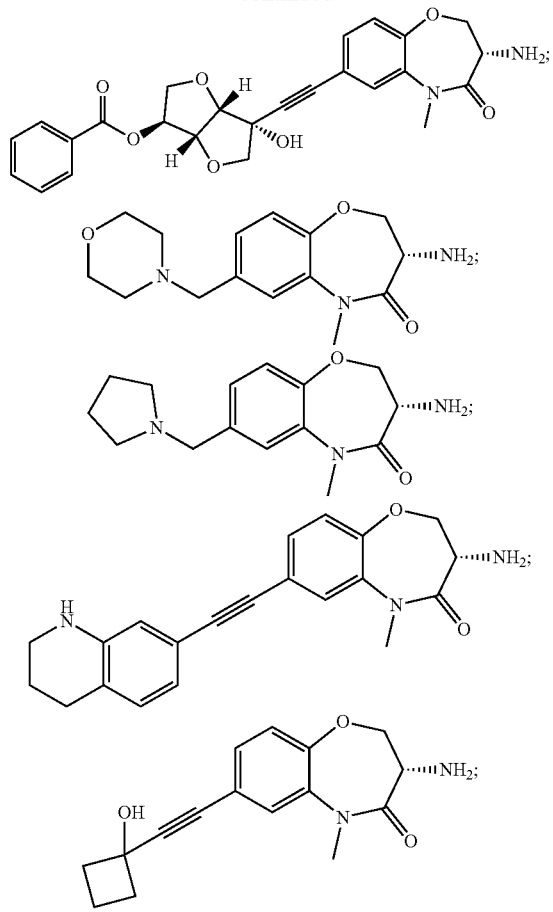
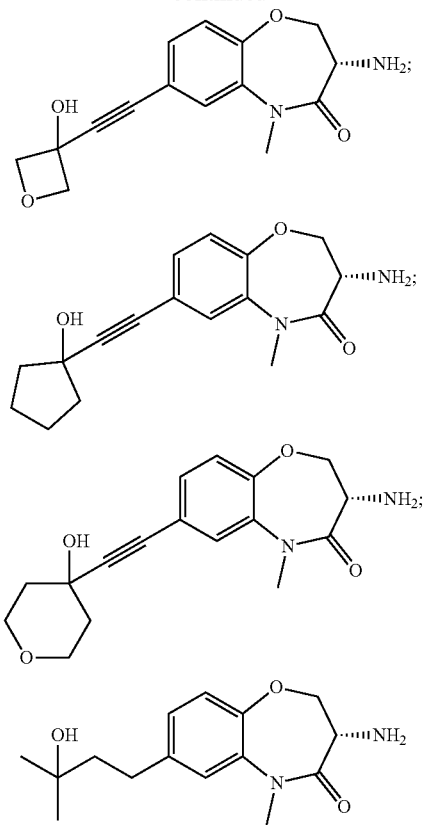
or an HCl salt thereof.

UNITED STATES PATENT AND TRADEMARK OFFICE
CERTIFICATE OF CORRECTION

PATENT NO. : 11,472,782 B2
APPLICATION NO. : 17/072862
DATED : October 18, 2022
INVENTOR(S) : Esteban Masuda et al.

Page 1 of 1

It is certified that error appears in the above-identified patent and that said Letters Patent is hereby corrected as shown below:

In the Claims

In Claim 9, Column 192, Line 27, after " 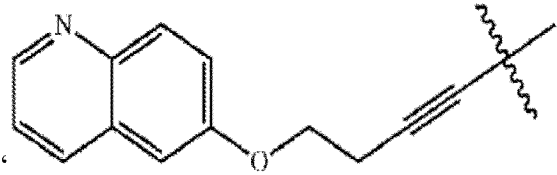 " insert -- ; --.

In Claim 11, Column 197, Line 17, after "group;" insert -- and --.

Signed and Sealed this
Seventh Day of February, 2023

Katherine Kelly Vidal
*Director of the United States Patent and Trademark Office*